US011186863B2

(12) United States Patent
Sekedat et al.

(10) Patent No.: US 11,186,863 B2
(45) Date of Patent: Nov. 30, 2021

(54) METHODS, SYSTEMS, AND COMPOSITIONS FOR COUNTING NUCLEIC ACID MOLECULES

(71) Applicant: Progenity, Inc., San Diego, CA (US)

(72) Inventors: Matthew Sekedat, Ann Arbor, MI (US); Jeffrey Buis, Ann Arbor, MI (US); Ronald David Beaubien, Jr., Jackson, MI (US); Sharat Singh, Rancho Santa Fe, CA (US); Jeff Perry, Ann Arbor, MI (US); Steven Lockton, San Diego, CA (US); Chandni Jain, San Diego, CA (US); Natalie Mae Jameson-Kiesling, San Diego, CA (US)

(73) Assignee: Progenity, Inc., San Diego, CA (US)

( * ) Notice: Subject to any disclaimer, the term of this patent is extended or adjusted under 35 U.S.C. 154(b) by 0 days.

(21) Appl. No.: 17/150,079

(22) Filed: Jan. 15, 2021

(65) Prior Publication Data
US 2021/0164029 A1 Jun. 3, 2021

Related U.S. Application Data

(63) Continuation of application No. PCT/US2020/026456, filed on Apr. 2, 2020.

(60) Provisional application No. 62/913,543, filed on Oct. 10, 2019, provisional application No. 62/913,542, filed on Oct. 10, 2019, provisional application No. 62/910,397, filed on Oct. 3, 2019, provisional application No. 62/910,394, filed on Oct. 3, 2019, provisional application No. 62/828,397, filed on Apr. 2, 2019.

(51) Int. Cl.
*C12Q 1/6837* (2018.01)
*C12Q 1/6853* (2018.01)

(52) U.S. Cl.
CPC ......... *C12Q 1/6837* (2013.01); *C12Q 1/6853* (2013.01)

(58) Field of Classification Search
None
See application file for complete search history.

(56) References Cited

U.S. PATENT DOCUMENTS

| 5,011,769 A | 4/1991 | Duck et al. |
| 5,124,246 A | 6/1992 | Urdea et al. |
| 5,288,609 A | 2/1994 | Engelhardt et al. |
| 5,401,632 A | 3/1995 | Wang et al. |
| 5,403,711 A | 4/1995 | Walder et al. |
| 5,409,818 A | 4/1995 | Davey et al. |
| 5,432,272 A | 7/1995 | Benner |
| 5,591,841 A | 1/1997 | Ji et al. |
| 5,624,802 A | 4/1997 | Urdea et al. |
| 5,660,988 A | 8/1997 | Duck et al. |
| 5,710,264 A | 1/1998 | Urdea et al. |
| 5,792,614 A | 8/1998 | Western et al. |
| 5,817,921 A | 10/1998 | Tom et al. |
| 5,846,717 A | 12/1998 | Brow et al. |
| 5,849,481 A | 12/1998 | Urdea et al. |
| 5,851,770 A | 12/1998 | Babon et al. |
| 5,866,337 A | 2/1999 | Schon |
| 5,882,867 A | 3/1999 | Ullman et al. |
| 5,888,740 A | 3/1999 | Han |
| 5,912,340 A | 6/1999 | Kutyavin et al. |
| 5,914,230 A | 6/1999 | Liu et al. |
| 5,942,391 A | 8/1999 | Zhang et al. |
| 5,958,692 A | 9/1999 | Cotton et al. |
| 5,976,790 A | 11/1999 | Pinkel et al. |
| 5,985,557 A | 11/1999 | Prudent et al. |
| 5,994,069 A | 11/1999 | Hall et al. |
| 6,001,567 A | 12/1999 | Brow et al. |
| 6,001,983 A | 12/1999 | Benner |
| 6,013,170 A | 1/2000 | Meade |
| 6,027,889 A | 2/2000 | Barany et al. |
| 6,037,120 A | 3/2000 | Benner |
| 6,063,573 A | 5/2000 | Kayyem |
| 6,090,543 A | 7/2000 | Prudent et al. |
| 6,100,029 A | 8/2000 | Lapidus et al. |
| 6,110,677 A | 8/2000 | Western et al. |
| 6,110,684 A | 8/2000 | Kemper et al. |
| 6,121,001 A | 9/2000 | Western et al. |
| 6,127,121 A | 10/2000 | Meyer, Jr. et al. |
| 6,140,496 A | 10/2000 | Benner |
| 6,143,496 A | 11/2000 | Brow et al. |
| 6,143,877 A | 11/2000 | Meyer et al. |
| 6,150,097 A | 11/2000 | Tyagi et al. |
| 6,183,960 B1 | 2/2001 | Lizardi |
| 6,210,884 B1 | 4/2001 | Lizardi |

(Continued)

FOREIGN PATENT DOCUMENTS

| WO | WO 1998/44151 | 10/1998 |
| WO | WO 2000/18957 | 4/2000 |

(Continued)

OTHER PUBLICATIONS

2001 International Symposiums on Circulating Nucleic Acids in Plasma and Serum, (CNAPS-2) (Feb. 20-21, 2001), Clin. Chem. 47(2):361-370.

(Continued)

*Primary Examiner* — Christopher M Gross

(74) *Attorney, Agent, or Firm* — Casimir Jones, S.C.

(57) ABSTRACT

Compositions and methods, systems, and kits for detecting and quantifying variations in numbers of molecules, particularly variations in gene dosage, e.g., due to gene duplication, or to variations from the normal euploid complement of chromosomes, e.g., trisomy of one or more chromosomes that are normally found in diploid pairs, without digital sequencing.

23 Claims, 67 Drawing Sheets

Specification includes a Sequence Listing.

(56) References Cited

U.S. PATENT DOCUMENTS

| | | |
|---|---|---|
| 6,221,583 B1 | 4/2001 | Kayyem et al. |
| 6,235,502 B1 | 5/2001 | Weissman et al. |
| 6,248,229 B1 | 6/2001 | Meade |
| 6,335,167 B1 | 1/2002 | Pinkel et al. |
| 6,391,559 B1 | 5/2002 | Brown et al. |
| 6,399,397 B1 | 6/2002 | Zarling et al. |
| 6,440,706 B1 | 8/2002 | Vogelstein et al. |
| 6,558,928 B1 | 5/2003 | Landegren |
| 6,753,147 B2 | 6/2004 | Vogelstein et al. |
| 6,852,487 B1 | 2/2005 | Barany et al. |
| 6,858,412 B2 | 2/2005 | Willis et al. |
| 6,872,816 B1 | 3/2005 | Hall et al. |
| 7,320,860 B2 | 1/2008 | Landegren et al. |
| 7,351,528 B2 | 4/2008 | Landegren |
| 7,459,315 B2 | 12/2008 | Brown |
| 7,618,937 B2 | 11/2009 | Messersmith et al. |
| 7,632,641 B2 | 12/2009 | Dirks et al. |
| 7,709,197 B2 | 5/2010 | Drmanac |
| 7,790,418 B2 | 9/2010 | Mayer |
| 7,858,679 B2 | 12/2010 | Messersmith et al. |
| 7,888,017 B2 | 2/2011 | Quake et al. |
| 8,105,778 B2 | 1/2012 | Dirks et al. |
| 8,361,720 B2 | 1/2013 | Oldham-Haltom et al. |
| 8,532,930 B2 | 9/2013 | Rabinowitz et al. |
| 8,541,060 B2 | 9/2013 | Messersmith et al. |
| 8,715,937 B2 | 5/2014 | Zou et al. |
| 8,815,793 B2 | 8/2014 | Messersmith et al. |
| 8,916,344 B2 | 12/2014 | Zou et al. |
| 9,057,730 B2 | 6/2015 | Mir |
| 9,096,893 B2 | 8/2015 | Allawi et al. |
| 9,212,392 B2 | 12/2015 | Allawi et al. |
| 9,376,677 B2 | 6/2016 | Mir |
| 9,481,883 B2 | 11/2016 | Mir |
| 9,556,429 B2 | 1/2017 | Mir |
| 9,637,597 B2 | 5/2017 | Messersmith et al. |
| 9,982,293 B2 | 5/2018 | Fu et al. |
| 2003/0087338 A1 | 5/2003 | Messersmith et al. |
| 2004/0209299 A1 | 3/2004 | Pinter et al. |
| 2004/0091864 A1 | 5/2004 | French et al. |
| 2004/0137470 A1 | 7/2004 | Dhallan |
| 2004/0185495 A1 | 9/2004 | Schueler et al. |
| 2005/0064476 A1 | 3/2005 | Huang et al. |
| 2005/0130173 A1 | 6/2005 | Leamon et al. |
| 2005/0164252 A1 | 7/2005 | Yeung et al. |
| 2006/0009550 A1 | 1/2006 | Messersmith et al. |
| 2006/0046258 A1 | 3/2006 | Lapidus et al. |
| 2006/0228721 A1 | 10/2006 | Leamon et al. |
| 2007/0072208 A1 | 3/2007 | Drmanac |
| 2007/0099208 A1 | 5/2007 | Drmanac et al. |
| 2007/0178478 A1 | 8/2007 | Dhallan et al. |
| 2008/0050739 A1 | 2/2008 | Stoughton et al. |
| 2008/0070792 A1 | 3/2008 | Stoughton et al. |
| 2008/0247984 A1 | 10/2008 | Messersmith et al. |
| 2008/0254474 A1 | 10/2008 | Laird et al. |
| 2009/0029377 A1 | 1/2009 | Lo et al. |
| 2010/0184043 A1 | 6/2010 | Mitchell et al. |
| 2010/0330025 A1 | 12/2010 | Messersmith et al. |
| 2013/0275103 A1 | 10/2013 | Struble et al. |
| 2014/0342354 A1 | 11/2014 | Evans et al. |
| 2017/0204459 A1 | 7/2017 | Barany et al. |
| 2018/0030519 A1 | 2/2018 | Bashkirov et al. |
| 2018/0066309 A1 | 3/2018 | Hengen et al. |
| 2018/0171409 A1 | 6/2018 | Rabinowitz et al. |
| 2018/0346984 A1 | 12/2018 | Quake et al. |
| 2019/0211383 A1 | 7/2019 | Ohman et al. |
| 2019/0292585 A1 | 9/2019 | Scholl et al. |
| 2020/0140922 A1 | 5/2020 | Dahl et al. |
| 2020/0294625 A1 | 9/2020 | Kim et al. |
| 2021/0040539 A1 | 2/2021 | Bashkirov et al. |
| 2021/0164029 A1 | 6/2021 | Sekedat et al. |

FOREIGN PATENT DOCUMENTS

| | | |
|---|---|---|
| WO | WO 2002/44411 | 6/2002 |
| WO | WO 2002/070755 | 9/2002 |
| WO | WO 2003/012119 | 2/2003 |
| WO | WO 2005/039389 | 5/2005 |
| WO | WO 2006/091226 | 8/2006 |
| WO | WO 2007/052006 | 5/2007 |
| WO | WO 2007/147073 | 12/2007 |
| WO | WO 2007/147074 | 12/2007 |
| WO | WO 2008/049108 | 4/2008 |
| WO | WO 2008/091386 | 7/2008 |
| WO | WO 2008/115497 | 9/2008 |
| WO | WO 2009/013492 | 1/2009 |
| WO | WO 2009/062146 | 5/2009 |
| WO | WO 2012/125693 | 9/2012 |
| WO | WO 2014/116812 | 7/2014 |
| WO | WO 2014/165267 | 10/2014 |
| WO | WO 2015/083002 | 6/2015 |
| WO | WO 2015/148503 | 10/2015 |
| WO | WO 2016/134191 | 8/2016 |
| WO | WO 2017/020023 | 2/2017 |
| WO | WO 2017/020024 | 2/2017 |
| WO | WO 2017/147145 | 8/2017 |
| WO | WO 2019/036378 | 2/2019 |
| WO | WO 2019/195346 | 10/2019 |
| WO | WO 2020/206170 | 10/2020 |

OTHER PUBLICATIONS

2003 International Symposiums on Circulating Nucleic Acids in Plasma and Serum, (CNAPS-3) (Nov. 9-12, 2003) Clin. Chem. 49(11):1-32.

2005 International Symposiums on Circulating Nucleic Acids in Plasma and Serum, (Cnaps Iv) (Sep. 4-6, 2005) Clin. Chem. 51(1):1-38.

Affidavit of Elizabeth Rosenberg, Internet Archive, regarding Illumina SNP Genotyping GoldenGate Assay Workflow, http://www.illumina.com/Products/prod_snp.ilmn, Internet Archive Web Capture, Dec. 4, 2004, 8 pages.

Ali et al., Rolling circle amplification: a versatile tool for chemical biology, materials science and medicine. Chen. Soc Rev. May 21, 2014;43(10):3324-41.

Ambardar et al., High Throughput Sequencing: An Overview of Sequencing Chemistry. Indian J Microbiol. Dec. 2016;56(4):394-404.

American College of Obstetricians and Gynecologists, ACOG Practice Bulletin No. 88, Dec. 2007. Invasive prenatal testing for aneuploidy. Obstet Gynecol. Dec. 2007;110(6):1459-67.

Avgidou et al., Prospective first-trimester screening for trisomy 21 in 30,564 pregnancies. Am J Obstet Gynecol. Jun. 2005;192(6):1761-7.

Baner et al., Signal amplification of padlock probes by rolling circle replication. Nucleic Acids Res. Nov. 15, 1998;26(22):5073-8.

Barany, Genetic disease detection and DNA amplification using cloned thermostable ligase. Proc Natl Acad Sci USA. Jan. 1, 1991;88(1):189-93.

Bauer et al., A prospective analysis of cell-free fetal DNA concentration in maternal plasma as an indicator for adverse pregnancy outcome. Prenat Diagn. Sep. 2006;26(9):831-6.

Baxter et al., Discovery and genetic localization of Down syndrome cerebellar phenotypes using the Ts65Dn mouse. Hum Mol Genet. Jan. 22, 2000;9(2):195-202.

Bennett et al., Toward the $1,000 human genome. Pharmacogenomics. Jun. 2005;6(4):373-82.

Bianchi, Circulating fetal DNA: its origin and diagnostic potential-a review. Placenta. Apr. 2004;25 Suppl A:S93-S101.

Blow, The Personal side of genomics. Nature. Oct. 2007;449:627-30.

Brewster et al., Copy number imbalances between screen- and symptom-detected breast cancers and impact on disease-free survival. Cancer Prev Res (Phila). Oct. 2011;4(10):1609-16.

Burmester et al., DMET microarray technology for pharmacogenomics-based personalized medicine. Methods Mol Biol. 2010;632:99-124.

Caldwell et al., CYP4F2 genetic variant alters required warfarin dose. Blood. Apr. 15, 2008;111(8):4106-12.

Ceska et al., Structure-specific DNA cleavage by 5' nucleases. Trends Biochem Sci. Sep. 1998;23(9):331-6.

(56) References Cited

OTHER PUBLICATIONS

Chan et al., Size distributions of maternal and fetal DNA in maternal plasma. Clin Chem. Jan. 2004;50(1):88-92.
Chitty et al., Noninvasive Prenatal Screening for Genetic Diseases Using Massively Parallel Sequencing of Maternal Plasma DNA. Cold Spring Harb Perspect Med. Jul. 17, 2015;5(9):a023085.
Chiu et al., Non-invasive prenatal diagnosis by single molecule counting technologies. Trends Genet. Jul. 2009;25(7):324-31.
Chiu et al., Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
Corstjens et al., Infrared up-converting phosphors for bioassays. IEE Proc Nanobiotechnol. Apr. 2005;152(2):64-72.
Dahl et al., Imaging single DNA molecules for high precision NIPT. Sci Rep. Mar. 14, 2018;8(1):4549.
Dalsin et al., Mussel Adhesive Protein Mimetic Polymers for the Preparation of Nonfouling Surfaces. J Am Chem. Soc. Apr. 9, 2003;125(14):4253-8.
Daly et al., Multiplex assay for comprehensive genotyping of genes involved in drug metabolism, excretion, and transport. Clin Chem. Jul. 2007;53(7):1222-30.
De Rijke et al., Up-converting phosphor reporters for nucleic acid microarrays. Nat Biotechnol. Mar. 2001;19(3):273-6.
Deeken et al., A pharmacogenetic study of docetaxel and thalidomide in patients with castration-resistant prostate cancer using the DMET genotyping platform. Pharmacogenomics J. Jun. 2010;10(3):191-9.
Deeken, The Affymetrix DMET platform and pharmacogenetics in drug development. Curr Opin Mol Ther. Jun. 2009;11(3):260-8.
Devor et al., Strategies for Attaching Oligonucleotides to Solid Supports. Integrated DNA Technologies, 2005, 24 pages.
Dhallan et al., A non-invasive test for prenatal diagnosis based on fetal DNA present in maternal blood: a preliminary study. Lancet. Feb. 10, 2007;369(9560):474-81.
Di et al., Dynamic model based algorithms for screening and genotyping over 100 K SNPs on oligonucleotide microarrays. Bioinformatics. May 1, 2005;21(9):1958-63.
Dietmaier et al., Multiple mutation analyses in single tumor cells with improved whole genome amplification. Am J Pathol. Jan. 1999;154(1):83-95.
Ding et al., MS analysis of single-nucleotide differences in circulating nucleic acids: Application to noninvasive prenatal diagnosis. Proc Natl Acad Sci U S A. Jul. 20, 2004;101(29):10762-7.
Dirks et al., Triggered amplification by hybridization chain reaction. Proc Natl Acad Sci U S A. Oct. 26, 2004;101(43):15275-8.
Dominak et al., Polymeric crowding agents improve passive biomacromolecule encapsulation in lipid vesicles. Langmuir. Aug. 17, 2010;26(16):13195-200.
Doty et al., Strand Separation and Specific Recombination in Deoxyribonucleic Acids: Physical Chemical Studies. Proc Natl Acad Sci U S A. Apr. 1960;46(4):461-76.
Dressman et al., Transforming single DNA molecules into fluorescent magnetic particles for detection and enumeration of genetic variations. Proc Natl Acad Sci U S A. Jul. 22, 2003;100(15):8817-22.
Dumaual et al., Comprehensive assessment of metabolic enzyme and transporter genes using the Affymetrix Targeted Genotyping System. Pharmacogenomics. Mar. 2007;8(3):293-305.
Engler et al., A one pot, one step, precision cloning method with high throughput capability. PLoS One. 2008;3(11):e3647.
Epstein et al., High-density fiber-optic genosensor microsphere array capable of zeptomole detection limits. Anal Chem. Apr. 15, 2002;74(8):1836-40.
Fan et al., Highly Parallel SNP Genotyping. Cold Spring Harb Symp Quant Biol. 2003;68:69-78.
Fan et al., Noninvasive diagnosis of fetal aneuploidy by shotgun sequencing DNA from maternal blood. Proc Natl Acad Sci U S A. Oct. 21, 2008;105(42):16266-71.

Fleischhacker et al., Methods for isolation of cell-free plasma DNA strongly affect DNA yield. Clin Chim Acta. Nov. 20, 2011;412(23-24):2085-8.
Fuchs et al., Salt concentration effects on equilibrium melting curves from DNA microarray. Biophys J. Sep. 22, 2010;99(6):1886-95.
Gautier et al., Fetal RhD genotyping by maternal serum analysis: a two-year experience. Am J Obstet Gynecol. Mar. 2005;192(3):666-9.
Geiersbach et al., Unknown partner for USP6 and unusual SS18 rearrangement detected by fluorescence in situ hybridization in a solid aneurysmal bone cyst. Cancer Genet. Apr. 2011;204(4):195-202.
Geiss et al., Direct multiplexed measurement of gene expression with color-coded probe pairs. Nat Biotechnol. Mar. 2008;26(3):317-25.
Glass et al., Organosilane deposition for microfluidic applications. Biomicrofluidics. Sep. 2011; 5(3):036501-036501-7.
Griffiths et al., "An introduction to genetic analysis" 6th ed., W.H. Freeman, New York (1996), TOC.
Hagen et al., Hapten-Anti-Hapten Technique for Two-Color IHC Detection of Phosphorylated EGFR and H2AX Using Primary Antibodies Raised in the Same Host Species.Methods Mol Biol. 2017;1554:155-160.
Hall et al., Sensitive detection of DNA polymorphisms by the serial invasive signal amplification reaction. Proc Natl Acad Sci U S A. Jul. 18, 2000;97(15):8272-7.
Hardenbol et al., Highly multiplexed molecular inversion probe genotyping: over 10,000 targeted SNPs genotyped in a single tube assay. Genome Res. Feb. 2005;15(2):269-75.
Hardenbol et al., Multiplexed genotyping with sequence-tagged molecular inversion probes. Nat Biotechnol. Jun. 2003;21(6):673-8.
Hatch et al., Rolling circle amplification of DNA immobilized on solid surfaces and its application to multiplex mutation detection. Genetic Analysis: Biomolecular Engineering. 1999;15:35-40.
Hegab et al., Single-Step Assembly of Multifunctional Poly(tannic acid)-Graphene Oxide Coating To Reduce Biofouling of Forward Osmosis Membranes. ACS Appl Mater Interfaces. Jul. 13, 2016;8(27):17519-28.
Hong et al., Fluorometric Detection of MicroRNA Using Isothermal Gene Amplification and Graphene Oxide. Anal Chem. Mar. 15, 2016;88(6):2999-3003.
Hosono et al., Unbiased whole-genome amplification directly from clinical samples. Genome Res. May 2003;13(5):954-64.
Hsu, Prenatal diagnosis of chromosomal abnormalities through amniocentesis. In: Milunsky A, editor. Genetic Disorders and the Fetus. 1998. 4 ed. Baltimore: The Johns Hopkins University Press. 179-180.
Huang et al., Molecular beacon lighting up on graphene oxide. Anal Chem. May 2012 1;84(9):4192-8.
Illumina, GoldenGate(TM) Assay Workflow. Product Fact Sheet. 2004, 2 pages.
Illumina, History of sequencing by synthesis, available at https://www.illumina.com/science/technology/next-generation-sequencing/illumina-sequencing-history.html, last accessed Jun. 8, 2021, 3 pages.
Illumina, Illumina Announces Benchtop SNP Genotyping System. Press Release. Nov. 5, 2003, 3 pages.
Illumina, Illumina Begins Shipment of Beadstation 500G Benchtop Genotyping System. Press Release. Apr. 15, 2004, 3 pages.
Illumina, Illumina Extends BeadArray Technology to Address Wider Range of SNP Genotyping Projects; New Microarray Offerings Enable Genotyping at 384 and 786 Multiplex. Press Release. May 4, 2004, 2 pages.
Illumina, Prepareing Samples of Sequencing Genomic DNA, Part#1003806 Rev. A., 2007, retrieved from http://zazil.ibt.unam.mx/usmb/wp-content/uploads/2016/05/1003806_Genomic_DNA_Sample_Prep.pdf, Jun. 8, 2021, 20 pages.
Innan et al., The pattern of polymorphism on human chromosome 21. Genome Res. Jun. 2003;13(6A):1158-68.

(56) References Cited

OTHER PUBLICATIONS

Institute of Medicine (US) Committee on Improving Birth Outcomes, Reducing Birth Defects: Meeting the Challenge in the Developing World. Eds. Bale, Stoll, Lucas, 2003, National Academies Press, 271 pages.
Jarvie, Next generation sequencing technologies. Drug Discov Today Technol. Autumn 2005;2(3):255-60.
Jett et al., Clinical and genetic aspects of neurofibromatosis 1. Genet Med. Jan. 2010;12(1):1-11.
Ji et al., Molecular inversion probe analysis of gene copy alterations reveals distinct categories of colorectal carcinoma. Cancer Res. Aug. 15, 2006;66(16):7910-9.
Jiang et al., Characterization of Escherichia coli endonuclease VIII. J Biol Chem. Dec. 19, 1997;272(51):32230-9.
Jiang et al., Surface Characteristics of a Self-Polymerized Dopamine Coating Deposited on Hydrophobic Polymer Films. Langmuir. Dec. 6, 2011;27(23):14180-7.
Kaiser et al., A comparison of eubacterial and archaeal structure-specific 5'-exonucleases. J Biol Chem. Jul. 23, 1999;274(30):21387-94.
Koile et al., Electrochemical Removal of Phenolic Films from a Platinum Anode. Anal. Chem. 1979;51(6):741-744.
Kumar et al., Silanized nucleic acids: a general platform for DNA immobilization. Nucleic Acids Res. Jul. 15, 2000;28(14):E71.
Lapierre et al., Analysis of uncultured amniocytes by comparative genomic hybridization: a prospective prenatal study. Prenat Diagn. Feb. 2000;20(2):123-31.
Lasken et al., Whole genome amplification: abundant supplies of DNA from precious samples or clinical specimens. Trends Biotechnol. Dec. 2003;21(12):531-5.
Lee et al., Facile Conjugation of Biomolecules onto Surfaces via Mussel Adhesive Protein Inspired Coatings. Adv Mater. Jan. 26, 2009;21(4):431-434.
Lee et al., Mussel-Inspired Surface Chemistry for Multifunctional Coatings. Science. Oct. 19, 2007;318(5849):426-30.
Li et al., Detection of paternally inherited fetal point mutations for beta-thalassemia using size-fractionated cell-free DNA in maternal plasma. JAMA. Feb. 16, 2005;293(7):843-9.
Li et al., Electrochemical quartz crystal microbalance study on growth and property of the polymer deposit at gold electrodes during oxidation of dopamine in aqueous solutions. Thin Solid Films. 2006;497(1-2):270- 278.
Li, et al., Detection of Single-Molecule DNA Hybridization Using Enzymatic Amplification in an Array of Femtoliter-Sized Reaction Vessels. J Am Chem. Soc. Sep. 24, 2008;130(38):12622-3.
Lin et al., Synthesis and duplex stability of oligonucleotides containing cytosinethymine analogues. Nucleic Acids Res. Dec. 25, 1989;17(24):10373-83.
Lin et al., Synthesis of oligodeoxyribonucleotides containing degenerate bases and their use as primers in the polymerase chain reaction. Nucleic Acids Res. Oct. 11, 1992;20(19):5149-52.
Lindhal et al., DNA N-glycosidases: properties of uracil-DNA glycosidase from Escherichia coli. J Biol Chem. May 25, 1977;252(10):3286-94.
Lindhal, DNA repair enzymes. Annu Rev Biochem. 1982;51:61-8.
Liu et al., Flap endonuclease 1: a central component of DNA metabolism. Annu Rev Biochem. 2004;73:589-615.
Lo et al., Digital PCR for the molecular detection of fetal chromosomal aneuploidy. Proc Natl Acad Sci U S A. Aug. 7, 2007;104(32):13116-21.
Lo et al., Plasma placental RNA allelic ratio permits noninvasive prenatal chromosomal aneuploidy detection. Nat Med. Feb. 2007;13(2):218-23.
Lo et al., Presence of fetal DNA in maternal plasma and serum. Lancet. Aug. 16, 1997;350(9076):485-7.
Lo et al., Quantitative analysis of fetal DNA in maternal plasma and serum: implications for noninvasive prenatal diagnosis. Am J Hum Genet. Apr. 1998;62(4):768-75.
Lo, Fetal DNA in maternal plasma: biology and diagnostic applications. Clin Chem. Dec. 2000;46(12):1903-6.
Lyamichev et al., Polymorphism identification and quantitative detection of genomic DNA by invasive cleavage of oligonucleotide probes. Nat Biotechnol. Mar. 1999;17(3):292-6.
Mahajan et al., Oligonucleotide Microarrays: Immobilization of Phosphorylated Oligonucleotides on Epoxylated Surface. Bioconjug Chem. Sep.-Oct. 2006;17(5):1184-9.
Man et al., Genetic variation in metabolizing enzyme and transporter genes: comprehensive assessment in 3 major East Asian subpopulations with comparison to Caucasians and Africans. J Clin Pharmacol. Aug. 2010;50(8):929-40.
Marmur et al., Strand Separation and Specific Recombination in Deoxyribonucleic Acids: Biological Studies. Natl Acad Sci U S A. Apr. 1960;46(4):453-61.
Masuzaki et al., Detection of cell free placental DNA in maternal plasma: direct evidence from three cases of confined placental mosaicism. J Med Genet. Apr. 2004;41(4):289-92.
Matsui et al., Molecular and biochemical characterization of a serine proteinase predominantly expressed in the medulla oblongata and cerebellar white matter of mouse brain. J Biol Chem. Apr. 14, 2000;275(15):11050-7.
Mcdonald et al., CYP4F2 is a vitamin KI oxidase: An explanation for altered warfarin dose in carriers of the V433M variant. Mol Pharmacol. Jun. 2009;75(6):1337-46.
Mega et al., Cytochrome p-450 polymorphisms and response to clopidogrel. N Engl J Med. Jan. 22, 2009;360(4):354-62.
Melamede et al., Isolation and characterization of endonuclease VIII from Escherichia coli. Biochemistry. Feb. 8, 1994;33(5):1255-64.
Mikkelson et al., Genome-wide Maps of Chromatin State in Plutipotent and Lineage-Committed Cells. Nature. Aug. 2, 2007;448(7153):553-60.
Mohsen et al., The Discovery of Rolling Circle Amplification and Rolling Circle Transcription. Acc Chem Res. Nov. 15, 2016; 49(11):2540-2550.
Morin et al., Nanopore-Based Target Sequence Detection. PLoS One. May 5, 2016;ll(5):e0154426.
Morris et al., Trends in Down's syndrome live births and antenatal diagnoses in England and Wales from 1989 to 2008: analysis of data from the National Down Syndrome Cytogenetic Register. BMJ. Oct. 26, 2009;339:b3794.
Nagalla et al., Proteomic analysis of maternal serum in down syndrome: identification of novel protein biomarkers. J Proteome Res. Apr. 2007;6(4):1245-57.
Nallur et al., Signal amplification by rolling circle amplification on DNA microarrays. Nuc Acid Res. 2011;29(23):el l8.
Nilsson et al., Padlock probes: circularizing oligonucleotides for localized DNA detection. Science. Sep. 30, 1994;265(5181):2085-8.
Nilsson et al., Real-time monitoring of rolling-circle amplification using a modified molecular beacon design. Nucleic Acids Res. Jul. 15, 2002;30(14):e66.
Nishigaki et al., Random PCR-Based Genome Sequencing: A Non-Divide-And-Conquer Strategy. DNA Res. Feb. 28, 2000;7(1):19-26.
Oliphant et al., BeadArray(TM) Technology: Enabling an Accurate, Cost-Effective Approach to High-Throughput Genotyping. BioTechniques Jun. 2002;32:S56-S61.
Orishchin et al., Rapid Deposition of Uniform Polydopamine Coatings on Nanoparticle Surfaces with Controllable Thickness. Langmuir . Jun. 20, 2017;33(24):6046-6053.
Ostermayer, Preparation and properties of infrared-to-visible conversion phosphors. Metall.Trans. 1971;752:747-55.
Pan et al., Tannic-Acid-Coated Polypropylene Membrane as a Separator for Lithium-Ion Batteries. ACS Appl Mater Interfaces. Jul. 29, 2015;7(29):16003-10.
Pask et al., Investigating the utility of combining phi29 whole genome amplification and highly multiplexed single nucleotide polymorphism BeadArray genotyping. BMC Biotechnol. Jul. 27, 2004;4:15.
Patil et al., Blocks of limited haplotype diversity revealed by high-resolution scanning of human chromosome 21. Science. Nov. 23, 2001;294(5547):1719-23.

(56) References Cited

OTHER PUBLICATIONS

Paunio et al., Preimplantation diagnosis by whole-genome amplification, PCR amplification, and solid-phase minisequencing of blastomere DNA. Clin Chem. Sep. 1996;42(9):1382-90.

Peterson et al., The effect of surface probe density on DNA hybridization. Nucleic Acids Res. Dec. 15, 2001;29(24):5163-8.

Philip et al., Late first-trimester invasive prenatal diagnosis: results of an international randomized trial. Clinical Trial Obstet Gynecol. Jun. 2004;103(6):1164-73.

Phillip et al., Common crowding agents have only a small effect on protein-protein interactions. Biophys J. Aug. 5, 2009;97(3):875-85.

Pont-Kingdon et al., Rapid detection of aneuploidy (Trisomy 21) by allele quantification combined with melting curves analysis of single-nucleotide polymorphism loci. Clin Chem. Jul. 2003;49(7):1087-94.

Press et al., Ovarian carcinomas with genetic and epigenetic BRCA1 loss have distinct molecular abnormalities. BMC Cancer. Jan. 22, 2008;8:17.

Quanterix Whitepaper 1.0, Scientific Principle of Simoa (Single Molecule Array) Technology, 2013, 2 pages.

Quanterix Whitepaper 6.0, Practical Application of Simoa™ HD-1 Analyzer for Ultrasensitive Multiplex Immunodetection of Protein Biomarkers, 2015, 3 pages.

Quinlan, Amniocentesis: indications and risks. Virtual Mentor. May 1, 2008;10(5):304-6.

Reeves et al., Too much of a good thing: mechanisms of gene action in Down syndrome. Trends Genet. Feb. 2001;17(2):83-8.

Rissin et al., Digital concentration readout of single enzyme molecules using femtoliter arrays and Poisson statistics. Nano Lett. Mar. 2006;6(3):520-3.

Robertson et al., Genome-wide profiles of STAT1 DNA association using chromatin immunoprecipitation and massively parallel sequencing. Nat Methods. Aug. 2007;4(8):651-7.

Rogaeva, The Solved and Unsovled Mysteries of the Genetics of Early-Onset Alzheimer's Disease. Neuromolecular Med. 2002;2(1):1-10.

Roman et al., Non-radioisotopic AFLP method using PCR primers fluorescently labeled with Cy5. Biotechniques. Feb. 1999;26(2):236-8.

Roy et al., A practical guide to single-molecule FRET. Nat Methods. Jun. 2008;5(6):507-16.

Ruano et al., Haplotype of multiple polymorphisms resolved by enzymatic amplification of single DNA molecules. Proc Natl Acad Sci U S A. Aug. 1990;87(16):6296-300.

Schiffman et al., Molecular inversion probes reveal patterns of 9p21 deletion and copy number aberrations in childhood leukemia. Cancer Genet Cytogenet. Aug. 2009;193(1):9-18.

Schiffman et al., Oncogenic BRAF mutation with CDKN2A inactivation is characteristic of a subset of pediatric malignant astrocytomas. Cancer Res. Jan. 15, 2010;70(2):512-9.

Schubert, Research Highlights, Picking out Prenatal DNA, Nat. Med. Aug. 2004;10(8):785.

Schweiizer et al., Hydrophobic, Non-Hydrogen-Bonding Bases and Base Pairs in DNA. J Am Chem. Soc. Feb. 22, 1995;117(7):1863-1872.

Schweitzer et al., Immunoassays with rolling circle DNA amplification: a versatile platform for ultrasensitive antigen detection. Proc Natl Acad Sci U S A. Aug. 29, 2000;97(18):10113-9.

Selvin, Fluorescence resonance energy transfer. Methods Enzymol. 1995;246:300-34.

Seppo et al., Detection of circulating fetal cells utilizing automated microscopy: potential for noninvasive prenatal diagnosis of chromosomal aneuploidies. Prenat Diagn. Sep. 2008;28(9):815-21.

Shen et al., High-throughput SNP genotyping on universal bead arrays. Mutat Res. Jun. 3, 2005;573(1-2):70-82.

Shendure et al., Accurate Multiplex Polony Sequencing of an Evolved Bacterial Genome. Science. Sep. 9, 2005;309(5741):1728-32.

Signal Transduction Immonohistochemistry: Methods and Protocols, Second Edition. Ed. Kalyuzhny, Humana Press. 2017, 289 pages.

Sissung et al., Clinical pharmacology and pharmacogenetics in a genomics era: the DMET platform. Pharmacogenomics. Jan. 2010;11(1):89-103.

Sivertsson et al., Pyrosequencing as an alternative to single-strand conformation polymorphism analysis for detection of N-ras mutations in human melanoma metastases. Clin Chem. Dec. 2002;48(12):2164-70.

Spencer et al., Maternal serum levels of dimeric inhibin A in pregnancies affected by trisomy 21 in the first trimester. Prenat Diagn. Jun. 2001;21(6):441-4.

Spencer et al., Maternal serum levels of total activin-A in first-trimester trisomy 21 pregnancies. Prenat Diagn. Apr. 2001;21(4):270-3.

Staebler et al., Should determination of the karyotype be systematic for all malformations detected by obstetrical ultrasound? Prenat Diagn. Jul. 2005;25(7):567-73.

Steinberg-Tatman et al., Synthetic Modification of Silica Beads That Allows for Sequential Attachment of Two Different Oligonucleotides. Bioconjug Chem. May-Jun. 2006;17(3):841-8.

Stryer, Fluorescence energy transfer as a spectroscopic ruler. Annu Rev Biochem. 1978;47:819-46.

Swinkels et al., Effects of blood-processing protocols on cell-free DNA quantification in plasma. Clin Chem. Mar. 2003;49(3):525-6.

Syvanen, Toward genome-wide SNP genotyping. Nat Genet. Jun. 2005;37 Suppl:S5-10.

Tian et al., Carbon nanotube enhanced label-free detection of microRNAs based on hairpin probe triggered solid-phase rolling-circle amplification. Nanoscale. 2013. Electronic Supplementary Information. 8 pages.

Tong et al., Noninvasive prenatal detection of fetal trisomy 18 by epigenetic allelic ratio analysis in maternal plasma: Theoretical and empirical considerations. Clin Chem. Dec. 2006;52(12):2194-202.

Turner et al., Massively parallel exon capture and library-free resequencing across 16 genomes. Nat Methods. May 2009;6(5):315-6.

Tyagi et al., Wavelength-shifting molecular beacons. Nat Biotechnol. Nov. 2000;18(ll):1191-6.

Van Der Los et al., Multiple immunoenzyme staining techniques. Use of fluoresceinated, biotinylated and unlabelled monoclonal antibodies. J Immunol Methods. Feb. 8, 1989;117(l):45-52.

Vogelstein et al., Digital PCR. Proc Natl Acad Sci U S A. Aug. 3, 1999;96(16):9236-41.

Von Eggeling et al., Applications of random PCR. Cell Mol Biol (Noisy-le-grand). Jul. 1995;41(5):653-70.

Wang et al., Allele quantification using molecular inversion probes (MIP). Nucleic Acids Res. Nov. 28, 2005;33(21):e183.

Wang et al., Analysis of molecular inversion probe performance for allele copy number determination. Genome Biol. 2007;8(11):R246.

Wang et al., High quality copy No. and genotype data from FFPE samples using Molecular Inversion Probe (MIP) microarrays. BMC Med Genomics. Feb. 19, 2009;2:8.

Wei et al., Detection and quantification by homogeneous PCR of cell-free fetal DNA in maternal plasma. Clin Chem. Feb. 2001;47(2):336-8.

Wen et al., Micellar effects on the electrochemistry of dopamine and its selective detection in the presence of ascorbic acid. Talanta. Dec. 6, 1999;50(5):1027-33.

Wen et al., Study on Rolling Circle Amplification of Ebola Virus and Fluoresence Detection Based on Graphene Oxide. Sensors and Actuators B. Jan. 2016;227:655-9.

Winsor et al., Maternal cell contamination in uncultured amniotic fluid. Prenat Diagn. Jan. 1996;16(l):49-54.

Zeng et al., Synthesis and Characterization of DOPA-PEG Conjugates. Polymer Preprints. 2000;41(1): 989.

Zhang et al., Automated multiplexing quantum dots in situ hybridization assay for simultaneous detection of ERG and PTEN gene status in prostate cancer. J Mol Diagn. Nov. 2013;15(6):754-64.

Zhang et al., Detection of target nucleic acids and proteins by amplification of circularizable probes. Expert Rev Mol Diagn. Mar. 2003;3(2):237-48.

(56) References Cited

OTHER PUBLICATIONS

Zheng et al., Whole Genome Amplification Increases the Efficiency and Validity of Buccal Cell Genotyping in Pediatric Populations. Cancer Epidemiol Biomarkers Prev. Jun. 2001;10(6):697-70.
Zimmerman et al., Digital PCR: a powerful new tool for noninvasive prenatal diagnosis? Prenat Diagn. 2008;28:1087-93.
Zimmerman et al., Noninvasive prenatal aneuploidy testing of chromosomes 13, 18, 21, X, and Y, using targeted sequencing of polymorphic loci. Prenat Diagn. Dec. 2012;32(13):1233-41.
Zimmerman et al., Novel Real-Time Quantitative PCR Test for Trisomy 21. Clin Chem. 2002;48(2):362-363.
Zimmerman et al., Optimized real-time quantitative PCR measurement of male fetal DNA in maternal plasma. Clin Chem. Sep. 2005;51(9):1598-604.
Zimmerman et al., Real-Time Quantitative Polymerase Chain Reaction Measurement of Male Fetal DNA in Maternal Plasma. Chapter 5 In Methods in Molecular Medicine: Single Cell Diagnostics: Methods and Protocols. Ed. Thornhill, Humana Press, Totowa, NJ, 2007, 7 pages.
Zimmerman et al., Use of Real-Time Polymerase Chain Reaction for the Detection of Fetal Aneuploidies. Chapter 8 In Methods in Molecular Biology. Vol 336: Clinical Applications of PCR. Eds Lo et al., 2006, 18 pages.
Zlotogora, Penetrance and expressivity in the molecular age. Genet Med. Sep.-Oct. 2003;5(5):347-52.
U.S. Appl. No. 10/712,616, filed Nov. 12, 2003.
U.S. Appl. No. 60/742,305, filed Dec. 6, 2005.
U.S. Appl. No. 60/754,396, filed Dec. 29, 2005.
U.S. Appl. No. 60/774,976, filed Feb. 21, 2006.
U.S. Appl. No. 60/789,506, filed Apr. 4, 2006.
U.S. Appl. No. 60/817,741, filed Jun. 30, 2006.
U.S. Appl. No. 60/846,610, filed Sep. 22, 2006.
U.S. Appl. No. 60/918,292, filed Mar. 16, 2007.
U.S. Appl. No. 60/926,198, filed Apr. 25, 2007.
U.S. Appl. No. 60/932,456, filed May 31, 2007.
U.S. Appl. No. 60/934,440, filed Jun. 30, 2007.
U.S. Appl. No. 60/951,438, filed Jul. 23, 2007.
U.S. Appl. No. 61/003,101, filed Nov. 13, 2007.
U.S. Appl. No. 61/008,637, filed Dec. 21, 2007.
International Search Report and Written Opinion for PCT/US2019/025462, dated Jul. 23, 2019, 18 pages.

- Tile chromosomes 13, 18, 21, X, and Y with 10,000-100,000 MIPs each
- Similar number of MIPs targeting reference sites (genome-wide)
- Ligation occurs when the arms anneal to their target
- MIP backbone may comprise unique feature-specific sequences

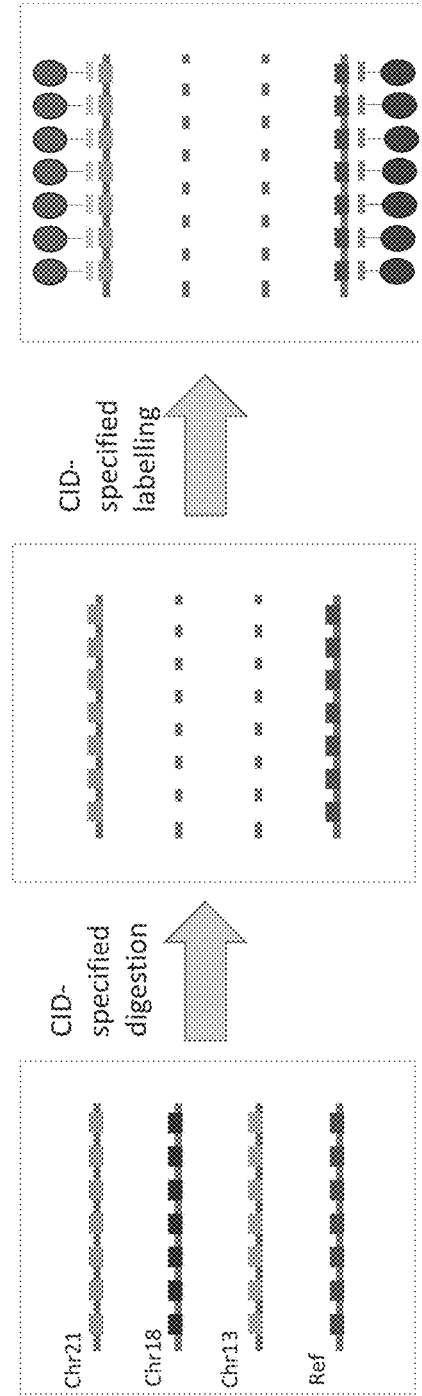
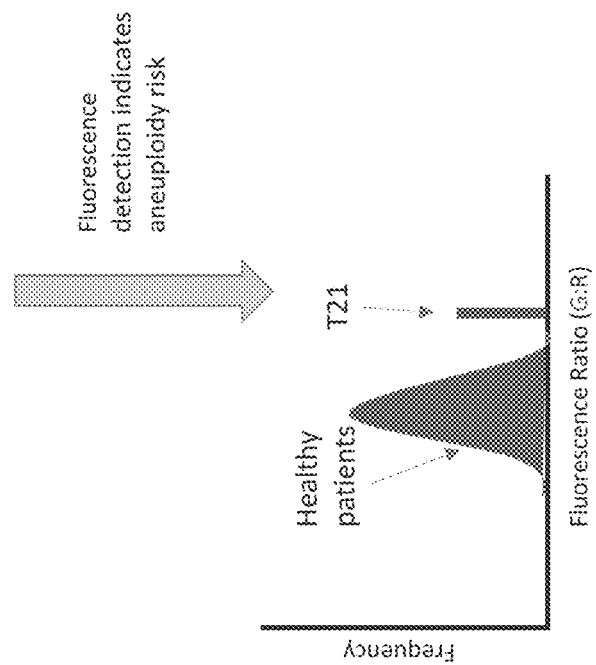
FIG. 12

FIG. 26
PEG 200
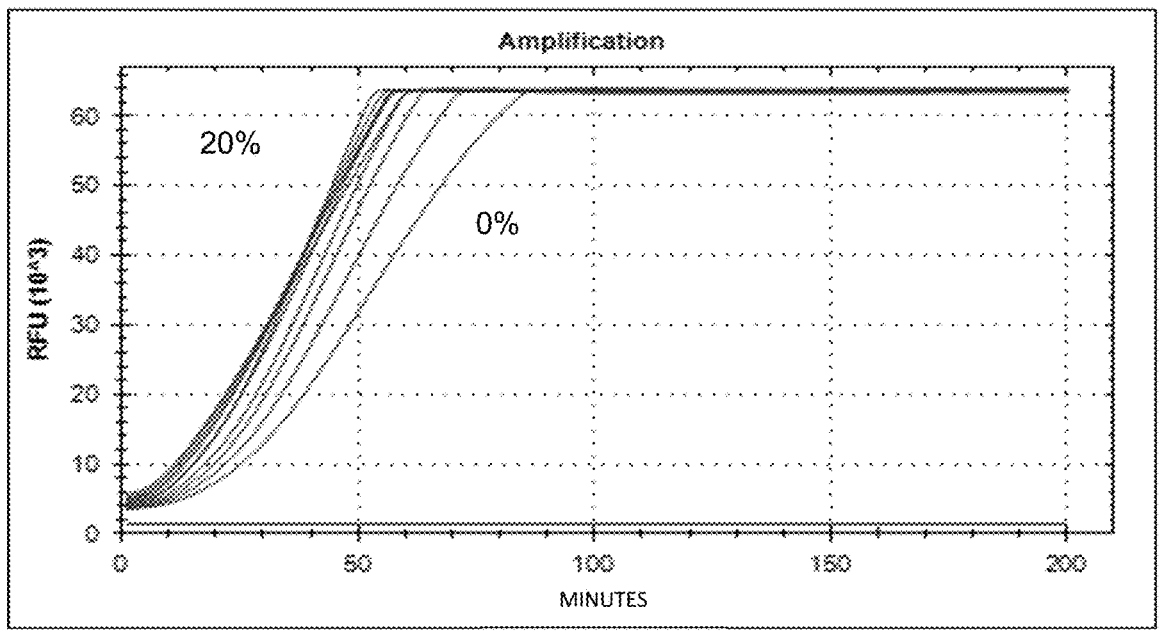
PEG 8000
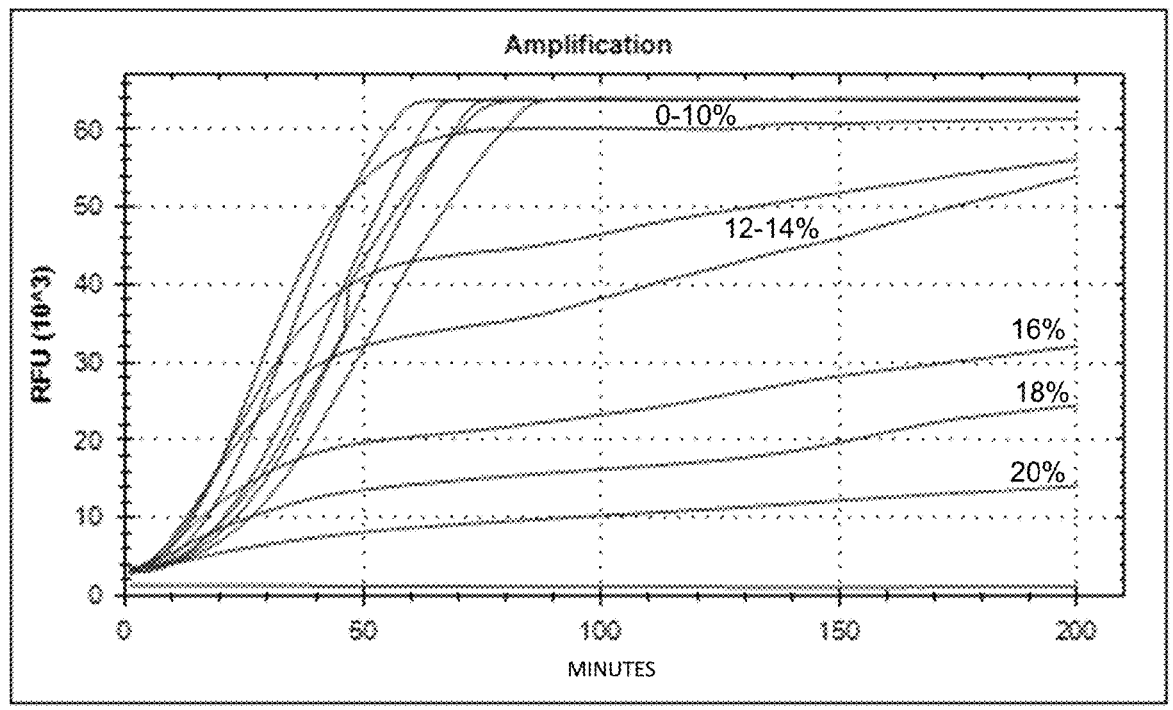

FIG. 27A
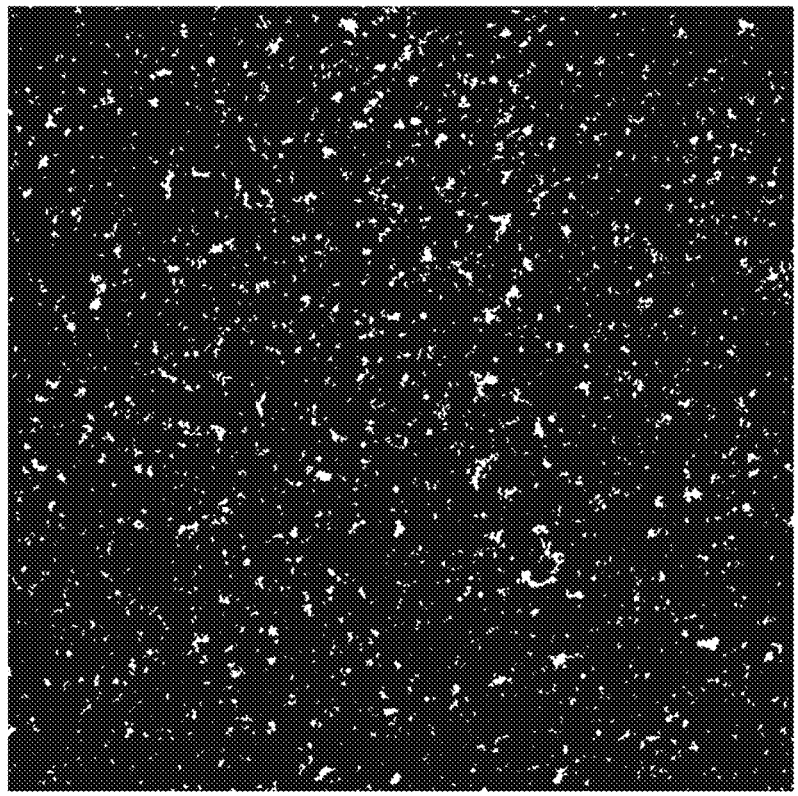
RCA + 20% PEG200, 140 min.
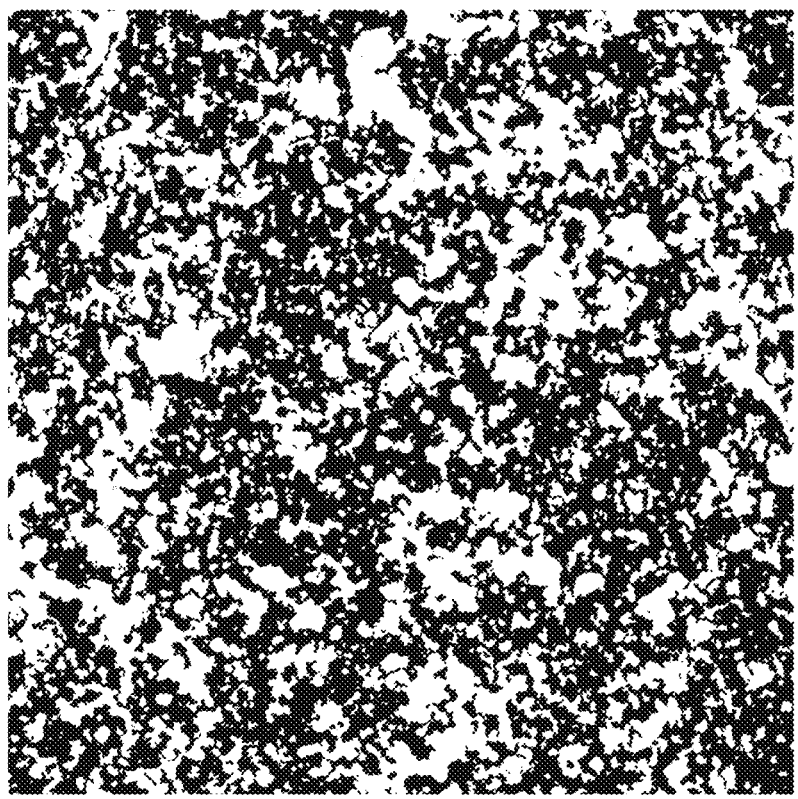
RCA without PEG, 140 min.

FIG. 27B
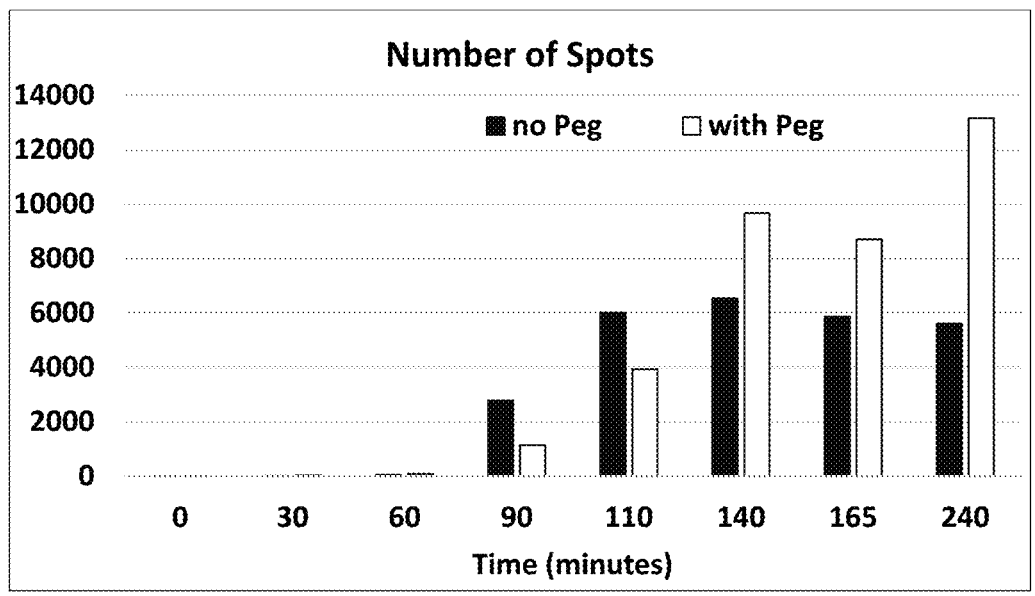
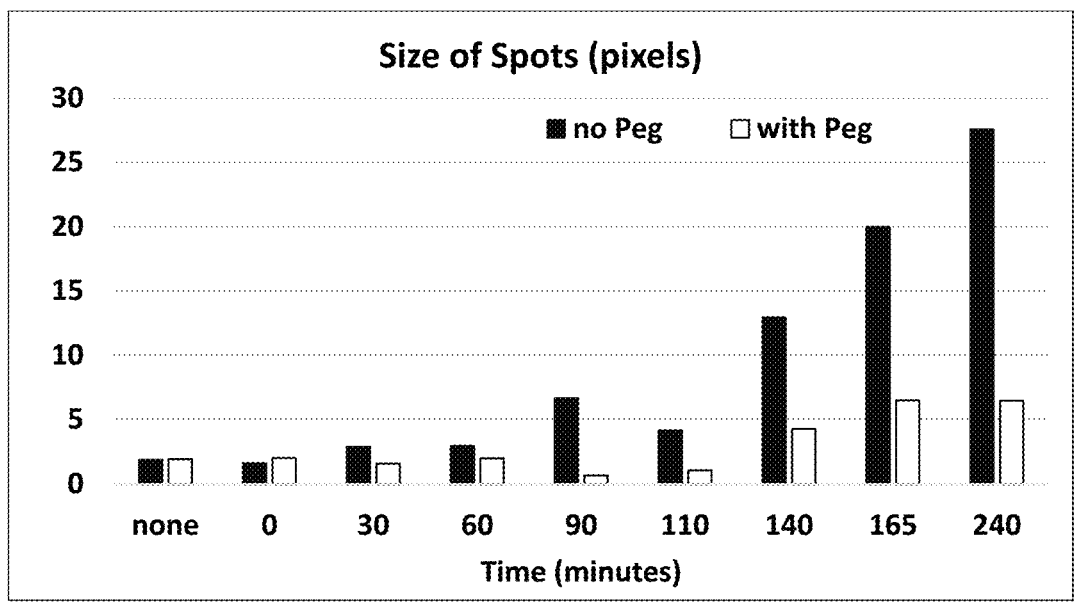

FIG. 29A
1 hour hybridization;
RCA with 20% PEG 600, 140 min.
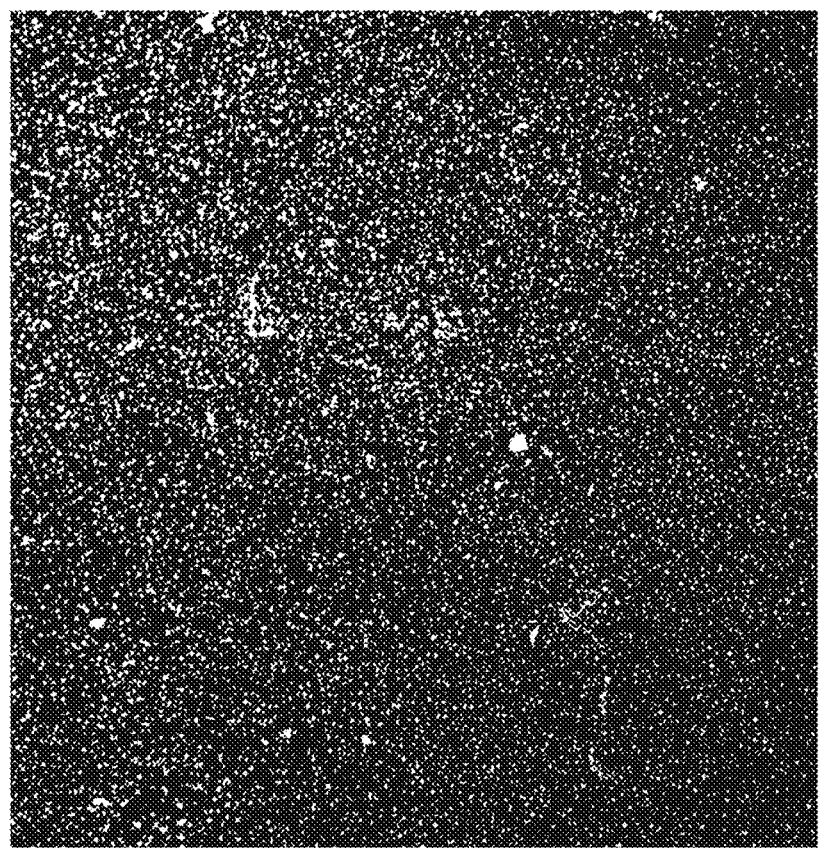
18 hour hybridization;
RCA with 20% PEG 600, 140 min.

FIG. 33
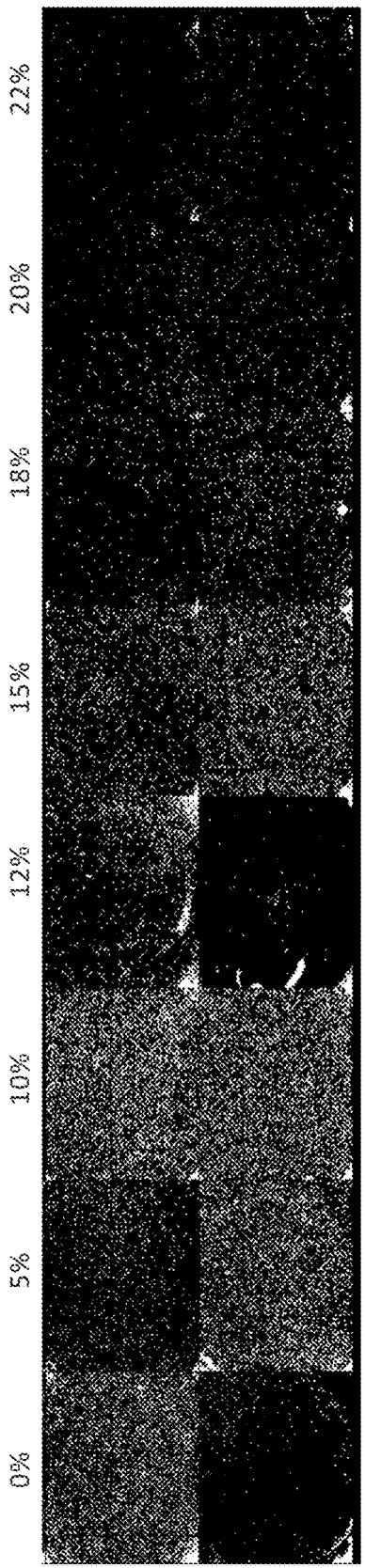
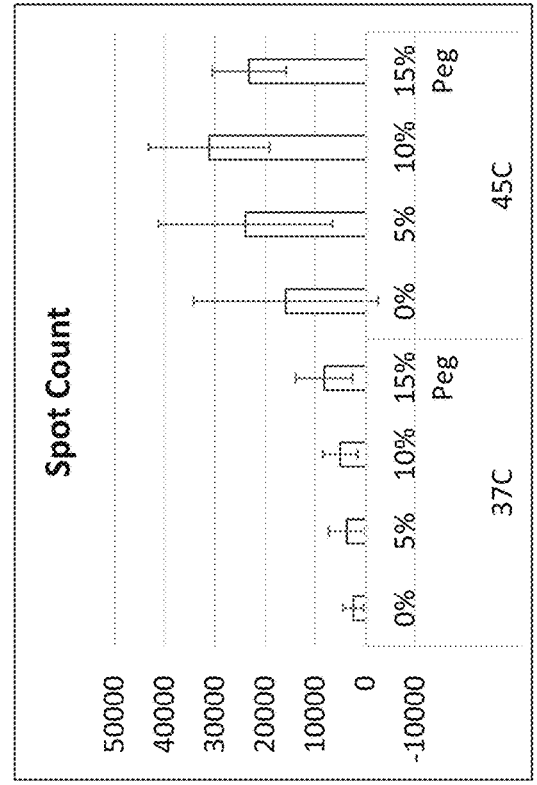
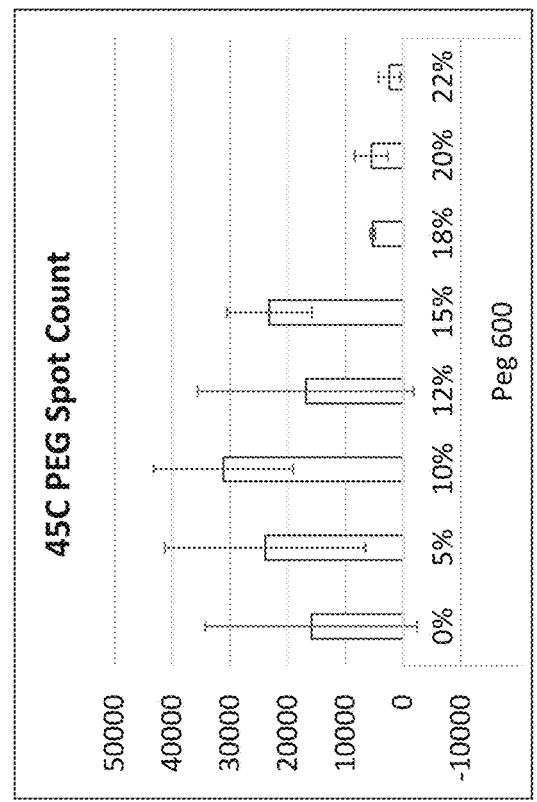

FIG. 45

N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}
N (C6) CGTCGTAGGTCACTTAACATAGAGUUU {AF488}

(SEQ ID NO: 7)

FIG. 46

/5Alex488N/CTCTATGTTAAGTGACCTACGACG
             GCAGCATAACTTGCATGGAGCTCGC (6C) N /5Alex488N/CTCTATGTTAAGTGACCTACGACG
                GCAGCATAACTTGCATGGAGCTCGC (6C) N GAGATACAACTTGCATGGAGCTCGC (6C) N
     /5Alex488N/CTCTATGTTAAGTGACCTACGACG /5Alex488N/CTCTATGTTAAGTGACCTACGACG
                GAGATACAACTTGCATGGAGCTCGC (6C) N GAGATACAACTTGCATGGAGCTCGC (6C) N
     /5Alex488N/CTCTATGTTAAGTGACCTACGACG (SEQ ID NO: 9)
             GAGATACAACTTGCATGGAGCTCGC (6C) N
/5Alex488N/CTCTATGTTAAGTGACCTACGACG
(SEQ ID NO: 8)

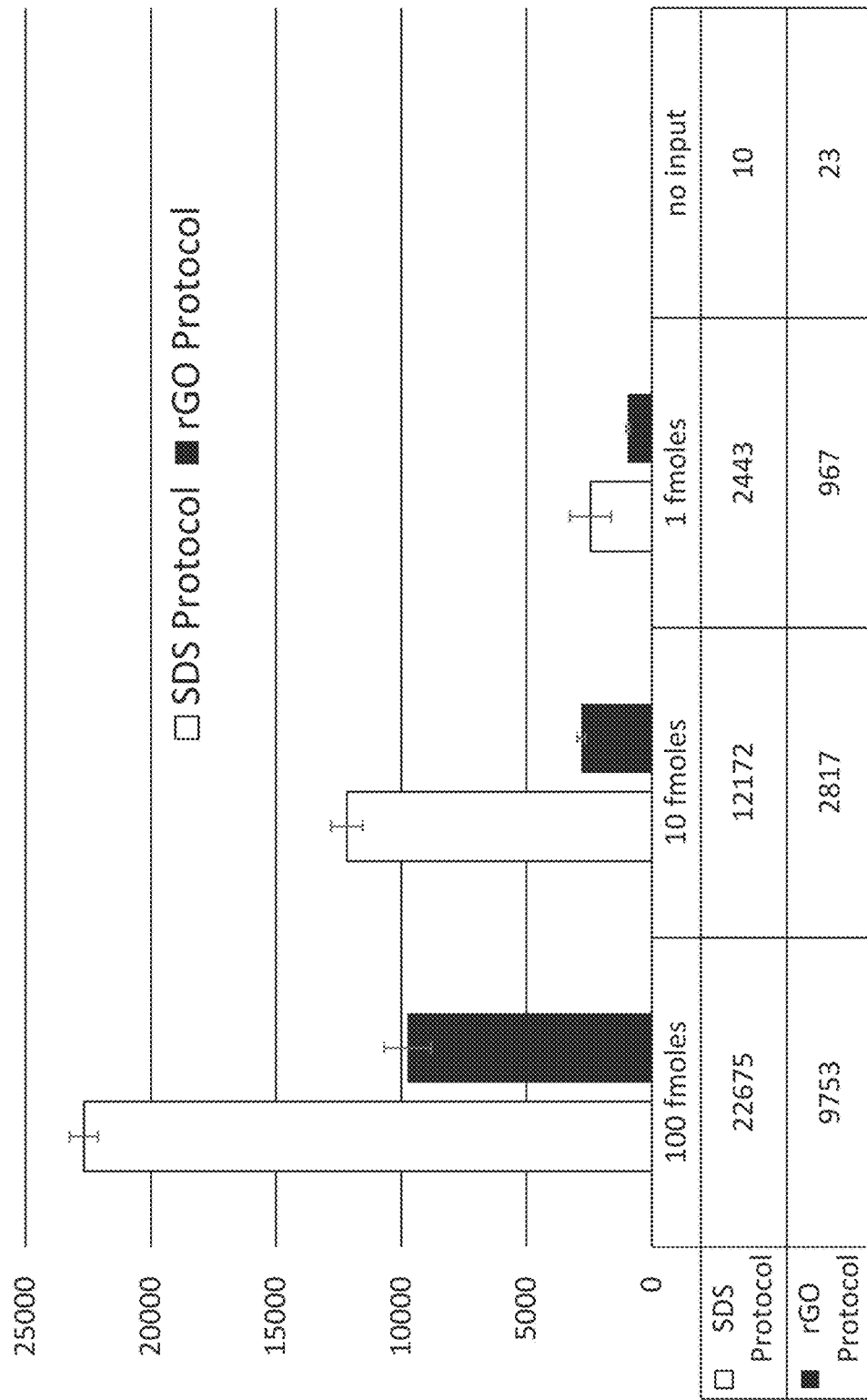

FIG. 51
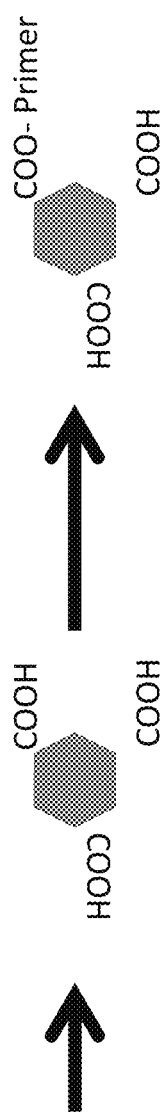
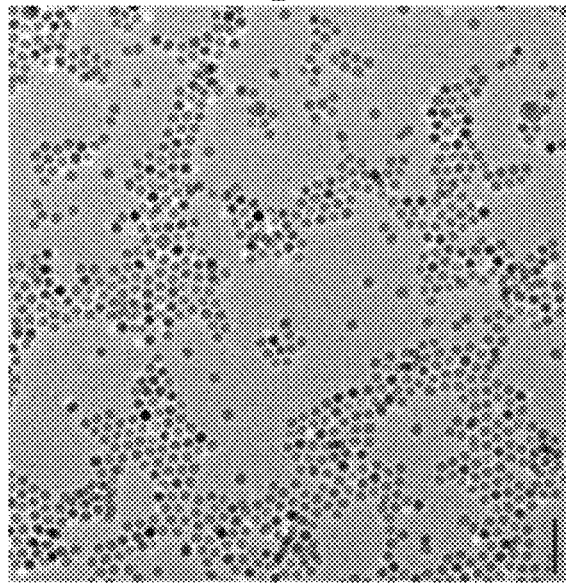

FIG. 57A

IN-SOLUTION PRIMERS:

In-sol-1: 5'TCGGTCCGAGGGTCT/iSp18/iSp18/CGTCGTAGGTCACTTAACATAGAG/TT/3BioTEG/3'
(SEQ ID NO:10)

In-sol-2: 5'TGGGTTGCCGTGGTT/iSp18//iSp18/CGTCGTAGGTCACTTAACATAGAG/TT/3BioTEG/3'
(SEQ ID NO:11)

In-sol-3: 5'TTCATTTGGCAGTGGGTC/iSp18/iSp18/CGTCGTAGGTCACTTAACATAGAG/TT/3BioTEG/3'
(SEQ ID NO:12)

In-sol-4: 5'TGGAAAGAGGCTGCTAGT/iSp18/iSp18/CGTCGTAGGTCACTTAACATAGAG/TT/3BioTEG/3'
(SEQ ID NO:13)

In-sol-5: 5'GTCGTTTACTGTCCATTGC/iSp18/iSp18/CGTCGTAGGTCACTTAACATAGAG/TT/3BioTEG/3'
(SEQ ID NO:14)

In-sol-6: 5'CTGCGCTAGTCATTCATTTG/iSp18/iSp18/CGTCGTAGGTCACTTAACATAGAG/TT/3BioTEG/3'
(SEQ ID NO:15)

In-sol-7: 5'TTTTTTTT/iSp18/iSp18/CGTCGTAGGTCACTTAACATAGAG/TT/3BioTEG/3'
(SEQ ID NO:16)

FIG. 57B

SUPPORT-CONJUGATED PRIMERS:

AUP
Control: 5'UniAmM/CGTCGTAGGTCACTTAACATAGAG3'
(SEQ ID NO:17)

AUP-1: 5'UniAmM/T/iUniAmM/TTTTCGTCGTAGGTCACTTAACATAGAG3'
(SEQ ID NO:18)

AUP-2: 5'UniAmM/T/iUniAmM/T/iUniAmM/TCGTCGTAGGTCACTTAACATAAG3'
(SEQ ID NO:19)

AUP-3: 5'UniAmM/T/iUniAmM/T/iUniAmM/T/iSp18/ iSp18/CGTCGTAGGTCACTTAACATAGAG3'
(SEQ ID NO:20)

AUP-4: 5'UniAmM/T/iUniAmM/T/iUniAmM/T/iUniAmM/T/iSp18/iSp18/iSp18/CGTCGTAGGTCACTTAACATAGAG3'
(SEQ ID NO:21)

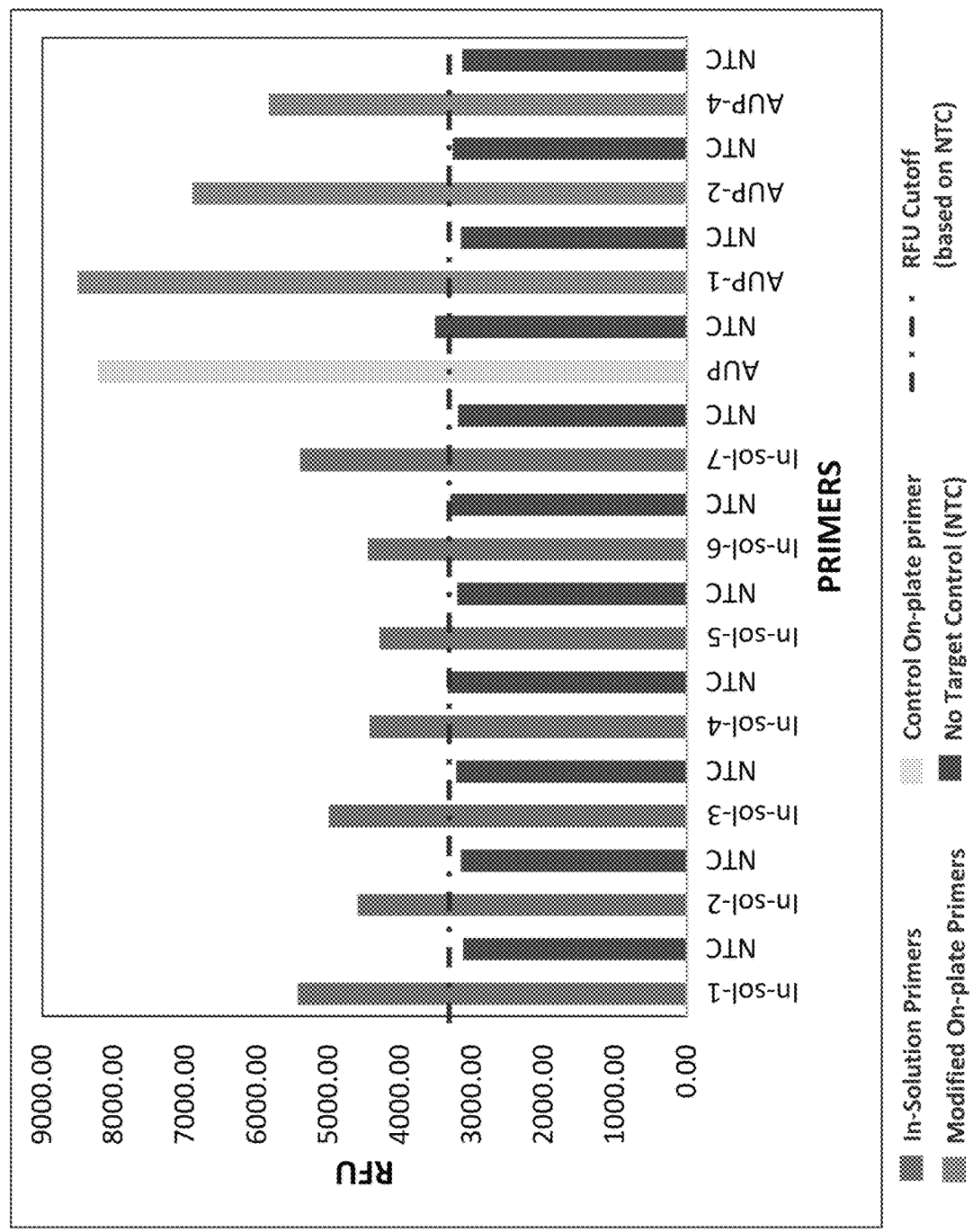

METHODS, SYSTEMS, AND COMPOSITIONS FOR COUNTING NUCLEIC ACID MOLECULES

The present application is a continuation of PCT/US2020/026456, filed Apr. 2, 2020, which claims priority to U.S. Provisional Application Ser. No. 62/828,397, filed Apr. 2, 2019; U.S. Provisional Application Ser. Nos. 62/910,394 and 62/910,397, both filed Oct. 3, 2019; and U.S. Provisional Application Ser. Nos. 62/913,542 and 62/913,543, both filed Oct. 10, 2019, each of which is incorporated herein by reference.

FIELD OF THE INVENTION

The present invention relates to compositions and methods for determining numbers of copies of individual molecules, such as nucleic acid molecules, without digital sequencing. The technologies find use, for example, in analysis of variations in copy numbers of specific nucleic acids sequences that may arise, e.g., from variations in chromosome number, gene copy number, expression level, etc. The technologies find particular application in genetic screening, e.g., prenatal testing, particularly for non-invasive prenatal testing (NIPT). NIPT is directed to the analysis of cell-free DNA (cfDNA) from a fetus that circulates in the blood of a woman carrying the fetus in utero. Analysis of cell-free DNA in maternal blood can be used to assess the health of the fetus. The technology herein relates to methods, systems, and kits for detecting and quantifying variations in numbers of molecules, particularly variations in gene dosage, e.g., due to gene duplication, or to variations from the normal euploid complement of chromosomes, e.g., trisomy of one or more chromosomes that are normally found in diploid pairs.

BACKGROUND OF THE INVENTION

Detection of the presence of, or variations in the numbers of molecules in a sample is a useful way of characterizing the sample and the source of the sample. For example, variations in gene dosage are clinically significant indicators of disease states, e.g., in a subject from whom a sample is collected. Variations in gene dosage arise due to errors in DNA replication and can occur in germ line cells, leading to congenital defects and even embryonic demise, or in somatic cells, often resulting in cancer. These replication anomalies can cause deletion or duplication of parts of genes, full-length genes and their surrounding regulatory regions, megabase-long portions of chromosomes, or entire chromosomes. Analysis of other biomolecules is also clinically important. For example, variations in amounts of RNA or protein may indicate changes in expression of a gene associated with a disease state.

Chromosomal abnormalities can affect either the number or structure of chromosomes. Conditions wherein cells, tissues, or individuals have one or more whole chromosomes or segments of chromosomes either absent, or in addition to the normal euploid complement of chromosomes can be referred to as aneuploidy. Germline replication errors due to chromosome non-disjunction result in either monosomies (one copy of an autosomal chromosome instead of the usual two or only one sex chromosome) or trisomies (three copies). Such events, when they do not result in outright embryonic demise, typically lead to a broad array of disorders often recognized as syndromes, e.g., trisomy 21 and Down's syndrome, trisomy 18 and Edward's syndrome, and trisomy 13 and Patau's syndrome. Structural chromosome abnormalities affecting parts of chromosomes arise due to chromosome breakage, and result in deletions, inversions, translocations or duplications of large blocks of genetic material. These events are often as devastating as the gain or loss of the entire chromosome and can lead to such disorders as Prader-Willi syndrome (del 15q11-13), retinoblastoma (del 13q14), Cri du chat syndrome (del 5p), and others listed in U.S. Pat. No. 5,888,740, herein incorporated in its entirety by reference.

Major chromosomal abnormalities are detected in nearly 1 of 140 live births and in a much higher fraction of fetuses that do not reach term or are still-born. Hsu (1998) Prenatal diagnosis of chromosomal abnormalities through amniocentesis. In: Milunsky A, editor. Genetic Disorders and the Fetus. 4 ed. Baltimore: The Johns Hopkins University Press. 179-180; Staebler et al. (2005) "Should determination of the karyotype be systematic for all malformations detected by obstetrical ultrasound?" Prenat Diagn 25: 567-573. The most common aneuploidy is trisomy 21 (Down syndrome), which currently occurs in 1 of 730 births. Hsu; Staebler et al. Though less common than trisomy 21, trisomy 18 (Edwards Syndrome) and trisomy 13 (Patau syndrome) occur in 1 in 5,500 and 1 in 17,200 live births, respectively. Hsu. A large variety of congenital defects, growth deficiencies, and intellectual disabilities are found in children with chromosomal aneuploidies, and these present life-long challenges to families and societies. Jones (2006) Smith's recognizable patterns of human malformation. Philadelphia: Elsevier Saunders. There are a variety of prenatal tests that can indicate increased risk for fetal aneuploidy, including invasive diagnostic tests such as amniocentesis or chorionic villus sampling, which are the current gold standard but are associated with a non-negligible risk of fetal loss. American College of Obstetricians and Gynecologists (2007) ACOG Practice Bulletin No. 88, December 2007. Invasive prenatal testing for aneuploidy. Obstet Gynecol 110: 1459-1467. More reliable, non-invasive tests for fetal aneuploidy have therefore long been sought. The most promising of these are based on the detection of fetal DNA in maternal plasma. It has been demonstrated that massively parallel sequencing of libraries generated from maternal plasma can reliably detect chromosome 21 abnormalities. See, e.g., Chiu et al., Non-invasive prenatal diagnosis of fetal chromosomal aneuploidy by massively parallel genomic sequencing of DNA in maternal plasma. Proc Natl Acad Sci USA 105:20458-20463 (2008); Fan et al., Noninvasive diagnosis of fetal aneuploidy by shotgun sequencing DNA from maternal blood. Proc Natl Acad Sci USA 105: 16266-16271 (2008). See also U.S. Pat. No. 7,888,017.

Quantifying variations in numbers of molecules is not limited to NIPT analysis, but finds application broadly in analyzing nucleic acids for any purpose, e.g., for characterizing nucleic acids and nucleic acid mixtures, such as nucleic acids indicative of cancer or other disease in a subject, nucleic acids indicative of microbes, e.g., viral and bacterial microbes and mixtures of microbes in a sample, etc.

Current methods for quantifying variations in numbers of molecules, for example performing aneuploidy screening, that rely on next generation sequencing (NGS) are often time-consuming, expensive, and require extensive bioinformatics analysis.

SUMMARY OF THE INVENTION

The present invention provides compositions, methods, and systems for the detection and characterization of samples by counting particular molecules (e.g., small molecules, haptens, proteins, antibodies, lipids, carbohydrates, and nucleic acids, such as genes or other DNA molecules or fragments, and/or RNAs, e.g., messenger RNAs, microRNAs and other non-coding RNAs) that may be represented in the samples. The technology finds application, for example, in monitoring gene expression, measuring non-coding RNA abundance, and in analyzing genetic variations, including but not limited to alterations in gene dosage, such as, e.g., aneuploidy. In preferred embodiments, the technology provides methods for detecting and thereby counting single copies of target molecules, including nucleic acids, without the use of "next generation" sequencing (NGS) technologies, such as those described by Chiu et al. and Fan, et al., supra, or on single-molecule amplification technologies that rely on separating amplification reactions for individual target molecules in different physically discrete elements, e.g., micro-vessels or emulsion droplets. While embodiments of the technology provided herein are discussed in relation particular applications, e.g., measuring DNA, it will be appreciated that the technology is not limited to these applications, and that it is readily adapted to analysis of many different types of molecules, modifications on molecules (e.g., glycosylation, phosphorylation, methylation), or moieties capable of binding to a partner molecule in a specific manner, e.g., antigens with antibodies, nucleic acids with complementary nucleic acids, nucleic acid structures (e.g., stem-loops, bulged nucleotides, flaps, promoter sequences) with proteins that bind such structures, lectins with carbohydrates, proteins with protein binding partners, proteins with lipids (e.g., SH2 domains with lipids), etc.

In general, these compositions, methods, and systems offer improved means to detect genomic deletions and duplications of various sizes, including complete chromosomes, arms of chromosomes, microscopic deletions and duplications, submicroscopic deletions and deletions, and single nucleotide features, including single nucleotide polymorphisms, deletions, and insertions. In certain embodiments, the methods of the disclosure can be used to detect sub-chromosomal genetic lesions, e.g., microdeletions. Exemplary applications of the methods include pediatric and prenatal diagnosis of aneuploidy, testing for product of conception or risk of premature abortion, noninvasive prenatal testing (both qualitative and quantitative genetic testing, such as detecting Mendelian disorders, insertions/deletions, and chromosomal imbalances), testing preimplantation genetics, tumor characterization, postnatal testing including cytogenetics, and mutagen effect monitoring.

In some embodiments, the technology herein provides methods for characterizing nucleic acid, preferably DNA, more preferably circulating cell-free DNA (ccfDNA) from blood or plasma, in a sequence-specific and quantitative manner. In preferred embodiments, single copies of the DNA are detected and counted, without polymerase chain reaction or DNA sequencing. Embodiments of the technology provide methods, compositions, and systems for detecting target DNA using methods for amplifying signals that are indicative of the presence of the target DNA in the sample. In preferred embodiments, the detectable signal from a single target molecule is amplified to such an extent and in such a manner that the signal derived from the single target molecule is detectable and identifiable, in isolation from signal from other targets and from other copies of the target molecule.

Embodiments of the technology provide methods for counting products formed by rolling circle replication, e.g., in a rolling circle amplification (RCA) reaction. In some embodiments the technology provides methods of counting RCA product molecules formed by replication from circularized nucleic acid probe molecules, e.g., molecular inversion probes (MIPs), including, e.g., padlock probes. Circularized nucleic acid probes may be formed, for example, by hybridization of a linear probe molecule having unique polynucleotide arms designed to hybridize immediately upstream and downstream of a specific target sequence (or site) in a nucleic acid target, e.g., in an RNA, cfDNA, or genomic nucleic acid sample and ligating the arms together to form a circularized nucleic acid probe. In some embodiments a MIP probe forms a ligatable nick upon hybridization to the nucleic acid target, while in some embodiments, the MIP probe is modified or repaired (e.g., by gap filling, flap cleavage, etc.) to form a nick prior to ligation. In embodiments, a number or amount of circularized nucleic acid probes formed in a reaction mixture is indicative of a number or amount of target nucleic acids in the reaction mixture.

In embodiments of the technology, a method is provided for counting circularized nucleic acid probes, comprising:
a) providing a ligation mixture comprising circularized nucleic acid probes and linear nucleic acids;
b) treating the ligation mixture with at least one exonuclease, wherein circularized nucleic acid probes are not substrate for the at least one exonuclease;
c) forming a plurality of complexes, each complex comprising an oligonucleotide primer hybridized to a circularized nucleic acid probe from the treated ligation mixture;
d) detecting formation of the plurality of complexes in a process comprising:
  i) extending primers in the complexes in a rolling circle amplification (RCA) reaction to form RCA products that comprise primer portions;
  ii) hybridizing labeled probes to the RCA products, wherein RCA products with hybridized labeled probes are localized to a support at dispersed loci, wherein at least a portion of the RCA products localized at the dispersed loci are individually detectable by detection of hybridized labeled probes; and
  iii) counting RCA products at dispersed loci on the support, preferably the counting RCA products at dispersed loci on the support by microscopy.

In some embodiments, the primers are localized at the dispersed loci prior to the extending, while in some embodiments, the primer portions of the RCA products are localized to the dispersed loci after the extending.

In any of the embodiments described above, embodiments are provided wherein:
a) the primers or primer portions are bound to one or more surfaces, preferably covalently linked to the one or more surfaces, or
b) the primers or primer portions are hybridized to capture oligonucleotides, wherein the capture oligonucleotides are bound to one or more surfaces, preferably covalently linked to the one or more surfaces.

In particular embodiments, the primers are bound to the one or more surfaces, preferably covalently linked to the one or more surfaces, or are hybridized to capture oligonucleotides bound to the one or more surfaces, preferably covalently linked to the one or more surfaces, before the extending.

In any of the embodiments described above, the technology further provides embodiments wherein the support comprises one or more surfaces selected from a portion of an assay plate, preferably a multi-well assay plate, preferably a glass-bottom assay plate; a portion of a slide; and one or more particles, preferably nanoparticles, wherein the particles are preferably paramagnetic particles, preferably ferromagnetic nanoparticles, preferably iron oxide nanoparticles.

In certain of any of the embodiments described above, the primers are bound to surfaces on particles, preferably covalently linked to surfaces on the particles, and wherein the RCA products with hybridized labeled probes are localized to dispersed loci by one or more of a magnet, centrifugation, and filtration.

In any one of the embodiments described above, the dispersed loci may be in an irregular dispersal or the dispersed loci may be in an addressable array.

Any of the embodiments described above comprise embodiments wherein hybridized labeled probes comprise oligonucleotides comprising a fluorescent label or a quencher moiety, or both a fluorescent label and a quencher moiety. The technology includes but is not limited to embodiments wherein a plurality of RCA products are hybridized to labeled probes that all comprise the same label, preferably the same fluorescent label, and embodiments wherein a plurality of RCA products are hybridized to labeled probes, that comprise two, three, four, five, six, seven or more different labels, preferably two, three, four, five, six, seven, or more different fluorescent labels.

In any of the embodiments above, forming RCA products may comprise extending the primers in the complexes in a reaction mixture comprising polyethylene glycol (PEG), preferably at least 2 to 10% (w:v), preferably at least 12%, preferably at least 14%, preferably at least 16%, preferably at least 18% to 20% PEG. In any of these embodiments, PEG may have an average molecular weight between 200 and 8000, preferably between 200 and 1000, preferably between 400 and 800, preferably 600.

In any of the embodiments above, forming RCA products may comprise incubating a reaction mixture for an incubation period having a beginning and an end, wherein the reaction mixture is treated by mixing one or more times between the beginning of the incubation period and the end of the incubation period, wherein the mixing preferably comprises one or more of vortexing, bumping, rocking, tilting, and ultrasonic mixing.

In any of the embodiments above, providing the ligation mixture comprising circularized nucleic acid probes and linear nucleic acids may comprise ligating MIP probes, preferably padlock probes, in the presence of a target nucleic acid target nucleic acid, preferably a target nucleic acid from a sample, preferably a target nucleic acid from a sample, to form the circularized nucleic acid probes. The target nucleic acid is not limited to any particular type of target nucleic acid, any may comprise, e.g., DNA, RNA, genomic DNA, cfDNA, synthetic DNA, etc.

In any of the embodiments above, the at least one exonuclease may comprise one or more of Exonuclease I (Exo I, *E. coli*), Thermolabile Exonuclease I; Exonuclease VII (Exo VII, *E. coli*), Exonuclease T (or "RNase T") and RecJ$_f$, a recombinant fusion protein of *E. coli* RecJ and maltose binding protein (MBP). In any of these embodiments, treating the ligation mixture with at least one exonuclease may comprise inactivating the at least one exonuclease, preferably heat-inactivating the at least one exonuclease, prior to forming the plurality of complexes.

In embodiments described above, forming RCA products may comprise extending the primers in the complexes in a reaction mixture that comprises the labeled probes, and/or may comprise embodiments wherein RCA products are localized at the dispersed loci prior to hybridizing the labeled probes to the RCA products. In some embodiments, RCA products with hybridized labeled probes are treated with graphene oxide prior to counting the RCA products at the dispersed loci.

Any of the embodiments above may comprise embodiments wherein RCA products with hybridized labeled probes are treated with one or more detergents prior to counting the RCA products at the dispersed loci, preferably one or more detergents comprising agents selected from anionic agents, preferably sodium dodecyl sulfate; sodium lauryl sulfate; ammonium lauryl sulfate; cationic agents, preferably benzalkonium chloride; cetyltrimethylammonium bromide; linear alkylbenzene sulfonates, preferably sodium dodecylbenzene sulfonate; non-ionic agents, preferably a TWEEN detergent selected from polyoxyethylene (20) sorbitan-monolaurate; -monopalmitate; -monostearate; or -monooleate; a TRITON detergent preferably selected from s polyethylene glycol p-(1,1,3,3-tetramethylbutyl)-phenyl ether, and steroid and steroidal glycosides, preferably saponin or digitonin; and zwitterionic agents, preferably 3-[(3-cholamidopropyl)dimethylammonio]-1-propane-sulfonate (CHAPS); and mixtures of detergent agents, preferably TEEPOL® detergent, comprising sodium dodecylbenzene sulfonate, and sodium $C_{12}$-$C_{15}$ alcohol ether sulfate.

Any of the embodiments above may comprise embodiments wherein the support comprises a an organic coating, the coating preferably comprising a polymeric coating polymerized from surface-modifying monomers, wherein the surface-modifying monomers preferably comprise one or more of dopamine, tannic acid, caffeic acid, pyrogallol, gallic acid, epigallocatechin gallate, and epicatechin gallate monomers, preferably dopamine and tannic acid. In some embodiments, the polymeric coating is homopolymeric. See, e.g., US 2003/0087338, which is incorporated herein by reference for all purposes.

Any of the embodiments above may comprise embodiments wherein prior to localizing RCA products at the dispersed loci, the primers, primer portions, or capture oligonucleotides comprise one or more immobilization moieties, preferably selected from a reactive amine, a reactive thiol group, biotin, and a hapten, wherein the immobilization moieties are exposed to a surface under conditions wherein the immobilization moieties interact with the surface to bind the primers, primer portions, or capture oligonucleotides to the surface. In certain embodiments, prior to localizing RCA products at the dispersed loci the surface comprises at least one of:
  acrylic groups;
  thiol-containing groups;
  reactive amine groups;
  carboxyl groups,
  streptavidin,
  antibodies,
  haptens,
  carbohydrates,
  lectins.

Embodiments of the technology provide a method for counting circularized nucleic acid probes, comprising:
  a) providing a ligation mixture comprising circularized nucleic acid probes and linear nucleic acids;
  b) forming a plurality of complexes, each complex comprising an oligonucleotide primer hybridized to a circularized nucleic acid probe from the ligation mixture, wherein the primer is bound to a nanoparticle, preferably a paramagnetic nanoparticle;

c) detecting formation of the plurality of complexes in a process comprising:

i) extending primers in the complexes in a rolling circle amplification (RCA) reaction to form RCA products bound to nanoparticles, wherein at least a portion of the RCA products on nanoparticles are individually detectable; and iii) counting RCA products on the nanoparticles.

Some embodiments comprise hybridizing labeled probes to the RCA products, wherein at least a portion of the RCA products are individually detectable by detection of hybridized labeled probes. Any of the embodiments described above comprise embodiments wherein hybridized labeled probes comprise oligonucleotides comprising a fluorescent label or a quencher moiety, or both a fluorescent label and a quencher moiety. The technology includes but is not limited to embodiments wherein a plurality of RCA products are hybridized to labeled probes that all comprise the same label, preferably the same fluorescent label, and embodiments wherein a plurality of RCA products are hybridized to labeled probes, that comprise two, three, four, five, six, seven or more different labels, preferably two, three, four, five, six, seven, or more different fluorescent labels.

In any of the embodiments wherein the primer is bound to a nanoparticle, the method comprises embodiments wherein the nanoparticles are paramagnetic nanoparticles, preferably iron oxide nanoparticles. In embodiments the nanoparticles have an average diameter of less than about 1000 nm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 5 nm, or 1 nm in diameter, wherein the nanoparticles are preferably from 1 to 50 nm, preferably from 5 to 20 nm average diameter. In some embodiments, the nanoparticles comprise an inorganic core of about 2.5 to about 55 nm diameter, and an organic coating, the organic coating preferably having an overall thickness of about 3 to 5 nm. Preferably the nanoparticles are predominantly spheroid or spherical, and in certain embodiments, the nanoparticles are essentially uniform in diameter.

In any of the embodiments wherein the primer is bound to a nanoparticle include embodiments wherein prior to binding primers, the nanoparticles have a surface comprising reactive groups, the reactive groups preferably comprising at least one of:

acrylic groups;
thiol-containing groups;
reactive amine groups;
carboxyl groups, wherein the primers comprise reactive groups suitable for forming covalent bonds with reactive groups on the surface of the nanoparticles, and wherein the primers and the nanoparticles are treated together under conditions wherein the primers are covalently linked to the nanoparticles.

In any of the embodiments wherein the primer is bound to a nanoparticle, counting RCA products on nanoparticles may comprise at least one of fluorescence microscopy, flow cytometry, and nanopore sensing.

In any of the embodiments wherein the primer is bound to a nanoparticle, counting RCA products on nanoparticles may comprise localizing RCA products to a support at dispersed loci wherein at least a portion of the RCA products localized at the dispersed loci are individually detectable by detection of hybridized labeled probes and counting RCA products at dispersed loci on the support. In preferred embodiments, RCA products with hybridized labeled probes are localized to dispersed loci by one or more of a magnet, centrifugation, and filtration.

Any of the embodiments wherein the primer is bound to a nanoparticle include embodiments wherein prior to forming the plurality of complexes, the ligation mixture is treated with at least one exonuclease, wherein circularized nucleic acid probes are not substrate for the at least one exonuclease. In preferred embodiments, the at least one exonuclease comprises at least one exonuclease selected from Rec Jf, Exo VII, Exo T, and Thermolabile Exo I.

Embodiments of the technology provide a composition comprising a plurality of complexes bound to a surface of an organic coating on one or more supports, wherein the one or more supports preferably comprise one or more of an assay plate, preferably a glass-bottom assay plate, and a nanoparticle, preferably a paramagnetic nanoparticle, more preferably a ferromagnetic nanoparticle, preferably an iron oxide nanoparticle, each complex comprising an oligonucleotide primer hybridized to a circularized nucleic acid probe, wherein the primer is bound to the surface of the organic coating on the support, and a reaction mixture comprising:

Phi29 DNA polymerase, preferably at least 0.2 units per µL, preferably at least 0.8 units per µL of Phi29 DNA polymerase;

a buffer;

a mixture of dNTPs, preferably at least 400 µM, preferably at least 600 µM, more preferably at least 800 µM total dNTPs;

PEG, preferably at least 2 to 10% (w:v), preferably at least 12%, preferably at least 14%, preferably at least 16%, preferably at least 18% to 20% PEG.

In some embodiments, the PEG has an average molecular weight between 200 and 8000, preferably between 200 and 1000, preferably between 400 and 800, preferably 600.

Embodiments include any of the compositions described above, wherein the reaction mixture further comprises at least one labeled probe, preferably a fluorescently labeled probe, more preferably a molecular beacon probe, preferably least 100 nM of labeled probe, more preferably at least 1000 nM of labeled probe.

Embodiments of the technology further provide a composition comprising a plurality of RCA products bound to a surface of an organic coating on one or more supports, wherein the one or more supports preferably comprise one or more of an assay plate, preferably a glass-bottom assay plate, and a nanoparticle, preferably a paramagnetic nanoparticle, more preferably a ferromagnetic nanoparticle, preferably an iron oxide nanoparticle, each RCA product comprising a primer portion bound to the surface of the organic coating on the support, and a buffer comprising Mg', the solution further comprising:

one or more labeled probes hybridized to RCA products; and one or more of:
graphene oxide;
one or more detergents.

Embodiments of such compositions include embodiments wherein the labeled probes comprise fluorescent labels and embodiments wherein the labeled probes comprise quencher moieties. In some embodiments, a plurality of RCA products are hybridized to labeled probes that all comprise the same label, preferably the same fluorescent label, while in some embodiments, a plurality of RCA products are hybridized to a set of labeled probes that all comprise a label, wherein the set of labeled probes comprises two, three, four, five, six, seven, or more different labels, preferably two, three, four, five, six, seven, or more different fluorescent labels.

Embodiments include any of the compositions above in which the one or more detergents comprise agents selected from anionic agents, preferably sodium dodecyl sulfate; sodium lauryl sulfate; ammonium lauryl sulfate; cationic agents, preferably benzalkonium chloride; cetyltrimethylammonium bromide; linear alkylbenzene sulfonates, preferably sodium dodecylbenzene sulfonate; non-ionic agents, preferably a TWEEN detergent selected from polyoxyethylene (20) sorbitan-monolaurate; -monopalmitate; -monostearate; or -monooleate; a TRITON detergent preferably selected from s polyethylene glycol p-(1,1,3,3-tetramethylbutyl)-phenyl ether, and steroid and steroidal glycosides, preferably saponin or digitonin; and zwitterionic agents, preferably 3[(3-cholamidopropyl)dimethylammonio]-1-propanesulfonate (CHAPS); and mixtures of detergent agents, preferably TEEPOL® detergent, comprising sodium dodecylbenzene sulfonate, and sodium $C_{12}$-$C_{15}$ alcohol ether sulfate.

Any of the embodiments above include embodiments of the composition wherein the organic coating is a polymeric coating polymerized from surface-modifying monomers, wherein the surface-modifying monomers preferably comprise one or more of dopamine, tannic acid, caffeic acid, pyrogallol, gallic acid, epigallocatechin gallate, and epicatechin gallate monomers, preferably dopamine and tannic acid. In some embodiments, the polymeric coating is homopolymeric.

Any of the embodiments above include embodiments of the composition wherein the solution comprising a labeled probe comprises a fluorescently labeled probe, preferably a molecular beacon probe, preferably more than 100 nM of labeled probe, preferably at least 1000 nM of labeled probe, and/or wherein the buffer comprising Mg' is a Phi29 DNA polymerase buffer.

Embodiments of the technology comprise systems, for example, a system comprising:
  i) a plurality of complexes bound to a surface of an organic coating on one or more supports, wherein the one or more supports preferably comprise one or more of an assay plate, preferably a glass-bottom assay plate, and a nanoparticle, preferably a paramagnetic nanoparticle, more preferably a ferromagnetic nanoparticle, preferably an iron oxide nanoparticle, each complex comprising an oligonucleotide primer hybridized to a circularized nucleic acid probe, wherein the primer is bound to the surface of the organic coating on the support;
  ii) DNA polymerase, preferably Phi29 DNA polymerase;
  iii) one or more labeled probes, preferably fluorescently labeled probes.

In some embodiments, a system further comprises one or more of:
  iv) a buffer comprising Mg++, preferably a buffer comprising $MgCl_2$, preferably a Phi29 DNA polymerase buffer;
  v) PEG, preferably PEG having an average molecular weight between 200 and 8000, preferably between 200 and 1000, preferably between 400 and 800, preferably 600;
  vi) one or more detergents, preferably one or more detergents comprising agents selected from anionic agents, preferably sodium dodecyl sulfate; sodium lauryl sulfate; ammonium lauryl sulfate; cationic agents, preferably benzalkonium chloride; cetyltrimethylammonium bromide; linear alkylbenzene sulfonates, preferably sodium dodecylbenzene sulfonate; non-ionic agents, preferably a TWEEN detergent selected from polyoxyethylene (20) sorbitan-monolaurate; -monopalmitate; -monostearate; or -monooleate; a TRITON detergent preferably selected from s polyethylene glycol p-(1,1,3,3-tetramethylbutyl)-phenyl ether, and steroid and steroidal glycosides, preferably saponin or digitonin; and zwitterionic agents, preferably 3-[(3-cholamidopropyl)dimethylammonio]-1-propanesulfonate (CHAPS); and mixtures of detergent agents, preferably TEEPOL® detergent, comprising sodium dodecylbenzene sulfonate, and sodium $C_{12}$-$C_{15}$ alcohol ether sulfate;
  vii) as solution comprising dNTPs; and
  viii) graphene oxide.

In some embodiments, the organic coating is a polymeric coating polymerized from surface-modifying monomers, wherein the surface-modifying monomers preferably comprise one or more of dopamine, tannic acid, caffeic acid, pyrogallol, gallic acid, epigallocatechin gallate, and epicatechin gallate monomers, preferably dopamine and tannic acid, and in some embodiments, the polymeric coating is homopolymeric.

In some embodiments, the support comprises a first surface. In some embodiments, the support, or the first surface of the support, comprises a solid or a porous material. In embodiments, the support or the first surface of the support can comprise ceramic, silanized material, metal, polymer, stone, paper, fabric, a carbon material, or a combination thereof. As used herein, the term "carbon materials" refer to elemental carbon materials, such as graphite, carbon fiber, carbon nanotube, graphene, carbon black, activated carbon, fullerene and diamond. In embodiments, the silanized material is quartz or glass, such as a glass slide, a glass bead, or a glass plate, such as the surface of a glass bottom assay plate. In some embodiments, the polymer is an organic polymer. In some embodiments, the polymer is a fluropolymer (e.g., Teflon®) or an organic polymer. Suitable organic polymers include but are not limited to polyesters (e.g., polyethylene terephthalate or polyethylene naphthalates), polyacrylates (e.g., polymethyl methacrylate or "PMMA"), poly(vinyl acetate) ("PVAC"), poly(vinyl butyral) ("PVB"), poly(ethyl acrylate) ("PEA"), poly(diphenoxyphosphazene) ("PDPP"), polycarbonate ("PC"), polypropylene ("PP"), high density polyethylene ("HDPE"), low density polyethylene ("LDPE"), polysulfone ("PS"), polyether sulfone ("PES"), polyurethane ("PUR"), polyamide ("PA"), poly(dimethylsiloxane) ("PDMS"), polyvinyl chloride ("PVC"), polyvinylidene fluoride ("PY dF"), polystyrene ("PSy") and polyethylene sulfide; cellulose derivatives, polyimide, polyimide benzoxazole, polybenzoxazole, poly(glycolic acid), poly(lactic acid), poly(lactic-co-glycolic acid).

In some embodiments, the technology provides a method of preparing a support, such as a solid support. In some embodiments, the method comprises a) providing a first surface (or substrate; or substrate having a first surface); b) modifying the first surface with one or more surface modifying agent(s) (SMA(s)); c) thereby providing a support comprising a second surface (or coating]). In some embodiments, the second surface coats at least a portion of the first surface. In some embodiments, the second surface (or coating) comprises functional groups capable of forming complexes with one or more analytes. Thus, in some embodiments, the method thereby provides a support referred to herein as a "surface functionalized substrate" (SFS). In some embodiments, the functional groups capable of complexing with the one or more analytes is an amine group (e.g., a primary, secondary, tertiary or quaternary amine), a carboxylate or carboxylic acid group, or a combination thereof.

In some further embodiments, the modification of the first surface with the one or more SMAs comprises contacting the first surface with a mixture comprising a carrier and the one or more SMAs. In some embodiments, the mixture further comprises one or more initiators, for example, one or more initiators of polymerization. In some embodiments, the mixture is a solution or a suspension. Thus, in some embodiments, the modification of the first surface comprises contacting the first surface with a mixture comprising one or more SMAs, one or more initiators, and a carrier. In some further embodiments, the carrier is a liquid carrier, and the mixture is a solution or suspension. In yet further embodiments, the liquid carrier is an aqueous vehicle, and the mixture is an aqueous solution or suspension. Thus, in some more particular embodiments, the modification of the first surface comprises contacting the first surface with a mixture comprising a carrier, one or more SMAs and one or more initiators; optionally, the mixture is an aqueous solution or suspension. In some preferred embodiments, the mixture is an aqueous solution.

In some embodiments, at least one of the one or more SMAs is a vinyl monomer. In some embodiments, the vinyl monomer can comprise acrylamides such as acrylamide, methacrylamide, dialkylaminoalkyl acrylamides, such as dimethylaminoethyl acrylamide and methacrylamide, acrylates such as acrylic acid and methacrylic acid, dialkylaminoalkyl acrylates, such as dimethylaminoethyl acrylate, dimethylaminoethyl methacrylate, vinyl pyridine, methyl vinyl pyridine, vinyl pyrrolidone, amino styrene such as p-dimethylaminomethyl styrene, vinyl sulfuric acid, trimethyl ammonium ethyl acrylate (chloride), or a combination thereof. In some embodiments, the vinyl monomer can comprise a carboxylic acid group, an amine group, or both. In some embodiments, the vinyl monomer can be water or alcohol soluble. In embodiments, the vinyl monomer can comprise an acrylate monomer. In embodiments, the acrylate monomer can comprise a carboxylic acid, an amine, or a combination thereof. In embodiments, the acrylate monomer comprises acrylic acid, methacrylate, ethyl acrylate, propyl acrylate, a butyl acrylate, or a combination thereof. In some embodiments, the acrylate monomer comprises 2-aminoethyl methacrylate (AEMA), acrylic acid (AA), or a combination thereof.

In some embodiments, at least one of the one or more SMAs is a phenol monomer (i.e., a monomer comprising a phenol group). The phenol monomer can comprise two or more phenolic hydroxyl groups. For example, the phenol monomer can comprise a galloyl group, a catechol group, or a combination thereof. As used herein, the term "galloyl group" comprises a structure:

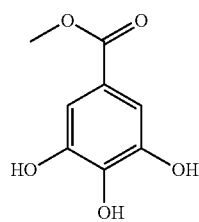

As used herein, the term "catechol group" comprises a 1,2-dihydroxybenzene. The galloyl group and catechol group used herein can be further substituted. In embodiments, the phenol monomer can comprise dopamine, tannic acid, caffeic acid, pyrogallol, gallic acid, epigallocatechin gallate, epicatechin gallate, epigallocatechin, or a combination thereof. In embodiments, the phenol monomer can comprise dopamine. In embodiments, the phenol monomer can comprise tannic acid.

In some embodiments, the method of modifying the first surface comprises polymerizing the one or more SMAs in the presence of the first surface. Thus, in some embodiments, the method of modifying the first surface comprises contacting the first surface with a mixture comprising a carrier and one or more SMAs, wherein the one or more SMAs polymerizes in the presence of the first surface, thereby providing the second surface. In some more particular embodiments, the mixture further comprises one or more initiators, wherein the initiator(s) initiate polymerization of the one or more SMAs. In some embodiments, the mixture comprises one SMA and the polymerization provides a homopolymer. In other embodiments, the mixture comprises at least two SMAs and the polymerization provides a copolymer. The homopolymer or the copolymer forms or is deposited on the first surface, thereby providing the second surface. In some embodiments, the second surface coats at least a portion of the first surface. In some embodiments, the second surface comprises functional groups capable of forming complexes with one or more analytes. Thus, in some embodiments, the method thereby provides a support which is a surface functionalized substrate (SFS). In some embodiments, the functional groups capable of complexing with the one or more analytes is an amine group (e.g., a primary, secondary, tertiary or quaternary amine), a carboxylate or carboxylic acid group, or a combination thereof.

In some embodiments, the polymerization or copolymerization of the SMA(s) can be performed in the presence of an initiator. The initiator can initiate polymerization, such as the homopolymerization or copolymerization of monomers. In some embodiments, the initiator can initiate the polymerization via a radical polymerization. In embodiments, the initiator can comprise an oxidant, a base, or a combination thereof. In embodiments, the initiator can comprise halogens, azo compounds, organic peroxides, inorganic peroxides, or a combination thereof. In embodiments, the initiator can comprise ammonium persulfate (APS), N,N,N',N'-tetramethylethylenediamine (TEMED), or a combination thereof. In embodiments, the initiator can initiate polymerization thermally, under ambient conditions or a combination thereof. In some embodiments, SMAs comprise photopolymers and polymerization is initiated by light, e.g., from a halogen, argon, xenon or LED light source.

In some more particular embodiments, the method of preparing the support comprises a) providing a substrate having a first surface; b) modifying the first surface by contacting the first surface with a mixture comprising a carrier, a first SMA which is dopamine, a second SMA which is AEMA, and one or more initiators; c) thereby providing a support comprising a second surface, wherein the second surface comprises a copolymer derived from the dopamine and the AEMA, and wherein the support is a surface functionalized substrate. In some embodiments, the second surface coats at least a portion of the first surface. In some embodiments, the second surface comprises functional groups capable of forming complexes with one or more analytes. In some embodiments, the functional groups capable of complexing with the one or more analytes is an amine group, a carboxylate or carboxylic acid group, or a combination thereof. In some embodiments, the initiator is ammonium persulfate, TEMED, or a combination thereof. In some other embodiments, the initiator is a photoinitiator. In some embodiments, the mixture is an aqueous solution. In some embodiments, the first surface is a silanized surface, such as glass. In some other embodiments, the first surface comprises an organic polymer, such as polystyrene.

In some more particular embodiments, the method of preparing the support comprises a) providing a substrate having a first surface; b) modifying the first surface by contacting the first surface with a mixture comprising a carrier, a first SMA which is dopamine, a second SMA which is acrylic acid, and one or more initiators; c) thereby providing a support comprising a second surface, wherein the second surface comprises a copolymer derived from the dopamine and the acrylic acid, and wherein the support is a surface functionalized substrate. In some embodiments, the second surface coats at least a portion of the first surface. In some embodiments, the second surface comprises functional groups capable of forming complexes with one or more analytes. In some embodiments, the functional groups capable of complexing with the one or more analytes is an amine group, a carboxylate or carboxylic acid group, or a combination thereof. In some embodiments, the initiator is ammonium persulfate, TEMED, or a combination thereof. In some other embodiments, the initiator is a photoinitiator. In some embodiments, the mixture is an aqueous solution. In some embodiments, the first surface is a silanized surface, such as glass. In some other embodiments, the first surface comprises an organic polymer, such as polystyrene.

In some more particular embodiments, the method of preparing the support comprises a) providing a substrate having a first surface; b) modifying the first surface by contacting the first surface with a mixture comprising a carrier, a first SMA which is tannic acid, a second SMA which is AEMA, and one or more initiators; c) thereby providing a support comprising a second surface, wherein the second surface comprises a copolymer derived from the tannic acid and the AEMA, and wherein the support is a surface functionalized substrate. In some embodiments, the second surface coats at least a portion of the first surface. In some embodiments, the second surface comprises functional groups capable of forming complexes with one or more analytes. In some embodiments, the functional groups capable of complexing with the one or more analytes is an amine group, a carboxylate or carboxylic acid group, or a combination thereof. In some embodiments, the initiator is ammonium persulfate, TEMED, or a combination thereof. In some other embodiments, the initiator is a photoinitiator. In some embodiments, the mixture is an aqueous solution. In some embodiments, the first surface is a silanized surface, such as glass. In some other embodiments, the first surface comprises an organic polymer, such as polystyrene.

In some more particular embodiments, the method of preparing the support comprises a) providing a substrate having a first surface; b) modifying the first surface by contacting the first surface with a mixture comprising a carrier, a first SMA which is tannic acid, a second SMA which is acrylic acid, and one or more initiators; c) thereby providing a support comprising a second surface, wherein the second surface comprises a copolymer derived from the tannic acid and the acrylic acid, and wherein the support is a surface functionalized substrate. In some embodiments, the second surface coats at least a portion of the first surface. In some embodiments, the second surface comprises functional groups capable of forming complexes with one or more analytes. In some embodiments, the functional groups capable of complexing with the one or more analytes is an amine group, a carboxylate or carboxylic acid group, or a combination thereof. In some embodiments, the initiator is ammonium persulfate, TEMED, or a combination thereof. In some other embodiments, the initiator is a photoinitiator. In some embodiments, the mixture is an aqueous solution. In some embodiments, the first surface is a silanized surface, such as glass. In some other embodiments, the first surface comprises an organic polymer, such as polystyrene.

In some embodiments, the technology provides a method for counting target molecules on a support, comprising: a) providing a first surface; b) modifying the first surface with at least one SMA to provide a surface functionalized substrate (SFS); optionally, the SFS comprises functional groups selected from at least one of carboxylate, carboxylic acid and amine groups; c) contacting the SFS with one or more analytes; d) thereby forming a plurality of complexes between the functional groups on the SFS and the one or more analytes; and e) counting the plurality of complexes. In some embodiments, the first surface (or substrate) is a silanized surface. In some embodiments, the silanized surface is glass, while in some embodiments, the surface is unsilanized glass. In certain preferred embodiments, the silanized surface comprises a surface treated with 3-aminopropyltriethoxysilane or 3-(trimethoxysilyl) propyl methacrylate. See, e.g., WO 2019/195346 A1 to Sekedat, et al., Methods, Systems, and Compositions for Counting Nucleic Acids (2019), which is incorporated herein by reference in its entirety, for all purposes. In some embodiments, the one or more analytes comprises at least one of an RCA product comprising a plurality of hybridized labeled probes and a double-stranded scaffold product comprising a plurality of concatemerized labeled scaffold oligonucleotides, wherein formation of a complex is indicative of the presence of a target molecule on the glass surface, and wherein forming said plurality of complexes comprises exposing the glass surface to a solution comprising graphene oxide. The surfaces are not limited to any particular format. For example, in any of the embodiments of described above, the support may comprise a surface in an assay plate, preferably a glass-bottom assay plate. In some embodiments, the assay plate is a multi-well assay plate, preferably a microtiter plate.

In some embodiments of the technology, the primer of any of the embodiments described above is bound directly to the support, preferably covalently linked to the support. For example, in some embodiments, the primer comprises a biotin moiety and the support comprises avidin, preferably streptavidin. In certain embodiments, the complex or complexes comprise an antibody bound to an antigen or hapten, and in some embodiments, the complex comprises an antigen or hapten bound directly to the support. In certain embodiments, the antigen or hapten is covalently attached to the support. In some embodiments, the primer is covalently linked to a support by conjugation of an amide bond between an amine and carboxylic acid.

In any of the embodiments described herein, forming a complex or plurality of complexes may comprise exposing the support to a solution comprising a crowding agent. In some embodiments, the crowding agent comprises polyethylene glycol (PEG), preferably at least 2 to 10% (w:v), preferably at least 12%, preferably at least 14%, preferably at least 16%, preferably at least 18% to 20% PEG. In certain preferred embodiments, the PEG has an average molecular weight between 200 and 8000, preferably between 200 and 1000, preferably between 400 and 800, preferably 600.

In any of the embodiments described above, forming a complex or plurality of complexes may comprise a step of exposing the support to a solution comprising graphene oxide. In preferred embodiments, the support is exposed to graphene oxide prior to step detecting hybridized labeled probe. In particularly preferred embodiments, the support is exposed to a solution that comprises a mixture of labeled probe and graphene oxide. In some embodiments, the support or the glass surface exposed to a solution comprising graphene oxide is washed with a solution comprising one or more detergents prior to the detecting or counting. In certain preferred embodiments, the one or more detergents comprises Tween 20.

In any of the embodiments described above, forming a complex or plurality of complexes may comprise comprising a step of exposing the support to a solution comprising one or more detergents or surfactants. In preferred embodiments, the support is exposed to a solution comprising one or more detergents or surfactants prior to a step of detecting hybridized labeled probe. In certain embodiments, the support is exposed to a solution that comprises a mixture of labeled probe and one or more detergents or surfactants. In some embodiments, the support or the glass surface is washed with a solution comprising one or more detergents or surfactants. In some embodiments, the detergent comprises an agent selected from anionic agents (e.g., sodium dodecyl sulfate; sodium lauryl sulfate; ammonium lauryl sulfate), cationic agents (e.g., benzalkonium chloride; cetyltrimethylammonium bromide; linear alkylbenzene sulfonates, such as sodium dodecylbenzene sulfonate), non-ionic agents (e.g., a TWEEN detergent, such as polyoxyethylene (20) sorbitan-monolaurate; -monopalmitate; -monostearate; or -monooleate; a TRITON, such as polyethylene glycol p-(1,1,3,3-tetramethylbutyl)-phenyl ether, or TRITON X-100; steroid and steroidal glycosides such as saponin and digitonin), and zwitterionic agents (e.g., CHAPS, which is 3-[(3-cholamidopropyl)dimethylammonio]-1-propanesulfonate), mixtures of detergent agents (e.g., TEEPOL® 610 S detergent, comprising sodium dodecylbenzene sulfonate, sodium $C_{12}$-$C_{15}$ alcohol ether sulfate), or a mixture thereof.

The technology finds use in detecting many different kinds of molecules, including, e.g., molecules as depicted schematically in FIG. 38. In some embodiments, a target molecule comprises nucleic acid, preferably DNA from a sample from a subject, preferably a blood or blood product sample. In certain preferred embodiments, the DNA is cell-free DNA from a blood or blood product sample, including but not limited to venous blood, menstrual blood, or other sources of blood and blood products that may be drawn from a body, collected from a tissue of a body, in a body, expelled or issued, etc., from a body of a subject. In some embodiments, the cell-free DNA comprises maternal and/or fetal DNA from a maternal blood sample.

Any of the embodiments described herein may comprise forming an RCA product in a process comprises extending a primer on a circularized nucleic acid probe in a reaction mixture. Preferably the reaction mixture comprises at least 0.2 units per μL, preferably at least 0.8 units per μL of Phi29 DNA polymerase and at least 400 μM, preferably at least 600 μM, more preferably at least 800 μM total dNTPs. In some embodiments, forming an RCA product comprising a plurality of hybridized labeled probes comprises forming the RCA product in a reaction mixture that further comprises more than 10 nM fluorescently-labeled oligonucleotide, e.g., a molecular beacon probe, preferably at least 100 nM fluorescently-labeled oligonucleotides probe, preferably at least 1000 nM fluorophore-labeled probe in the reaction mixture. In some embodiments, forming an RCA product comprising a plurality of hybridized labeled probes comprises forming the RCA product in a reaction mixture that does not comprise labeled probe, then treating the RCA product on the support with a solution that comprises one more labeled probes, preferably a solution that comprises $Mg^{++}$, preferably $MgCl_2$. In some embodiments, RCA product is removed from the reaction mixture, and in some embodiments washed, e.g., with a buffer, prior to treatment with the solution comprising one or more labeled probes.

In any of the embodiments described herein, complexes immobilized on a surface may comprise at least one polypeptide, e.g., an antibody, a lectin, and/or they may comprise at least one specifically-bindable molecule selected from a hapten, a carbohydrate, and a lipid.

In some embodiments of the technology, forming an RCA product comprises incubating the reaction mixture at least 37° C., preferably at least 42° C., preferably at least 45° C. In certain embodiments, the reaction mixture comprises PEG, preferably at least 2 to 10% (w:v), preferably at least 12%, preferably at least 14%, preferably at least 16%, preferably at least 18% to 20% PEG.

The technology also provides compositions related to practice of the methods. In some embodiments, the technology provides a composition comprising a silanized surface or non-silanized surface, preferably a surface modified using one or more surface modifying agents to provide a second surface bound to a plurality of complexes, each comprising an oligonucleotide primer hybridized to a circularized nucleic acid probe, wherein the primer is localized to a support, and a reaction mixture comprising at least 0.1 units per μL, preferably at least 0.2 to 0.8 units per μL of Phi29 DNA polymerase; a buffer; at least 400 μM, preferably at least 600 μM, more preferably at least 800 μM total dNTP; and PEG, preferably at least 2 to 20% (w:v), preferably 12 to 18%, preferably 14 to 16%, preferably 15% PEG. In some embodiments, the PEG has an average molecular weight of between 200 and 8000, preferably between 200 and 1000, preferably between 400 and 800, preferably 600. In some embodiments, the reaction mixture further comprises at least 10 nM fluorescently labeled oligonucleotide, e.g., molecular beacon probe, preferably at least 100 nM fluorescently labeled oligonucleotide, preferably at least 1000 nM fluorescently labeled oligonucleotide. In some embodiments, RCA product is removed from the reaction mixture, and in some embodiments washed, e.g., with a buffer, prior to treatment with the solution comprising one or more labeled probes.

In some embodiments of the composition, the primers are localized to the support in an irregular dispersal, while in some embodiments, the primers are localized to the support in an addressable array. In certain embodiments, the primer is covalently linked to the support, while in some embodiments, wherein the primer comprises a biotin moiety and the support comprises avidin, preferably streptavidin. In other embodiments, the primer is covalently bound to a bead or particle, preferably a small nanoparticle, more preferably a paramagnetic small nanoparticle, and the nanoparticle-bound primer is localized to a surface by an application of force, e.g., with a magnet or centrifuge In some embodiments, the complexes comprise an antibody bound to an antigen or hapten and in some embodiments, the complexes comprise an antigen or hapten bound directly to the support. In some embodiments, the antigen or hapten is covalently attached to the support.

In some embodiments of the compositions herein, complexes comprise at least one polypeptide. In some preferred embodiments, the at least one polypeptide comprises an antibody or a lectin. In some embodiments, the complexes comprise at least one specifically-bindable molecule selected from a hapten, a carbohydrate, and a lipid.

Embodiments of the composition described above may comprise a silanized surface bound to a plurality of complexes each comprising an RCA product comprising a plurality of hybridized labeled probes, and a solution comprising graphene oxide.

In some embodiments, the silanized surface is glass. In some preferred embodiments, the silanized surface comprises a surface, preferably a glass surface, treated with 3-aminopropyltriethoxysilane or 3-(trimethoxysilyl) propyl methacrylate. In some embodiments, the surface, preferably a glass surface is not silanized. In certain preferred embodiments, the surface comprises a polymeric coating formed by polymerization of one or more monomers, including but not limited to e.g., tannic acid, acrylic acid, dopamine, etc. In preferred embodiments, the support comprises a surface comprising polytannic acid or polydopamine.

In some embodiments, the solution comprising graphene oxide further comprises a fluorescently labeled probe, e.g., a molecular beacon probe, preferably more than 10 nM of fluorescently labeled probe, preferably at least 100 nM fluorescently labeled probe, preferably at least 1000 nM fluorescently labeled probe.

In some embodiments of the composition, the solution comprising graphene oxide comprises a buffer solution comprising $MgCl_2$. In certain embodiments, the buffer comprising $MgCl_2$ is a Phi29 DNA polymerase buffer.

The technology provided herein is not limited to any particular use or application. In some embodiments, the technology finds use in analysis of chromosomal aberrations, e.g., aneuploidy, preferably in the context of non-invasive prenatal testing. For example, some embodiments of applications of the technology comprise obtaining a maternal sample that comprises both maternal and fetal genetic material, and measuring a plurality of target nucleic acids, wherein the target nucleic acids comprise specific sequences associated with a first chromosome, wherein the first chromosome is suspected of being variant (e.g., in gene dosage or chromosome count) in the fetal material, and wherein the target nucleic acid further comprises specific sequences associated with a second chromosome, which is not suspected of being variant in the fetal material. The method comprises analyzing an amount of the target nucleic acids associated with the first chromosome and the amount of target nucleic acids associated with the second chromosome in the sample to determine whether the amount of the target nucleic acids associated with the first chromosome differs sufficiently from the amount the target nucleic acid associated with the second chromosome to indicate a chromosomal or gene dosage variant in the fetus. In preferred embodiments, the target nucleic acids associated the first and second chromosomes are present in both the maternal and fetal genetic material and are the maternal and fetal nucleic acids the assay is not specific for one over the other. In preferred embodiments, the maternal sample is cell-free DNA from maternal blood. Statistical methods for analyzing chromosomal aberrations based on measuring amounts of DNA in a sample, including determining aberrations in the fetal DNA when the fetal DNA is a small fraction of the total DNA in a maternal sample, are known in the art. See, e.g., U.S. Pat. No. 6,100,029, which is incorporated herein by reference.

Definitions

To facilitate an understanding of the present invention, a number of terms and phrases are defined below:

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, the terms "subject" and "patient" refer to any organisms including plants, microorganisms and animals (e.g., mammals such as dogs, cats, livestock, and humans).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as canines, felines, ungulates, bear, fish, lagomorphs, rodents, marsupials, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "target" as used herein refers to a molecule sought to be sorted out from other molecules for assessment, measurement, or other characterization. For example, a target nucleic acid may be sorted from other nucleic acids in a sample, e.g., by probe binding, amplification, isolation, capture, etc. When used in reference to a hybridization-based detection, e.g., polymerase chain reaction, "target" refers to the region of nucleic acid bounded by the primers used for polymerase chain reaction, while when used in an assay in which target DNA is not amplified, e.g., in capture by molecular inversion probes (MIPS), a target comprises the site bounded by the hybridization of the target-specific arms of the MIP, such that the MIP can be ligated and the presence of the target nucleic acid can be detected.

The term "source of target nucleic acid" refers to any sample that contains nucleic acids (RNA or DNA). Particularly preferred sources of target nucleic acids are biological samples including, but not limited to blood, plasma, serum, saliva, urine, feces, gastrointestinal fluid, cerebral spinal fluid, pleural fluid, milk, lymph, sputum, and semen.

The term "gene dosage" as used herein refers to the copy number of a gene, a genic region, a chromosome, or fragments or portions thereof. Normal individuals carry two copies of most genes or genic regions, one on each of two chromosomes. However, there are certain exceptions, e.g., when genes or genic regions reside on the X or Y chromosomes, or when genes sequences are present in pseudogenes.

The term "aneuploidy" as used herein refers to conditions wherein cells, tissues, or individuals have one or more whole chromosomes or segments of chromosomes either absent, or in addition to the normal euploid complement of chromosomes.

As used herein, the "sensitivity" of a given assay (or set of assays used together) refers to the percentage of samples that report a particular form or variant, e.g., a mutation, gene duplication, chromosome duplication, above a threshold value that distinguishes between samples exhibiting a variant phenotype (e.g., cancerous cells, aneuploidy) and samples exhibiting a normal or wild-type phenotype (e.g., non-cancerous cells, euploidy). In some embodiments, a "positive" is defined as a clinically-confirmed variant that reports an assay result associated with the presence of the disease or condition to be detected, and a false negative is defined as a clinically-confirmed variant that reports an assay result associated with the absence of the disease or condition. The value of sensitivity, therefore, reflects the probability that a given diagnostic assay performed on a known variant or diseased sample will produce a result indicative of the presence of the variation or disease. As defined here, the clinical relevance of a calculated sensitivity value represents an estimation of the probability that a given assay would detect the presence of a clinical condition when applied to a subject with that condition. Using the technology described herein, it may be possible to achieve a certain level of accuracy without the need for generating sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

As used herein, the "specificity" of a given assay (or set of assays used together) refers to the percentage of normal samples that report an assay result associated with the presence of the disease or condition to be detected, and a false positive is defined as a clinically-confirmed normal sample that reports an assay result associated with the presence of the disease or condition. The value of specificity, therefore, reflects the probability that a given diagnostic assay performed on a known normal sample will produce a result indicative of the presence of the variation or disease. As defined here, the clinical relevance of the calculated specificity value represents an estimation of the probability that a given marker would detect the absence of a clinical condition when applied to a subject without that condition.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full-length coding sequence or by any portion of the coding sequence so long as the desired activity or function is retained.

The term "genic region" as used herein refers to a gene, its exons, its introns, and its regions flanking it upstream and downstream, e.g., 5 to 10 kilobases 5' and 3' of the transcription start and stop sites, respectively.

The term "genic sequence" as used herein refers to the sequence of a gene, its introns, and its regions flanking it upstream and downstream, e.g., 5 to 10 kilobases 5' and 3' of the transcription start and stop sites, respectively.

The term "chromosome-specific" as used herein refers to a sequence that is found only in that particular type of chromosome.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated, e.g., in the presence of nucleotides and a suitable nucleic acid polymerase. An oligonucleotide "primer" may occur naturally, may be made using molecular biological methods, e.g., purification of a restriction digest, or may be produced synthetically. In preferred embodiments, a primer is composed of or comprises DNA.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include base analogs, and comprise modified forms of deoxyribonucleotides as well as ribonucleotides, and include but are not limited to modified bases and nucleotides described in U.S. Pat. Nos. 5,432,272; 6,001,983; 6,037,120; 6,140,496; 5,912,340; 6,127,121 and 6,143,877, each of which is incorporated herein by reference in their entireties; heterocyclic base analogs based on the purine or pyrimidine ring systems, and other heterocyclic bases.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As applied to polynucleotides, the term "substantial identity" denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence, which may include deletions or additions which total 20 percent or less of the reference sequence over the window of comparison. The reference sequence may be a subset of a larger sequence, for example, as a splice variant of the full-length sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxigenin; luminogenic, phosphorescent or fluorogenic moieties; mass tags; and fluorescent dyes alone or in combination with moieties that can suppress ("quench") or shift emission spectra by fluorescence resonance energy transfer (FRET). FRET is a distance-dependent interaction between the electronic excited states of two molecules (e.g., two dye molecules, or a dye molecule and a non-fluorescing quencher molecule) in which excitation is transferred from a donor molecule to an acceptor molecule without emission of a photon. (Stryer et al., 1978, Ann. Rev. Biochem., 47:819; Selvin, 1995, Methods Enzymol., 246: 300, each incorporated herein by reference). As used herein, the term "donor" refers to a fluorophore that absorbs at a first wavelength and emits at a second, longer wavelength. The term "acceptor" refers to a moiety such as a fluorophore, chromophore, or quencher that has an absorption spectrum that overlaps the donor's emission spectrum, and that is able to absorb some or most of the emitted energy from the donor when it is near the donor group (typically between 1-100 nm). If the acceptor is a fluorophore, it generally then re-emits at a third, still longer wavelength; if it is a chromophore or quencher, it then releases the energy absorbed from the donor without emitting a photon. In some embodiments, changes in detectable emission from a donor dye (e.g. when an acceptor moiety is near or distant) are detected. In some embodiments, changes in detectable emission from an acceptor dye are detected. In preferred embodiments, the emission spectrum of the acceptor dye is distinct from the emission spectrum of the donor dye such that emissions from the dyes can be differentiated (e.g., spectrally resolved) from each other.

In some embodiments, a donor dye is used in combination with multiple acceptor moieties. In a preferred embodiment, a donor dye is used in combination with a non-fluorescing quencher and with an acceptor dye, such that when the donor dye is close to the quencher, its excitation is transferred to the quencher rather than the acceptor dye, and when the quencher is removed (e.g., by cleavage of a probe), donor dye excitation is transferred to an acceptor dye. In particularly preferred embodiments, emission from the acceptor dye is detected. See, e.g., Tyagi, et al., Nature Biotechnology 18:1191 (2000), which is incorporated herein by reference.

Labels may provide signals detectable by fluorescence (e.g., simple fluorescence, FRET, time-resolved fluorescence, fluorescence polarization, etc.), radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

In some embodiment a label comprises a particle for detection. In preferred embodiments, the particle is a phosphor particle. In particularly preferred embodiments, the phosphor particle is an up-converting phosphor particle (see, e.g., Ostermayer, F. W. Preparation and properties of infrared-to-visible conversion phosphors. Metall. Trans. 752, 747-755 [1971]). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. While the present invention is not limited to any particular mechanism, in some embodiments the UPT up-converts infrared light to visible light by multi-photon absorption and subsequent emission of dopant-dependent phosphorescence. See, e.g., U.S. Pat. No. 6,399,397, Issued Jun. 4, 2002 to Zarling, et al.; van De Rijke, et al., Nature Biotechnol. 19(3):273-6 [2001]; Corstjens, et al., IEE Proc. Nanobiotechnol. 152(2):64 [2005], each incorporated by reference herein in its entirety.

As used herein, the terms "solid support" or "support" refer to any material that provides a substrate structure to which another material can be attached. A support or substrate may be, but need not be, solid. Support materials include smooth solid supports (e.g., smooth metal, glass, quartz, plastic, silicon, wafers, carbon (e.g., diamond), and ceramic surfaces, etc.), as well as textured and porous materials. Solid supports need not be flat. Supports include any type of shape, including spherical shapes (e.g., beads). Support materials also include, but are not limited to, gels, hydrogels, aerogels, rubbers, polymers, and other porous and/or non-rigid materials.

As used herein, the terms "bead" and "particle" are used interchangeably, and refer to a small support, typically a solid support, that is capable of moving about when in a solution (e.g., it has dimensions smaller than those of the enclosure or container in which the solution resides). In some embodiments, beads may settle out of a solution when the solution is not mixed (e.g., by shaking, thermal mixing, vortexing), while in other embodiments, beads may be suspended in solution in a colloidal fashion. In some embodiments, beads are completely or partially spherical or cylindrical. However, beads are not limited to any particular three-dimensional shape. In some embodiments, beads or particles may be paramagnetic. For example, in some embodiments, beads and particles comprise a magnetic material, e.g., ferrous oxide.

A bead or particle is not limited to any particular size, and in a preparation comprising a plurality of particles, the particles may be essentially uniform in size (e.g., in diameter) or may be a mixture of different sizes. In some embodiments, beads comprise or consist of nanoparticles, e.g., particles of less than about 1000 nm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 5 nm, or 1 nm in diameter. In some embodiments, the nanoparticle beads between 5 and 20 nm average diameter.

Materials attached to a solid support may be attached to any portion of the solid support (e.g., may be attached to an interior portion of a porous solid support material, or to an exterior portion, or to a flat portion on an otherwise non-flat support, or vice versa). In preferred embodiments of the technology, biological molecules such as nucleic acid or protein molecules are attached to solid supports. A biological material is "attached" to a solid support when it is affixed to the solid support through chemical or physical interaction. In some embodiments, attachment is through a covalent bond. However, attachments need not be covalent and need not be permanent. In some embodiments, an attachment may be undone or disassociated by a change in condition, e.g., by temperature, ionic change, addition or removal of a chelating agent, or other changes in the solution conditions to which the surface and bound molecule are exposed.

In some embodiments, materials are attached to a first support and are localized to the surface of a second support. For example, in some embodiments, materials that comprise a ferrous or magnetic particle may be magnetically localized to a surface or a region of a surface, such as a planar surface of a slide or well.

As used herein in reference to a support or substrate, e.g., for a coating or for attachment of a molecule, the term "surface" broadly refers to a portion of a support or substrate that is accessible for a purpose. For example, a portion of a bead or vessel or plate that is accessible to be coated, functionalized, attached to a moiety, e.g., an oligonucleotide or other macromolecule, or otherwise treated, may be considered a "surface" of the bead or plate, even if the surface is on an interior portion of the bead or vessel (e.g., within a pore, within a sintered matrix, inside a well, etc.) Similarly, a portion of a matrix that is flexible and/or porous (e.g., a hydrogel, aerogel, mesh, and that is accessible for a purpose, e.g., to be coated, functionalized, attached to a moiety, derivatized, etc., may be considered a surface of the matrix. In certain embodiments, a support may comprise a support surface, sometimes termed a first surface, which is the surface of the structural support material, e.g., in the absence of a coating or modifying layer, and may further comprise substrate surface, sometimes termed a second surface, which is the surface that is accessible for a purpose after the support surface is modified, e.g., by coating with a polymer or other coating. In some embodiments, the substrate surface comprises functional groups capable of complexing covalently or non-covalently with the one or more analytes, such as oligonucleotides or polypeptides that comprise reactive or binding groups suitable for complexing with the substrate surface functional groups.

As used herein, the term "detergent" refers any of a group of synthetic, organic, liquid or water-soluble agents that have wetting-agent and emulsifying-agent properties, and include anionic agents (e.g., sodium dodecyl sulfate, sodium lauryl sulfate, ammonium lauryl sulfate, cationic (e.g., benzalkonium chloride, cetyltrimethylammonium bromide) linear alkylbenzene sulfonates (e.g., sodium dodecylbenzene sulfonate), non-ionic (e.g., a TWEEN (e.g., polyoxyethylene (20) sorbitan-monolaurate, -monopalmitate, -monostearate, or -monooleate); TRITON (polyethylene glycol p-(1,1,3,3-tetramethylbutyl)-phenyl ether, steroid and steroidal al glycosides (e.g., saponin, digitonin); and zwitterionic (net neutral) agents such as 3-[(3-cholamidopropyl) dimethylammonio]-1-propanesulfonate (CHAPS), compounds. some embodiments, a "detergent" comprises a mixture of agents, e.g., TEEPOL® detergent, comprising sodium dodecylbenzene sulfonate, sodium $C_{12}$-$C_{15}$ alcohol ether sulfate.

In some embodiments, a target molecule, e.g., a biological material, is attached to a solid support through a "spacer molecule" or "linker group." Such spacer molecules are molecules that have a first portion that attaches to the biological material and a second portion that attaches to the solid support. Spacer molecules typically comprise a chain of atoms, e.g., carbon atoms, that provide additional distance between the first portion and the second portion. Thus, when attached to the solid support, the spacer molecule permits separation between the solid support and the biological material, but is attached to both. Examples of linkers and spacers include but are not limited to carbon chains, e.g., C3 and C6 (hexanediol), 1',2'-dideoxyribose (dSpacer); photocleavable (PC) spacers; triethylene glycol (TEG); and hexaethylene glycol spacers (Integrated DNA Technologies, Inc.).

As used herein, the terms "array" and "microarray" refer a surface or vessel comprising a plurality of pre-defined loci that are addressable for analysis of the locus, e.g., to determine a result of an assay. Analysis at a locus in an array is not limited to any particular type of analysis and includes, e.g., analysis for detection of an atom, molecule, chemical reaction, light or fluorescence emission, suppression, or alteration (e.g., in intensity or wavelength) indicative of a result at that locus. Examples of pre-defined loci include a grid or any other pattern, wherein the locus to be analyzed is determined by its known position in the array pattern. Microarrays, for example, are described generally in Schena, "Microarray Biochip Technology," Eaton Publishing, Natick, Mass., 2000. Examples of arrays include but are not limited to supports with a plurality of molecules non-randomly bound to the surface (e.g., in a grid or other regular pattern) and vessels comprising a plurality of defined reaction loci (e.g., wells) in which molecules or signal-generating reactions may be detected. In some embodiments, an array comprises a patterned distribution of wells that receive beads, e.g., as described above for the SIMOA technology. See also U.S. Pat. Nos. 9,057,730; 9,556,429; 9,481,883; and 9,376,677, each of which is incorporated herein by reference in its entirety, for all purposes.

As used herein, the terms "dispersed" and "dispersal" as used in reference to loci or sites, e.g., on a support or surface, refers to a collection of loci or sites that are distributed or scattered on or about the surface, wherein at least some of the loci are sufficiently separated from other loci that they are individually detectable or resolvable, one from another, e.g., by a detector such as a microscope. Dispersed loci may be in an ordered array, or they may be in an irregular distribution or dispersal, as described below.

As used herein, the term "irregular" as used in reference to a dispersal or distribution of loci or sites, e.g., on a solid support or surface, refers to distribution of loci on or in a surface in a non-arrayed manner. For example, molecules may be irregularly dispersed on a surface by application of a solution of a particular concentration that provides a desired approximate average distance between the molecules on the surface, but at sites that are not pre-defined by or addressable any pattern on the surface or by the means of applying the solution (e.g., inkjet printing). In such embodiments, analysis of the surface may comprise finding the locus of a molecule by detection of a signal wherever it may appear (e.g., scanning a whole surface to detect fluorescence anywhere on the surface). This contrasts to locating a signal by analysis of a surface or vessel only at predetermined loci (e.g., points in a grid array), to determine how much (or what type of) signal appears at each locus in the grid.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717; 5,985,557; 5,994,069; 6,001,567; 6,090,543; and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle amplification (e.g., U.S. Pat. Nos. 6,210,884, 6,183,960 and 6,235,502, herein incorporated by reference in their entireties); the variation of rolling circle amplification called "RAM amplification" (see, e.g., U.S. Pat. No. 5,942,391, incorporated herein by reference in its entirety; NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barany Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification plus invasive cleavage detection configurations, termed the QuARTS method, are described in, e.g., in U.S. Pat. Nos. 8,361,720; 8,715,937; 8,916,344; and 9,212,392, each of which is incorporated herein by reference for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

As used herein, the terms "digital PCR," "single molecule PCR" and "single molecule amplification" refer to PCR and other nucleic acid amplification methods that are configured to provide amplification product or signal from a single starting molecule. Typically, samples are divided, e.g., by serial dilution or by partition into small enough portions (e.g., in microchambers or in emulsions) such that each portion or dilution has, on average as assessed according to Poisson distribution, no more than a single copy of the target nucleic acid. Methods of single molecule PCR are described, e.g., in U.S. Pat. No. 6,143,496, which relates to a method comprising dividing a sample into multiple chambers such that at least one chamber has at least one target, and amplifying the target to determine how many chambers had a target molecule; U.S. Pat. No. 6,391,559; which relates to an assembly for containing and portioning fluid; and U.S. Pat. No. 7,459,315, which relates to a method of dividing a sample into an assembly with sample chambers where the samples are partitioned by surface affinity to the chambers, then sealing the chambers with a curable "displacing fluid." See also U.S. Pat. Nos. 6,440,706 and 6,753,147, and Vogelstein, et al., Proc. Natl. Acad. Sci. USA Vol. 96, pp. 9236-9241, August 1999. See also US 20080254474, describing a combination of digital PCR combined with methylation detection.

The term "sequencing", as used herein, is used in a broad sense and may refer to any technique known in the art that allows the order of at least some consecutive nucleotides in at least part of a nucleic acid to be identified, including without limitation at least part of an extension product or a vector insert. In some embodiments, sequencing allows the distinguishing of sequence differences between different target sequences. Exemplary sequencing techniques include targeted sequencing, single molecule real-time sequencing, electron microscopy-based sequencing, transistor-mediated sequencing, direct sequencing, random shotgun sequencing, Sanger dideoxy termination sequencing, targeted sequencing, exon sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, ion semiconductor sequencing, nanoball sequencing, nanopore sequencing, 454 sequencing, Solexa Genome Analyzer sequencing, miSeq (Illumina), HiSeq 2000 (Illumina), HiSeq 2500 (Illumina), Illumina Genome Analyzer (Illumina), Ion Torrent PGM™ (Life Technologies), MinION™ (Oxford Nanopore Technologies), real-time SMRT™ technology (Pacific Biosciences), the Probe-Anchor Ligation (cPAL™) (Complete Genomics/BGI), SOLiD® sequencing, MS-PET sequencing, mass spectrometry, and a combination thereof. In some embodiments, sequencing comprises detecting the sequencing product using an instrument, for example but not limited to an ABI PRISM® 377 DNA Sequencer, an ABI PRISM® 310, 3100, 3100-Avant, 3730, or 373OxI Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique, for example but not limited to, massively parallel signature sequencing (MPSS).

As used herein, the terms "peptide," "polypeptide," and "protein" are used interchangeably in reference to a chain of two or more amino acids linked together by peptide bonds. Polypeptides may be synthetic or naturally occurring, and may be short, e.g., between two about 30 amino acid residues, or may be hundreds or thousands of amino acid residues in length. Polypeptides may be composed of the 20 main naturally-occurring amino acids, or may comprise one or more non-natural amino acids, e.g., peptide nucleic acid residues, which comprise pyrimidine or purine bases on a peptide chain backbone, or modified versions of natural amino acids (e.g., modified in the structure of the side groups).

As used herein, the term "antibody" (Ab) refers to antigen-binding immunoglobulins, and includes monoclonal antibodies (mAbs) and polyclonal Abs. The term further includes all modified forms of antibodies that have the ability to bind to an antigen, e.g., fragment antibodies (fAbs) comprising portions of an immunoglobulin structure.

As used herein, the term "lectins" refers to a class of non-antibody proteins that specifically binds to sugars and to sugar moieties (e.g., sugar moieties on glycoproteins and glucolipids, or within complex carbohydrates).

As used herein, the terms "crowding agent" and "volume excluder," as used in reference to a component of a fluid reaction mixture, are used interchangeably and refer to compounds, generally polymeric compounds, that reduce available fluid volume in a reaction mixture, thereby increasing the effective concentration of reactant macromolecules (e.g., nucleic acids, enzymes, etc.) Crowding reagents include, e.g., glycerol, ethylene glycol, polyethylene glycol, ficoll, serum albumin, casein, and dextran.

As used herein, the terms "digital sequencing," "single-molecule sequencing," and "next generation sequencing (NGS)" are used interchangeably and refer to determining the nucleotide sequence of individual nucleic acid molecules. Systems for individual molecule sequencing include but are not limited to the 454 FLX™ or 454 TITANIUM™ (Roche), the SOLEXA™/Illumina Genome Analyzer (Illumina), the HELISCOPE™ Single Molecule Sequencer (Helicos Biosciences), and the SOLID™ DNA Sequencer (Life Technologies/Applied Biosystems) instruments), as well as other platforms still under development by companies such as Intelligent Biosystems and Pacific Biosystems. See also U.S. Pat. No. 7,888,017, entitled "Non-invasive fetal genetic screening by digital analysis," relating to digital analysis of maternal and fetal DNA, e.g., cfDNA.

As used herein, the term "probe" or "hybridization probe" refers to an oligonucleotide (i.e., a sequence of nucleotides), whether occurring naturally as in a purified restriction digest or produced synthetically, recombinantly or by PCR amplification, that is capable of hybridizing, at least in part, to another oligonucleotide of interest. A probe may be single-stranded or double-stranded. Probes are useful in the detection, identification and isolation of particular sequences. In some preferred embodiments, probes used in the present invention will be labeled with a "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "MIP" as used herein, refers to a molecular inversion probe (or a circular capture probe). Molecular inversion probes (or circular capture probes) are nucleic acid molecules that comprise a pair of unique polynucleotide arms that hybridize to a target nucleic acid to form a nick or gap and a polynucleotide linker (e.g., a universal backbone linker). In some embodiments, the unique polynucleotide arms hybridize to a target strand immediately adjacent to each other to form a ligatable nick (generally termed "padlock probes") while in some embodiments, one the hybridized MIP must be further modified (e.g., by polymerase extension, base excision, and/or flap cleavage) to form a ligatable nick. Ligation of a MIP probe to form a circular nucleic acid is typically indicative of the presence of the complementary target strand. In some embodiments, MIPs comprise one or more unique molecular tags (or unique molecular identifiers). See, for example, FIG. 1. In some embodiments, a MIP may comprise more than one unique molecular tags, such as, two unique molecular tags, three unique molecular tags, or more. In some embodiments, the unique polynucleotide arms in each MIP are located at the 5' and 3' ends of the MIP, while the unique molecular tag(s) and the polynucleotide linker are located internal to the 5' and 3' ends of the MIP. For example, the MIPs that are used in some embodiments of this disclosure comprise in sequence the following components: first unique polynucleotide arm—first unique molecular tag—polynucleotide linker—second unique molecular tag—second unique polynucleotide arm. In some embodiments, the MIP is a 5' phosphorylated single-stranded nucleic acid (e.g., DNA) molecule. See, for example, WO 2017/020023, filed Jul. 29, 2016, and WO 2017/020024, filed Jul. 29, 2016, each of which is incorporated by reference herein for all purposes.

As used herein, the terms "circular nucleic acid" and "circularized nucleic acid" as used, for example, in reference to probe nucleic acids, refers to nucleic acid strands that are joined at the ends, e.g., by ligation, to form a continuous circular strand of nucleic acid.

The unique molecular tag may be any tag that is detectable and can be incorporated into or attached to a nucleic acid (e.g., a polynucleotide) and allows detection and/or identification of nucleic acids that comprise the tag. In some embodiments the tag is incorporated into or attached to a nucleic acid during sequencing (e.g., by a polymerase). Non-limiting examples of tags include nucleic acid tags, nucleic acid indexes or barcodes, radiolabels (e.g., isotopes), metallic labels, fluorescent labels, chemiluminescent labels, phosphorescent labels, fluorophore quenchers, dyes, proteins (e.g., enzymes, antibodies or parts thereof, linkers, members of a binding pair), the like or combinations thereof. In some embodiments, particularly sequencing embodiments, the tag (e.g., a molecular tag) is a unique, known and/or identifiable sequence of nucleotides or nucleotide analogues (e.g., nucleotides comprising a nucleic acid analogue, a sugar and one to three phosphate groups). In some embodiments, tags are six or more contiguous nucleotides. A multitude of fluorophore-based tags are available with a variety of different excitation and emission spectra. Any suitable type and/or number of fluorophores can be used as a tag. In some embodiments 1 or more, 2 or more, 3 or more, 4 or more, 5 or more, 6 or more, 7 or more, 8 or more, 9 or more, 10 or more, 20 or more, 30 or more, 50 or more, 100 or more, 500 or more, 1000 or more, 10,000 or more, 100,000 or more different tags are utilized in a method described herein (e.g., a nucleic acid detection and/or sequencing method). In some embodiments, one or two types of tags (e.g., different fluorescent labels) are linked to each nucleic acid in a library. In some embodiments, chromosome-specific tags are used to make chromosomal counting faster or more efficient. Detection and/or quantification of a tag can be performed by a suitable method, machine or apparatus, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In the MIPs, the unique polynucleotide arms are designed to hybridize immediately upstream and downstream of a specific target sequence (or site) in a nucleic acid target, e.g., in an RNA, cfDNA, or genomic nucleic acid sample. In some embodiments, hybridization of a MIP to a target sequence produces a ligatable nick without a gap, i.e., the two arms of the MIP hybridize to contiguous sequences in the target strand such that no overlap or gap is formed upon hybridization. Such zero-gap MIPs are generally termed "padlock" probes. See, e.g., M. Nilsson, et al. "Padlock probes: circularizing oligonucleotides for localized DNA detection". Science. 265 (5181): 2085-2088 (1994); J. Banér, et al., *Nucleic Acids Res.*, 26 (22):5073-5078 (1998). In other embodiments the hybridized MIP/target nucleic acid complex requires modification to produce a ligatable nick. For example, in some embodiments, hybridization leaves a gap that is filled, e.g., by polymerase extending a 3' end of the MIP, prior to ligation, while in other embodiments, hybridization forms an overlapping flap structure that must be modified, e.g., by a flap endonuclease or a 3' exonuclease, to produce a ligatable nick. In some embodiments, MIPS comprise unique molecular tags are short nucleotide sequences that are randomly generated. In some embodiments, the unique molecular tags do not hybridize to any sequence or site located on a genomic nucleic acid fragment or in a genomic nucleic acid sample. In some embodiments, the polynucleotide linker (or the backbone linker) in the MIPs are universal in all the MIPs used in embodiments of this disclosure.

In some embodiments, the MIPs are introduced to nucleic acid fragments derived from a test subject (or a reference subject) to perform capture of target sequences or sites (or control sequences or sites) located on a nucleic acid sample (e.g., a genomic DNA). In some embodiments, fragmenting aids in capture of target nucleic acid by molecular inversion probes. In some embodiments, for example, when the nucleic acid sample is comprised of cell free nucleic acid, fragmenting may not be necessary to improve capture of target nucleic acid by molecular inversion probes. For example, in some types of samples, cell free nucleic acid is fragmented in the sample such that further fragmentation is not necessary and may even be detrimental capture of the target nucleic acids. As described in greater detail herein, after capture of the target sequence (e.g., locus) of interest, the captured target may be subjected to enzymatic gap-filling and ligation steps, such that a copy of the target sequence is incorporated into a circle-like structure. In some embodiments, nucleic acid analogs, e.g., containing labels, haptens, etc., may be incorporated in the filled section, for use, e.g., in downstream detection, purification, or other processing steps. Capture efficiency of the MIP to the target sequence on the nucleic acid fragment can, in some embodiments, be improved by lengthening the hybridization and gap-filling incubation periods. (See, e.g., Turner E H, et al., Nat Methods. 2009 Apr. 6:1-2.).

In some embodiments, the MIPs that are used according to the disclosure to capture a target site or target sequence comprise in sequence the following components: first targeting polynucleotide arm—first unique targeting molecular tag—polynucleotide linker—second unique targeting molecular tag—second targeting polynucleotide arm.

In some embodiments, the MIPs that are used in the disclosure to capture a control site or control sequence comprise in sequence the following components: first control polynucleotide arm—first unique control molecular tag—polynucleotide linker—second unique control molecular tag—second control polynucleotide arm.

MIP technology may be used to detect or amplify particular nucleic acid sequences in complex mixtures. One of the advantages of using the MIP technology is in its capacity for a high degree of multiplexing, which allows thousands of target sequences to be captured in a single reaction containing thousands of MIPs. Various aspects of MIP technology are described in, for example, Hardenbol et al., "Multiplexed genotyping with sequence-tagged molecular inversion probes," Nature Biotechnology, 21(6): 673-678 (2003); Hardenbol et al., "Highly multiplexed molecular inversion probe genotyping: Over 10,000 targeted SNPs genotyped in a single tube assay," Genome Research, 15: 269-275 (2005); Burmester et al., "DMET microarray technology for pharmacogenomics-based personalized medicine," Methods in Molecular Biology, 632: 99-124 (2010); Sissung et al., "Clinical pharmacology and pharmacogenetics in a genomics era: the DMET platform," Pharmacogenomics, 11(1): 89-103 (2010); Deeken, "The Affymetrix DMET platform and pharmacogenetics in drug development," Current Opinion in Molecular Therapeutics, 11(3): 260-268 (2009); Wang et al., "High quality copy number and genotype data from FFPE samples using Molecular Inversion Probe (MIP) microarrays," BMC Medical Genomics, 2:8 (2009); Wang et al., "Analysis of molecular inversion probe performance for allele copy number determination," Genome Biology, 8(11): R246 (2007); Ji et al., "Molecular inversion probe analysis of gene copy alternations reveals distinct categories of colorectal carcinoma," Cancer Research, 66(16): 7910-7919 (2006); and Wang et al., "Allele quantification using molecular inversion probes (MIP)," Nucleic Acids Research, 33(21): e183 (2005), each of which is hereby incorporated by reference in its entirety for all purposes. See also in U.S. Pat. Nos. 6,858,412; 5,817,921; 6,558,928; 7,320,860; 7,351,528; 5,866,337; 6,027,889 and 6,852,487, each of which is hereby incorporated by reference in its entirety for all purposes.

MIP technology has previously been successfully applied to other areas of research, including the novel identification and subclassification of biomarkers in cancers. See, e.g., Brewster et al., "Copy number imbalances between screen- and symptom-detected breast cancers and impact on disease-free survival," Cancer Prevention Research, 4(10): 1609-1616 (2011); Geiersbach et al., "Unknown partner for USP6 and unusual SS18 rearrangement detected by fluorescence in situ hybridization in a solid aneurysmal bone cyst," Cancer Genetics, 204(4): 195-202 (2011); Schiffman et al., "Oncogenic BRAF mutation with CDKN2A inactivation is characteristic of a subset of pediatric malignant astrocytomas," Cancer Research, 70(2): 512-519 (2010); Schiffman et al., "Molecular inversion probes reveal patterns of 9p21 deletion and copy number aberrations in childhood leukemia," Cancer Genetics and Cytogenetics, 193(1): 9-18 (2009); Press et al., "Ovarian carcinomas with genetic and epigenetic BRCA1 loss have distinct molecular abnormalities," BMC Cancer, 8:17 (2008); and Deeken et al., "A pharmacogenetic study of docetaxel and thalidomide in patients with castration-resistant prostate cancer using the DMET genotyping platform," Pharmacogenomics, 10(3): 191-199 (2009), each of which is hereby incorporated by reference in its entirety for all purposes.

MIP technology has also been applied to the identification of new drug-related biomarkers. See, e.g., Caldwell et al., "CYP4F2 genetic variant alters required warfarin dose," Blood, 111(8): 4106-4112 (2008); and McDonald et al., "CYP4F2 Is a Vitamin K1 Oxidase: An Explanation for Altered Warfarin Dose in Carriers of the V433M Variant," Molecular Pharmacology, 75: 1337-1346 (2009), each of which is hereby incorporated by reference in its entirety for all purposes. Other MIP applications include drug development and safety research. See, e.g., Mega et al., "Cytochrome P-450 Polymorphisms and Response to Clopidogrel," New England Journal of Medicine, 360(4): 354-362 (2009); Dumaual et al., "Comprehensive assessment of metabolic enzyme and transporter genes using the Affymetrix Targeted Genotyping System," Pharmacogenomics, 8(3): 293-305 (2007); and Daly et al., "Multiplex assay for comprehensive genotyping of genes involved in drug metabolism, excretion, and transport," Clinical Chemistry, 53(7): 1222-1230 (2007), each of which is hereby incorporated by reference in its entirety for all purposes. Further applications of MIP technology include genotype and phenotype databasing. See, e.g., Man et al., "Genetic Variation in Metabolizing Enzyme and Transporter Genes: Comprehensive Assessment in 3 Major East Asian Subpopulations with Comparison to Caucasians and Africans," Journal of Clinical Pharmacology, 50(8): 929-940 (2010), which is hereby incorporated by reference in its entirety for all purposes.

The term "capture" or "capturing", as used herein, refers to the binding or hybridization reaction between a molecular inversion probe and its corresponding targeting site. In some embodiments, upon capturing, a circular replicon or a MIP replicon is produced or formed. In some embodiments, the targeting site is a deletion (e.g., partial or full deletion of one or more exons). In some embodiments, a target MIP is designed to bind to or hybridize with a naturally-occurring (e.g., wild-type) genomic region of interest where a target deletion is expected to be located. The target MIP is designed to not bind to a genomic region exhibiting the deletion. In these embodiments, binding or hybridization between a target MIP and the target site of deletion is expected to not occur. The absence of such binding or hybridization indicates the presence of the target deletion. In these embodiments, the phrase "capturing a target site" or the phrase "capturing a target sequence" refers to detection of a target deletion by detecting the absence of such binding or hybridization. As used in reference to other oligonucleotides, e.g., "capture oligonucleotide" the term refers to a binding or hybridization reaction between the capture oligonucleotide and a nucleic acid to be captured, e.g., to be immobilized, removed from solution, or otherwise be manipulated by hybridization to the capture oligonucleotide.

The term "MIP replicon" or "circular replicon", as used herein, refers to a circular nucleic acid molecule generated via a capturing reaction (e.g., a binding or hybridization reaction between a MIP and its targeted sequence). In some embodiments, the MIP replicon is a single-stranded circular nucleic acid molecule. In some embodiments, a targeting MIP captures or hybridizes to a target sequence or site. After the capturing reaction or hybridization, in some embodiments, a ligation reaction mixture is introduced to ligate the nick formed by hybridization of the two targeting polynucleotide arms to form single-stranded circular nucleotide molecules, i.e., a targeting MIP replicon, while in some embodiments, hybridization of the MIP leaves a gap, and a ligation/extension mixture is introduced to extend and ligate the gap region between the two targeting polynucleotide arms to form a targeting MIP replicon. In some embodiments, a control MIP captures or hybridizes to a control sequence or site. After the capturing reaction or hybridization, a ligation reaction mixture is introduced to ligate the nick formed by hybridization of the two control polynucleotide arms, or a ligation/extension mixture is introduced to extend and ligate the gap region between the two control polynucleotide arms to form single-stranded circular nucleotide molecules, i.e., a control MIP replicon. MIP replicons may be amplified through a polymerase chain reaction (PCR) to produce a plurality of targeting MIP amplicons, which are double-stranded nucleic acid molecules. MIP replicons find particular application in rolling circle amplification, or RCA. RCA is an isothermal nucleic acid amplification technique where a DNA polymerase continuously adds single nucleotides to a primer annealed to a circular template, which results in a long concatemer of single stranded DNA that contains tens to hundreds to thousands of tandem repeats (complementary to the circular template). See, e.g., M. Ali, et al. "Rolling circle amplification: a versatile tool for chemical biology, materials science and medicine". *Chemical Society Reviews*. 43 (10): 3324-3341, which is incorporated herein by reference in its entirety, for all purposes. See also WO 2015/083002, which is incorporated herein by reference in its entirety, for all purposes.

Polymerases typically used in RCA for DNA amplification are Phi29, Bst, and Vent exo-DNA polymerases, with Phi29 DNA polymerase being preferred in view of its superior processivity and strand displacement ability The term "amplicon", as used herein, refers to a nucleic acid generated via amplification reaction (e.g., a PCR reaction). In some embodiments, the amplicon is a single-stranded nucleic acid molecule. In some embodiments, the amplicon is a double-stranded nucleic acid molecule. In some embodiments, a targeting MIP replicon is amplified using conventional techniques to produce a plurality of targeting MIP amplicons, which are double-stranded nucleotide molecules. In some embodiments, a control MIP replicon is amplified using conventional techniques to produce a plurality of control MIP amplicons, which are double-stranded nucleotide molecules.

The term "probe oligonucleotide" or "flap oligonucleotide" when used in reference to a flap assay (e.g., an INVADER invasive cleavage assay), refers to an oligonucleotide that interacts with a target nucleic acid to form a cleavage structure in the presence of an invasive oligonucleotide.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archival thermophiles organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect. In such embodiments, the cassette may be referred to as a "FRET cassette." See, for example, U.S. Pat. No. 9,096,893, issued Aug. 4, 2015, which is incorporated herein by reference in its entirety, for all purposes.

As used herein, the phrase "not substantially complementary" as used in reference to a probe flap or arm means that the flap portion is sufficiently non-complementary not to hybridize selectively to a nucleic acid sequence, e.g., a target nucleic acid or amplified DNA, under the designated annealing conditions or stringent conditions, encompassing the terms "substantially non-complementary" and "perfectly non-complementary."

The term "signal" as used herein refers to any detectable effect, such as would be caused or provided by a label or by action or accumulation of a component or product in an assay reaction.

As used herein, the term "detector" refers to a system or component of a system, e.g., an instrument (e.g. a camera, fluorimeter, charge-coupled device, scintillation counter, solid state nanopore device, etc.) or a reactive medium (X-ray or camera film, pH indicator, etc.), that can convey to a user or to another component of a system (e.g., a computer or controller) the presence of a signal or effect. A detector is not limited to a particular type of signal detected, and can be a photometric or spectrophotometric system, which can detect ultraviolet, visible or infrared light, including fluorescence or chemiluminescence; a radiation detection system; a charge detection system; a system for detection of an electronic signal, e.g., a current or charge perturbation; a spectroscopic system such as nuclear magnetic resonance spectroscopy, mass spectrometry or surface enhanced Raman spectrometry; a system such as gel or capillary electrophoresis or gel exclusion chromatography; or other detection system known in the art, or combinations thereof.

The term "detection" as used herein refers to quantitatively or qualitatively identifying an analyte (e.g., DNA, RNA or a protein), e.g., within a sample. The term "detection assay" as used herein refers to a kit, test, or procedure performed for the purpose of detecting an analyte within a sample. Detection assays produce a detectable signal or effect when performed in the presence of the target analyte, and include but are not limited to assays incorporating the processes of hybridization, nucleic acid cleavage (e.g., exo- or endonuclease), nucleic acid amplification, nucleotide sequencing, primer extension, nucleic acid ligation, antigen-antibody binding, interaction of a primary antibody with a secondary antibody, and/or conformational change in a nucleic acid (e.g., an oligonucleotide) or polypeptide (e.g., a protein or small peptide).

As used herein, the term "prenatal or pregnancy-related disease or condition" refers to any disease, disorder, or condition affecting a pregnant woman, embryo, or fetus. Prenatal or pregnancy-related conditions can also refer to any disease, disorder, or condition that is associated with or arises, either directly or indirectly, as a result of pregnancy. These diseases or conditions can include any and all birth defects, congenital conditions, or hereditary diseases or conditions. Examples of prenatal or pregnancy-related diseases include, but are not limited to, Rhesus disease, hemolytic disease of the newborn, beta-thalassemia, sex determination, determination of pregnancy, a hereditary Mendelian genetic disorder, chromosomal aberrations, a fetal chromosomal aneuploidy, fetal chromosomal trisomy, fetal chromosomal monosomy, trisomy 8, trisomy 13 (Patau Syndrome), trisomy 16, trisomy 18 (Edwards syndrome), trisomy 21 (Down syndrome), X-chromosome linked disorders, trisomy X (XXX syndrome), monosomy X (Turner syndrome), XXY syndrome, XYY syndrome, XYY syndrome, XXXY syndrome, XXYY syndrome, XYYY syndrome, XXXXX syndrome, XXXXY syndrome, XXXYY syndrome, XXYYY syndrome, Fragile X Syndrome, fetal growth restriction, cystic fibrosis, a hemoglobinopathy, fetal death, fetal alcohol syndrome, sickle cell anemia, hemophilia, Klinefelter syndrome, dup(17)(p11.2p1.2) syndrome, endometriosis, Pelizaeus-Merzbacher disease, dup(22)(q11.2q11.2) syndrome, cat eye syndrome, cri-du-chat syndrome, Wolf-Hirschhorn syndrome, Williams-Beuren syndrome, Charcot-Marie-Tooth disease, neuropathy with liability to pressure palsies, Smith-Magenis syndrome, neurofibromatosis, Alagille syndrome, Velocardiofacial syndrome, DiGeorge syndrome, steroid sulfatase deficiency, Prader-Willi syndrome, Kallmann syndrome, microphthalmia with linear skin defects, adrenal hypoplasia, glycerol kinase deficiency, Pelizaeus-Merzbacher disease, testis-determining factor on Y, azospermia (factor a), azospermia (factor b), azospermia (factor c), 1p36 deletion, phenylketonuria, Tay-Sachs disease, adrenal hyperplasia, Fanconi anemia, spinal muscular atrophy, Duchenne's muscular dystrophy, Huntington's disease, myotonic dystrophy, Robertsonian translocation, Angelman syndrome, tuberous sclerosis, ataxia telangieltasia, open spina bifida, neural tube defects, ventral wall defects, small-for-gestational-age, congenital cytomegalovirus, achondroplasia, Marfan's syndrome, congenital hypothyroidism, congenital toxoplasmosis, biotinidase deficiency, galactosemia, maple syrup urine disease, homocystinuria, medium-chain acyl Co-A dehydrogenase deficiency, structural birth defects, heart defects, abnormal limbs, club foot, anencephaly, arhinencephaly/holoprosencephaly, hydrocephaly, anophthalmos/microphthalmos, anotia/microtia, transposition of great vessels, tetralogy of Fallot, hypoplastic left heart syndrome, coarctation of aorta, cleft palate without cleft lip, cleft lip with or without cleft palate, oesophageal atresia/stenosis with or without fistula, small intestine atresia/stenosis, anorectal atresia/stenosis, hypospadias, indeterminate sex, renal agenesis, cystic kidney, preaxial polydactyly, limb reduction defects, diaphragmatic hernia, blindness, cataracts, visual problems, hearing loss, deafness, X-linked adrenoleukodystrophy, Rett syndrome, lysosomal disorders, cerebral palsy, autism, aglossia, albinism, ocular albinism, oculocutaneous albinism, gestational diabetes, Arnold-Chiari malformation, CHARGE syndrome, congenital diaphragmatic hernia, brachydactlia, aniridia, cleft foot and hand, heterochromia, Dwarnian ear, Ehlers Danlos syndrome, epidermolysis bullosa, Gorham's disease, Hashimoto's disease, hydrops fetalis, hypotonia, Klippel-Feil syndrome, muscular dystrophy, osteogenesis imperfecta, progeria, Smith Lemli Opitz syndrome, chromatelopsia, X-linked lymphoproliferative disease, omphalocele, gastroschisis, pre-eclampsia, eclampsia, pre-term labor, premature birth, miscarriage, delayed intrauterine growth, ectopic pregnancy, hyperemesis gravidarum, morning sickness, or likelihood for successful induction of labor.

In some NIPT embodiments, the technology described herein further includes estimating a fetal fraction for a sample, wherein the fetal fraction is used to aid in the determination of whether the genetic data from the test subject is indicative of an aneuploidy. Methods for determining or calculating fetal fraction are known in the art.

As used herein, the term "valid detection assay" refers to a detection assay that has been shown to accurately predict an association between the detection of a target and a phenotype (e.g. medical condition). Examples of valid detection assays include, but are not limited to, detection assays that, when a target is detected, accurately predict the phenotype medical 95%, 96%, 97%, 98%, 99%, 99.5%, 99.8%, or 99.9% of the time. Other examples of valid detection assays include, but are not limited to, detection assays that qualify as and/or are marketed as Analyte-Specific Reagents (i.e. as defined by FDA regulations) or In-Vitro Diagnostics (i.e. approved by the FDA).

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, allele frequencies, RNA expression levels, protein expression, phenotypes correlating to genotypes, etc. "Allele frequency information" refers to facts or data pertaining allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

As used herein, the term "assay validation information" refers to genomic information and/or allele frequency information resulting from processing of test result data (e.g. processing with the aid of a computer). Assay validation information may be used, for example, to identify a particular candidate detection assay as a valid detection assay.

BRIEF DESCRIPTION OF THE DRAWINGS

FIG. 12 provides a schematic diagram of an embodiment of the technology comprising use of RCA of CIDS, followed by CID-specific digestion and CID-specific labeling.

FIG. 26 provides graphs comparing the effects on signal accumulation from signal amplification of single molecules by rolling circle amplification (RCA) of using different molecular weights of PEG at the percentages (w:v) shown.

FIGS. 27A-27B show results achieved in RCA reactions performed using primers bound to glass surfaces in an irregular dispersion, with detection using molecular beacon probes comprising a quencher and fluorophore.

FIG. 27A shows microscope images of surfaces of APTES-silanized plates, as described in Example 1, and compares RCA signal with or without PEG.

FIG. 27B provides graphs showing the effects of PEG on the number fluorescent spots and on the size of the spots in pixels for the spots shown in FIG. 27A.

FIG. 29A shows microscope images of surfaces of APTES-silanized plates, as described in Example 1, and compares RCA signal for reactions hybridized for 18 hours or 1 hour prior to initiating the RCA reaction.

FIG. 33 shows microscope images of surfaces of APTES-silanized plates, as described in Example 1, and compares RCA signal for reactions comprising PEG 600 at the indicated concentrations, performed at 37° C. or 45° C.

FIG. 45 illustrates primers immobilized via a 5' terminal amine modification. In the embodiment shown, the primer 3' ends contain three due bases and an AlexaFluor488 tag at the 3' terminus. The immobilized primers are treated with a mixture of uracil DNA glycosylase and DNA glycosylase-lyase Endonuclease VIII (abbreviated USER) to convert uracils to abasic sites and to cleave of the abasic sites. The resulting 3' end is polymerase extendible. The conversion of the immobilized oligonucleotides into extendible primers can be monitored by monitoring fluorescence released from the oligonucleotides, allowing measurement oligonucleotide immobilization and final primer density.

FIG. 46 illustrates primers immobilized via a 5' terminal amine modification, hybridized to oligonucleotides labeled with a fluorophore (e.g., AlexaFluor488, as shown). After hybridization of the fluor-tagged oligonucleotides to the immobilized primers, excess tagged oligonucleotides are removed, and the plate is washed. The bound tagged oligonucleotides can be melted off, e.g., with NaOH, the solution neutralized (e.g., with HCl) and the released fluorescence is measured (e.g., in a Spectramax plate reader). The embodiment illustrated allows for rapid characterization of hybridization conditions in a manner that is independent of rolling circle amplification efficiency.

FIG. 48 provides a graph illustrating the effect of treating a surface with a solution comprising sodium dodecyl sulfate (SDS) after exposing the bound RCA product to labeled probes.

FIG. 51 shows a TEM image of 10 nm iron oxide nanoparticles that are modified with an amphiphilic polymer coating and to comprising carboxylic acid functional groups (Ocean NanoTech, San Diego, Calif.). The organic layers consist of a monolayer of oleic acid and a monolayer of amphiphilic polymer, and have an average thickness of 4 nm, such that the particles have an average diameter about 8 to 10 nm larger than the inorganic core particle size. FIG. 51 illustrates conjugation of a primer oligonucleotide to an iron oxide nanoparticle.

FIG. 57A shows primer oligonucleotides designed for the in-solution RCA, e.g., in the embodiment shown schematically in FIG. 56, and containing different arrangements of spacers.

FIG. 57B shows primer oligonucleotides designed for use in on-support RCA, e.g., in the embodiment shown schematically in FIG. 35, and containing different combinations of spacers and amine modifications.

FIG. 58 provides a graph comparing end-point signal measured for reactions performed in solution or on on-plate using the primers shown in FIGS. 57A and 57B.

DETAILED DESCRIPTION OF THE INVENTION

Figure 1:
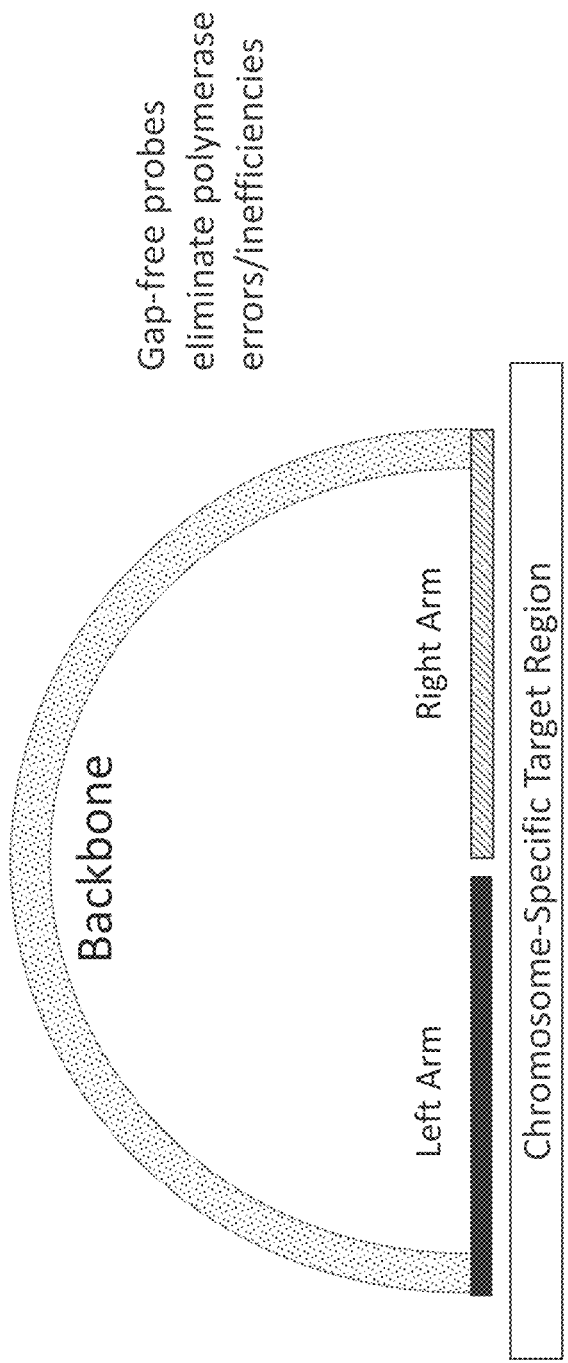
FIG. 1 provides a schematic diagram of a molecular inversion probe (MIP) for chromosome-specific recognition, suitable for use in massively multiplexed capture assays.

A goal in molecular diagnostics has been to achieve accurate, sensitive detection of analytes in as little time as possible with the least amount of labor and steps as possible. One manner in which this is achieved is the multiplex detection of analytes in samples, allowing multiple detection events in a single reaction vessel or solution. However, many of the existing diagnostic methods, including multiplex reaction, still require many steps, including sample preparation steps that add to the time, complexity, and cost of conducting reactions. The present invention, in some embodiments, provides solutions to these problems by providing assay that can be conducted directly in unpurified or untreated biological samples (e.g., blood or plasma).

In some embodiments, the technologies provided herein provide economical methods for testing samples in a manner that counts the number of copies of a specific nucleic acid or protein in a sample or portion of a sample in a digital manner, i.e., by detecting individual copies of the molecules, without use of a sequencing step (e.g., a digital or "next gen" sequencing step). The technologies find use for measuring target molecules such as nucleic acid molecules in any kind of sample, including but not limited to, e.g., samples collected for from a subject for diagnostic screening. Embodiments of the technology provided herein find use in, for example, non-invasive prenatal testing (NIPT) and other genetic analysis. Embodiments of the technology implement one or more steps of nucleic acid extraction, MIP probe design, MIP amplification/replication, and/or methods for measuring signal from circularized MIPs. In preferred embodiments, the technology provides methods for immobilizing MIPs on a surface and detecting immobilized MIPs. In preferred embodiments, immobilized MIPs are detected using rolling circle amplification.

In preferred embodiments, the methods of the technology comprise a target-recognition event, typically comprising hybridization of a target nucleic acid, e.g., a sample of patient DNA, to another nucleic acid molecule, e.g., a synthetic probe. In preferred embodiments, the target recognition event creates conditions in which a representative product is produced (e.g., a probe oligonucleotide that has been extended, ligated, and/or cleaved), the product then being indicative that the target is present in the reaction and that the probe hybridized to it.

A number of different "front-end" methods for recognizing target nucleic acid and producing a new product are described herein. For example, as shown in the exemplary embodiments in the Figures, the technology provides a number of ways to produce circularized molecules for use in a "back end" detection/readout step (see, e.g., FIGS., 1-3, 13-18, 34, 35, and 38-40). The technology also provides methods to signal the presence of a target nucleic acid using other probe types, such as a probe that can be cleaved by a flap endonuclease in the presence of the target nucleic acid (see, e.g., FIGS. 17-19). Each of these front-end embodiments can be used to produce a distinctive molecule, e.g., a circular or cleaved oligonucleotide.

These distinctive molecules may be configured to have one or more features useful for capture and/or identification in a downstream backend detection step. Examples of molecules and features produced in a front-end reaction include circularized MIPs having joined sequences (e.g., a complete target-specific sequence formed by ligation of the 3' and 5' ends of the probe), having added sequences (e.g., copied portions of a target template) and/or tagged nucleotides (e.g., nucleotides attached to biotin, dyes, quenchers, haptens, and/or other moieties), or products such as single-stranded arms released from a flap cleavage reaction (see, e.g., FIGS. 17-19). In some embodiments, the MIPs comprise a feature in a portion of the probe, e.g., in the backbone of the probe.

Examples of back-end analysis methods for amplifying and/or detecting the representative products of the front-end are provided, e.g., in FIGS. 2-3, 6-7, 9-12, 15-16, 20-21, 34, 35, and 38-41, 44-46, and 52

Figure 19:
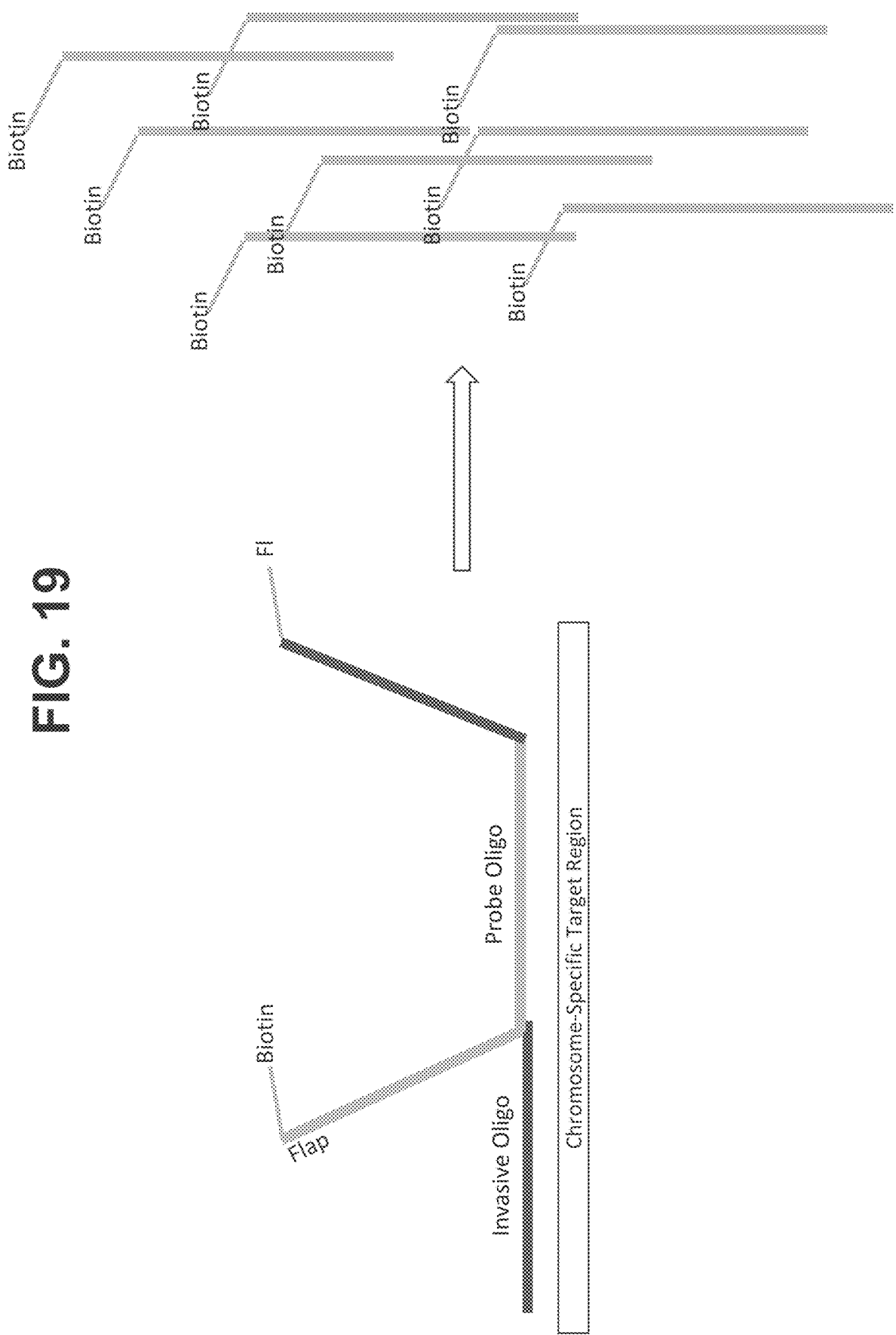
FIG. 19 provides an illustration of the accumulation of cleaved flap fragments in a flap endonuclease assay.
Figure 20:
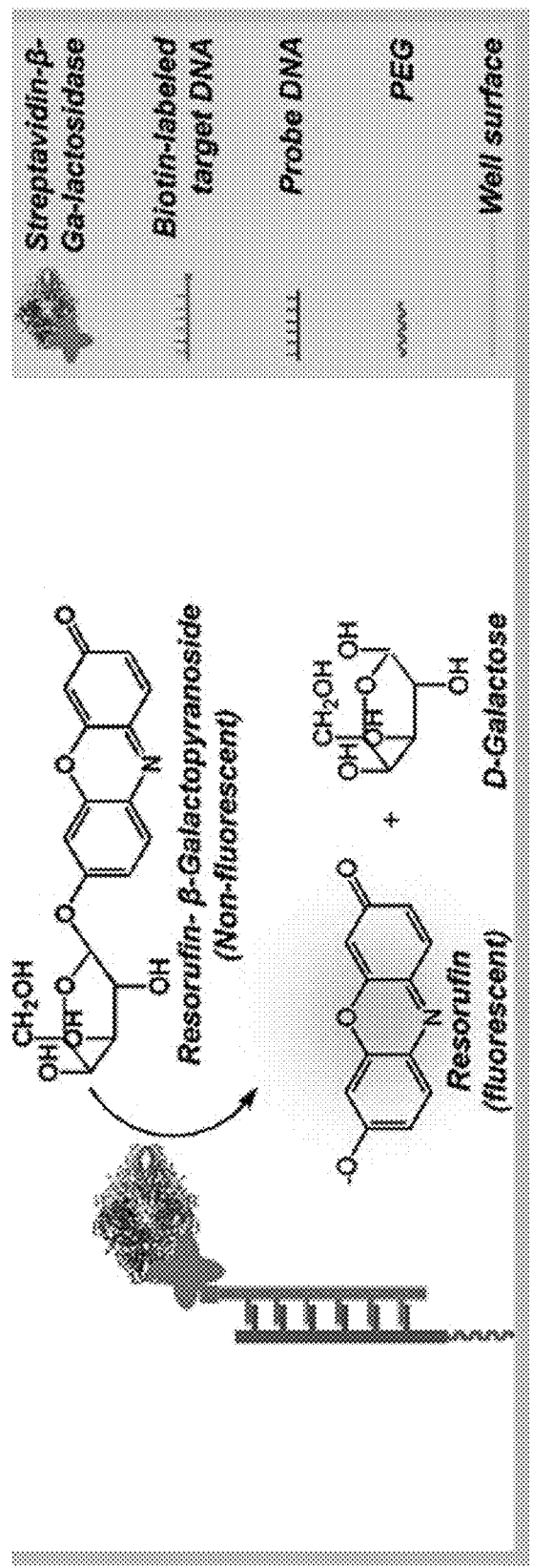
FIG. 20 illustrates an embodiment in which a cleaved biotinylated flap is captured using an immobilized complementary probe, and the biotin is reacted with streptavidin linked to an enzyme, e.g., β-galactosidase.

Although the technology is discussed by reference to particular embodiments, such as combinations of certain front-end target-dependent reactions with particular back-end signal amplification methods and detection platforms, e.g., biotin-incorporated MIP of FIGS. 13-16 coupled with an enzyme-free hybridization chain reaction back-end; biotin-tagged cleaved flaps (as in FIG. 19) coupled with capture to a surface, followed by hybridization to an enzyme-linked probe that produces fluorescence signal catalytically (as shown in FIG. 20), the invention is not limited to the particular combinations of front-end and back-end methods and configurations disclosed herein, or to any particular methods of detecting a signal from the assay products. It will be appreciated that the skilled person may readily adapt one front-end to work with an alternative back-end. For example, the circularized MIP of FIG. 14 may be captured and detected using the enzyme-linked probe of FIG. 20, or might alternatively be amplified in a rolling circle amplification assay, exemplified in FIGS. 2-3, 8-7, 9-12, 21, 34, 35, and 38-41, 44-46, and 52. Similarly, the cleaved flap as shown in FIG. 19 may be detected using a hybridization chain reaction, as depicted in FIGS. 19-20; and a circularized MIP or an RCA amplicon may be detected using an invasive cleavage reaction as diagrammed in FIG. 17, and so forth.

Further, although the technology is discussed in reference to particular target nucleic acids, e.g., cell-free DNA in plasma, the invention is not limited to any particular form of DNA, or to any particular type of nucleic acid, or to any particular type of variation in a nucleic acid. It will be appreciated that the skilled person may readily configure embodiments of the technology for detecting and counting mutations, insertions, deletions, single nucleotide polymorphisms (SNPs), and epigenetic variations in methylation (e.g., variations in methylation of particular CpG dinucleotides by analysis of DNA treated with a reagent that converts unmethylated cytosines to uracils, thereby creating detectable sequence variations that reflect cytosine methylation variations in target DNAs).

In some embodiments, assays are performed in a multiplexed manner. In some embodiments, multiplexed assays can be performed under conditions that allow different loci to reach more similar levels of amplification.

FIG. 1 provides a schematic diagram of a molecular inversion probe (MIP). The molecular inversion probe contains first and second targeting polynucleotide arms that are complementary to adjacent or proximal regions on a target nucleic acid to be detected, with a polynucleotide linker or "backbone" connecting the two arms (see FIG. 1).

In the presence of a complementary target nucleic acid, the MIP can be circularized to form a MIP replicon suitable for detection. In some embodiments, the MIP is simply ligated using a nick repair enzyme, e.g., T4 DNA ligase, AMPLIGASE thermostable DNA ligase, etc., while in some embodiments closing of the probe to form a circle comprises additional modification of the probe to create a ligatable nick, e.g., cleavage of an overlap between the termini, filling of a gap between the termini using a nucleic acid polymerase, etc.

A target site or sequence, as used herein, refers to a portion or region of a nucleic acid sequence that is sought to be sorted out from other nucleic acids in the sample that have other sequences, which is informative for determining the presence or absence of a genetic disorder or condition (e.g., the presence or absence of mutations, polymorphisms, deletions, insertions, aneuploidy etc.). A control site or sequence, as used herein, refers to a site that has known or normal copy numbers of a particular control gene. In some embodiments, the targeting MIPs comprise in sequence the following components: first targeting polynucleotide arm—first unique targeting molecular tag—polynucleotide linker—second unique targeting molecular tag—second targeting polynucleotide arm. In some embodiments, a target population of the targeting MIPs are used in the methods of the disclosure. In the target population, the pairs of the first and second targeting polynucleotide arms in each of the targeting MIPs are identical and are substantially complementary to first and second regions in the nucleic acid that, respectively, flank the target site. See, e.g., WO 2017/020023 and WO 2017/020024, each of which is incorporated herein by reference in its entirety.

In some embodiments, the length of each of the targeting polynucleotide arms is between 18 and 35 base pairs. In some embodiments, the length of each of the targeting polynucleotide arms is 18, 19, 20, 21, 22, 23, 24, 25, 26, 27, 28, 29, 30, 31, 32, 33, 34, or 35 base pairs, or any size range between 18 and 35 base pairs. In some embodiments, the length of each of the control polynucleotide arms is between 18 and 35 base pairs. In some embodiments, the length of each of the control polynucleotide arms is 18, 19, 20, 21, 22, 23, 24, 25, 26, 27, 28, 29, 30, 31, 32, 33, 34, or 35 base pairs, or any size ranges between 18 and 35 base pairs. In some embodiments, each of the targeting polynucleotide arms has a melting temperature between 55° C. and 70° C. In some embodiments, each of the targeting polynucleotide arms has a melting temperature at 56° C., 57° C., 58° C., 59° C., 60° C., 61° C., 62° C., 63° C., 64° C., 65° C., 66° C., 67° C., 68° C., 69° C., 70° C., or any temperature between 55° C. and 70° C. In some embodiments, each of the control polynucleotide arms has a melting temperature between 55° C. and 70° C. In some embodiments, each of the control polynucleotide arms has a melting temperature at 56° C., 57° C., 58° C., 59° C., 60° C., 61° C., 62° C., 63° C., 64° C., 65° C., 66° C., 67° C., 68° C., 69° C., 70° C., or any temperature between 55° C. and 70° C.

In some embodiments, each of the targeting polynucleotide arms has a GC content between 20% and 80%. In some embodiments, each of the targeting polynucleotide arms has a GC content of 20-30%, 30-40%, or 30-50%, or 30-60%, or 40-50%, or 40-60%, or 40-70%, or 50-60%, or 50-70%, or 50-80%, or any range of GC content between 20% and 80%, or any specific percentage between 20% and 80%. In some embodiments, each of the control polynucleotide arms has a GC content between 20% and 80%. In some embodiments, each of the control polynucleotide arms has a GC content of 20-30%, 30-40%, or 30-50%, or 30-60%, or 40-50%, or 40-60%, or 40-70%, or 50-60%, or 50-70%, or 50-80%, or any range of GC content between 20% and 80%, or any specific percentage between 20% and 80%.

In some embodiments, the polynucleotide linker is not substantially complementary to any genomic region of the sample or the subject. In some embodiments, the polynucleotide linker has a length of 30 to 40 base pairs. In some embodiments, the polynucleotide linker has a length of 31, 32, 33, 34, 35, 36, 37, 38, or 39 base pairs, or any interval between 30 and 40 base pairs, and including 30 or 40 base pairs. In some embodiments, the polynucleotide linker has a melting temperature of between 60° C. and 80° C. In some embodiments, the polynucleotide linker has a melting temperature of 60° C., 65° C., 70° C., 75° C., or 80° C., or any interval between 60° C. and 80° C., or any specific temperature between 60° C. and 80° C. In some embodiments, the polynucleotide linker has a GC content between 40% and 60%. In some embodiments, the polynucleotide linker has a GC content of 40%, 45%, 50%, 55%, or 60%, or any interval between 40% and 60%, or any specific percentage between 40% and 60%.

In some embodiments, targeting MIPs replicons are produced by: i) the first and second targeting polynucleotide arms, respectively, hybridizing to the first and second regions in the nucleic acid that, together, form a continuous target site; and ii) after the hybridization, using a ligation reaction mixture to ligate the nick region between the two targeting polynucleotide arms to form single-stranded circular nucleic acid molecules. In other embodiments, targeting MIPs replicons are produced by: i) the first and second targeting polynucleotide arms, respectively, hybridizing to the first and second regions in the nucleic acid that, respectively, flank the target site; and ii) after the hybridization, using a ligation/extension mixture to extend and ligate the gap region between the two targeting polynucleotide arms to form single-stranded circular nucleic acid molecules.

In certain embodiments, the methods described herein are used to detect exonic deletions or insertions or duplication. In some embodiments, the target site (or sequence) is a deletion or insertion or duplication in a gene of interest or a genomic region of interest. In some embodiments, the target site is a deletion or insertion or duplication in one or more exons of a gene of interest. In some embodiments, the target multiple exons are consecutive. In some embodiments, the target multiple exons are non-consecutive. In some embodiments, the first and second targeting polynucleotide arms of MIPs are designed to hybridize upstream and downstream of the deletion (or insertion, or duplication) or deleted (or inserted, or duplicated) genomic region (e.g., one or more exons) in a gene or a genomic region of interest. In some embodiments, the first or second targeting polynucleotide arm of MIPs comprises a sequence that is substantially complementary to the genomic region of a gene of interest that encompasses the target deletion or duplication site (e.g., exons or partial exons).

Circular DNA molecules such as ligated MIPs are suitable substrates for amplification using rolling circle amplification (RCA). In certain embodiments of RCA, a rolling circle replication primer hybridizes to a circular nucleic acid molecule, e.g., a ligated MIP, or circularized cfDNA. Extension of the primer using a strand-displacing DNA polymerase (e.g., φ29 (Phi29), Bst Large Fragment, and Klenow fragment of E. coli Pol I DNA polymerases) results in long single-stranded DNA molecules containing repeats of a nucleic acid sequence complementary to the MIP circular molecule.

In some embodiments, ligation-mediated rolling circle amplification (LM-RCA), which involves a ligation operation prior to replication, is utilized. In the ligation operation, a probe hybridizes to its complementary target nucleic acid sequence, if present, and the ends of the hybridized probe are joined by ligation to form a covalently closed, single-stranded nucleic acid. After ligation, a rolling circle replication primer hybridizes to probe molecules to initiate rolling circle replication, as described above. Generally, LM-RCA comprises mixing an open circle probe with a target sample, resulting in an probe-target sample mixture, and incubating the probe-target sample mixture under conditions promoting hybridization between the open circle probe and a target sequence, mixing ligase with the probe-target sample mixture, resulting in a ligation mixture, and incubating the ligation mixture under conditions promoting ligation of the open circle probe to form an amplification target circle (ATC, which is also referred to an RCA replicon). A rolling circle replication primer (RCRP) is mixed with the ligation mixture, resulting in a primer-ATC mixture, which is incubated under conditions that promote hybridization between the amplification target circle and the rolling circle replication primer. DNA polymerase is mixed with the primer-ATC mixture, resulting in a polymerase-ATC mixture, which is incubated under conditions promoting replication of the amplification target circle, where replication of the amplification target circle results in formation of tandem sequence DNA (TS-DNA), i.e., a long strand of single-stranded DNA that contains a concatemer of the sequence complementary to the amplification target circle.

Figure 2:
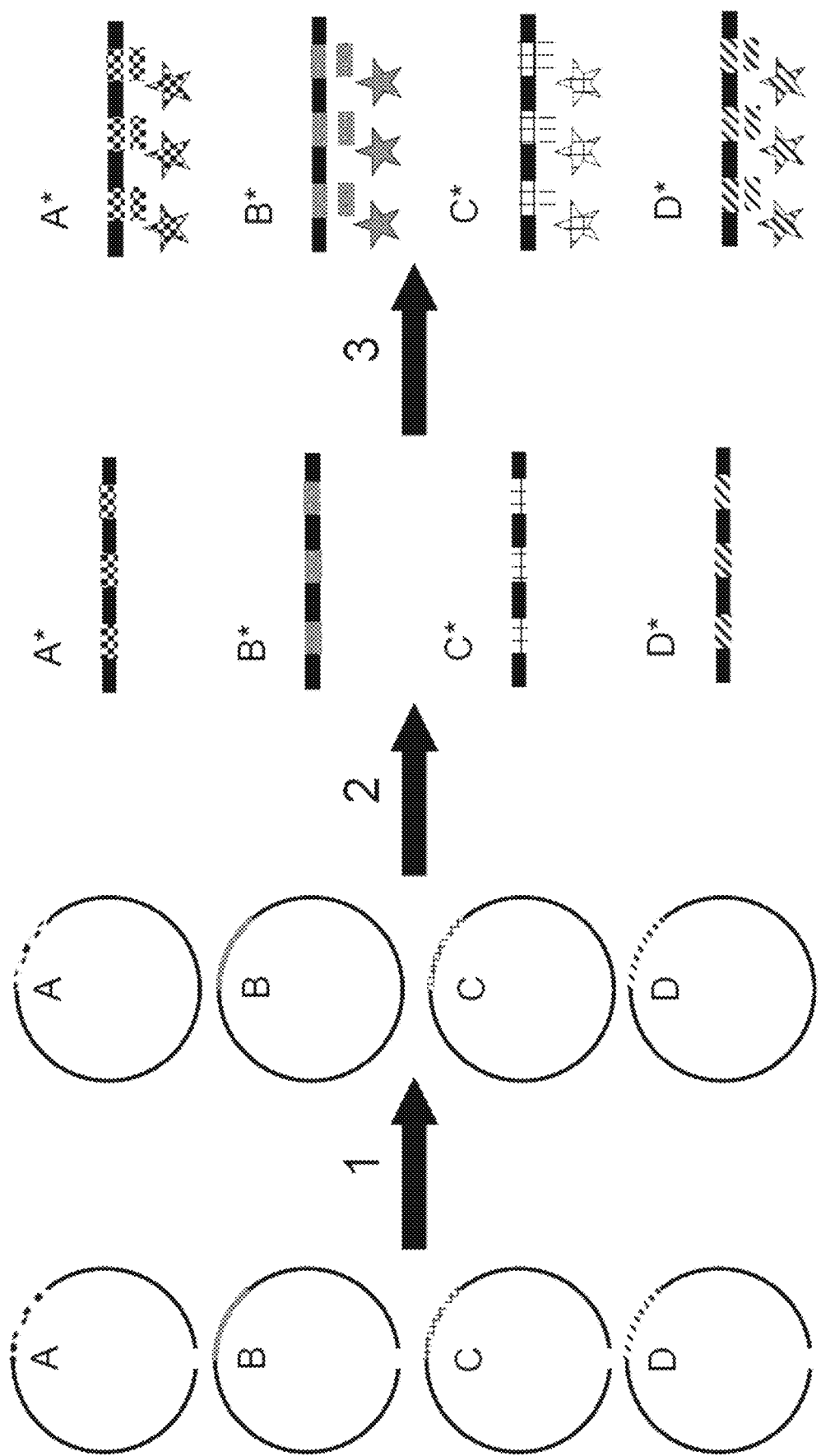
FIG. 2 provides a schematic diagram of an embodiment of multiplexed chromosome-specific rolling circle amplification.
Figure 3:
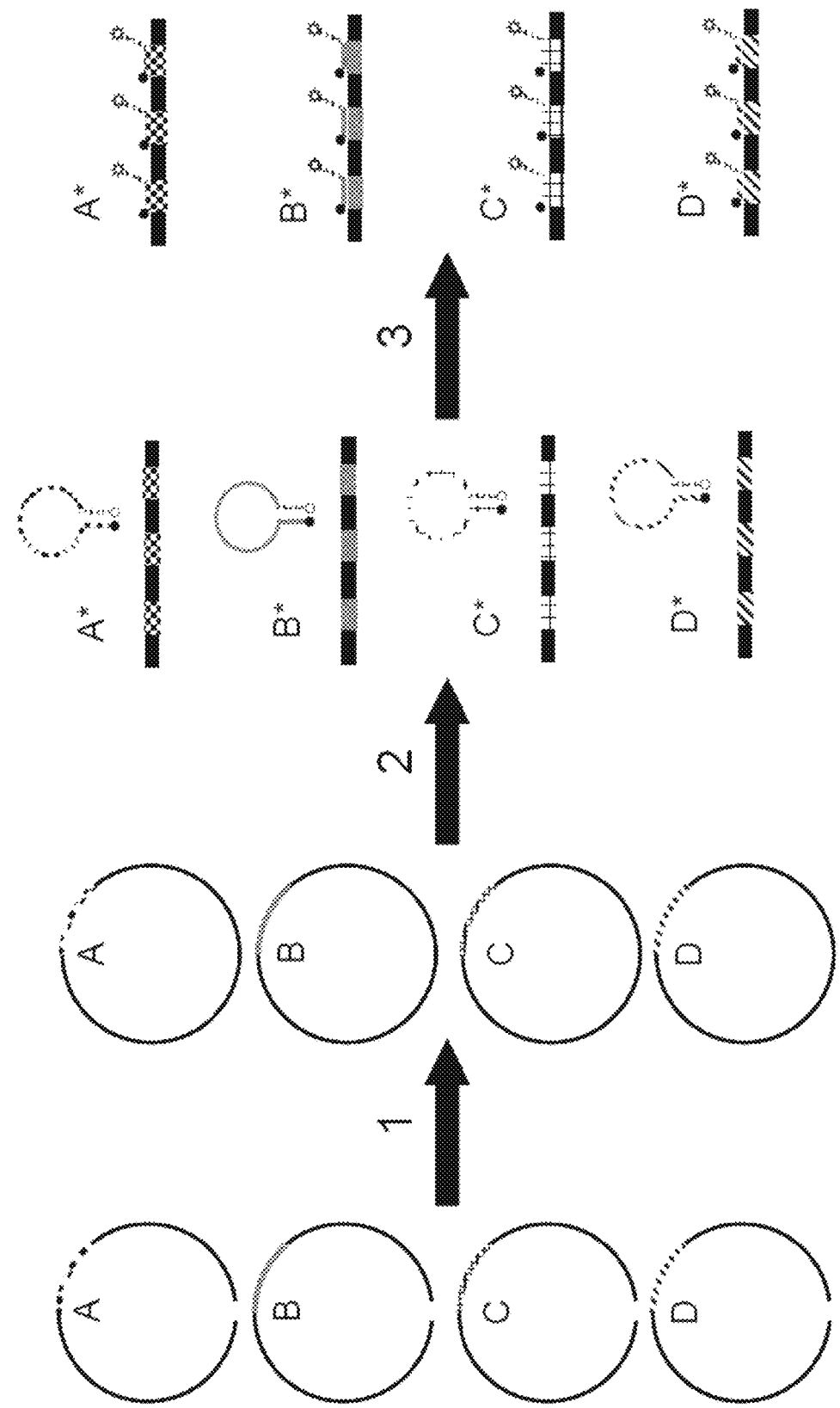
FIG. 3 provides a schematic diagram of an embodiment of multiplexed chromosome-specific rolling circle amplification using molecular beacon probes for detection.

In the embodiment illustrated in FIG. 2, circularized molecules A, B, C, and D consist of MIPs that are specific to chromosome 13, 18, 21, X, and/or Y, or to a reference chromosome such as Chr. 1. The sequence of the MIP surrounding the gap complements region of the targeted chromosome, and the backbone of the MIP contains a specific sequence that is used to hybridize a probe that will contain a specific fluorescent dye (FITC, ALEXA, Dylight, Cyan, Rhodamine dyes, quantum dots, etc.). Step 1 comprises hybridizing the MIPs to cfDNA, a single base pair extension (or longer extension), and ligation to circularize the extended MIP. Step 2 comprises rolling circle amplification of the circularized MIP so that the sequence required to hybridize to the fluorescently labeled oligonucleotide is amplified. A*, B*, C*, D* are the complement of the MIP sequence. Step 3 comprises hybridizing the fluorescently labeled probe to the rolling circle product. In the embodiment illustrated in FIG. 3, detection of the RCA product is facilitated by molecular probes instead of fluorescent dye labeled oligonucleotides.

There are multiple ways to immobilize the MIP to a surface (e.g., a bead or glass surface) For example, this may be accomplished by priming the rolling circle amplification with a modified oligonucleotide comprising a bindable moiety. Groups useful for modification of the priming oligonucleotide include but are not limited to thiol, amino, azide, alkyne, and biotin, such that the modified oligonucleotides can be immobilized using appropriate reactions, e.g., as outlined in Meyer et. al., "Advances in DNA-mediated immobilization" Current Opinions in Chemical Biology, 18:8: 8-15 (2014), which is incorporated herein by reference in its entirety, for all purposes.

Imaging of the fluorescent dye incorporated MIPs can be accomplished by using methods comprising immobilization of MIPs to a surface (e.g., glass slide or bead), e.g., using modifications of the MIP backbone to contain modified bases that can be immobilized using appropriate reactions as outlined above and in Meyer et. al., supra. and detected using an antibody. Once immobilized to a surface, an antibody directed to an incorporated tag can be used to form antibody-MIP complexes that can be imaged with microscopy. In some embodiments, the antibody may be conjugated to enhance or amplify detectable signal from the complexes. For example, conjugation of β-galactosidase to the antibody allows detection in a single molecule array ("SIMOA"), using the process described by Quanterix, wherein each complex is immobilized on a bead such that any bead has no more than one labeled immunocomplex, and the beads are distributed to an array of femtoliter-sized wells, such that each well contains, at most, one bead. With addition of resorufin-β-galactopyranoside, the β-galactosidase on the immobilized immunocomplexes catalyzes the production of resorufin, which fluoresces. Upon visualization, the fluorescence emitted in wells having an immobilized individual immunocomplexes can be detected and counted. See, e.g., Quanterix Whitepaper 1.0, Scientific Principle of Simoa (Single Molecule Array) Technology, 1-2 (2013); and Quanterix Whitepaper 6.0, Practical Application of Simoa™ HD-1 Analyzer for Ultrasensitive Multiplex Immunodetection of Protein Biomarkers, 1-3 (2015), each of which is incorporated herein by reference for all purposes In some embodiments, the antibody-MIP complex may be directly detected, e.g., using a solid state nanopore with an antibody labeled with poly(ethylene glycol) at various of molecular weights, as described in Morin et. al., "Nanopore-Based Target Sequence Detection" PLOS One, DOI: 10.1371/journal.pone.0154426 (2016), incorporated herein by reference.

Figure 4:
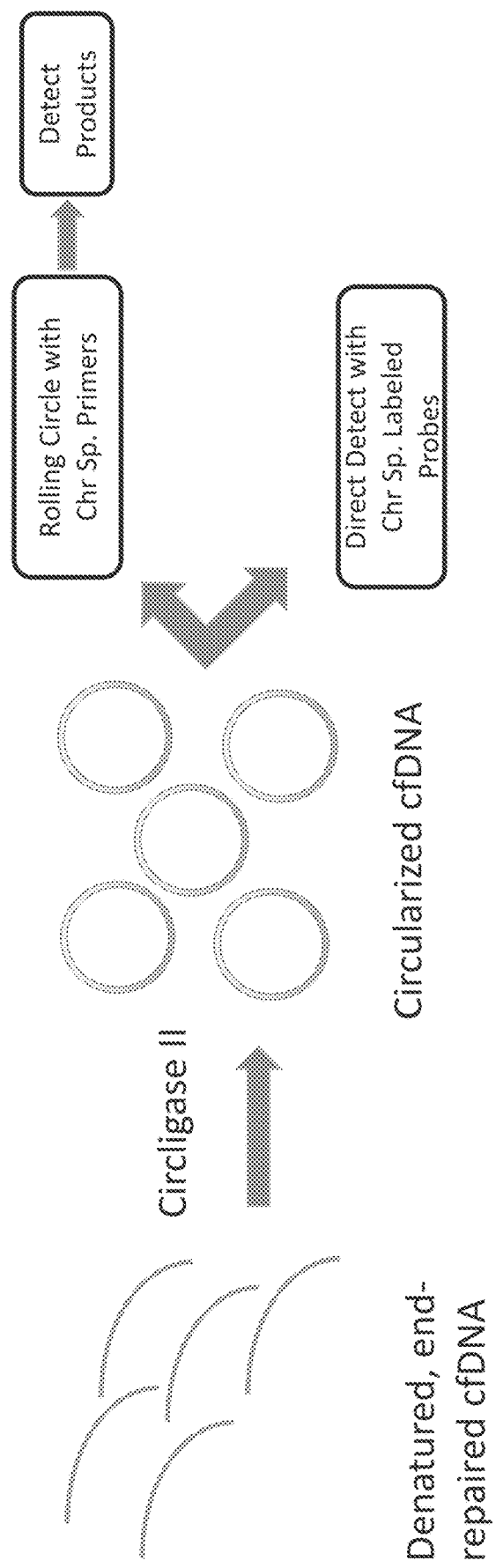
FIG. 4 provides a schematic diagram of an embodiment of the technology comprising circularizing cfDNA using a single-strand ligase (e.g., CircLigase™ thermostable RNA ligase) to make "native circles" for detection.
Figure 5:
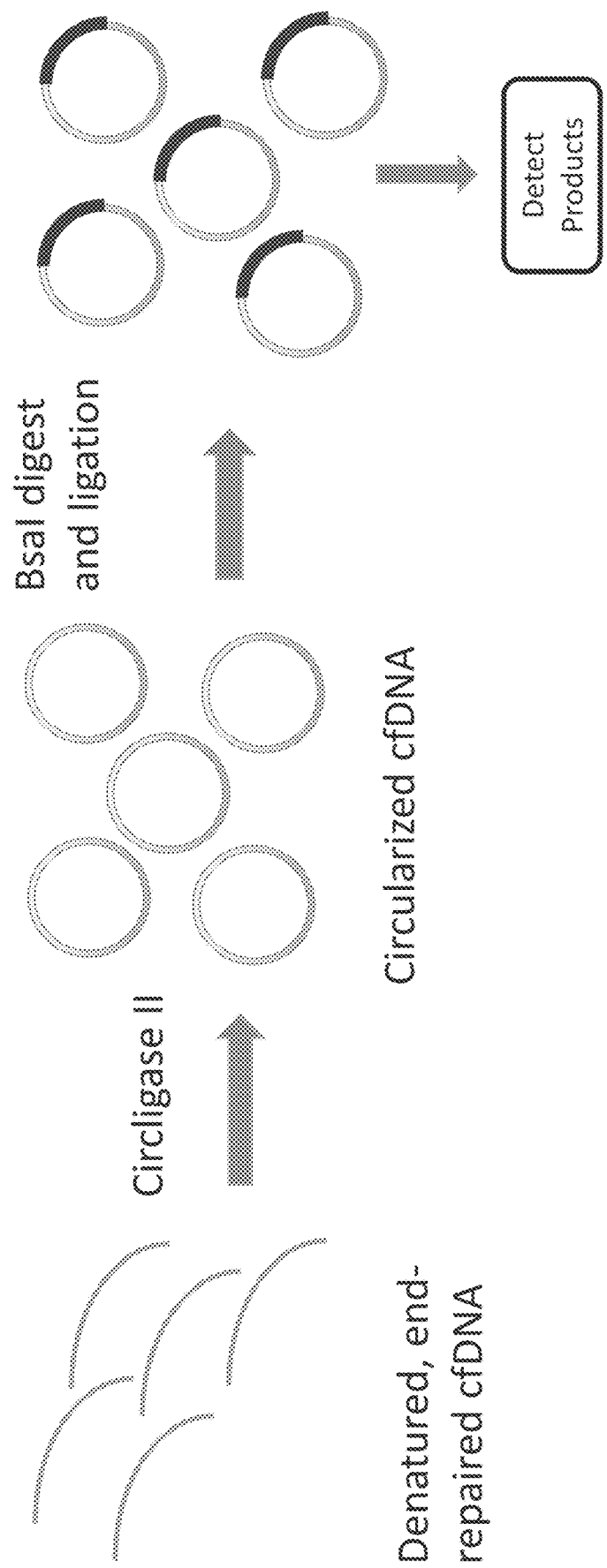
FIG. 5 provides a schematic diagram of an embodiment of the technology comprising circularizing cfDNA and using "Golden Gate Assembly" to add segments for detection (see, e.g., Engler, C., Kandzia, R., and Marillonnet, S. (2008) PLoS ONE 3, e3647.)

FIG. 4 provides a schematic diagram of an embodiment of the technology comprising circularizing circulating cfDNA (ccfDNA) using a single-strand ligase (e.g., CircLigase™ thermostable RNA ligase) to make "native circles" for detection. Once created, the circular ccfDNA may be detected using a number of different methods, including a number of RCA methods. For example, as diagrammed in FIG. 5, one embodiment of the technology comprising circularizing cfDNA and using "Golden Gate Assembly" to add segments for detection (see, e.g., Engler, C., Kandzia, R., and Marillonnet, S. (2008) PLoS ONE 3, e3647.)

Figure 6:
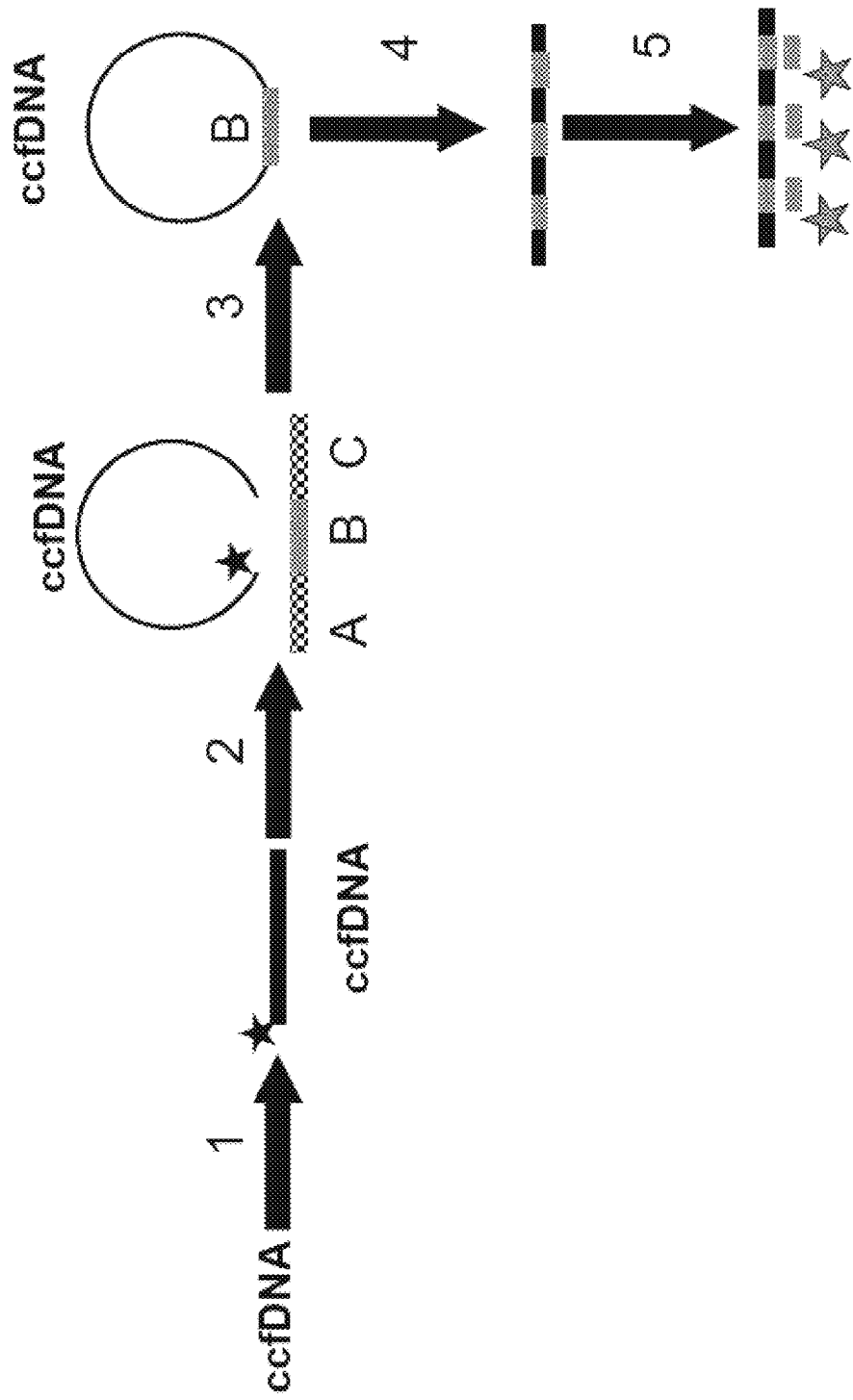
FIG. 6 provides a schematic diagram of an embodiment of the technology comprising circularizing cfDNA using extension ligation on a unique molecular inversion-inducing template, with detection using an embodiment of RCA.

FIG. 6 illustrates an additional method of detecting ccfDNA. In this embodiment, plasma samples are processed to purify ccfDNA, as previously described (see, e.g., M. Fleischhacker, et al., Methods for isolation of cell-free plasma DNA strongly affect DNA yield, Clin Chim Acta. 2011 Nov. 20; 412(23-24):2085-8). In Step 1, ccfDNA is heat denatured and treated with T4 polynucleotide kinase to create 5' phosphorylated and 3' hydroxyl end DNA fragments. Additional DNA repair, such as with T4 DNA polymerase, may be used to repair DNA before heat denaturation and T4 polynucleotide kinase treatment. A complementation oligonucleotide with a 3' protected end (so that it will not be extended by a polymerase) is hybridized to the ccfDNA. This complementary oligonucleotide consists of chromosome specific regions, A and C, and a universal sequence, B. ccfDNA is extended and ligated to complete the circular DNA molecule. Circularized ccfDNA is purified from the oligonucleotide and RCA is used by annealing an oligonucleotide to the universal sequence, B. After RCA, fluorescently labeled probes are hybridized to the rolling circle product.

Figure 7:
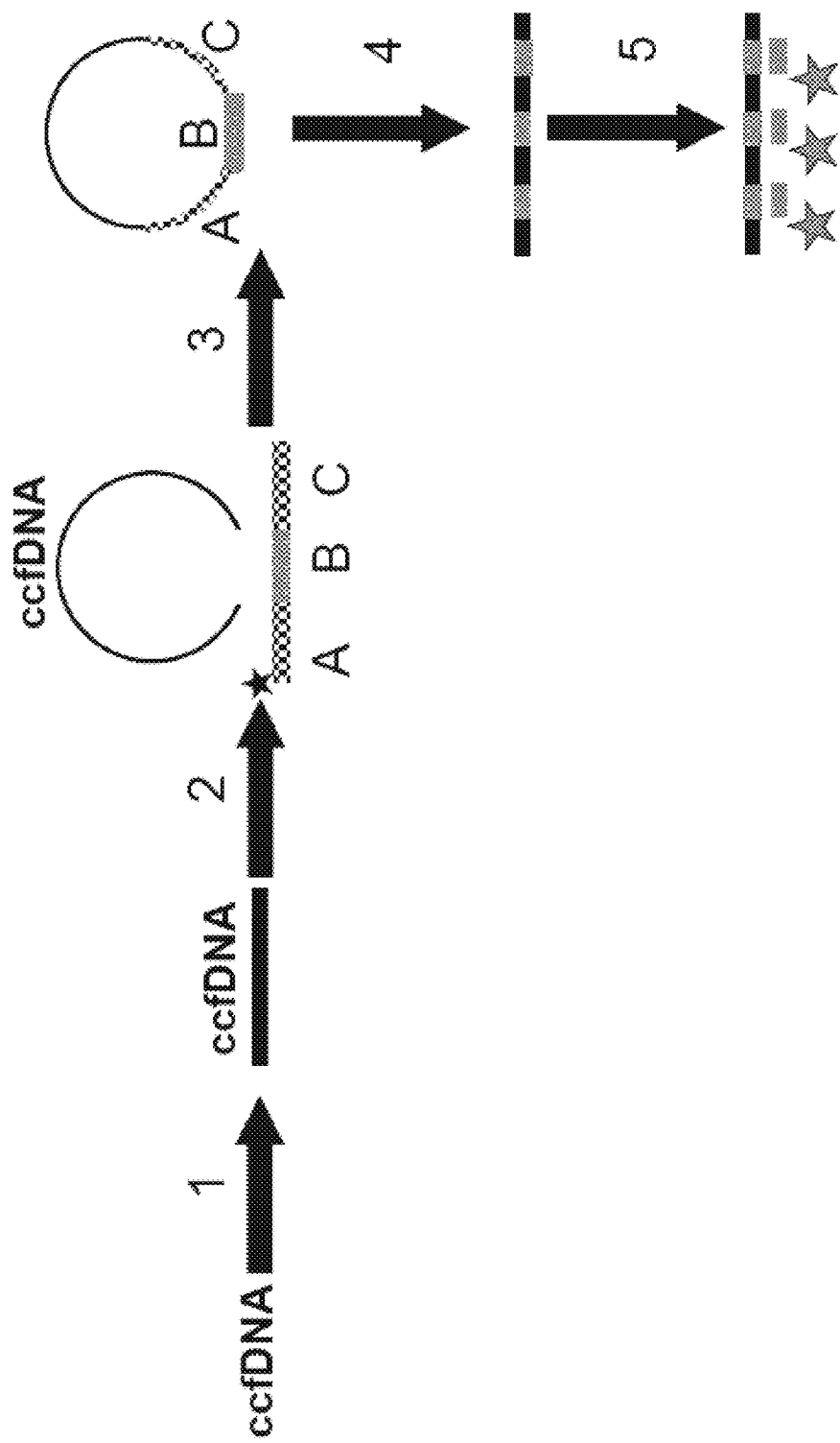
FIG. 7 provides a schematic diagram of an embodiment of the technology comprising a unique molecular inversion inducing template that is extended and ligated to create a circular DNA molecule, with detection using an embodiment of RCA.

FIG. 7 illustrates another method of detecting ccfDNA. Plasma samples are processed to purify ccfDNA as previously described. Step 1, ccfDNA is heat denatured. A complementation oligonucleotide with a phosphorylated 5 prime protected end is hybridized to the ccfDNA. This complementary oligonucleotide consists of chromosome specific regions, A and C, and a universal sequence, B. Both the ccfDNA and complimentary oligonucleotide is extended. However, only the complimentary oligonucleotide has a 5' phosphate to allow completion of a circular DNA molecule. Circularized complimentary oligonucleotide is amplified by rolling circle amplification using a primer complementary to the universal sequence, B. After rolling circle amplification, fluorescently labeled probes are hybridized to the rolling circle product.

Figure 8:
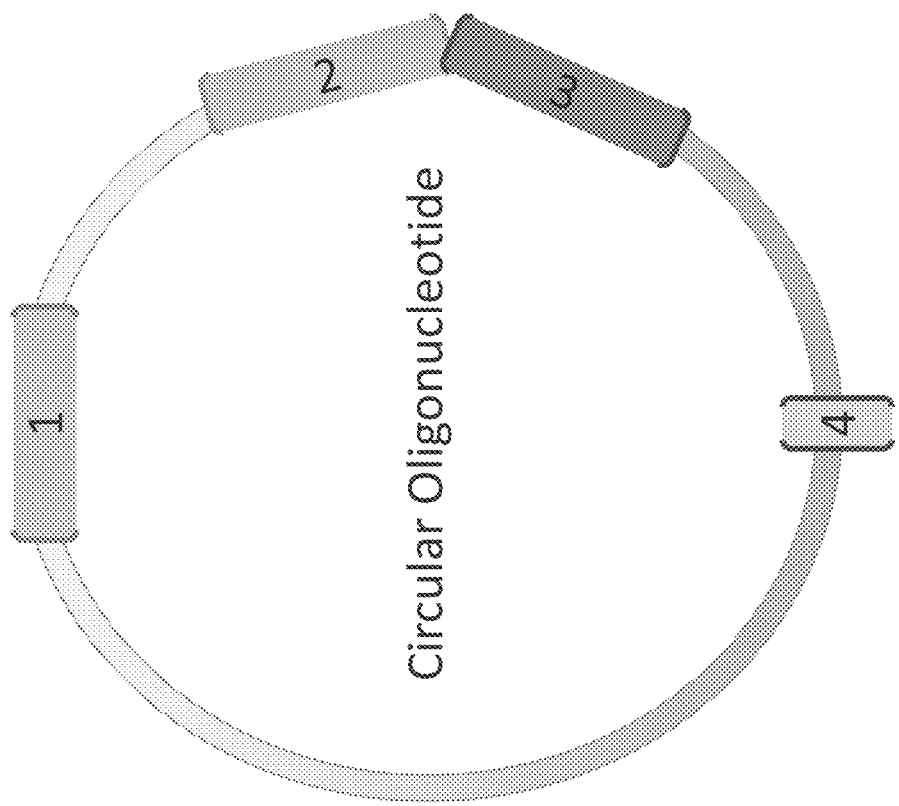
FIG. 8 provides a schematic diagram of an embodiment of the technology comprising a synthetic circular DNA comprising binding sites for probe binding and a primer binding site for replication, for use, e.g., as a template for rolling circle amplification.

FIG. 8 shows a schematic diagram of a synthetic circular DNA useful as a template for rolling circle amplification, and comprising binding rolling circle primer-binding site and two probe binding sites, and an optional binding moiety (e.g., biotin).

Figure 9:
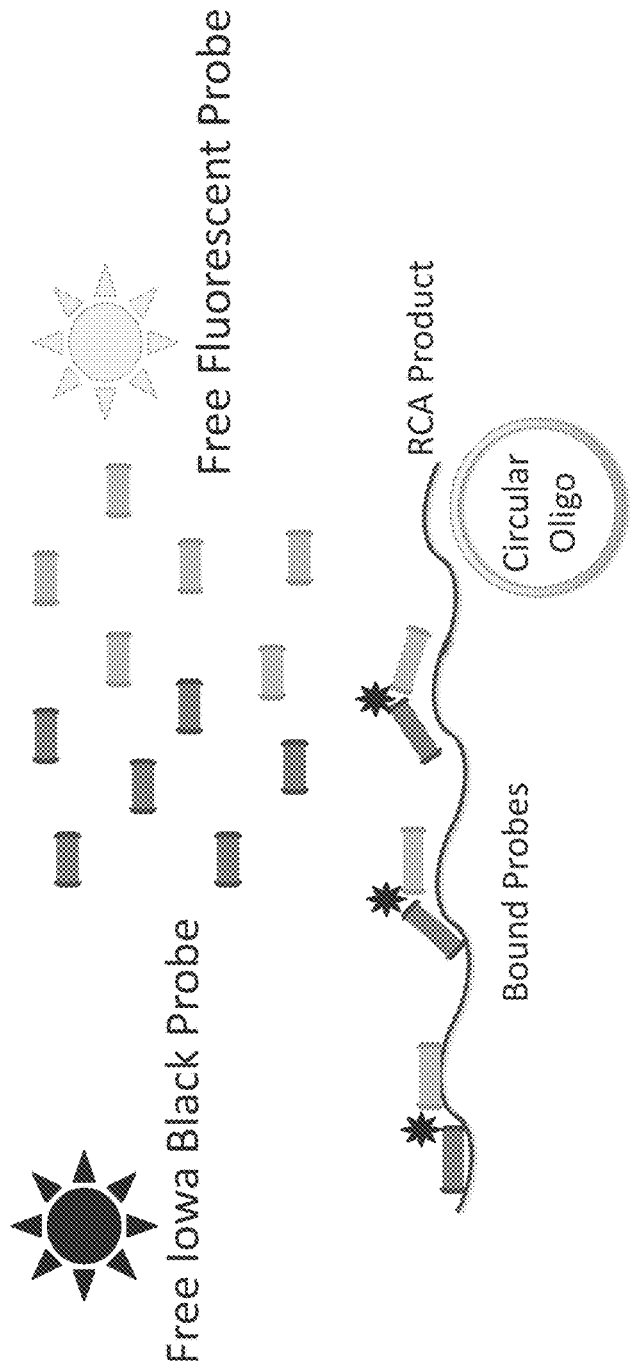
FIG. 9 provides a schematic diagram of an embodiment of the technology comprising use of pairs of probes configured for collisional quenching when hybridized to a strand of DNA, for use in detection of product from RCA.

FIG. 9 provides a schematic diagram of an embodiment of the technology comprising use of pairs of probes configured for collisional quenching when hybridized to a strand of DNA, for use in detection of product from RCA, e.g., of a circular DNA like the one shown in FIG. 8. In this embodiment, the dye-labeled probe in solution is not quenched, and produces signal. Probes hybridizing to the target near quencher-tagged probes would be quenched, thereby reducing the fluorescence signal. As the amount of RCA product increases, the fluorescence decreases.

Figure 10:
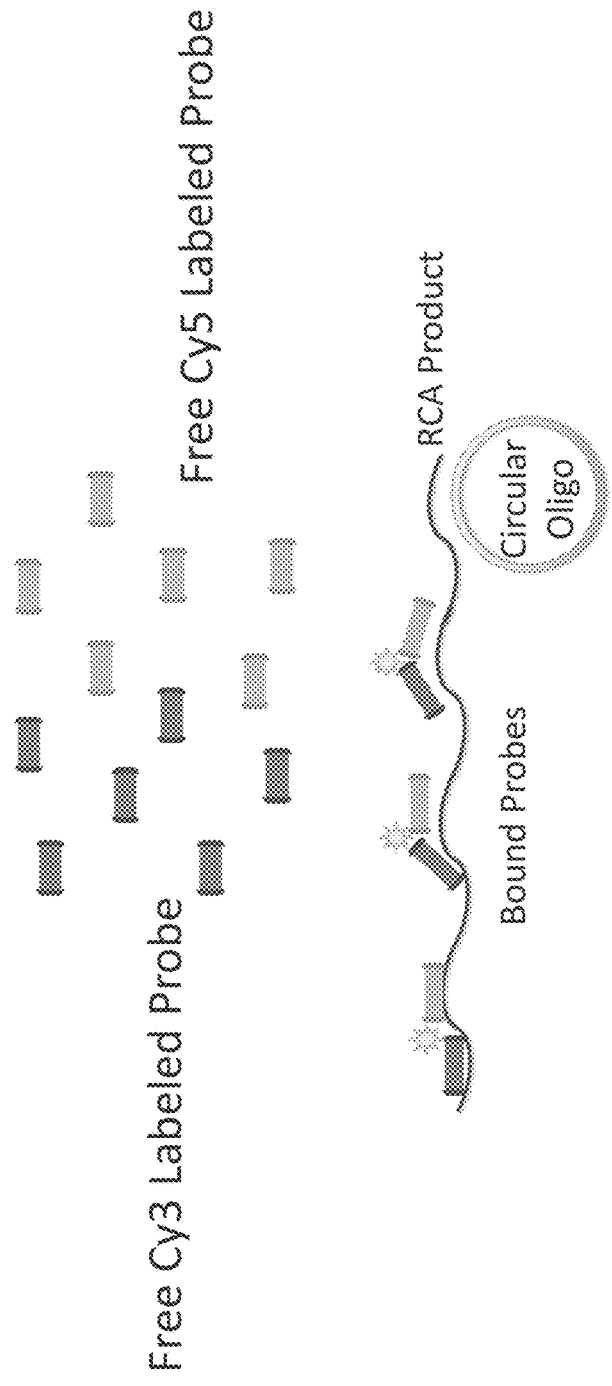
FIG. 10 provides a schematic diagram of an embodiment of the technology comprising use of pairs of probes configured for fluorescence resonance energy transfer (FRET) when hybridized to a strand of DNA, for use in detection of product from RCA.

FIG. 10 provides a schematic diagram of an embodiment of the technology comprising use of pairs of probes configured for fluorescence resonance energy transfer (FRET), as described above, when hybridized to a strand of DNA, for use in detection of product from RCA.

Figure 11:
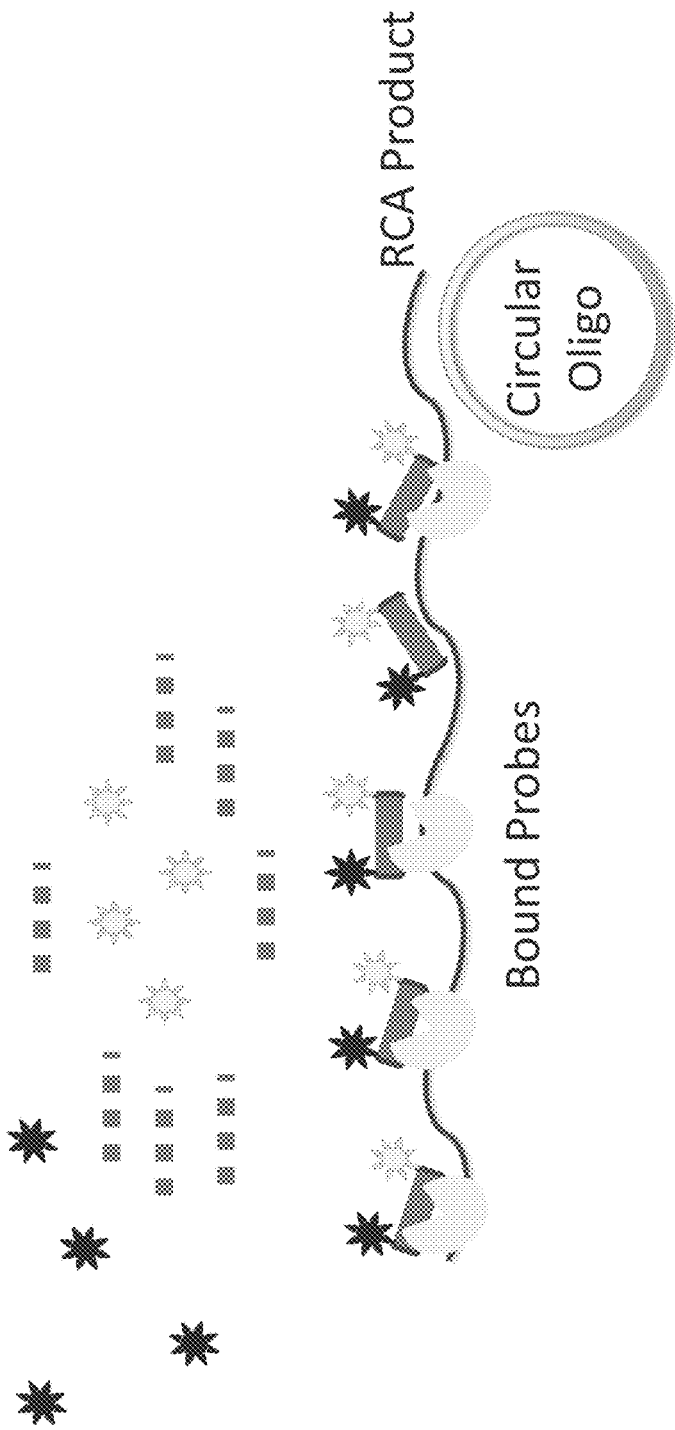
FIG. 11 provides a schematic diagram of an embodiment of the technology comprising use of probes comprising a dye and a quencher, configured to be cleaved, e.g., using a duplex-specific nuclease, such as a restriction enzyme, when hybridized to a strand of DNA, for use in detection of product from RCA.

FIG. 11 provides a schematic diagram of an embodiment of the technology comprising use of probes comprising a dye and a quencher, configured to be cleaved, e.g., using a duplex-specific nuclease, such as a restriction enzyme, when hybridized to a strand of DNA, for use in detection of product from RCA.

As diagrammed in FIG. 12, one embodiment of the technology comprising use of RCA of chromosome-specific identifier sequences (CIDs), followed by CID-specific digestion of non-targeted chromosomes, and CID-specific labeling directed to targeted CIDs. CIDs are amplified by RCA but maintain their individual single molecule identities. CID amplification increases the fluorescence signal from individual target molecules. Sequences from chromosomes that are not being analyzed are dually-repressed by enzymatic digestion and the use of labels specific only for the chromosomes being analyzed.

In some embodiments, a MIP may be detected using non-enzymatic method of signal amplification. For example, in some embodiments, a MIP is immobilized on a surface, and is detected using a method such as a triggered "hybridization chain reaction" (HCR), e.g., as described by R M Dirks, et al., Proc. Natl. Acad. Sci. USA 101(43):15275-15278 (2004), and U.S. Pat. No. 8,105,778, each of which are incorporated herein by reference. FIGS. 13-16 illustrate an exemplary configuration using HCR for signal amplification.

Figure 13:
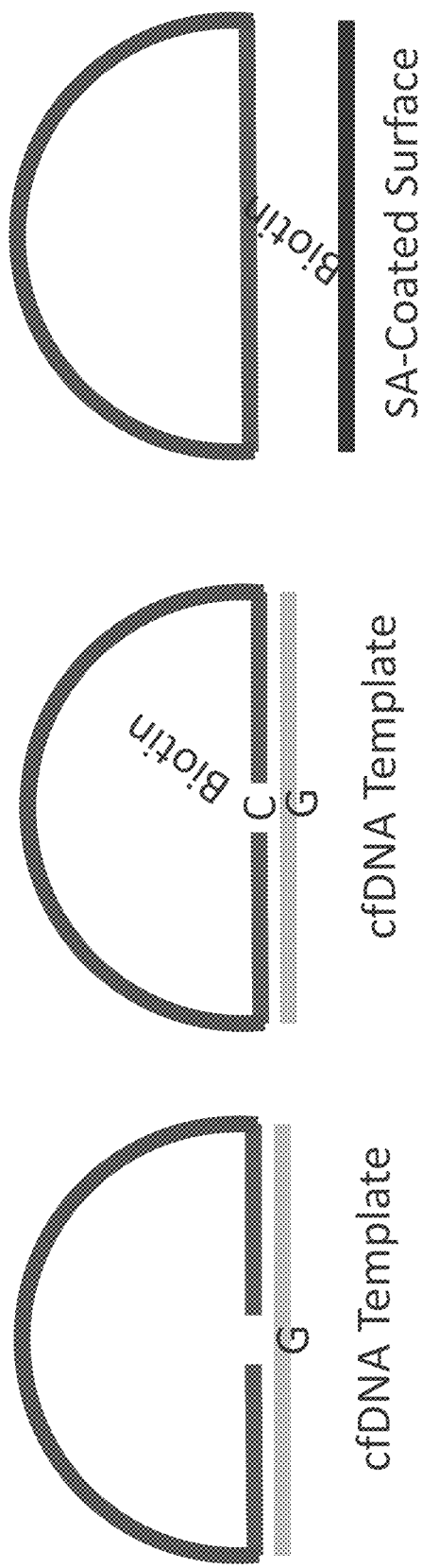
FIG. 13 illustrates an embodiment in which MIPs hybridize to target nucleic acid, e.g., cfDNA, leaving a single nucleotide gap. The gap is filled by extension to incorporate a biotinylated nucleotide and closed by ligation. The circularized MIPs may then be bound to a streptavidin-coated surface.
Figure 14:
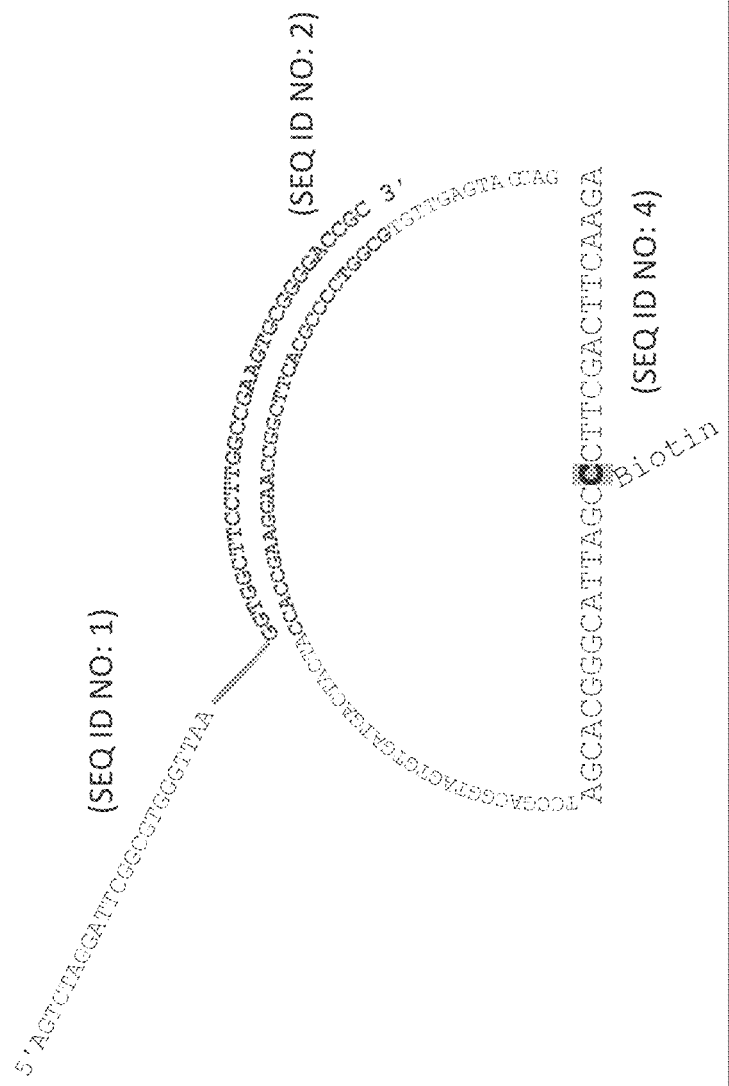
FIG. 14 shows a schematic diagram of an initiator oligonucleotide hybridized to a MIP immobilized on a surface.

FIG. 13 illustrates an embodiment in which MIPs hybridize to target nucleic acid, e.g., cfDNA, leaving a single nucleotide gap. The gap is filled by extension to incorporate a biotinylated nucleotide and closed by ligation. The circularized MIPs may then be bound to a streptavidin-coated surface, as illustrated in FIG. 14, and, after washing away any unbound MIPs, the backbone of the bound MIP is hybridized to an initiator oligonucleotide. In preferred embodiments, a spacer, e.g., an 18-atom hexa-ethyleneglycol spacer, is included between the initiator sequence and backbone-binding sequence. Preferably, the footprint of the MIP binding region is selected to have a high $T_m$ (e.g., approx. 79° C.), for stable binding. As discussed above, binding tags are than biotin, such as an amine group, a thiol group, an azide, or a hapten, may be used to tag and immobilize the MIP to an appropriately reactive surface.

Figure 15:
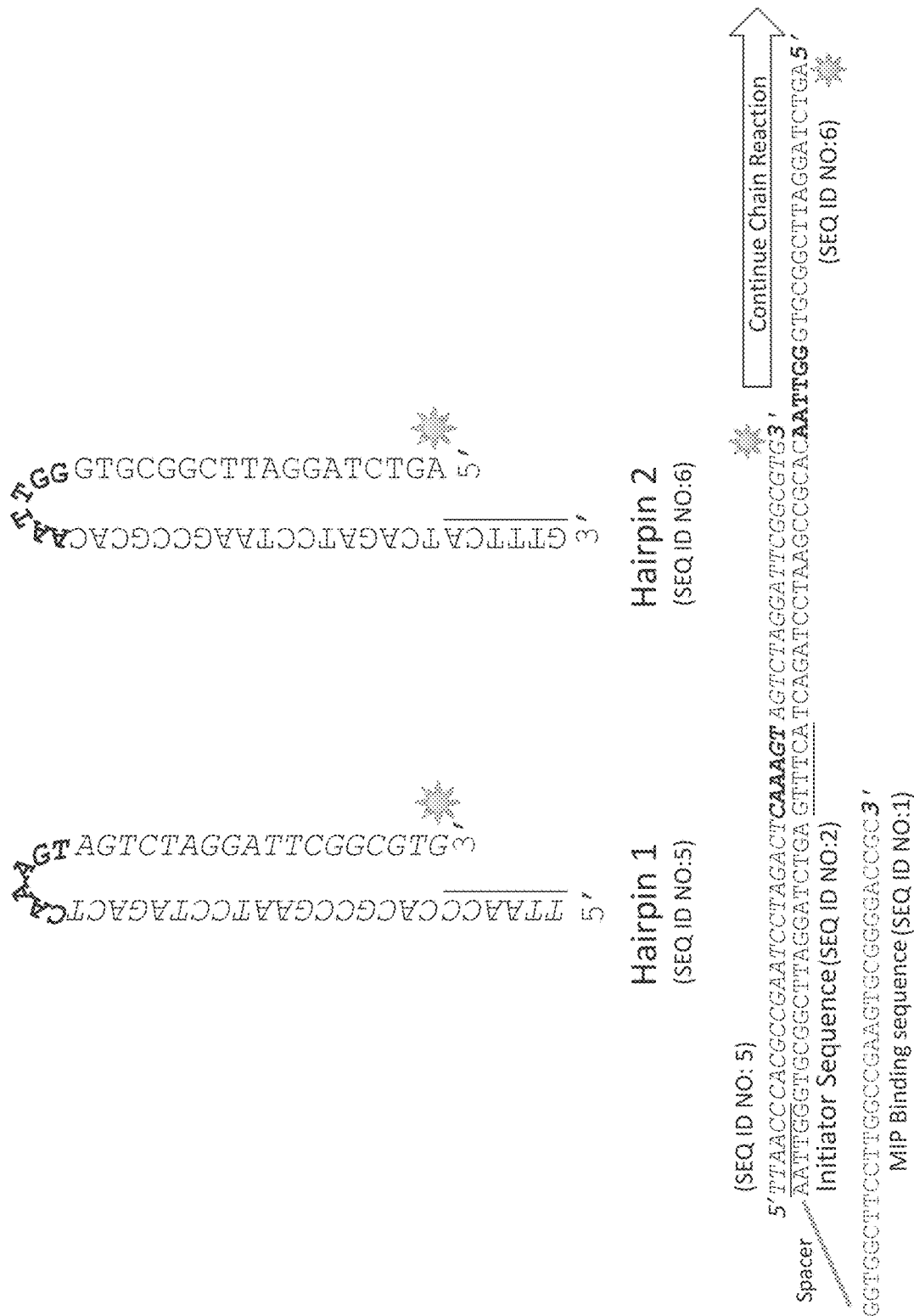
FIG. 15 shows a schematic diagram of hairpin oligonucleotides that work together to form a self-assembling scaffold in the presence of an initiator oligonucleotide.
Figure 16:
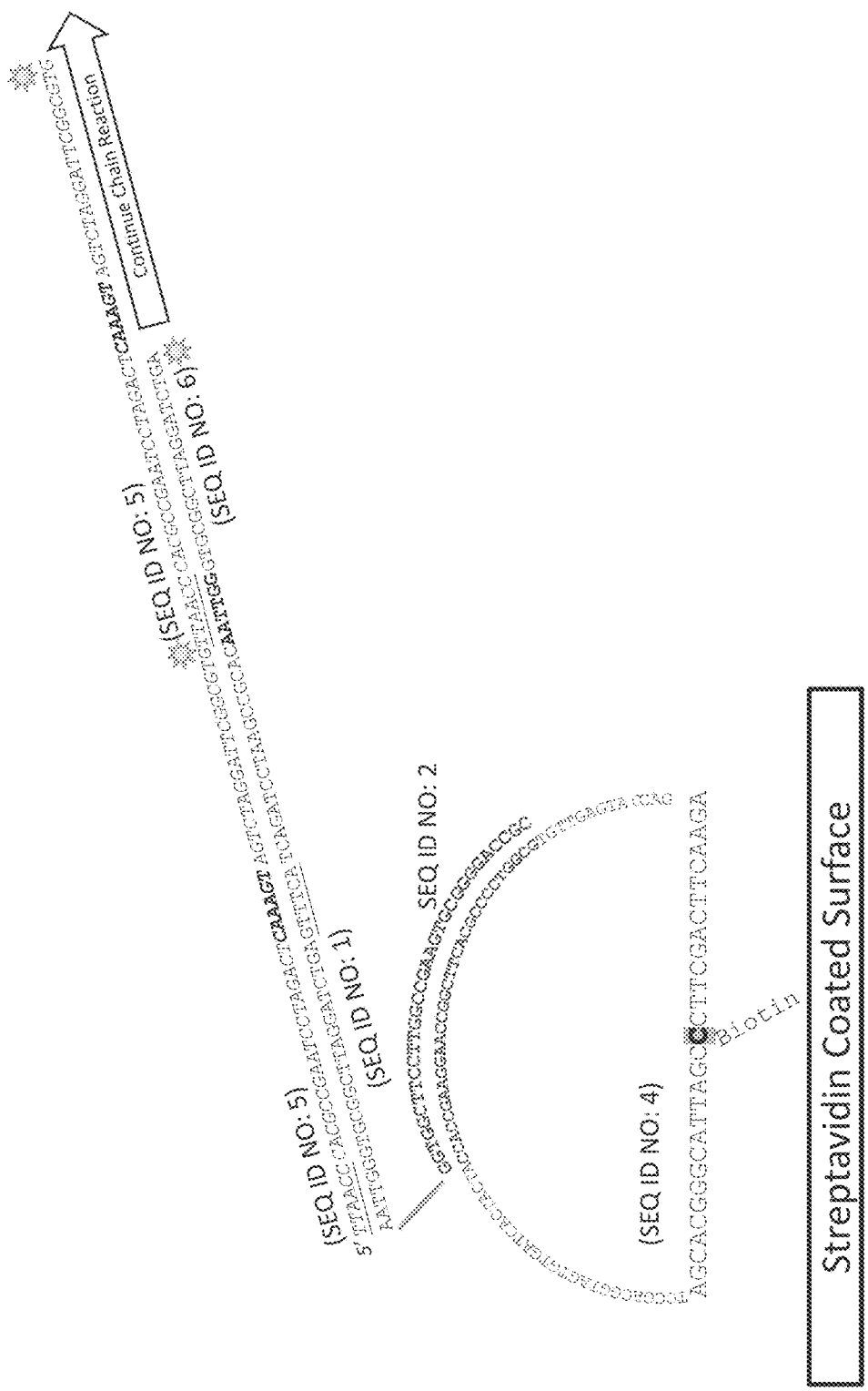
FIG. 16 illustrates a self-assembled scaffold comprising multiple labels, e.g., fluorescent dyes.

FIG. 15 shows examples of hairpin oligonucleotides used in the HCR to form a self-assembling scaffold. One or both oligonucleotides comprises at least one label, e.g., a fluorophore. In preferred embodiments, the dyes are positioned to provide a sufficiently large spacing in the assembled scaffold to prevent quenching effects. For example, in some embodiments, the dyes are positioned on opposite ends of the hairpins, as shown in FIG. 14. As shown in FIG. 16, once the reaction is initiated by hybridization to the initiator oligonucleotide bound to the MIP backbone, the HCR hairpins unfold and hybridize in in long strands, creating a scaffold comprising a large number of labels.

Figure 17:
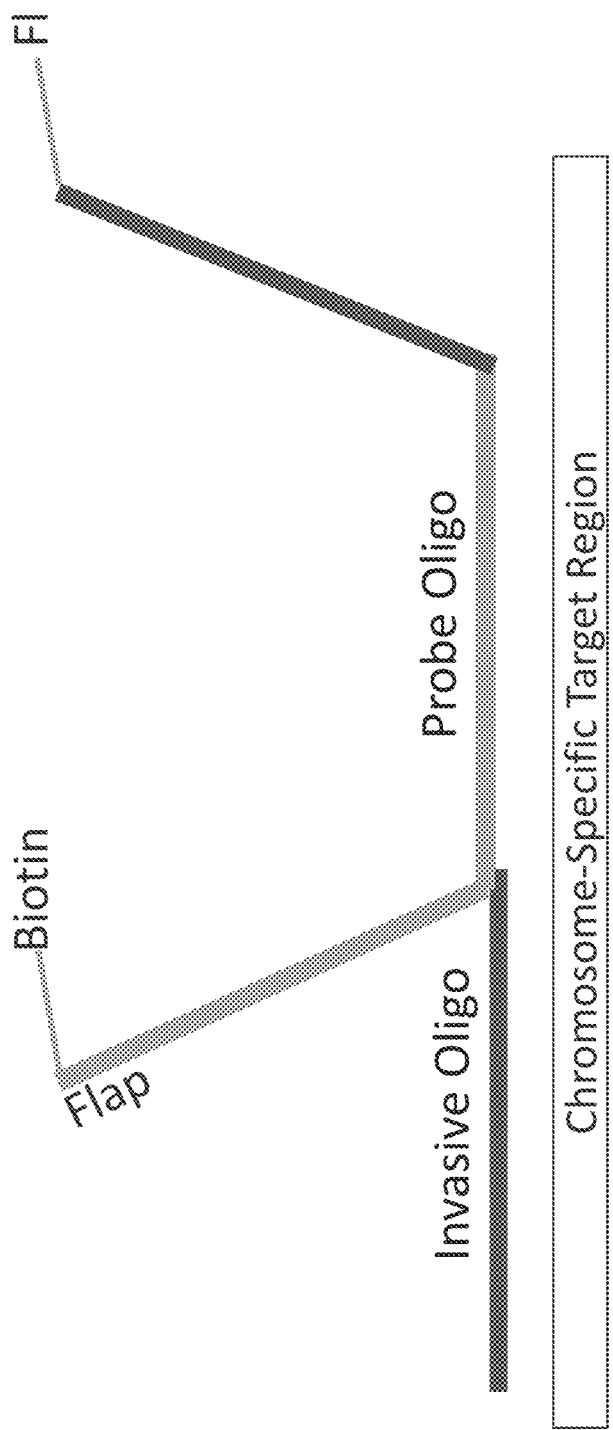
FIG. 17 provide a schematic diagram of an invasive cleavage structure according to an embodiment of the technology.

A flap endonuclease reaction (e.g., Invader assay) may be used for specific, quantitative detection of chromosomes. An exemplary embodiment is illustrated in FIGS. 17-20. FIG. 17 shows an Invader oligonucleotide and a probe oligonucleotide hybridized to a target region of a chromosome. The 3' end of the invasive oligonucleotide overlaps with the 5' end of the region of the probe oligonucleotide that is complementary to the target region. In this embodiment, the probe oligonucleotide comprises a 5' flap comprising a biotin moiety, and a 3' tail comprising a label, e.g., a fluorophore. A flap endonuclease, e.g., a FEN-1 nuclease, recognizes the overlapping invasive cleavage structure and cleaved the probe in a highly specific, structure-dependent manner, releasing the 5' flap. In preferred embodiments, the reaction is run isothermally and produces linear signal amplification, providing $10^3$ to $10^4$ cleaved probes per target in one to three hours, as shown schematically in FIG. 19.

Figure 18:
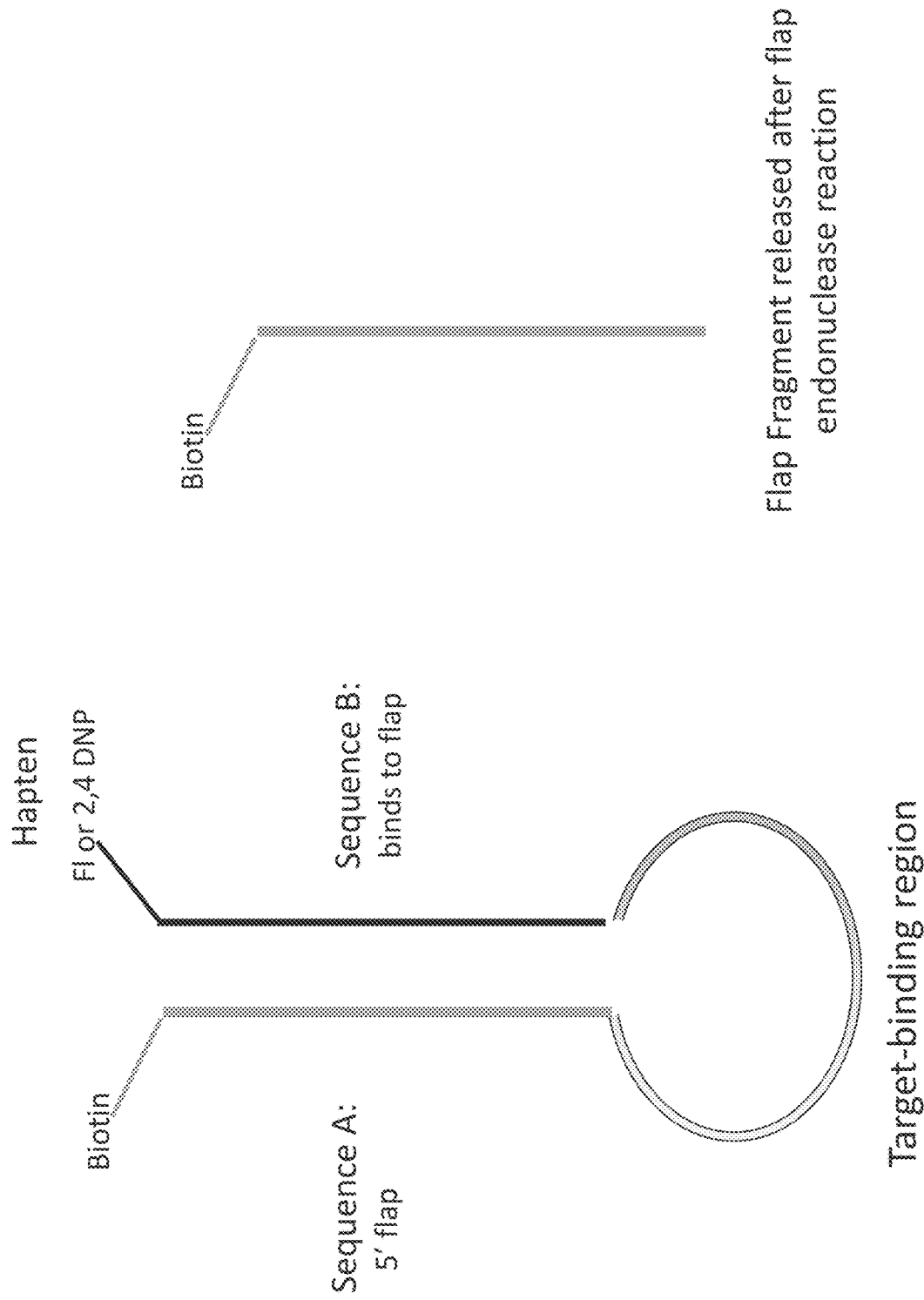
FIG. 18 provides an illustration of a hairpin probe for use in forming an invasive cleavage structure for a flap endonuclease assay, e.g., an Invader® assay, according to an embodiment of the technology.

In preferred embodiments, the probe oligonucleotide used comprises a hairpin structure in which the 5' flap and the 3' tail of the probe hybridize to each other, as illustrated in FIG. 18. The fluorophore or another moiety, e.g., 2,4 dinitrophenyl, may be used as haptens, such that uncleaved probes and/or the 3' portions of the cleaved probes may be removed from the reaction using an antibody to the hapten for capture.

Cleaved flaps from the flap endonuclease reaction may be detected in a number of ways. In a preferred embodiment, the cleaved flap is captured using an immobilized complementary probe, and the biotin is reacted with streptavidin linked to a detectable moiety, as illustrated in FIG. 20. In the embodiment shown, the streptavidin is coupled to β-galactosidase, and a fluorescence signal is generated by providing non-fluorescent resorufin-β-galactopyranoside, which is catalyzed by the β-galactosidase to produce the D-galactose and the fluorescent dye resorufin. Using femtoliter arrays and Poisson statistics to produce a digital readout forma, single hybridization events can be detected using such enzymatic signal amplification. See, e.g., D M Rissin and D R Walt, Digital Concentration Readout of Single Enzyme Molecules Using Femtoliter Arrays and Poisson Statistics. Nano Letters 6(3):520-523 (2006); Quanterix Whitepaper 1.0, Scientific Principle of Simoa (Single Molecule Array) Technology, 1-2 (2013); and Quanterix Whitepaper 6.0, Practical Application of Simoa™ HD-1 Analyzer for Ultrasensitive Multiplex Immunodetection of Protein Biomarkers, 1-3 (2015), each of which is incorporated herein by reference for all purposes. In certain preferred embodiments a kinetic readout, i.e., collecting signal from the array at two time points, is used.

Figure 21:
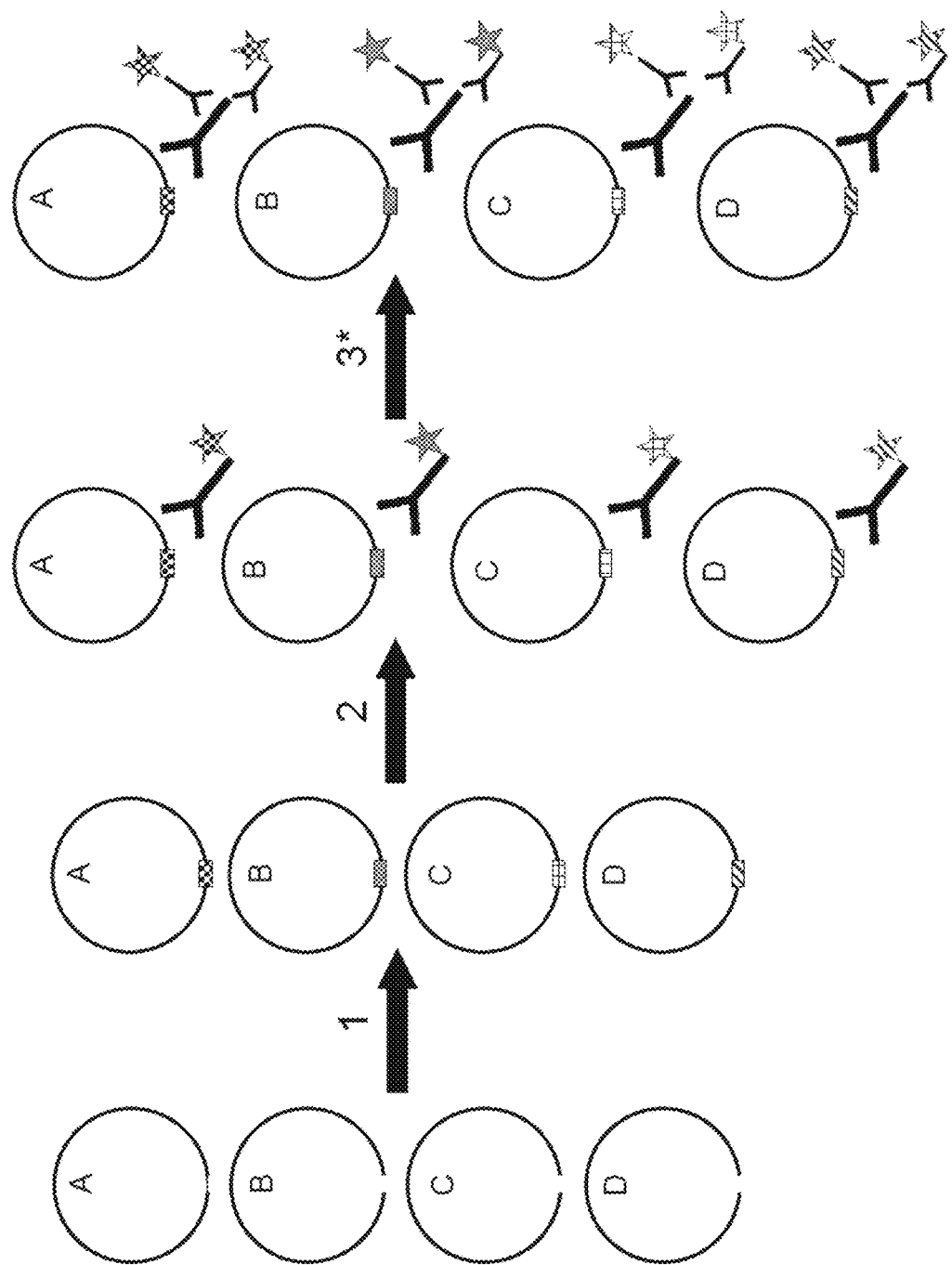
FIG. 21 illustrates an embodiment of the technology in which MIPs designed to target different chromosomes each require a different nucleotide to extend and ligate, and wherein the MIPs are extended and ligated in a chromosome-specific manner using nucleotides which carry different dyes or haptens for each different dNTP.

In the embodiment illustrated in FIGS. 21, A, B, C, and D consist of MIPs that are specific to chromosome 13, 18, 21, X, Y, or a reference chromosome such as 1. The sequence of the MIP surrounding the gap complements region of the targeted chromosome and is designed to contain a single nucleotide gap. Step 1: This gap is filled in with a dNTP conjugated to a hapten such as a fluorescent dye, biotin, etc. Filling the gap introduces a different hapten into MIPs targeted to each of the different specific chromosomes. For example, addition of an A completes only MIPs targeted to chromosome 21, T completes MIPs targeted to chromosome 18, G completes MIPs targeted to chromosome 13, and C completes MIPs targeted to a reference chromosome such as chromosome 1. This approach labels these four different MIPs with a four unique haptens. To increase the number of chromosomes investigated, samples can be split into two or more samples. These split samples can be reacted with different MIP pools to incorporate 8 or more different haptens using the same concept explained above in two or more separate reactions. Pools of MIPs targeted to each chromosome requiring a specific dNTP to complete the single extension and ligation are used to increase the number of capture events. Step 2 comprises incubating the hapten-containing MIPs with labeled antibodies specific to each hapten. The labels may comprise, e.g., a fluorescent dye, quantum dot, or other fluorescent particles. Step 3 comprises an optional step of exposing the immunocomplexes comprising the hapten-targeted primary antibodies to a labeled secondary antibody directed against the primary antibody, thereby amplifying the fluorescent signal.

As illustrated in FIG. 21, in this embodiment of the technology, MIPs designed to target different chromosomes each require a different nucleotide to extend and ligate, and wherein the MIPs are extended and ligated in a chromosome-specific manner using nucleotides which carry different dyes for each different dNTP. For example, in a preferred embodiment, CY2, CY3, CY5, and CY7 are used. The dye-tagged MIPs may be detected using antibodies specific for each different dye (and, by extension, for each different chromosome to be detected). Signal can be amplified by the use of secondary antibodies. For example, CY2 primary rabbit antibody is bound to the target MIP, and secondary goat anti-rabbit antibody is bound to primary antibody to amplify signal, etc.)

As discussed above, many different fluorescence labeling systems find application in the embodiments of the technology. In some embodiments, fluorescent dyes (e.g., fluorescein, Texas Red, TAMRA, Cy3, Cy5, may be used, e.g. attached to nucleotide analogs incorporated into oligonucleotides or extension products. In some embodiments, fluorescent particles, e.g., nanoparticles, nanocrystals, quantum dots, silica (e.g., mesoporous silica nanoparticles) polymer beads (e.g., latex), may be used.

Many options exist for detection and quantitation of fluorescence signal from the embodiments of the technology described hereinabove. Detection can be based on measuring, for example physicochemical, electromagnetic, electrical, optoelectronic or electrochemical properties, or characteristics of the immobilized molecule and/or target molecule. Two factors that are pertinent to single molecule detection of molecules on a surface are achieving sufficient spatial resolution to resolve individual molecules, and distinguishing the desired single molecules from background signals, e.g., from probes bound non-specifically to a surface. Exemplary methods for detecting single molecule-associated signals are found, e.g., in WO 2016/134191, which is incorporated by reference herein in its entirety for all purposes. In some embodiments, assays are configured for standard SBS micro plate detection, e.g., in a SpectraMax microplate reader or other plate reader. While this method typically requires low-variance fluorescence (multiple wells, multiple measurements), this format can be multiplexed and read on multiple different fluorescence channels. Additionally, the format is very high throughput.

Embodiments can also be configured for detection on a surface, e.g., a glass, gold, or carbon (e.g., diamond) surface. In some embodiments, signal detection is done by any method for detecting electromagnetic radiation (e.g., light) such as a method selected from far-field optical methods, near-field optical methods, epi-fluorescence spectroscopy, confocal microscopy, two-photon microscopy, optical microscopy, and total internal reflection microscopy, where the target molecule is labelled with an electromagnetic radiation emitter. Other methods of microscopy, such as atomic force microscopy (AFM) or other scanning probe microscopies (SPM) are also appropriate. In some embodiments, it may not be necessary to label the target. Alternatively, labels that can be detected by SPM can be used. In some embodiments, signal detection and/or measurement comprises surface reading by counting fluorescent clusters using an imaging system such as an ImageXpress imaging system (Molecular Devices, San Jose, Calif.), and similar systems.

Embodiments of the technology may be configured for detection using many other systems and instrument platforms, e.g., bead assays (e.g., Luminex), array hybridization, NanoString nCounter single molecule counting device. See, e.g., G K Geiss, et al., Direct multiplexed measurement of gene expression with color-coded probe pairs; Nature Biotechnology 26(3):317-25 (2008), U.S. Patent Publication 2018/0066309 A1 published Mar. 8, 2018, (P N Hengen, et. Al., Invent., Nanostring Technogies, Inc.), etc.

In the Luminex bead assay, color-coded beads, pre-coated with analyte-specific capture antibody for the molecule of interest, are added to the sample. Multiple analytes can be simultaneously detected in the same sample. The analyte-specific antibodies capture the analyte of interest. Biotinylated detection antibodies that are also specific to the analyte of interest are added, such that an antibody-antigen sandwich is formed. Phycoerythrin (PE)-conjugated streptavidin is added, and the beads are read on a dual-laser flow-based detection instrument. The beads are read on a dual-laser flow-based detection instrument, such as the Luminex 200™ or Bio-Rad® Bio-Plex® analyzer. One laser classifies the bead and determines the analyte that is being detected. The second laser determines the magnitude of the PE-derived signal, which is in direct proportion to the amount of bound analyte.

The NanoString nCounter is a single-molecule counting device for the digital quantification of hundreds of different genes in a single multiplexed reaction. The technology uses molecular "barcodes", each of which is color-coded and attached to a single probe corresponding to a gene (or other nucleic acid) of interest, in combination with solid-phase hybridization and automated imaging and detection. See, e.g. Geiss, et al., supra, which describes use of unique pairs of capture and reporter probes constructed to detect each nucleic acid of interest. In the embodiment described, probes are mixed together with the nucleic acid, e.g., unpartitioned cfDNA, or total RNA from a sample, in a single solution-phase hybridization reaction. Hybridization results in the formation of tripartite structures composed of a target nucleic acid bound to its specific reporter and capture probes, and unhybridized reporter and capture probes are removed e.g., by affinity purification. The hybridization complexes are exposed to an appropriate capture surface, e.g., a streptavidin-coated surface when biotin immobilization tags are used. After capture on the surface, an applied electric field extends and orients each complex in the solution in the same direction. The complexes are then immobilized in the elongated state and are imaged. Each target molecule of interest can thus be identified by the color code generated by the ordered fluorescent segments present on the reporter probe and tallied to count the target molecules.

Figure 22:
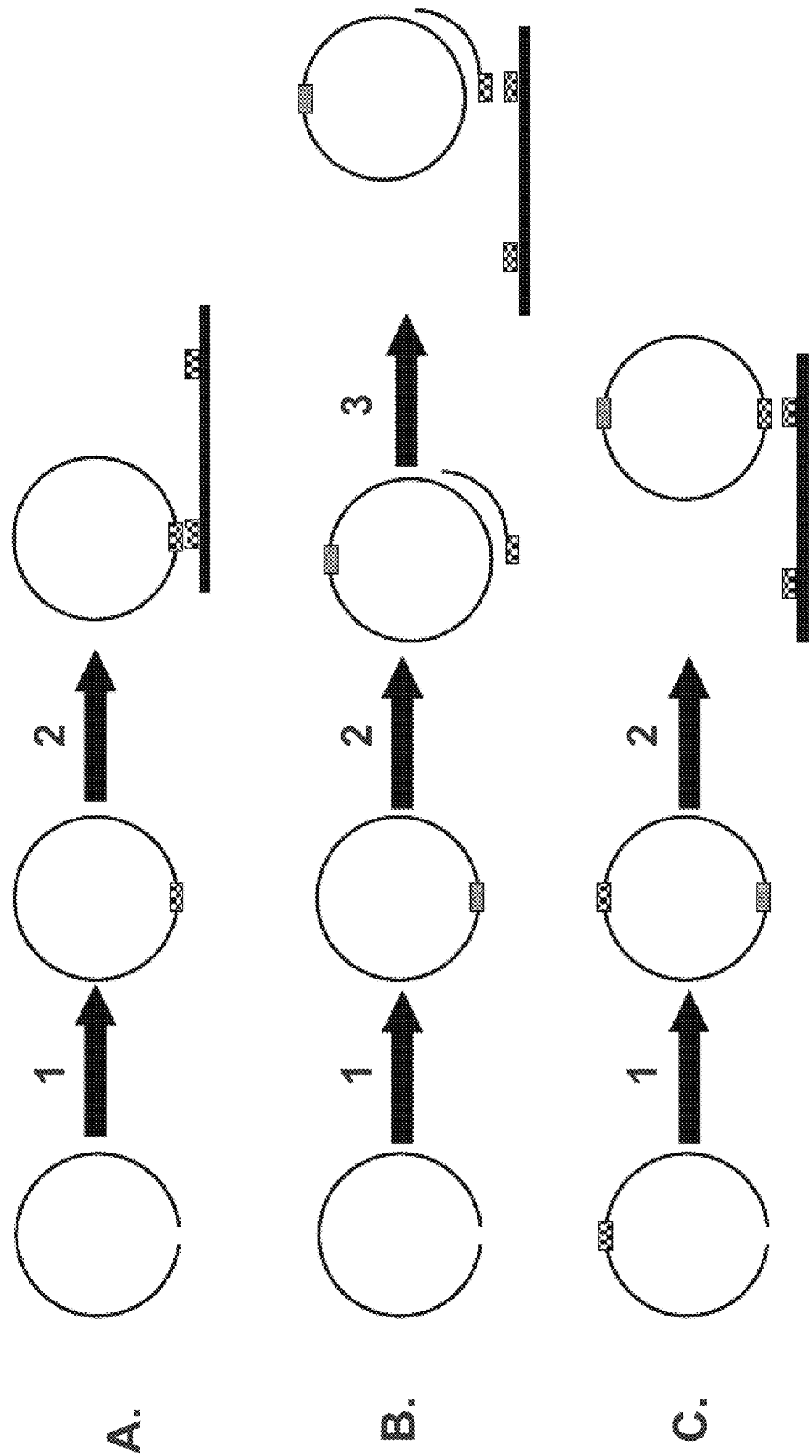
FIG. 22, panels A, B, and C, illustrate embodiments of the technology in which MIPs contain or are modified to contain an immobilization moiety, or are hybridized to an oligonucleotide containing an immobilization moiety, and are immobilized on a surface.

FIG. 22, panels A, B, and C, illustrate embodiments of the technology in which MIPs comprising or attached to an immobilization moiety are immobilized on a surface. While not limited to any particular embodiment for incorporating a representaati feature indicative of target recognition into a circularized MIP molecule, the embodiments of FIG. 22 are illustrated using an embodiment comprising extension of the linear MIP using a polymerase to copy one or more nucleotides of a target nucleic acid, followed by ligation to circularize the extended probe.

In the embodiment illustrated in panel A of FIG. 22, in step 1 MIPs are hybridized with the target DNA and are then extended by a DNA polymerase in the presence of modified dNTPs so that an immobilization moiety is incorporated into each MIP during extension. The MIP is then ligated to itself to complete the circularized probe. The modified dNTPs may comprise, but are not limited to, dNTPs comprising reactive chemistry species such as amine groups or thiol groups, or other bindable features, such as biotin or an antibody hapten. In step 2, circularized MIPs are exposed to a surface under conditions in which the surface interacts with the immobilization feature of the MIP to bind the MIP. Such surfaces include but are not limited to derivatized or underivatized glass, silica, diamond, gold, agarose, plastic, ferromagnetic material, alloys, etc., and may be in any form, e.g., slide, sample well, channel, bead, particle and/or nanoparticles, any of which may be porous or non-porous.

In the embodiment illustrated in panel B of FIG. 22, in step 1, MIPs are hybridized with target DNA and ligated to circularize. In the embodiment shown, the MIP is extended by a DNA polymerase to fill a sequence gap prior to ligation, while in other embodiments, the MIP may be designed to be simply hybridized to the target nucleic acid and ligated to circularize without use of a polymerization step, in the manner, e.g., of padlock probes See, e.g., M. Nilsson, et al. "Padlock probes: circularizing oligonucleotides for localized DNA detection". Science. 265 (5181): 2085-2088 (1994); J. Banér, et al., *Nucleic Acids Res.*, 26 (22):5073-5078 (1998). In step 2, the circular MIP is hybridized to a complementary oligonucleotide that contains an immobilization moiety as described above, e.g., a reactive amine, a reactive thiol group, biotin, a hapten, a capturable nucleic acid tag sequence, etc. In step 3, the hybrid MIP complex of the MIP and the oligonucleotide comprising the immobilization moiety is exposed to a surface under conditions in which the surface interacts with the immobilization feature of the MIP complex to bind the MIP complex. As described above, surfaces include but are not limited to derivatized or underivatized glass, silica, diamond, gold, agarose, plastic, ferromagnetic material, alloys, etc., and may be in any form, e.g., slide, sample well, channel, bead, particle and/or nanoparticles, any of which may be porous or non-porous.

In the embodiment illustrated in panel C of FIG. 22, in step 1, MIPs that contain an immobilization moiety built into the backbone of the probe are hybridized with DNA, extended by a DNA polymerase, and ligated to circularize the probe. As with the embodiment of panel B described above, the MIPs may be designed to be simply hybridized to a target nucleic acid and ligated to circularize without use of a polymerization step. In step 2, the circularized MIP containing the immobilization moiety is exposed to a surface under conditions in which the surface interacts with the immobilization feature of the MIP to bind the MIP. As described above, surfaces include but are not limited to derivatized or underivatized glass, silica, diamond, gold, agarose, plastic, ferromagnetic material, alloys, etc., and may be in any form, e.g., slide, sample well, channel, bead, particle and/or nanoparticles, any of which may be porous or non-porous.

In each of the embodiments illustrated in FIG. 22, once the MIPs have been immobilized to a surface, labeling and/or signal amplification (e.g., fluorescent labeling and/or amplification of fluorescent signal) and detection can be accomplished using any of the various back-end analysis methods discussed herein. Suitable methods for amplifying and/or detecting the unique immobilized MIP products include but are not limited to the NanoString nCounter technology described above, and the methods illustrated in FIGS. 2-3, 6-7, 9-12, 15-16 and 20-21. In some embodiments, labeling and/or signal amplification (e.g., fluorescent labeling and/or amplification of fluorescent signal) is done before the MIPs have been immobilized to a surface.

In preferred embodiments, a back-end process configured for single molecule visualization is used. For example, as described above, is the Quanterix platform uses an array of femtoliter-sized wells that capture beads having no more than one tagged complex, with the signal from the captured complexes developed using a resorufin-β-galactopyranoside/β-galactosidase reaction to produce fluorescent resorufin. Visualization of the array permits detection of the signal from each individual complex. In certain preferred embodiments, a solid state nanopore device, e.g., as described by Morin, et al., (see "Nanopore-Based Target Sequence Detection" PLoS ONE 11(5):e0154426 (2016)), is used. A solid-state nanopore is a nano-scale opening formed in a thin solid-state membrane that separates two aqueous volumes. A voltage-clamp amplifier applies a voltage across the membrane while measuring the ionic current through the open pore. When a single charged molecule such as a double-stranded DNA is captured and driven through the pore by electrophoresis, the measured current shifts, and the shift depth (SI) and duration are used to characterize the event. (Morin, et al., supra). Although DNA alone is detectable using this system, distinctive tags (e.g., different sizes of polyethylene glycol (PEG)) may be attached to highly sequence-specific probes (e.g., peptide nucleic acid probes, PNAs) to give any particular DNA-PNA-PEG complex a distinctive signature that represents the target nucleic acid detected in the front-end of the assay.

Figure 23:
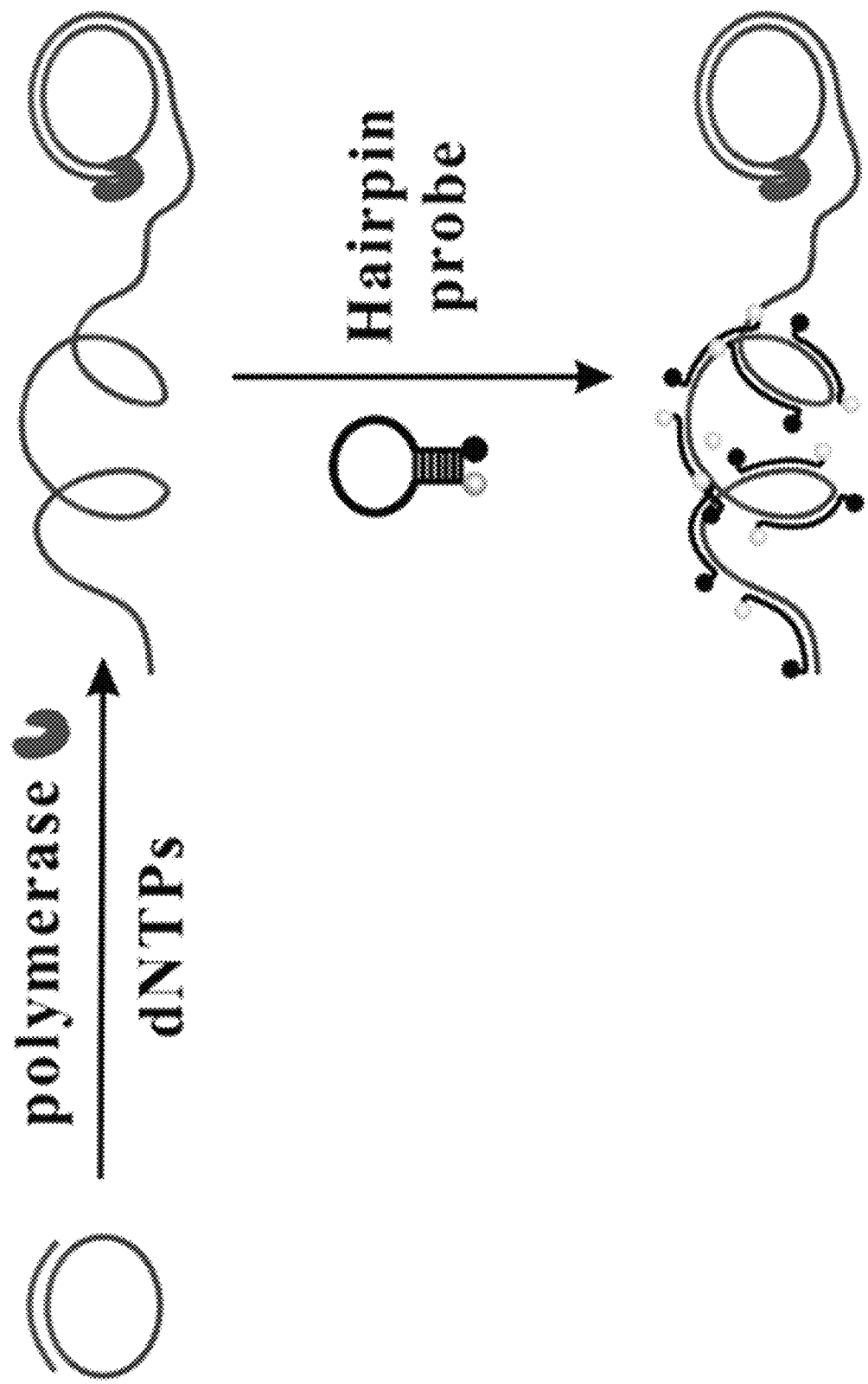
FIG. 23 provides a schematic diagram of a rolling circle amplification reaction.
Figure 24A:
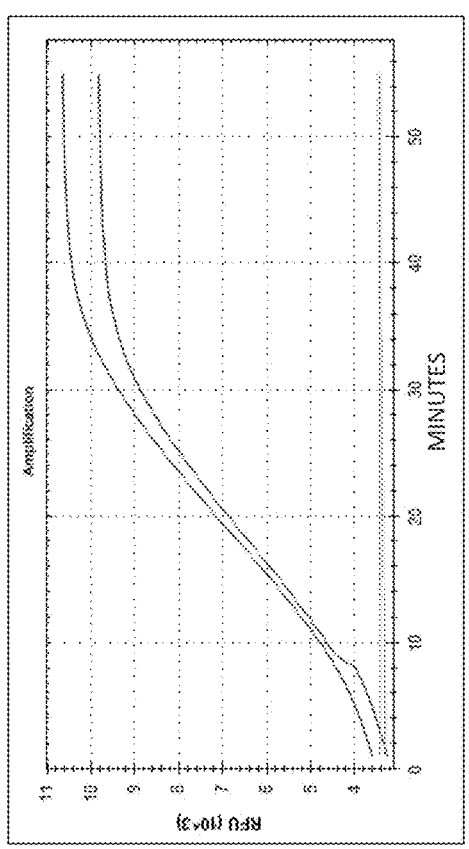
FIGS. 24A-24D provide graphs showing results from examining the effect on RCA signal of including biotin residues in the MIP complex.
Figure 24B:
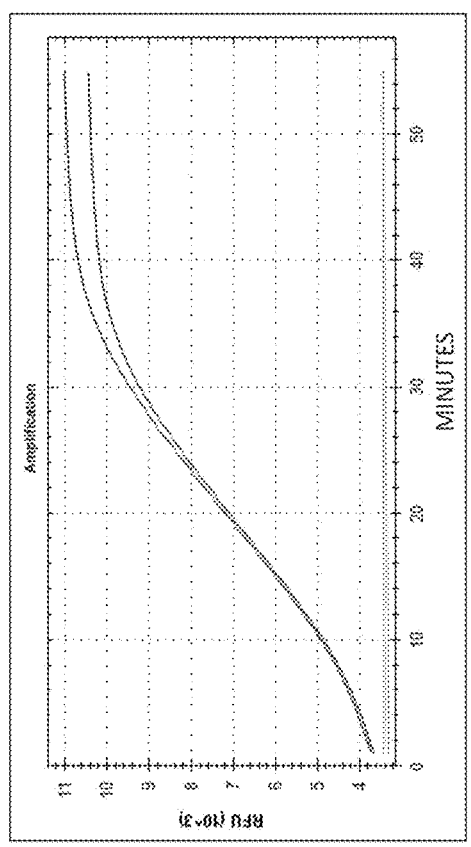
Figure 24C:
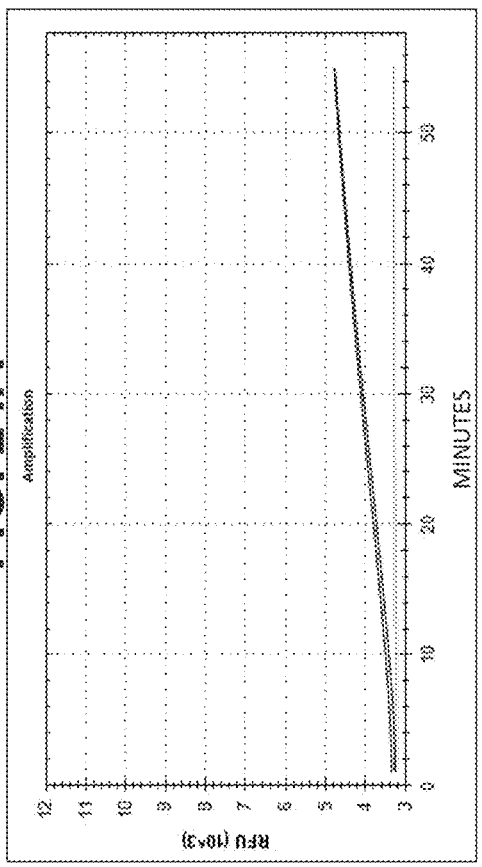
Figure 24D:
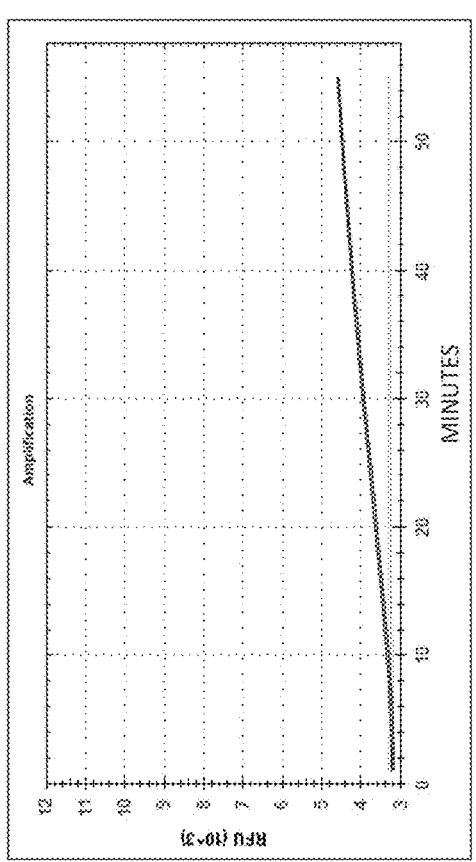

In the embodiment illustrated in FIG. 23, a complex is formed comprising an oligonucleotide primer and a circular probe, such as a MIP or ligated padlock probe. Extension of the primer in a rolling circle amplification reaction produces long strand of single-stranded DNA that contains a concatemer of the sequence complementary to the circular probe. The RCA product binds to a plurality of molecular beacon probes having a fluorophore and a quencher. Hybridization of the beacons separates the quencher from the fluorophore, allowing detection of fluorescence from the beacon. Accumulation of the RCA product may be monitored in real time by measuring an increase in fluorescence intensity that is indicative of binding of the beacons to the increasing amount of product over the time course of the reaction.

Real-time quantitation of accumulating fluorescence in reactions was used to examine the effects of attached biotin moieties on the MIP or on the primer. FIGS. 24A-24D show results from examining the effect on RCA signal of including biotin residues in the circularized MIP only (A), in the RCA primer only (B), in both (C), and in neither (D). In this experiment, the MIP contained the sequence:

```
(circularized)                       (SEQ ID NO: 23)
5'-CCTCCCATCATATTAAAGGCCTCTATGTTAAC[T]GACCTACGACG

ATGCTGCTGCTGTACTACGAGGCTAAGGCATTCTGCAAACAT-3'.
```

In the biotinylated MIP above, the boxed 'T' shows the site of attachment of a biotin (Integrated DNA Technologies, "Internal Biotin dT") in the MIP containing a biotin. The biotinylated primer comprised a biotin attached at the terminal '5' phosphate (Integrated DNA Technologies, "'5' Biotin-TEG"). The rolling circle reaction was conducted according to the "standard rolling circle reaction" procedure described below in Example 1, at 37° C. for one hour. These data show that the presence of biotin in the circularized MIP inhibits RCA, while the presence of biotin on the primer does not inhibit the reaction.

Figure 25A:
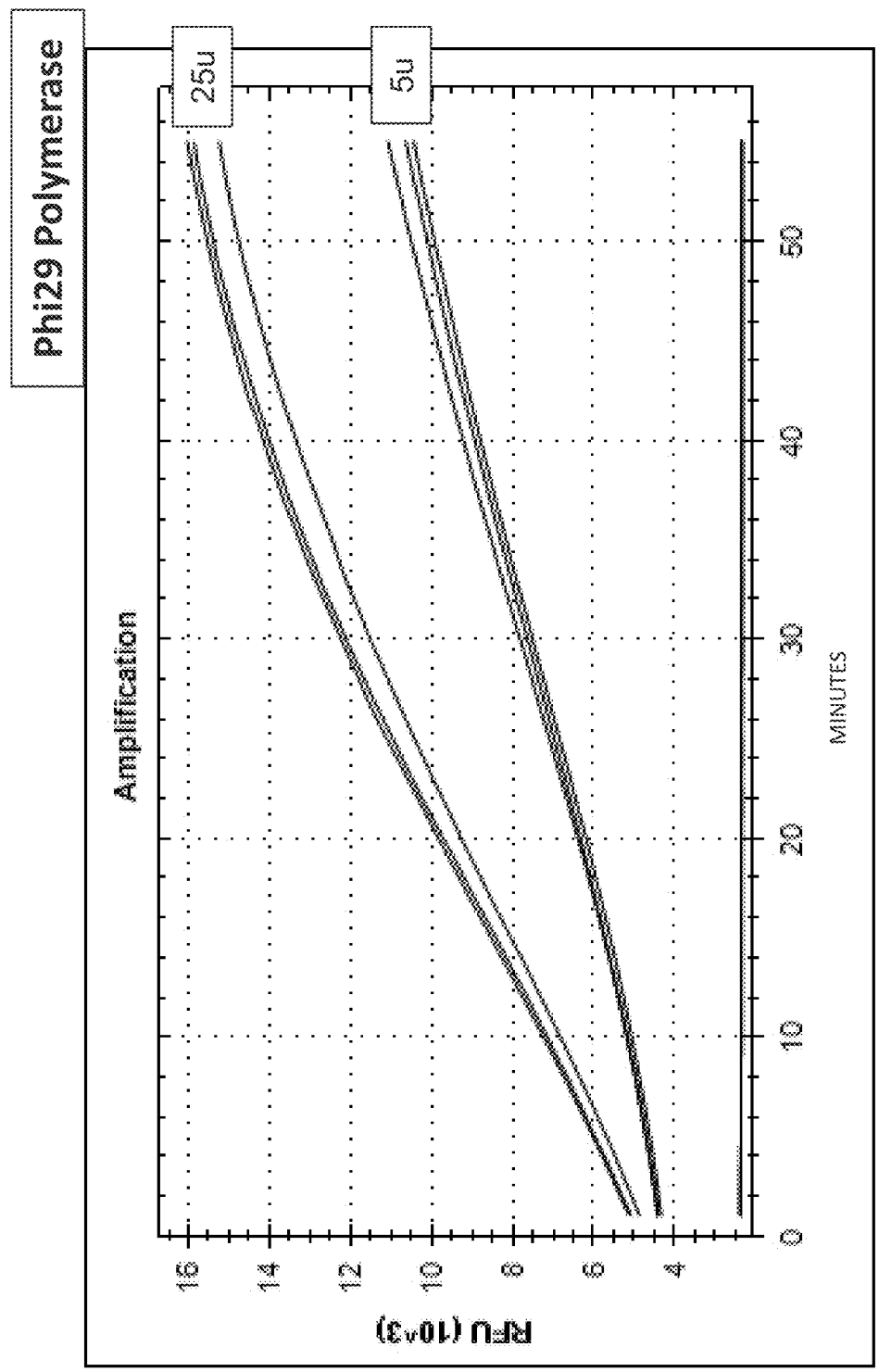
FIGS. 25A-25C provide graphs showing the results of varying amounts of components in standard RCA reactions in solution.
Figure 25B:
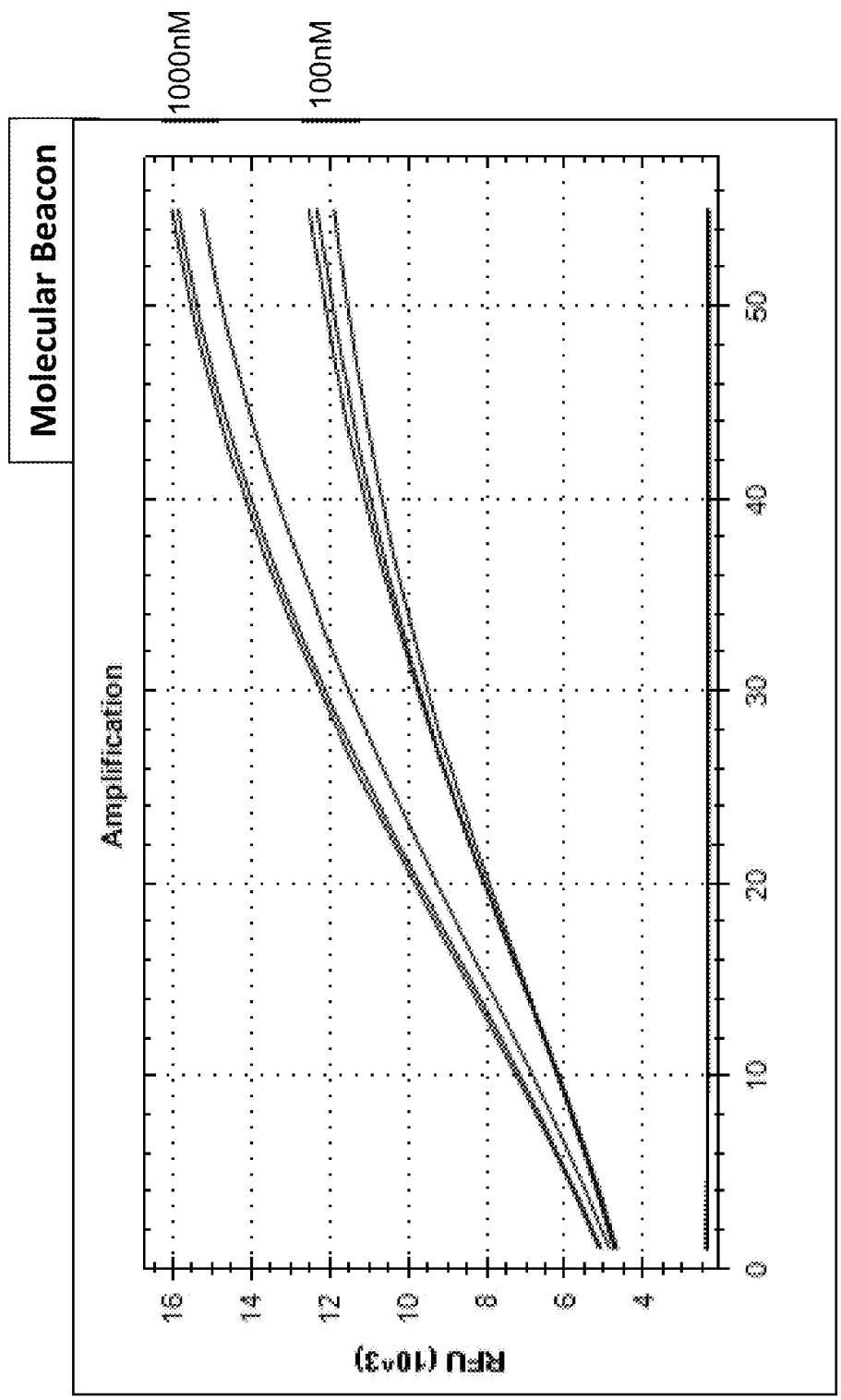
Figure 25C:
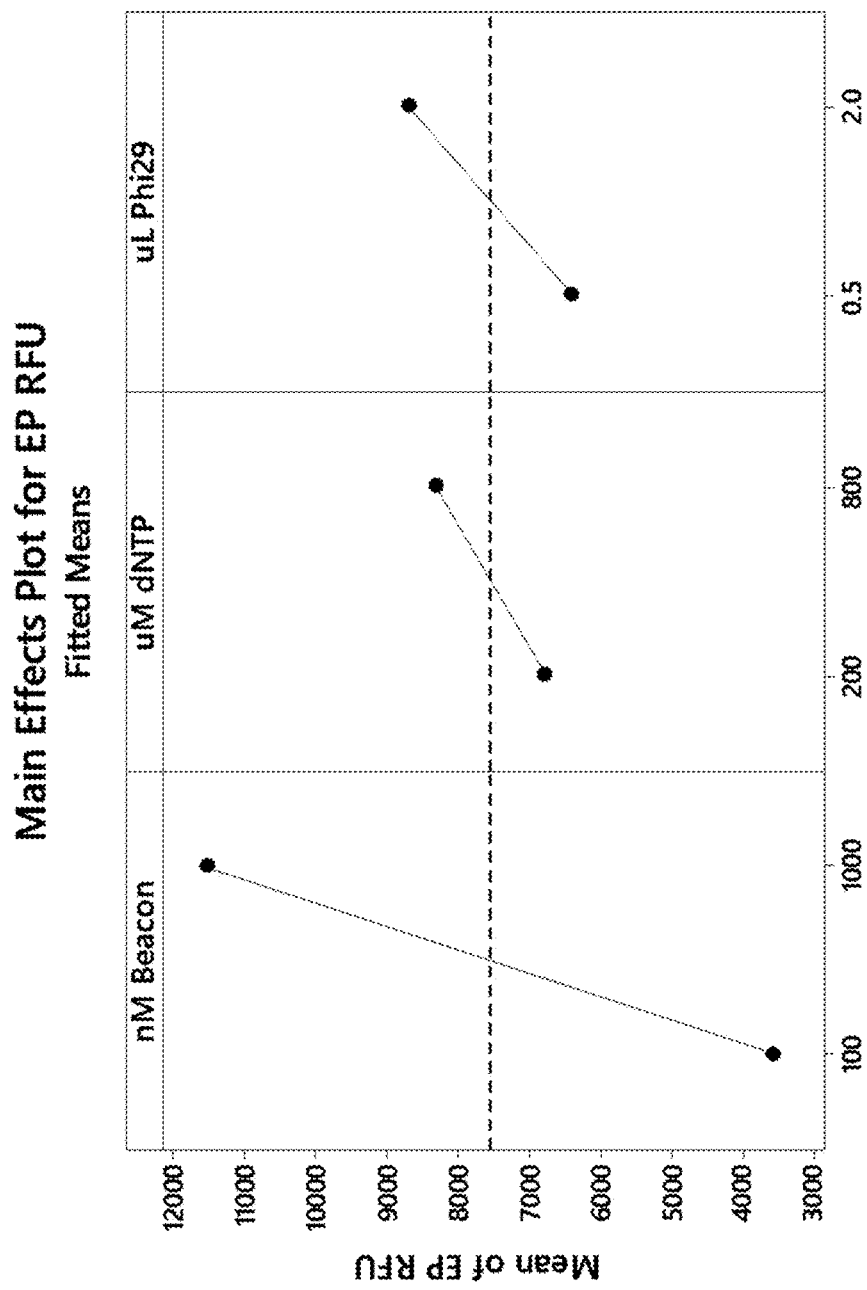

FIGS. 25 A-C show the results of varying amounts of components in standard RCA reactions in solution. FIG. 25A compares use of 5 units and 25 units of Phi29 polymerase in each reaction, and shows that the higher concentration of polymerase yielded consistently higher signal under the conditions tested. FIG. 25B shows the effects of using different concentrations of molecular beacon probe ("Beacon"); FIG. 25C compares the effects of using the different concentrations of Phi29 polymerase and molecular beacon probe to the effect on the standard reaction of using 200 μM or 800 μM total dNTPs. Based on these data, reactions adjusted to comprise 1000 nM beacon, 800 μM dNTPs, and 2000 nM phi 29 polymerase (80 units) were further tested.

The effects of adding different concentrations of PEG and of using different sizes of PEG to the enhanced RCA conditions (E-RCA, see Example 1, below) were examined. FIG. 26 compares the effects of using different sizes of PEG (200 and 8000) at the percentages (w:v) shown, in the E-RCA conditions. Under the conditions tested for this embodiment, PEG 200 provided superior results at all concentrations tested, with 20% PEG 200 providing the best results. In contrast, the PEG 8000 significantly reduced the efficiency of the RCA. Based on these data, RCA reactions comprising at least 20% w:v of PEG 200 were further tested.

As discussed above, single molecule detection on a surface, it is preferable that the spot size of the signal from any individual bound molecule be minimized, such that separation between spots is assured such that individual spots can be resolved by a light microscope. The effects of using PEG 200 on the spot size and the number of spots detected was examined. The assays were conducted using the E-RCA conditions described below, with or without 20% w:v PEG 200, incubated for 140 min. The results are shown in FIGS. 27A-27B and 28A-28B. FIG. 27A shows that the presence of PEG decreased the spot size, enhancing measurement of fluorescence signal from individual spots. FIG. 27B shows the effects of PEG on the number and fluorescence intensity of the spots shown in FIG. 27A, and shows that addition of PEG increased the number of detectable spots while reducing the size of the spots detected.

Figure 28:
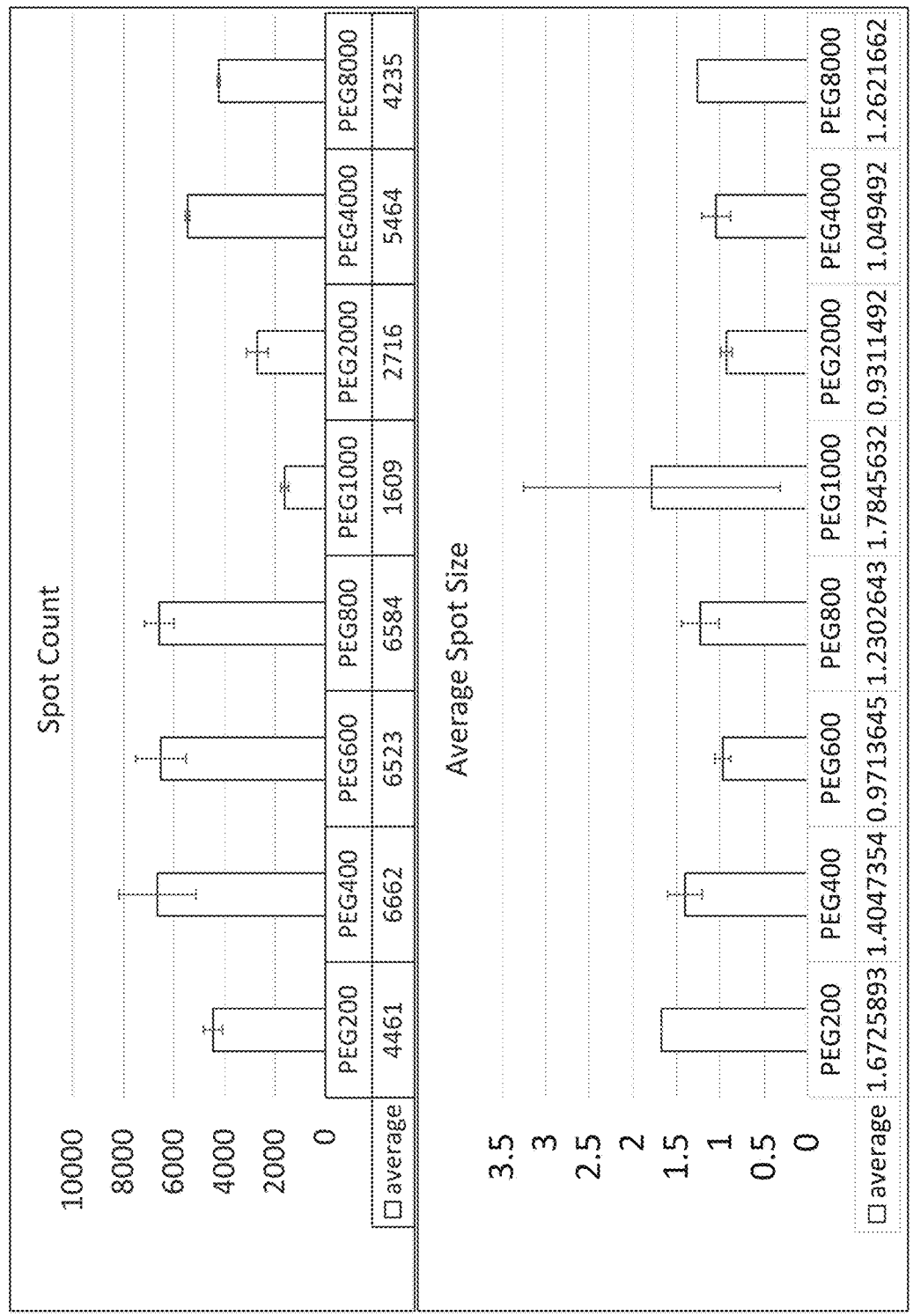
FIG. 28 provides graphs showing the effects of different molecular weights of PEG in a 20% solution on the number and pixel size of the spots on APTES-silanized plates, as described in Example 1.

The effects on spot count and spot size using different molecular weights of PEG in a 20% solution in reactions conducted on APTES-silanized plates were examined. Reactions on the APTES-treated surface were conducted as described in the "One-Step Rolling Circle Amplification On a Surface" in Example 1, with the PEG component modified as indicated in FIG. 28. FIG. 28 shows that spot number is maximized and spot size is minimized when the PEG used is smaller than 1000, preferably between 200 and 800, more preferably 600 average molecular weight.

Figure 29B:
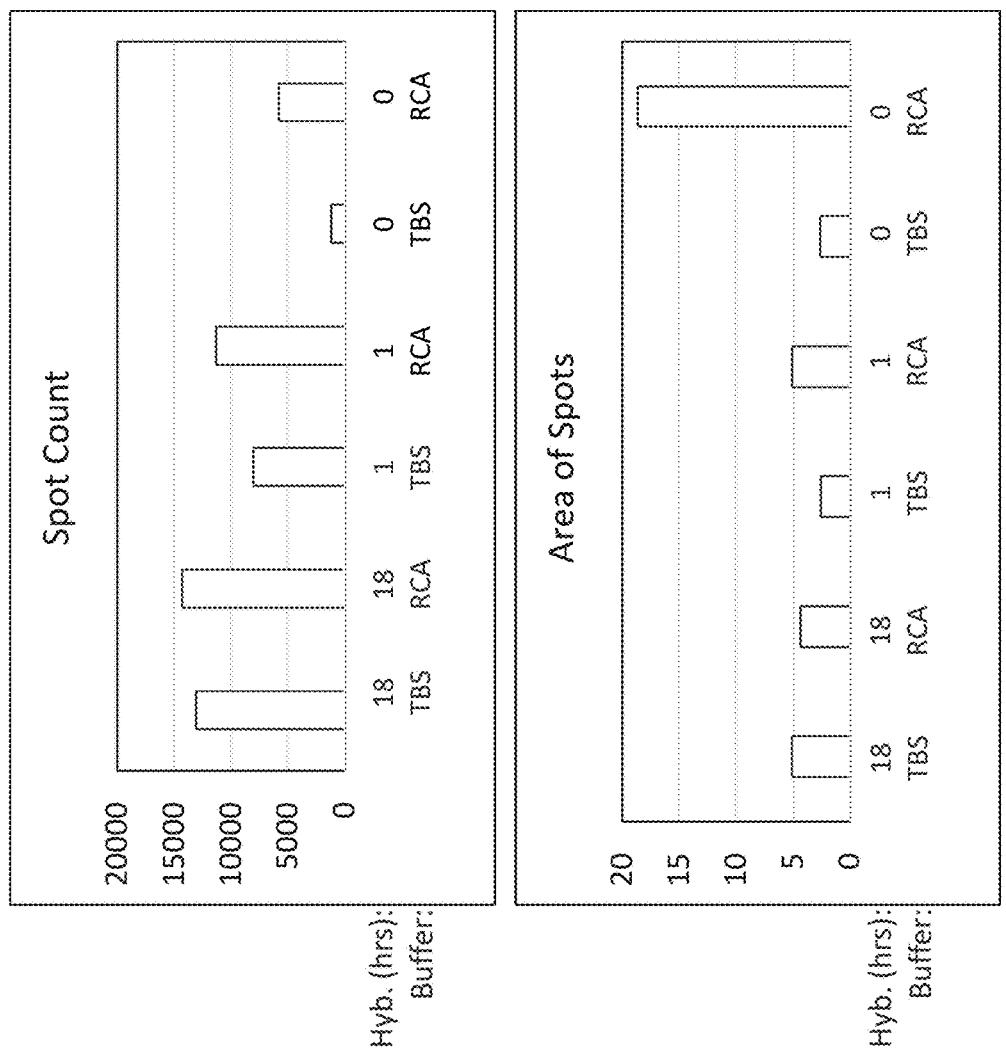
FIG. 29B provides graphs comparing the effects of hybridization time and buffer on the number and pixel size (area) of the spots shown in FIG. 29A.

The length of hybridization time prior to initiating the RCA reaction was examined. FIG. 29A shows microscope images of surfaces of APTES-silanized plates, as described in Example 1, and compares RCA signal for reactions hybridized for 18 hours or 1 hour prior to initiating the RCA reaction, in either TBS or RCA buffer The Enhanced RCA was performed as described above, with 20% PEG 600, for 140 minutes. FIG. 29B provides graphs comparing the effects of hybridization time and buffer on the number and fluorescence intensity (area) of the spots shown in FIG. 29A. These data show a substantial increase in the number of spots when with longer hybridization time.

Figure 30:
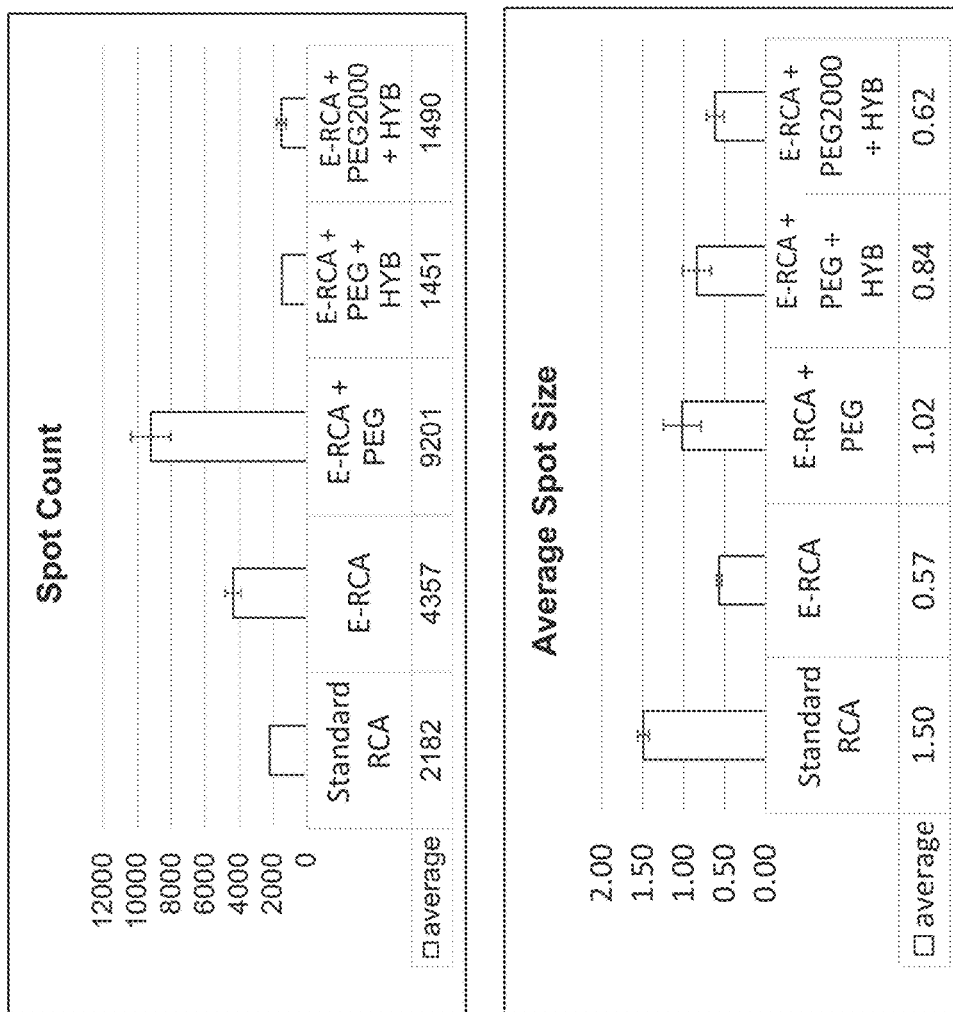
FIG. 30 provides graphs comparing the effects of PEG 200 on the standard RCA reaction conditions, with or without a 2-hour hybridization time, and the effect of PEG 2000 with 2-hour hybridization, on the number and pixel size (area) of the spots.
Figure 31:
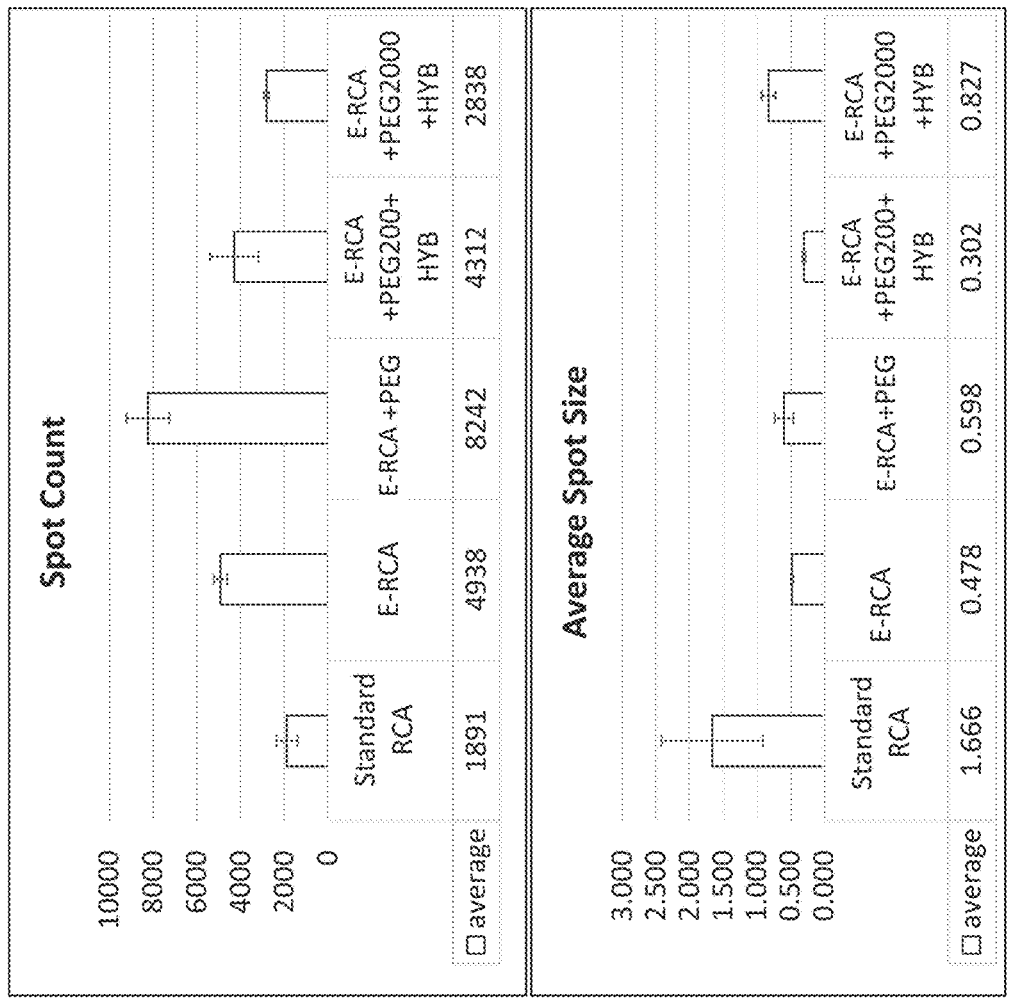
FIG. 31 provides graphs comparing the effects of PEG 200 on the standard RCA reaction conditions performed at 25° C., with or without a 2-hour hybridization time, and the effect of PEG 2000 with 2-hour hybridization, on the number and pixel size (area) of the spots.
Figure 32:
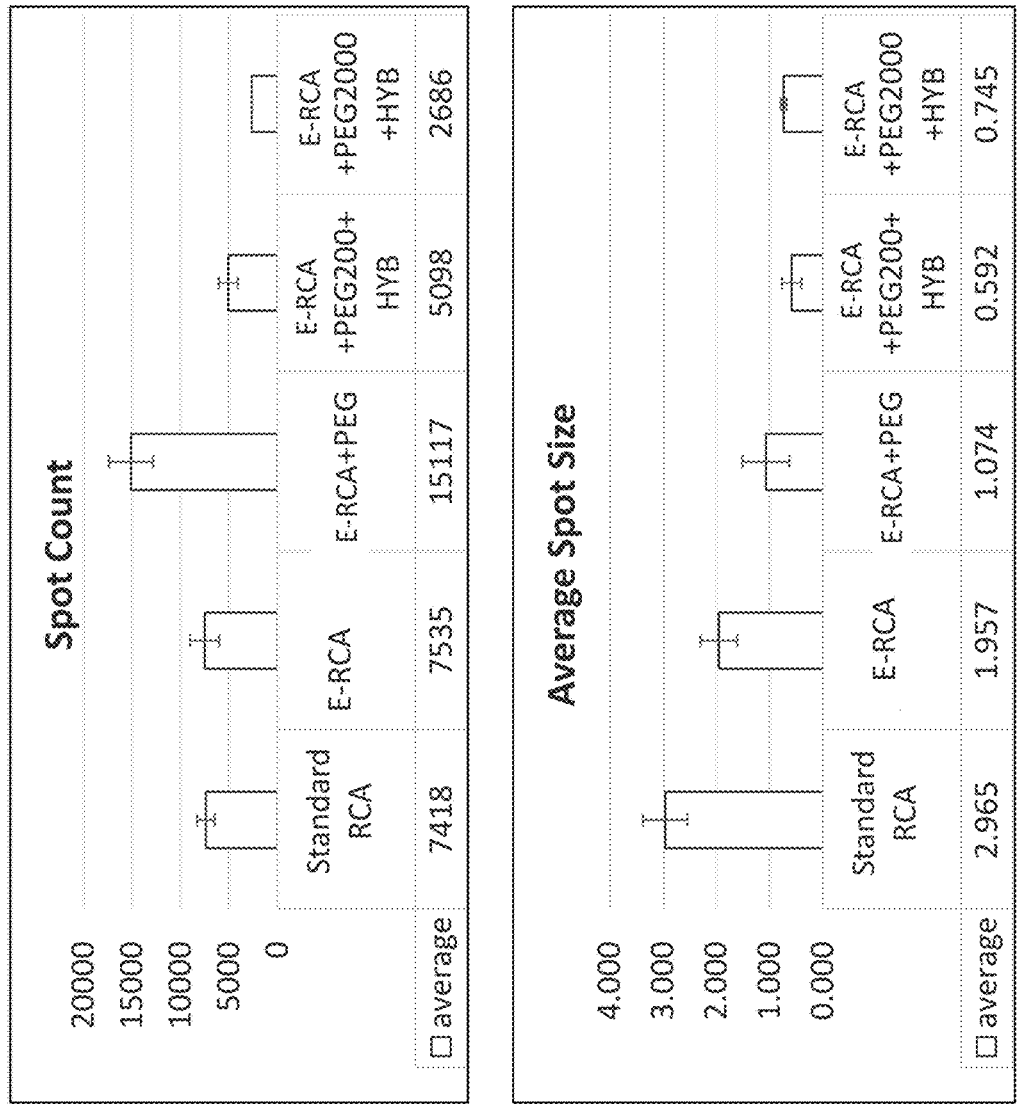
FIG. 32 provides graphs comparing the effects of PEG 200 on the standard RCA reaction conditions performed at 37° C., with or without a 2-hour hybridization time, and the effect of PEG 2000 with 2-hour hybridization, on the number and pixel size (area) of the spots.
Figure 34:
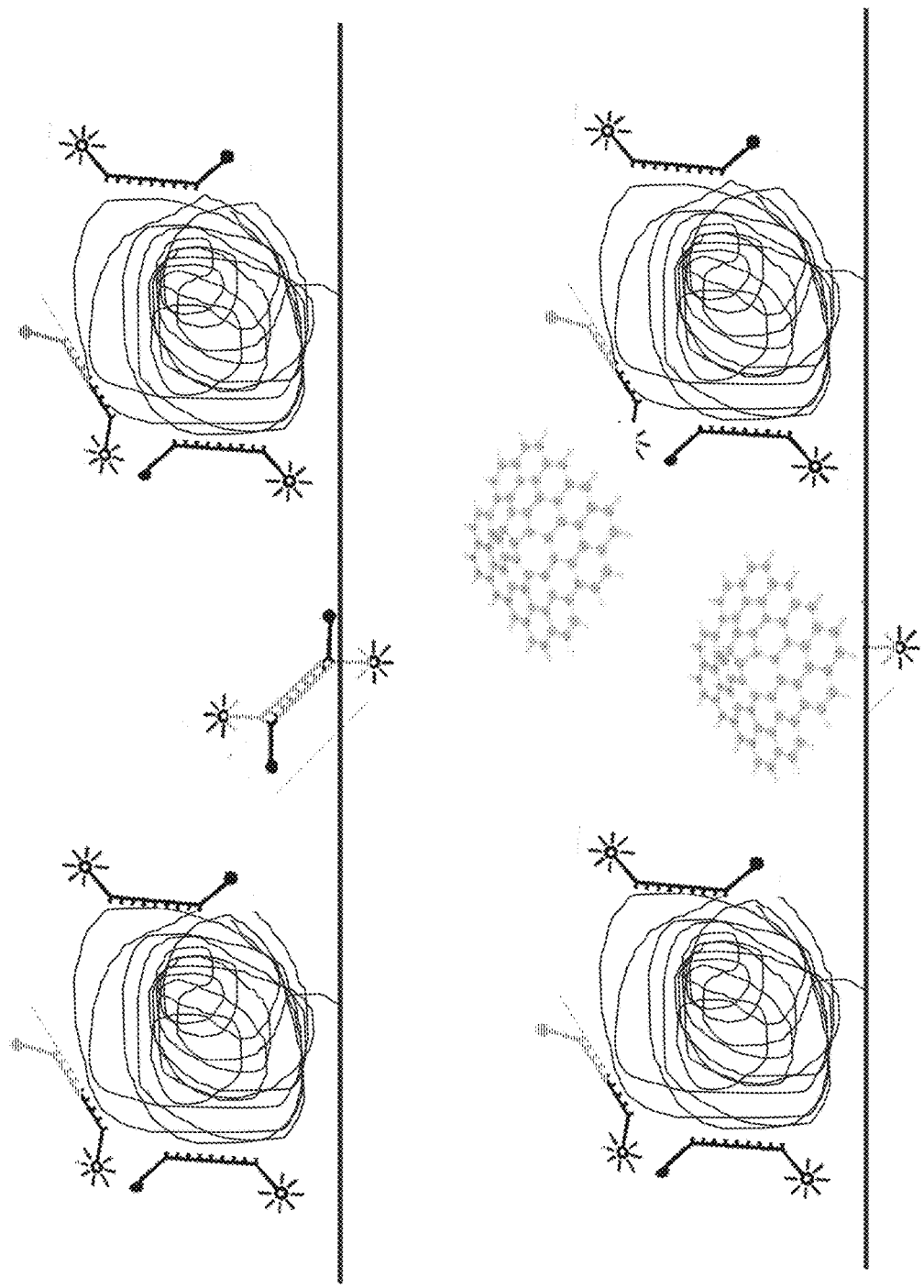
FIG. 34 provides a schematic diagram of RCA-molecular beacon products on a surface, with or without graphene oxide, with graphene oxide quenching fluorescence background from beacons bound non-specifically to the surface.
Figure 35:
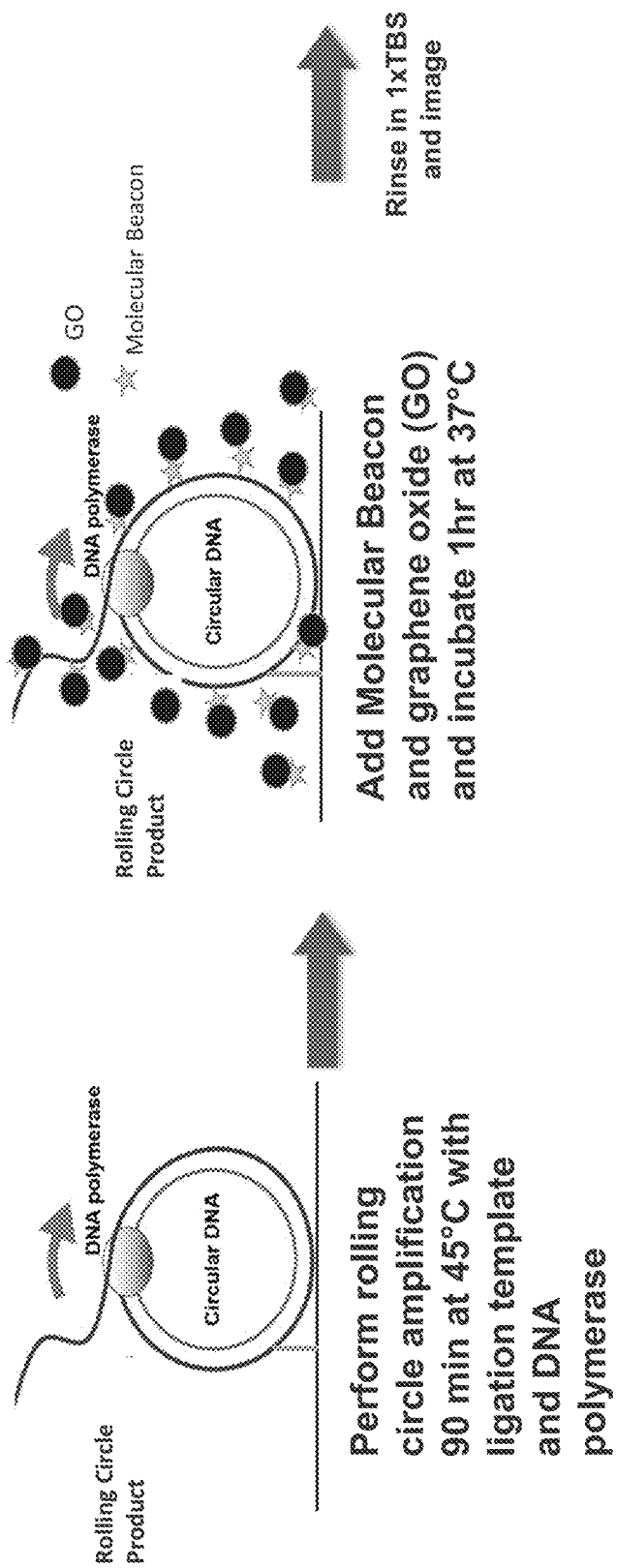
FIG. 35 provides a schematic diagram of a two-step RCA reaction, in which the rolling circle reaction is started, the molecular beacon and graphene oxide are added, and the RCA reaction is further incubated, as described in Example 1.

FIGS. 30, 31, and 32 provide graphs comparing the effects of PEG 200 on the standard RCA reaction conditions, on the enhanced RCA (E-RCA) conditions, and on the E-RCA conditions with additional variations, with or without a 2 hour hybridization time, and with PEG 2000 in place of PEG 200, with a 2 hour hybridization. The reactions in each figure were all performed at the same temperature, with the reactions performed at 30° C., 25° C., and 37° C. in FIGS. 30, 31, and 32, respectively.

The number and pixel size (area, in pixels) of the spots were assessed for each condition. Using the IXM4 microscope, a single pixel width is approximately 334 nm. These data show that in the presence of PEG 200, the 37° C. reaction temperature gave the best combination of high spot count and small spot size. The effect of varying the concentrations of beacon probe using higher RCA reaction temperatures was also examined. Reactions containing 1000, 2000, 4000, or 8000 nM molecular beacon probes were conducted at 37° C. or 45° C., and showed that at the higher temperature, the number of spots counted increased substantially (data not shown). While not limiting the technology to any particular mechanism of action, these data suggest that conducting the reactions at higher temperature, e.g., 45° C. or above, results in more RCA product and more bound beacon probe.

The effect of increased temperature in the presence of varying concentrations of PEG 600 was further examined. FIG. 33 shows microscope images of surfaces of APTES-silanized plates, as described in Example 1, and compares RCA signal for reactions comprising PEG 600 at the indicated concentrations, performed at 37° C. or 45° C. These data show that 45° C. reactions produced substantially higher spot counts, and that 10 to 15% w:v PEG 600 at 45° C. produced the best combination of spot count and spot size.

Figure 36:
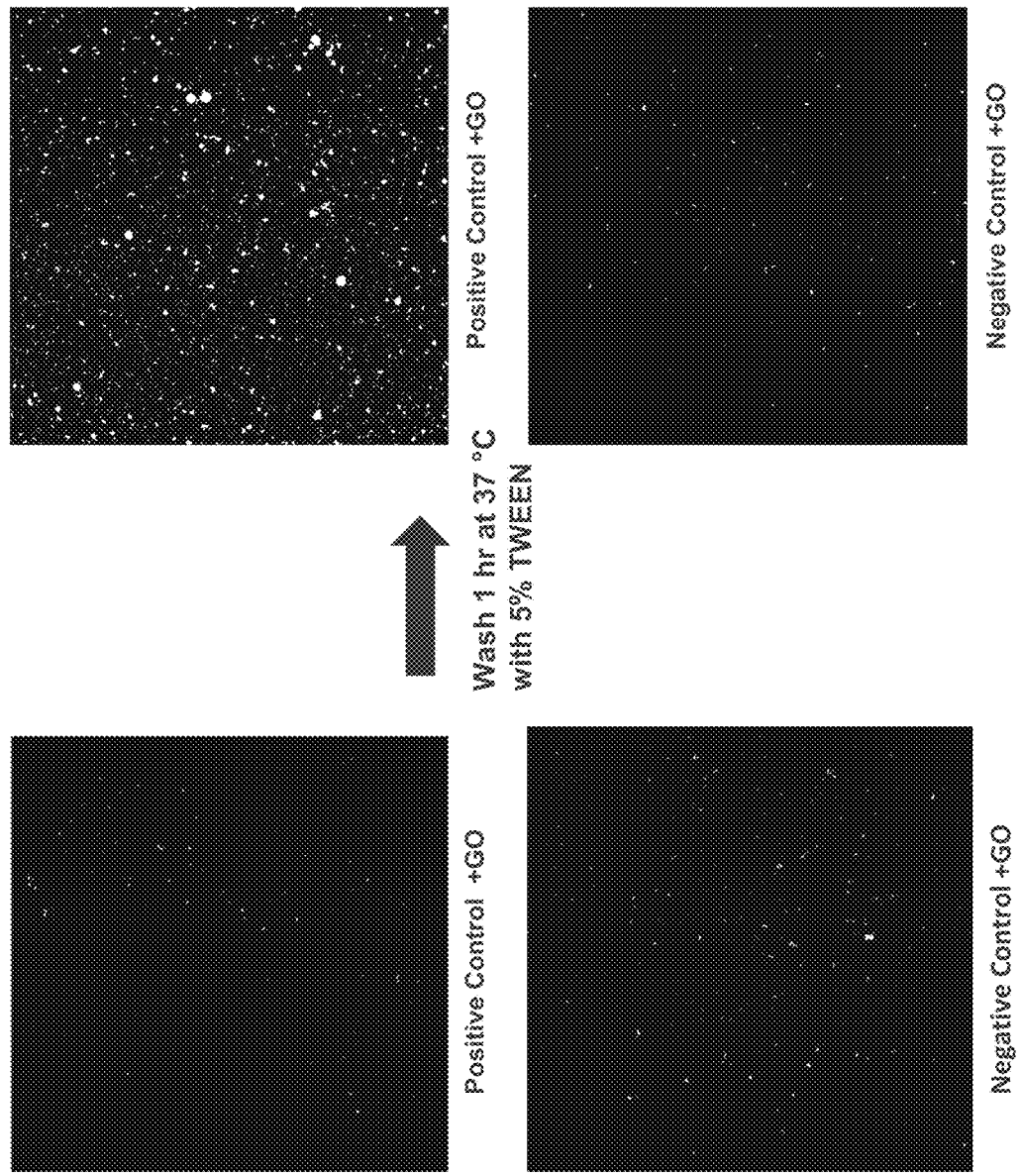
FIG. 36 shows microscope images of surfaces of APTES-silanized plates, as described in Example 1, and shows RCA signal for two-step reactions graphene oxide.
Figure 37:
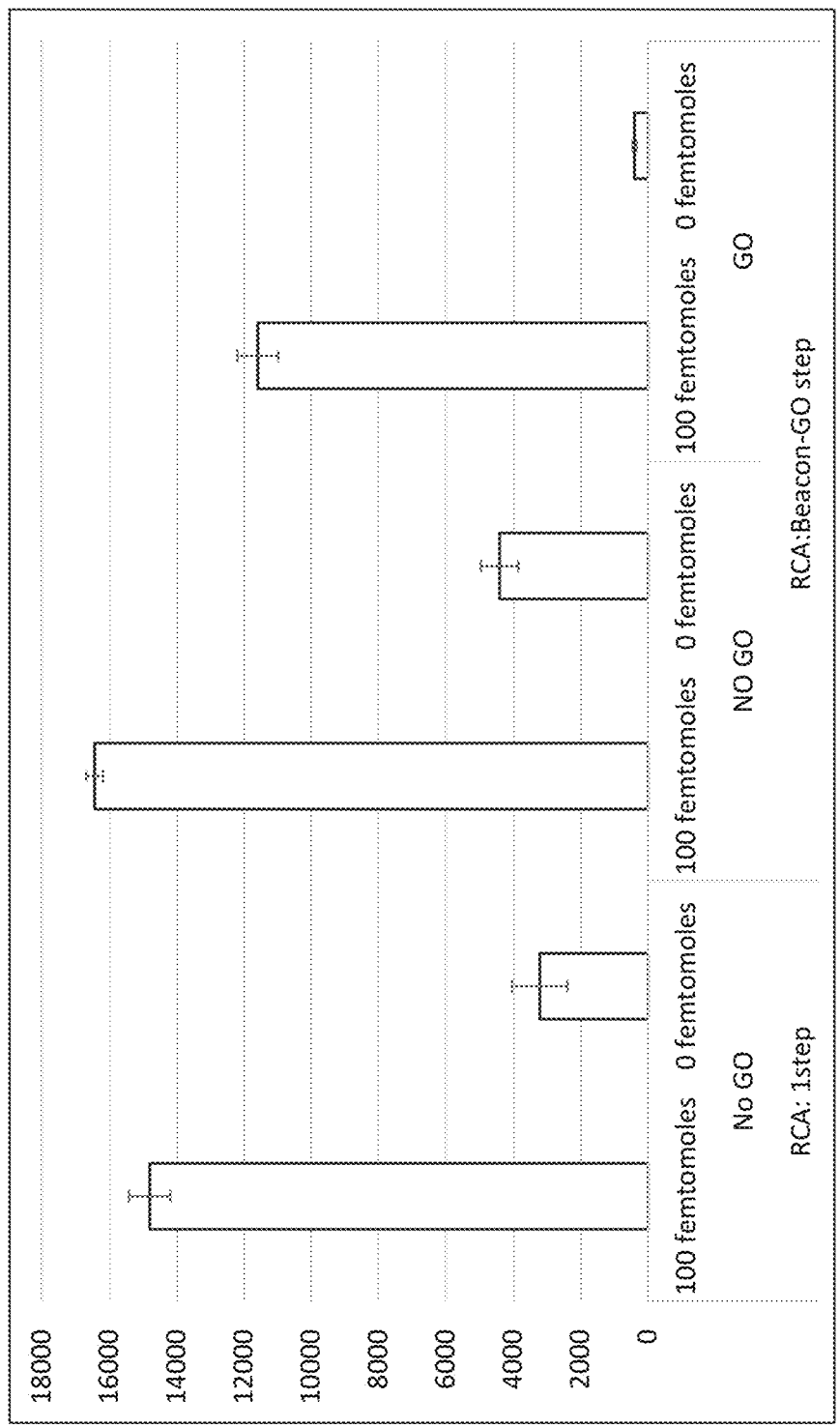
FIG. 37 provides a graph comparing spot counts for RCA reactions done one step (no GO) or two steps (with or without GO), comparing reactions with 100 fmol of circularized MIP to reactions with no circularized MIP.

The effect of adding graphene oxide to the RCA surface-bound reactions was examined. A two-step RCA procedure as described in Example 2 and shown schematically in FIG. 35, was developed. FIG. 36 shows microscope images of surfaces of APTES-silanized plates, as described in Example 1, and shows RCA signal for two-step reactions graphene oxide. The negative control contained no input target and shows background from the molecular beacon probe. FIG. 37 provides a graph comparing spot counts for RCA reactions done one step (no GO) or two steps (with or without GO), comparing reactions with 100 fmol of circularized MIP to reactions with no circularized MIP. These data show that use of GO substantially reduces the number of background spots in the no-target control reactions, improving the signal:background result in the assay.

Figure 38:
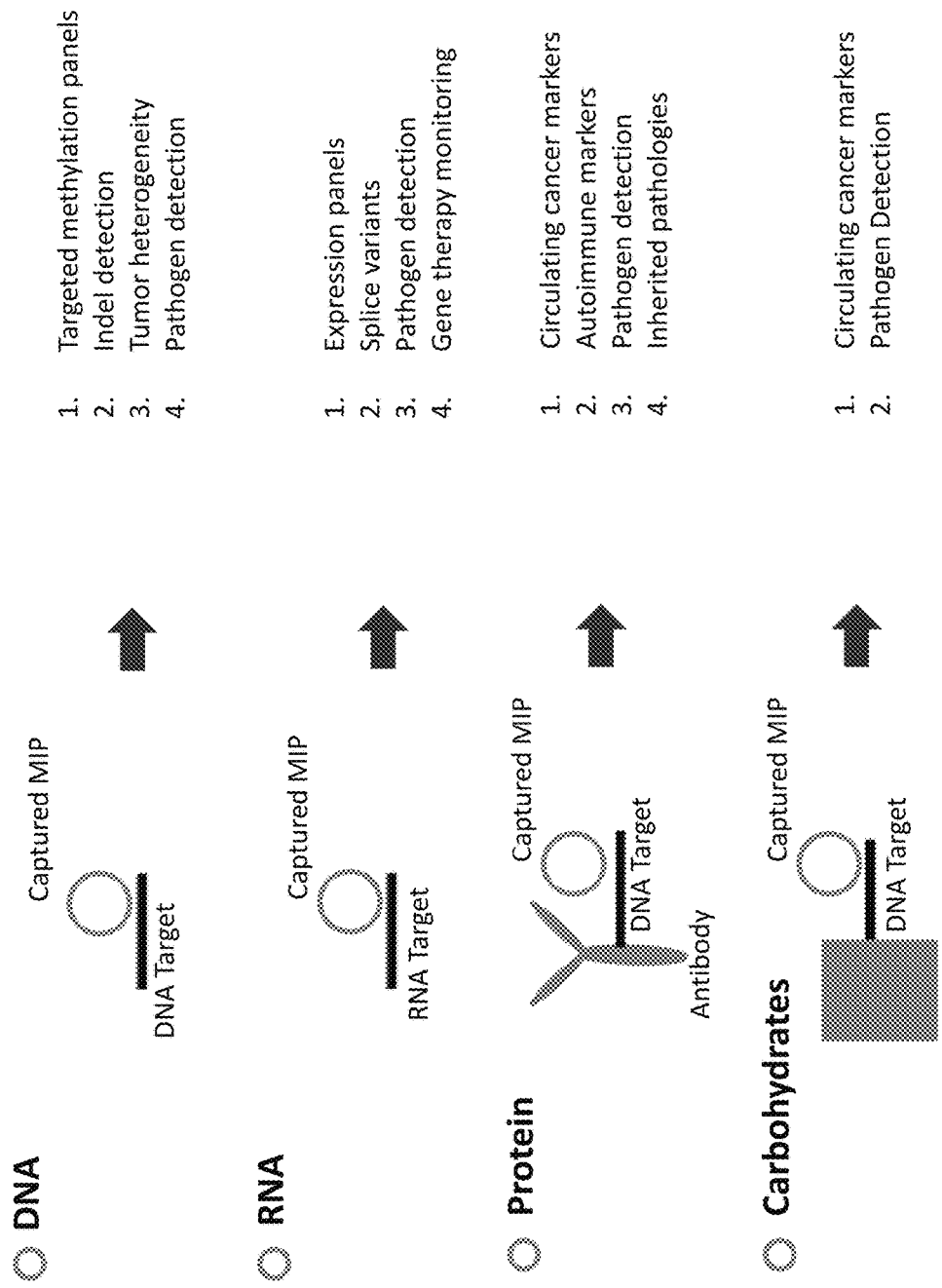
FIG. 38 provides schematic diagrams of different capture complexes for applications of embodiments of the technology to detection of different types of target molecules.
Figure 39:
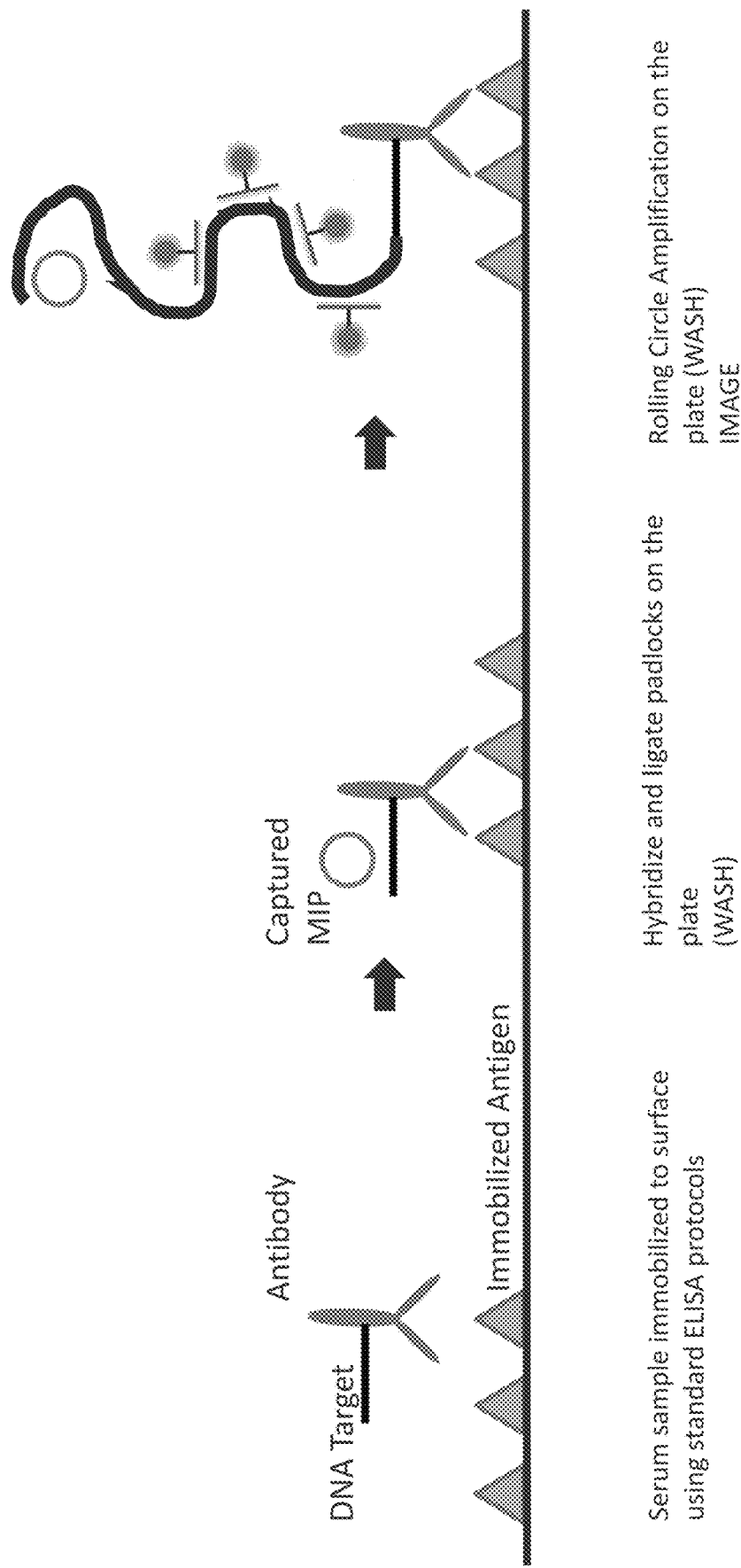
FIG. 39 provides a schematic diagram of applications of the technology to detection of immobilized antigens.
Figure 40:
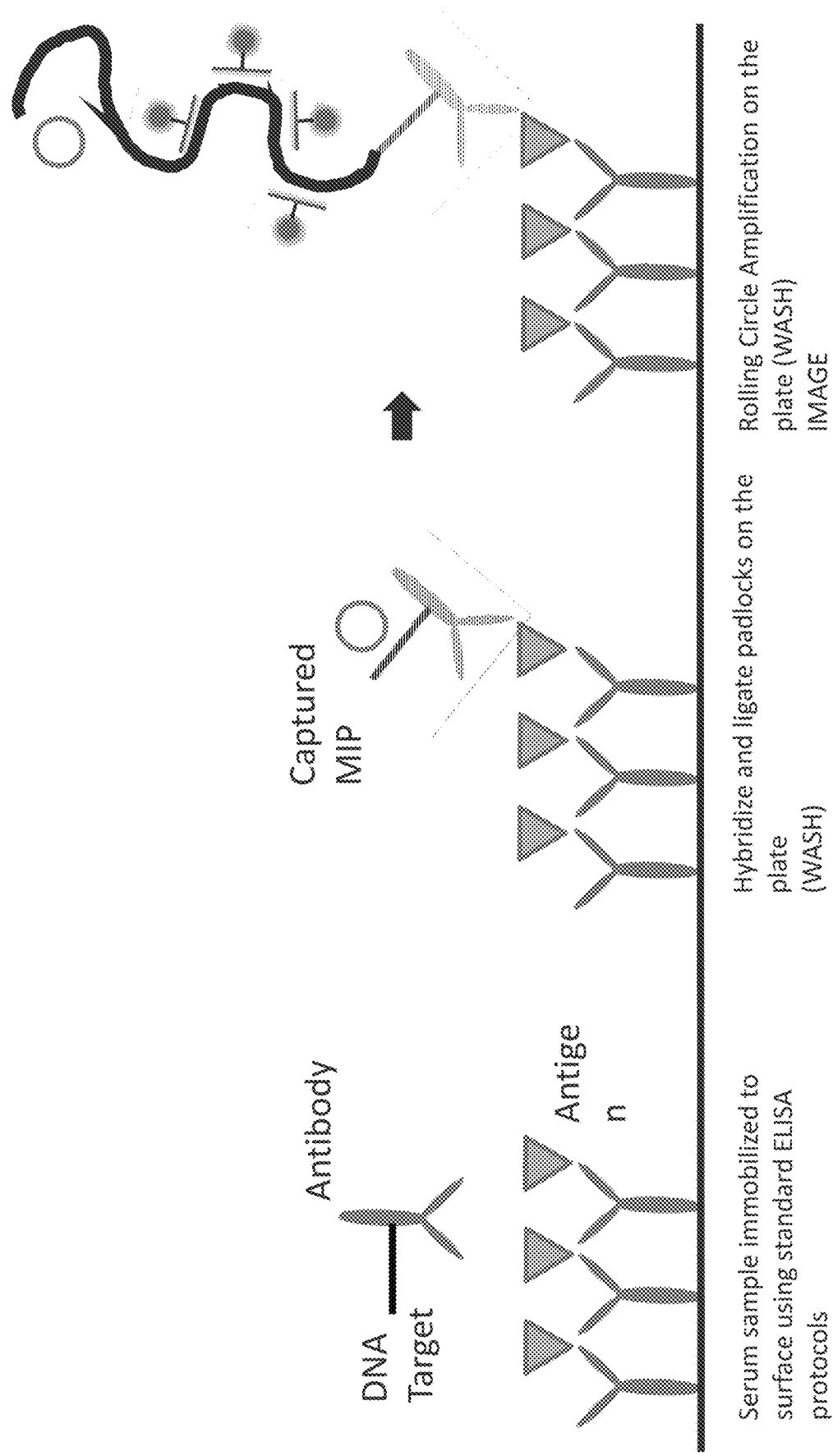
FIG. 40 provides a schematic diagram of applications of the technology to detection of immobilized antigen-antibody complexes.

The technology provided herein is not limited to counting of nucleic acid molecules, and may be applied, for example, to counting other molecules, e.g., macromolecules such as proteins and carbohydrates. FIGS. 38-40 provide schematic diagrams of different capture complexes for applications of embodiments of the technology to detection of different types of target molecules.

Generally, it is preferable to avoid loss of target material, e.g., target cfDNA so as to maximize the sensitivity of assay reactions. Target molecules such as nucleic acid are often lost during purification steps. For example, when matrix binding is used for purification (e.g., chaotrope-mediated binding to glass matrix prior to washing and elution), target material can be lost by incomplete capture from a sample and/or incomplete release from the matrix during elution. Similarly, when precipitation is used, sample can be lost by incomplete precipitation, or by incomplete dissolving after precipitation. Some embodiments of the present technology are configured to reduce or eliminate such purification steps between the steps of the assays. In preferred embodiments, the method is configured such that the fluid environment of each step is compatible with the fluid environment of the following step. A fluid environment for a follow-on step may be considered compatible with a prior step if, for example, it uses the same fluid environment (salts, buffer, detergents, reducing agents, e.g.,) or if the fluid environment of the prior step can be readily adjusted to suit the follow-on step (e.g., by addition of a reagent, buffer, additive, etc., to modify the fluid environment, or by dilution of all or part of the product of a prior step into a fluid environment compatible with the follow-on step). Accordingly, embodiments of the technology provided herein are preferably configured so that the products of each step flow to the next step without intervening purification or isolation steps.

Figure 41:
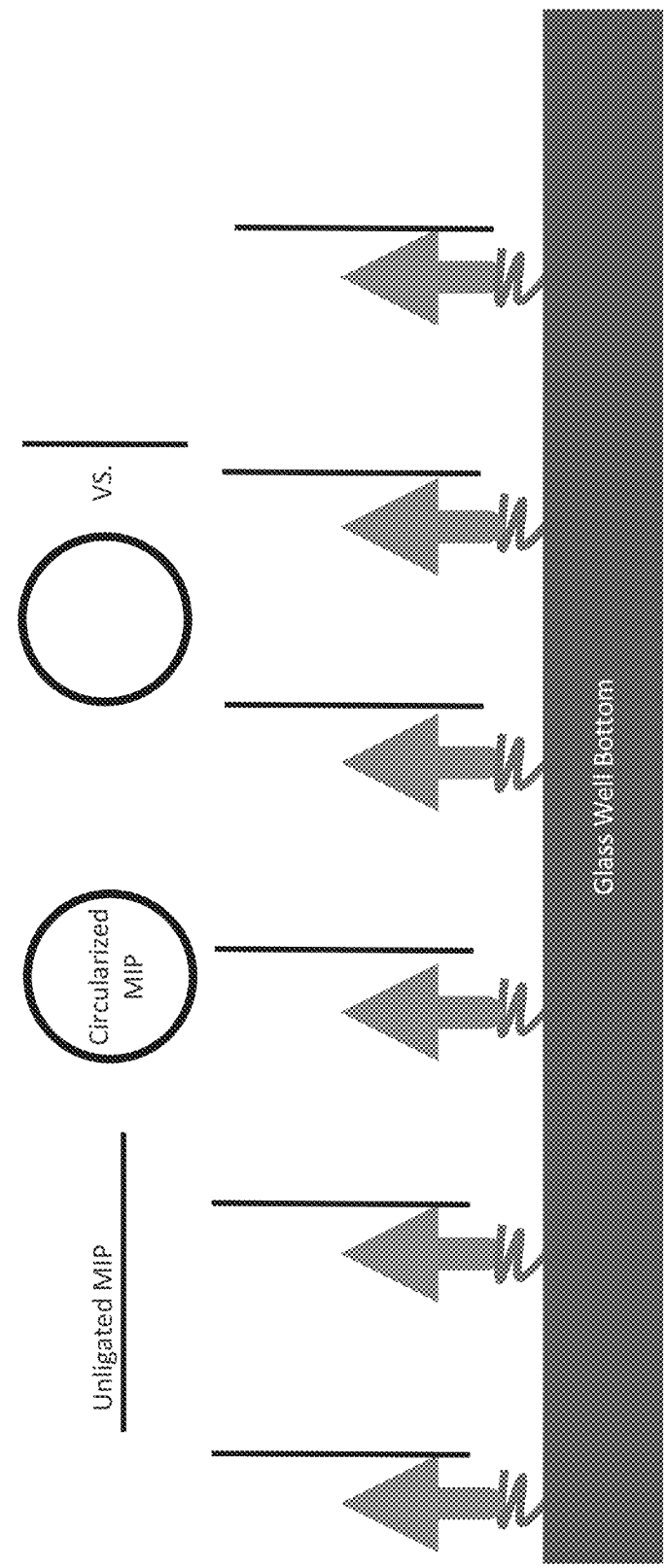
FIG. 41 provides a schematic diagram illustrating interference of surface hybridization of ligated (circularized) MIPs by unligated MIP probes, e.g., in an assay mixture.
Figure 42:
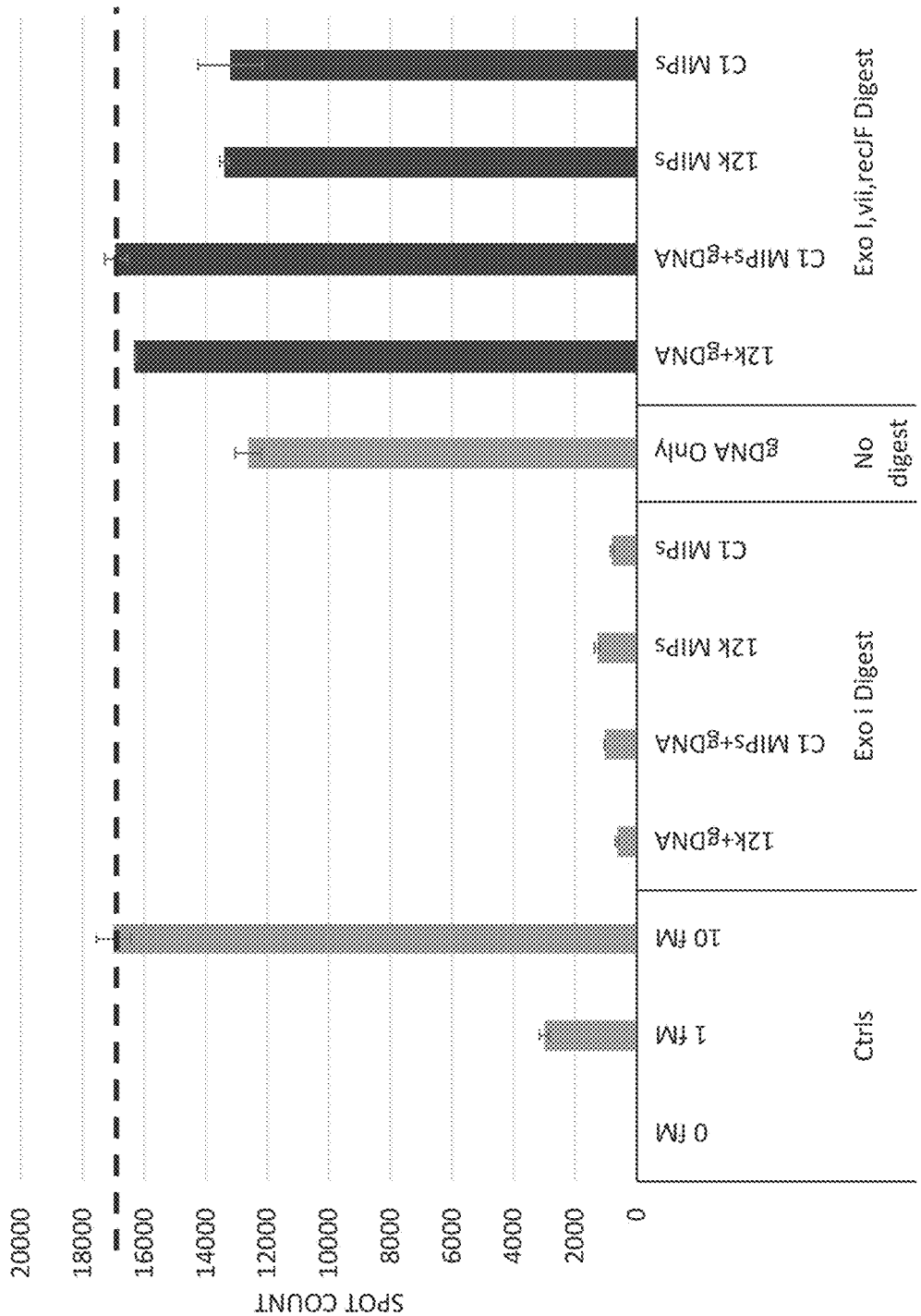
FIG. 42 provides graphs comparing the effects of treating assay mixtures to remove unligated MIP probes prior to hybridizing ligated, circularized MIPs to a surface. These data show the spots counted on a surface after hybridization and rolling circle signal amplification as described herein. These data illustrate that inhibition by excess unligated MIP proves is reduced by treatment of the mixture with a combination of Exo I, Exo VII, recJ$_f$ prior to hybridizing the product to immobilized primers on a surface. Treatment with Exo I alone showed substantial inhibition of circularized MIP hybridization, resulting in low spot counts. Treatment with Exo I in combination with Exo III also showed substantial inhibition of circularized MIP hybridization (data not shown).

In some embodiments, unligated MIP probes used in a capture reaction can inhibit follow-on steps. FIG. 41, for example, illustrates the problem of unligated MIP probes interfering with hybridization of the circular ligated MIPs to primers that are immobilized on a surface. Such inhibition reduces the sensitivity of assays configured to detect and count the ligated MIPs in an assay reaction. During development of the technology, it was determined that a combination of nuclease enzymes could be used to reduce or eliminate interference from the unligated MIP probes. As shown in FIG. 42, the effects of treating the ligated MIP assay mixtures with a single exonuclease, Exo I, were compared to the effects of treating the ligation mixture with a combination of exonucleases prior to hybridizing the circularized MIPs to primers immobilized on a surface. These data show the spots counted on a surface after hybridization and rolling circle signal amplification as described herein, and illustrate that inhibition of hybridization by excess unligated MIP is reduced by treatment of the mixture with the combination of Exo I, Exo VII, and recJ$_f$ prior to hybridizing the product to immobilized primers on a surface. Treatment with Exo I alone showed substantial inhibition of circularized MIP hybridization, resulting in low spot counts (granule counts). Based on these data, it was determined that at least 1000-fold excess of MIP probes could be used, e.g., to drive efficient target binding and ligation, then the excess could be removed by exonuclease treatment to remove inhibition of primer binding. After treatment with exonucleases, preferably with a cocktail of exonucleases selected from, e.g., Exo I, Exo VII, recJ$_f$, and/or Exo T, as described in Example 3, below, the nuclease enzymes are heat killed or otherwise disabled prior to exposing the nuclease-treated MIP mixture to additional single-single stranded and linear oligonucleotides, such as primers or capture probes. In the experiment shown in FIG. 42, the enzymes were heat killed prior to binding of the ligated MIPs to surface-immobilized primers. In other embodiments, nuclease may be selected such that 5' conjugated primers (e.g., conjugated to a nanoparticle or plate surface at the 5' end) and circular molecules such as MIPs are not substrates for the exonuclease activity. For example, these oligonucleotides are not substrate for flap nuclease or 5' to 3' exonucleases, which require a substrate to have a free 5' end for digestion. In addition to the benefits described above, the ability to perform the ligation capture reactions in the presence of a high concentration of MIP probe oligonucleotides also increases the complexity of multiplexing that can be performed using the technology.

Figure 43:
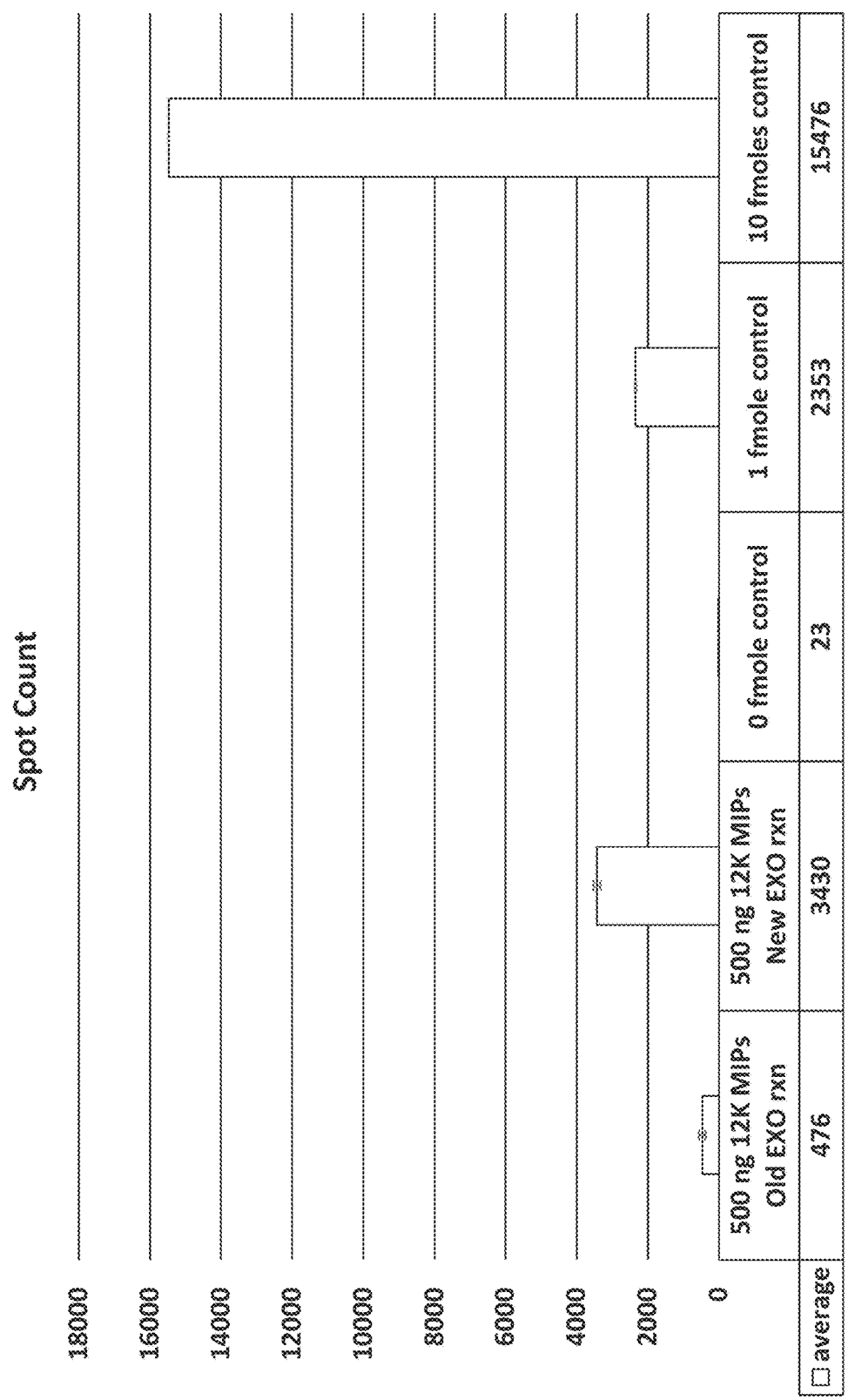
FIG. 43 provides a graph comparing the results of pretreatment of the reaction mixture with an original EXO reaction to the results using an improved nuclease digestion treatment as described herein, as reflected in spot counts indicative of hybridization of circularized MIP probes.

FIG. 43 provides a graph comparing the results of pre-treatment of the reaction mixture with an Exo I reaction to the results using a nuclease digestion treatment comprising Exo I, Exo VII and recJ$_f$, as described herein, as reflected in spot counts indicative of hybridization of circularized MIP probes.

Figure 44:
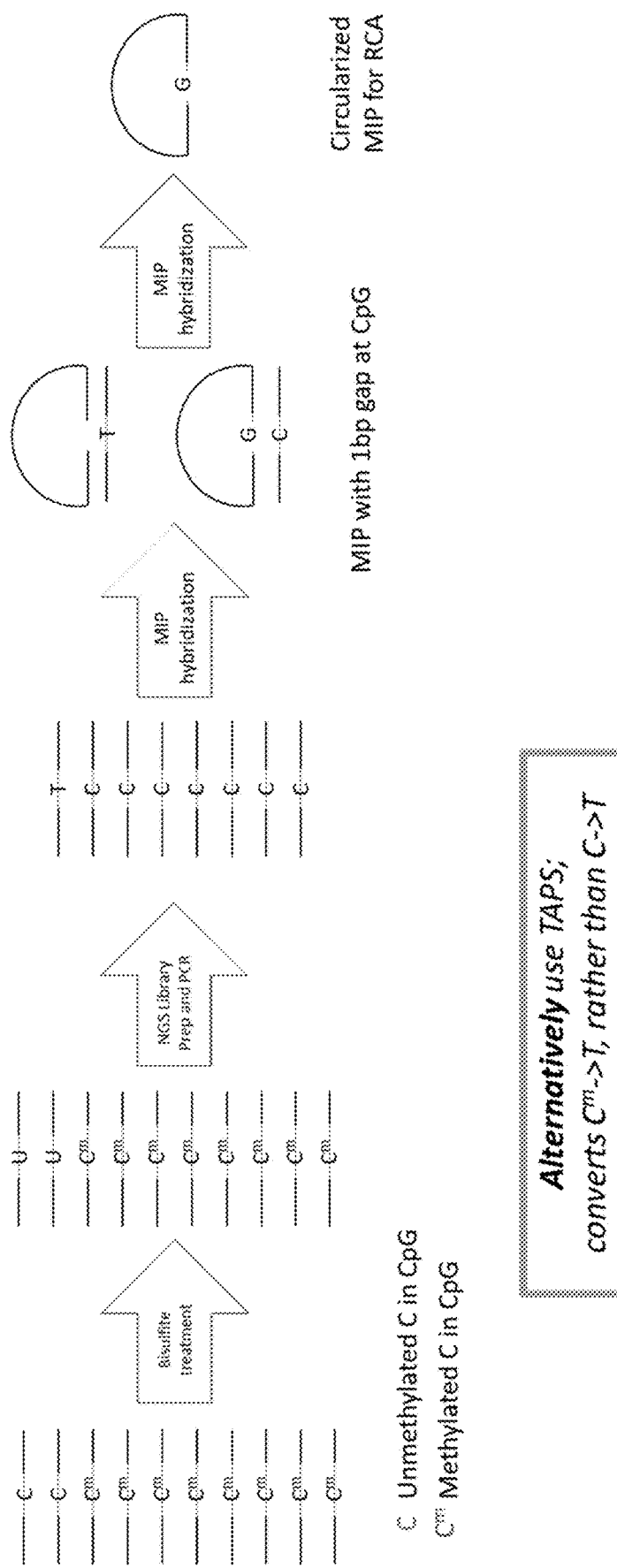
FIG. 44 provides a schematic diagram illustrating use of MIP probes for quantitation of methylation of C residues, e.g., in CpG dinucleotide loci of a hyper- or hypomethylated gene or gene control region. In the illustrated embodiments, unmethylated cytosines are converted to deoxyuracils by treatment with a bisulfite reagent (e.g., sodium bisulfite), such that the methyl C bases can be distinguished from uracils bases using MIP technology. In alternative embodiments, Tet-assisted pyridine borane system is used, in which methylated DNA is treated with ten-eleven translocation (Tet1) enzyme, which oxidizes both 5-methylcytosine (5mC) and 5-hydroxymethylcytosine (5hmC) to 5-carboxylcytosine (5caC). Pyridine borane is then used to reduce 5caC to dihydrouracil, a uracil derivative. Like the uracil in bisulfite converted DNA, the uracil is replaced by a thymine when the DNA is replicated, e.g., in a polymerase chain reaction. (See, e.g., Liu Y, et al., *Nat Biotechnol.* 2019 April; 37(4): 424-429.

FIG. 44 provides a schematic diagram illustrating use of MIP probes for quantitation of methylation of C residues, e.g., in CpG dinucleotide loci of a hyper- or hypo-methylated gene or gene control region. In the illustrated embodiments, unmethylated cytosines are converted to deoxyuracils by treatment with a bisulfite reagent (e.g., sodium bisulfite), such that the methyl C bases ($C^m$) can be distinguished from uracil bases using MIP technology. As illustrated, MIP probes at methylated C loci can be circularized by polymerase extension to incorporate a dG base, followed by ligation to close the resulting nick in the MIP strand.

In other embodiments, a Tet-assisted pyridine borane system is used, in which methylated DNA is treated with ten-eleven translocation (Tet1) enzyme, which oxidizes both 5-methylcytosine (5mC) and 5-hydroxymethylcytosine (5hmC) to 5-carboxylcytosine (5caC). Pyridine borane is then used to reduce 5caC to dihydrouracil, a uracil derivative. Like the uracil in bisulfite-converted DNA, dihydrouracil is recognized as a T base during probe hybridization and is replaced by a thymine when the modified DNA is replicated, e.g., in a polymerase chain reaction. (See, e.g., Liu Y, et al., *Nat Biotechnol.* 2019 April; 37(4):424-429.) Application of the present technology to the counting of methylated and unmethylated loci in molecules may, for example, be used to measure methylation levels without using sequencing methods, such as Illumina bisulfite sequencing. Target DNAs having CpG dinucleotides of known methylation levels (e.g., synthetic controls) can be used to establish standard curves for determining methylation level as measured by spot count. Measuring different degrees of methylation of DNAs finds application in characterizing a large number of disease states, including but not limited to cancers, imprinting disorders such as Prader-Willi disorder, and also in some embodiments, distinguishes between fetal and maternal DNAs.

Factors that influence immobilization and hybridization of oligonucleotides (e.g., primers) include but are not limited to primer density (e.g., overly high density can lead to poor hybridization); electrostatic interference (e.g., repulsion between negative charges of nucleic acid backbone, use of cations, e.g., sodium, potassium, magnesium, etc., to shield negative charges and reduce repulsion); and distance of oligonucleotides from the surface (e.g., direct attachment vs. use of spacer molecules to mimic solution kinetics). For example, higher concentrations of counterion (Na+) have been shown to yield higher densities of immobilized probes and faster immobilization, and heating of the probe film prior to hybridization has also been shown to increase hybridization efficiency. See, e.g., Fuchs, J., et al., Biophysical Journal Volume 99 September 2010 1886-1895; and Peterson, A W, et al, *Nucleic Acids Res.*, 29(24): 5163-5168 (2001), each of which is incorporated herein by reference in its entirety, for all purposes.

During development of the technology, molecules were configured in several different ways in order to measure immobilization and hybridization on a surface. For example, as illustrated in FIG. 45, in some embodiments, primers are immobilized, e.g., via a 5' terminal amine modification (or other functional group for conjugation to a surface). In the embodiment shown, the primer 3' ends contain three dU bases and an AlexaFluor488 tag at the 3' terminus. The immobilized primers are treated with a uracil-specific excision reagent, the USER enzyme cocktail (New England Biolabs) to convert uracils to abasic sites and to cleave of the abasic sites. USER Enzyme is a mixture of Uracil DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released and a polymerase extendible 3' OH is left. See, e.g., Lindhal, T., et al., (1977). J. Biol. Chem. 252, 3286-3294; Lindhal, T. (1982). Annu. Rev. Biochem. 51, 61-64; Melamede, R. J., et al., (1994). Biochemistry. 33, 1255-1264; and Jiang, D., et al., (1997). J. Biol. Chem. 272, 32230-32239. The conversion of the immobilized oligonucleotides into extendible primers can be monitored by monitoring fluorescence released from the oligonucleotides, allowing measurement oligonucleotide immobilization and final primer density.

Figure 47:
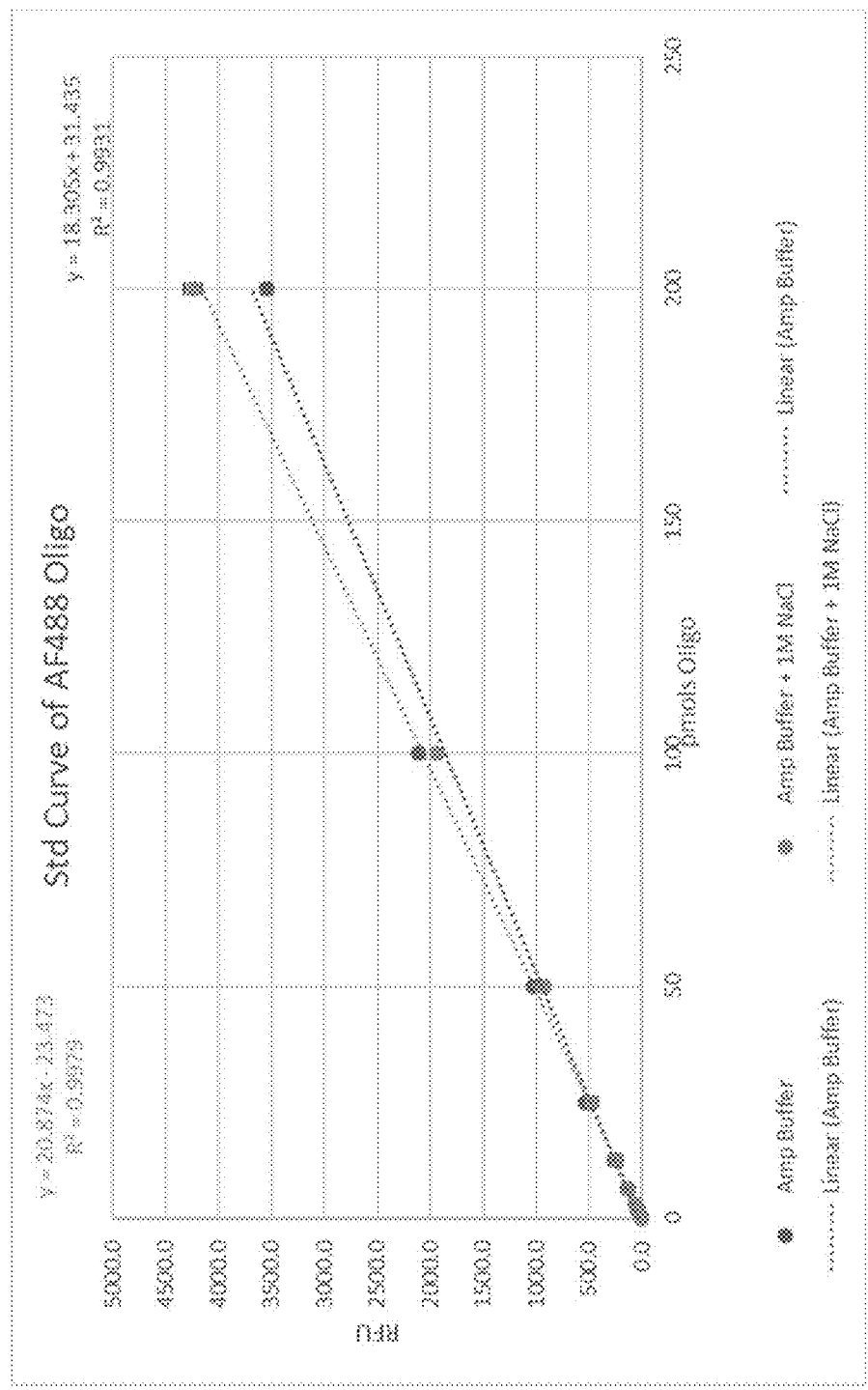
FIG. 47 provides graphs illustrating the correlation between the amount of oligonucleotide immobilized with the measured fluorescence using the method described above for FIG. 46, showing excellent linearity, as well as a limit of detection of less than 100 fmoles.
Figure 47:
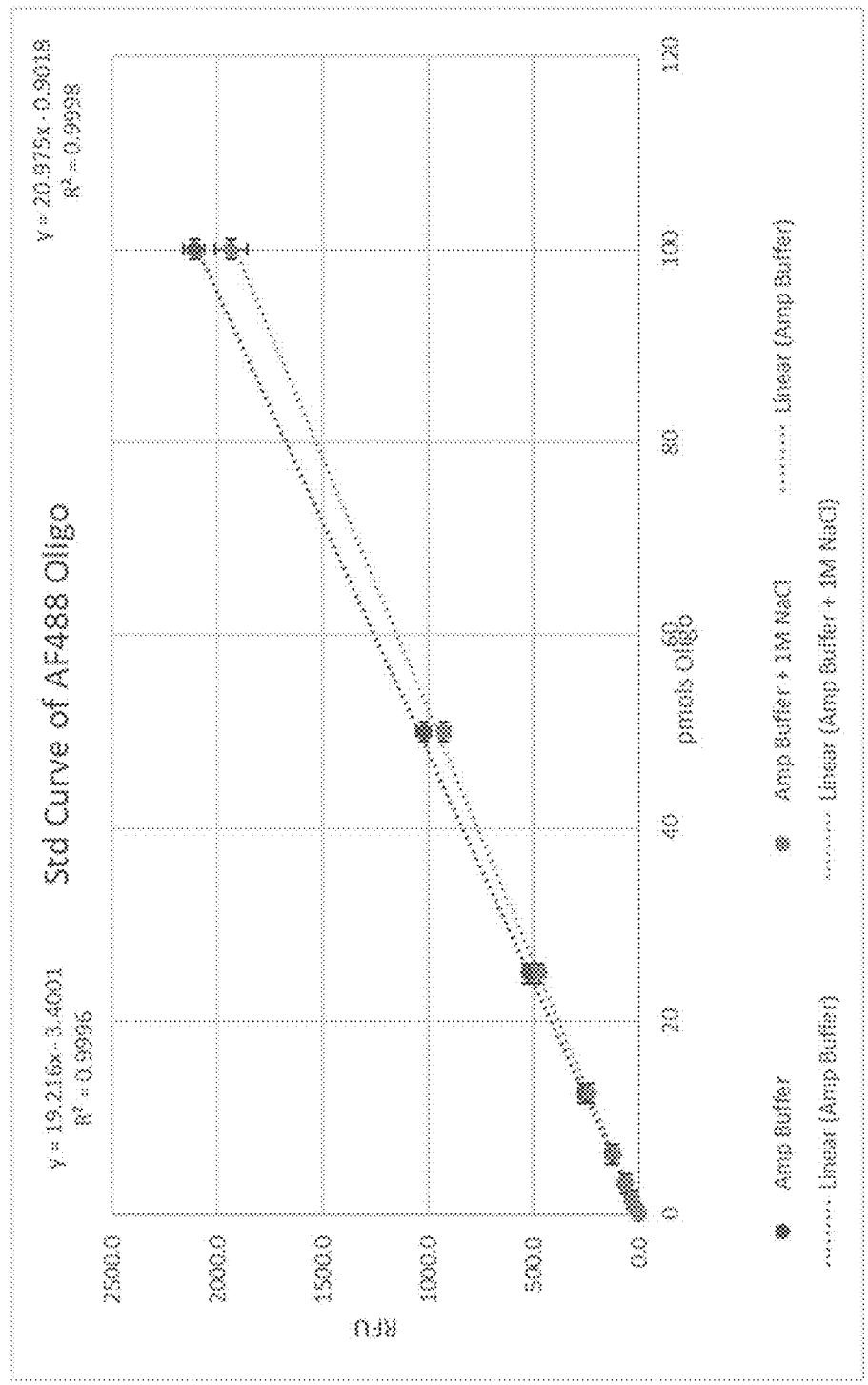

Hybridization to immobilized primers can be similarly tested by hybridization to fluorescently labeled test targets. As illustrated in FIG. 46, primers immobilized to a surface (e.g., via a 5' terminal amine modification) are hybridized to oligonucleotides labeled with a fluorophore (e.g., AlexaFluor488, as shown). After hybridization of the fluor-tagged oligonucleotides, excess tagged oligonucleotides are removed, and the plate is washed. The bound tagged oligonucleotides can be melted off, e.g., with NaOH, the solution neutralized (e.g., with HCl) and the fluorescence released into the solution can be measured (e.g., in a Spectramax plate reader). The embodiment illustrated allows for rapid characterization of hybridization conditions in a manner that is independent of rolling circle amplification efficiency, as illustrated in FIG. 47. The graphs in FIG. 47 show the correlation between the amount of fluorescently labeled oligonucleotide hybridized to immobilized oligonucleotides using the method described above for FIG. 46, with the measured fluorescence showing excellent linearity, as well as a limit of detection of less than 100 fmoles.

Figure 49A:
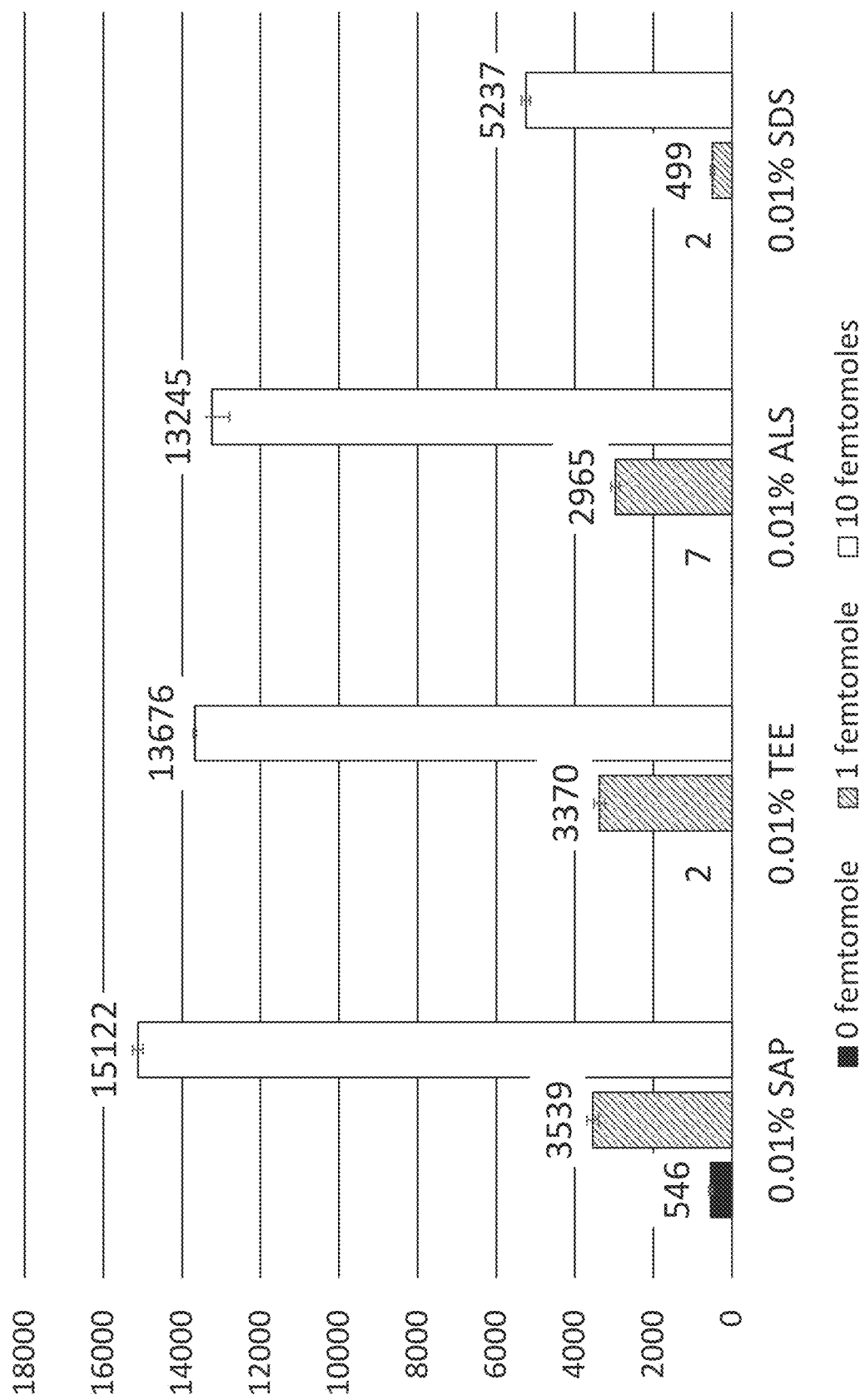
FIG. 49A shows the effects of addition of a detergent (Saponin, Teepol, Ammonium Lauryl Sulfate or SDS) addition on a 2-step protocol in which a molecular beacon probe and the detergent (without graphene oxide) are added after the RCA reaction and incubated for 1 hour at 37° C., as described below.
Figure 49B:
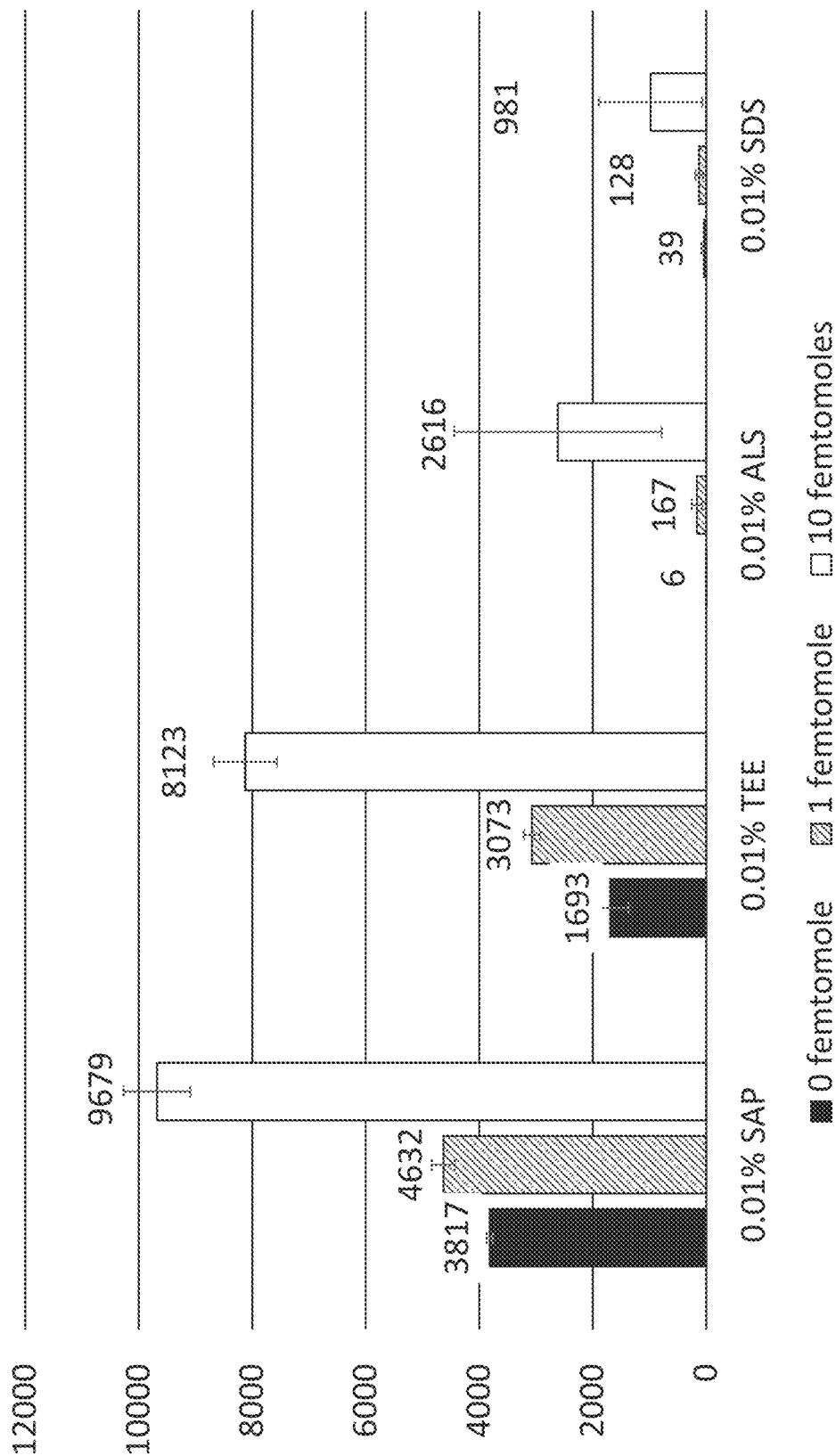
FIG. 49B shows that the effects of addition of a detergent (Saponin, Teepol, Ammonium Lauryl Sulfate or SDS) in a 2-step protocol.

As discussed above, for single molecule detection on a surface, it is preferable that the spot size of the signal (e.g., in pixel area or diameter) from any individual bound molecule be minimized, such that separation between spots is assured and the spots can be resolved by microscopy, e.g., with a light microscope. FIG. 48 shows a comparison of two protocols. The rolling circle-graphene oxide protocol (rGO) used graphene oxide to quench the background false positive signal observed in the no-target ("no input") control wells, but also decreased the overall signal from all wells, including target-containing wells. A two-step protocol was used to examine the effect of treatment with SDS detergent. In the first step, RCA was performed without fluorescent probe. In the second step, the fluorescently labeled probe oligonucleotide was added in the presence of the detergent, in 1× Phi29 polymerase buffer. These data show that the SDS detergent protocol reduced the no input false positive spots, but didn't decrease the signal from other wells, and produced higher spot counts compared to the reactions without SDS. As shown in FIG. 48, the effects treating with SDS during the post-RCA staining step (with molecular beacon probes only) were examined and compared to the graphene oxide protocol. While the use of SDS had a similar effect on reducing the signal in the negative control ("no input") these data show that use of SDS produced higher spot count compared to the use of RCA with molecular beacon stain and graphene oxide without a detergent step. We next tested multiple anionic detergents in this protocol. FIGS. 49A and 49B show that the effects of using detergent in staining RCA products on a surface using molecular beacon probes in either a 2-step protocol (FIG. 49A) or a 1-step protocol (FIG. 49B), as described hereinbelow. These data show that inclusion of detergent reduced background in the no-target control while not quenching fluorescence signal like the graphene oxide protocol on the samples having 1 or 10 fmol of input DNA (circular RCA template).

Figure 50A:
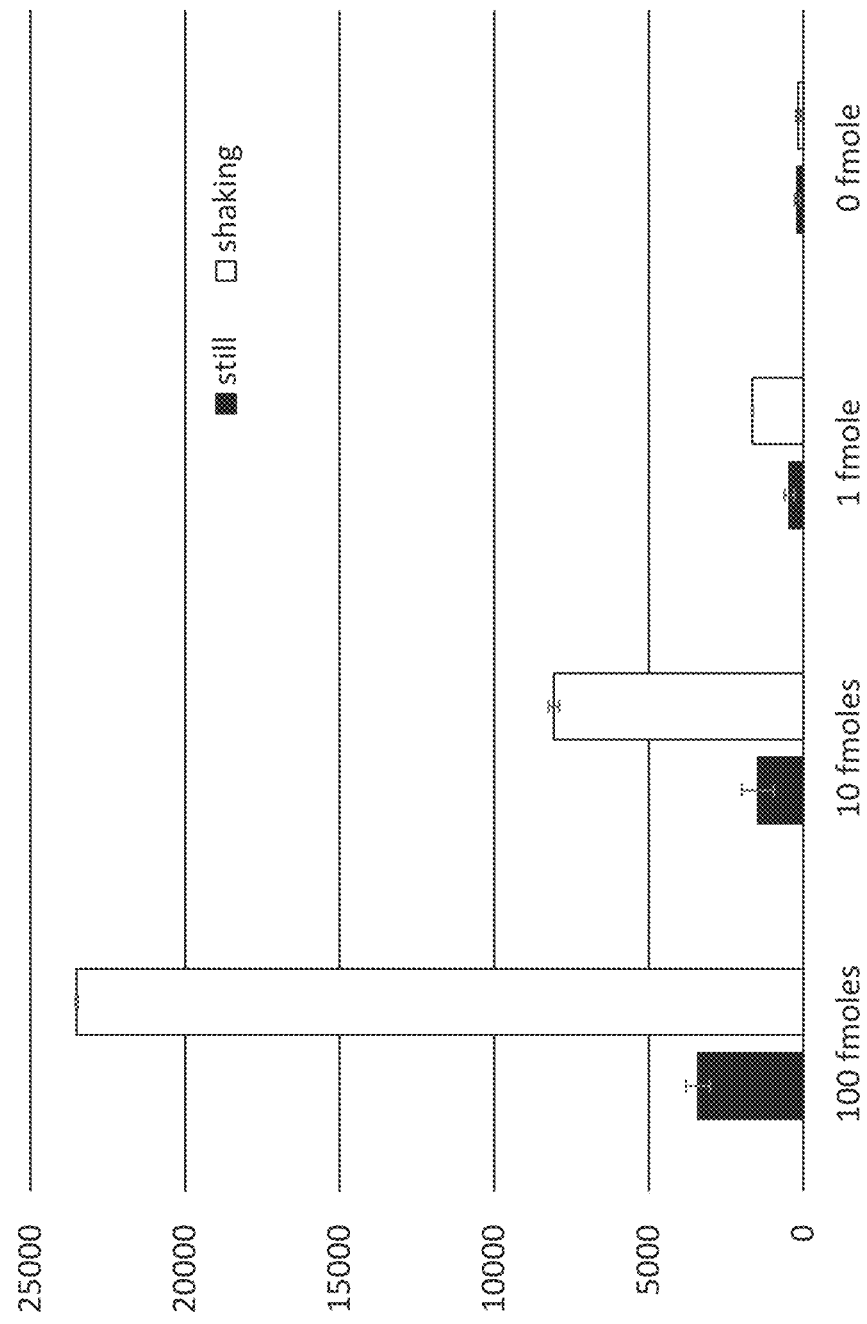
FIGS. 50A and 50B compare the number of spots developed on a during RCA amplification from MIPs localized on a surface in either still reactions, or when the surface is agitated to mix the reagents during the course of the amplification reaction.

When the amplification is performed using a primer conjugated to a fixed surface, e.g., a reaction well surface rather than a suspended bead surface, the amplification reagents may be locally depleted during the reaction. Accordingly, embodiments of the technology, e.g., the 1-step or 2-step reaction protocols described below, may include intermittent mixing steps (e.g., every 1, 2, 3, 4, 5, 6, 7, 8, 9, 10, 11, 12, 13, 14, 15, etc. minutes) to re-distribute reagents at time points throughout the reaction step incubations (e.g., during probe hybridization, rolling circle amplification, fluorescent probe hybridization, etc.). Mixing is not limited to any particular method and may comprising vortexing, bumping, rocking, tilting, or ultrasonic mixing. See, e.g., Ishigaki and Soto, *Micromachines* 2018, 9:272, which is incorporated herein by reference for all purposes. In FIG. 50A, the count of spots on a surface generated with surface-immobilized primers for RCA, in reactions performed without shaking ("still") or with intermittent shaking ("shaking") are compared. These data show that intermittent mixing produced a much larger number of detectable spots than the still reactions produced.

During development of the technology, the effects of shaking on different steps of the RCA assay were examined, as follows:

|  | 25° C. 90 min Input Hyb | 45° C. 90 min RCA | 37° C. 60 min RCA + GO + Beacon | 37° C. 60 min 5% Tween |
|---|---|---|---|---|
| Exp 1 | Shake | Still | Still | Still |
| Exp 2 | Still | Shake | Still | Still |
| Exp 3 | Still | Still | Shake | Still |
| Ctrl 1 | N/A | Still | N/A | N/A |
| Ctrl 2 | N/A | Shake | Still | Still |

Circular MIP oligonucleotides were hybridized to a surface-bound primer at 25° C. for 90 min. Rolling circle amplification was conducted at 45° C. for 90 min, and the RCA products were hybridized to fluorescent oligonucleotides in the presence of graphene oxide at 37° C. for 60 min. The products were washed with 5% Tween 20 at 37° C. for 60 min., then measured for the number of countable spots at concentration. Control 1 was a one step RCA protocol that was not shaken at any time and Control 2 was a two step control RCA that was shaken during the RCA and held still during the fluorescent stain with the detergent. All conditions had the same circularized MIPs as input. The shaking protocol incubating the RCA reactions at 45° C. for 90 minutes, with at-temperature mixing at 1500 rmp for the first 30 seconds of each 15 minute interval, as described below in Example 5.

Figure 50B:
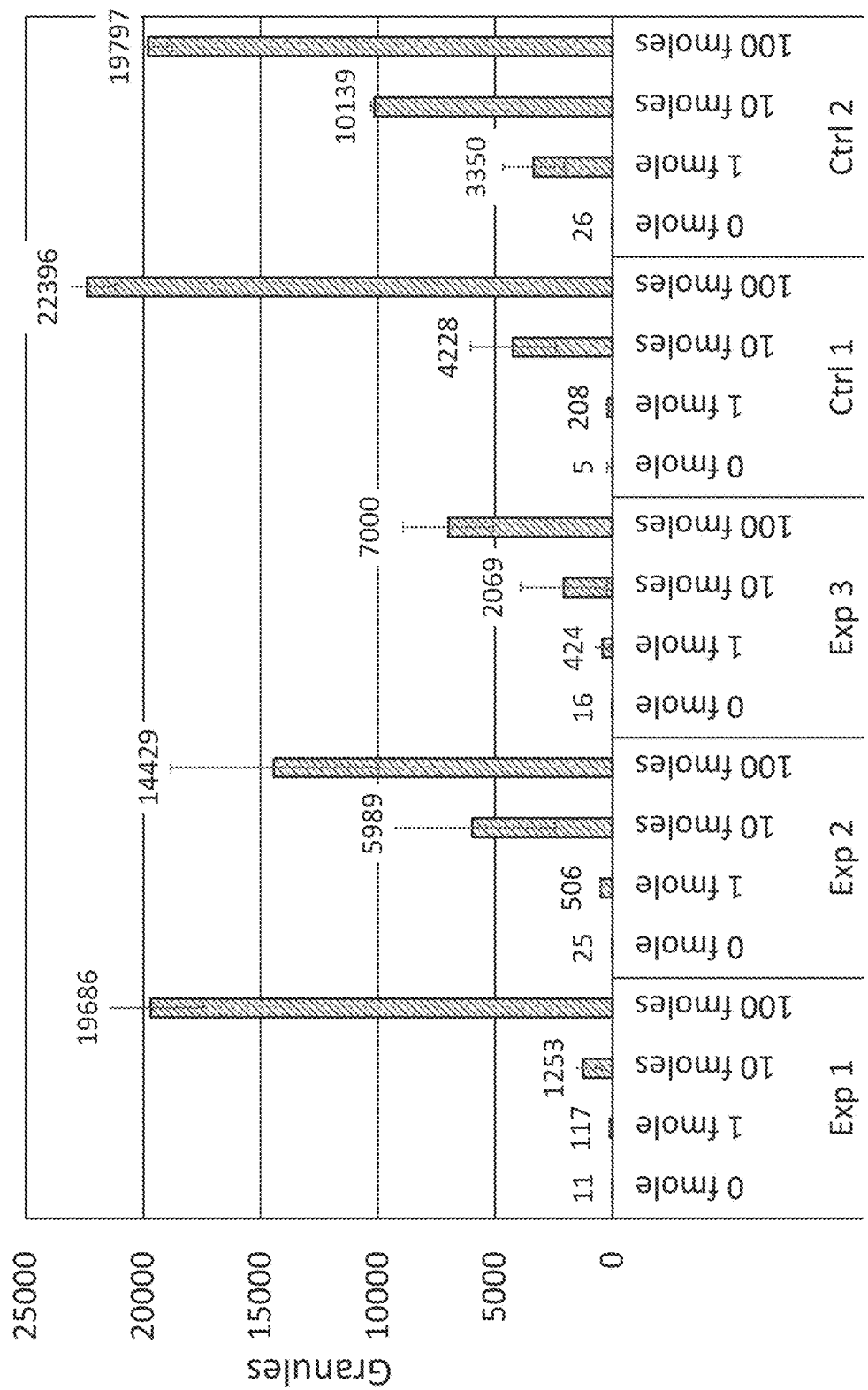
Figure 52:
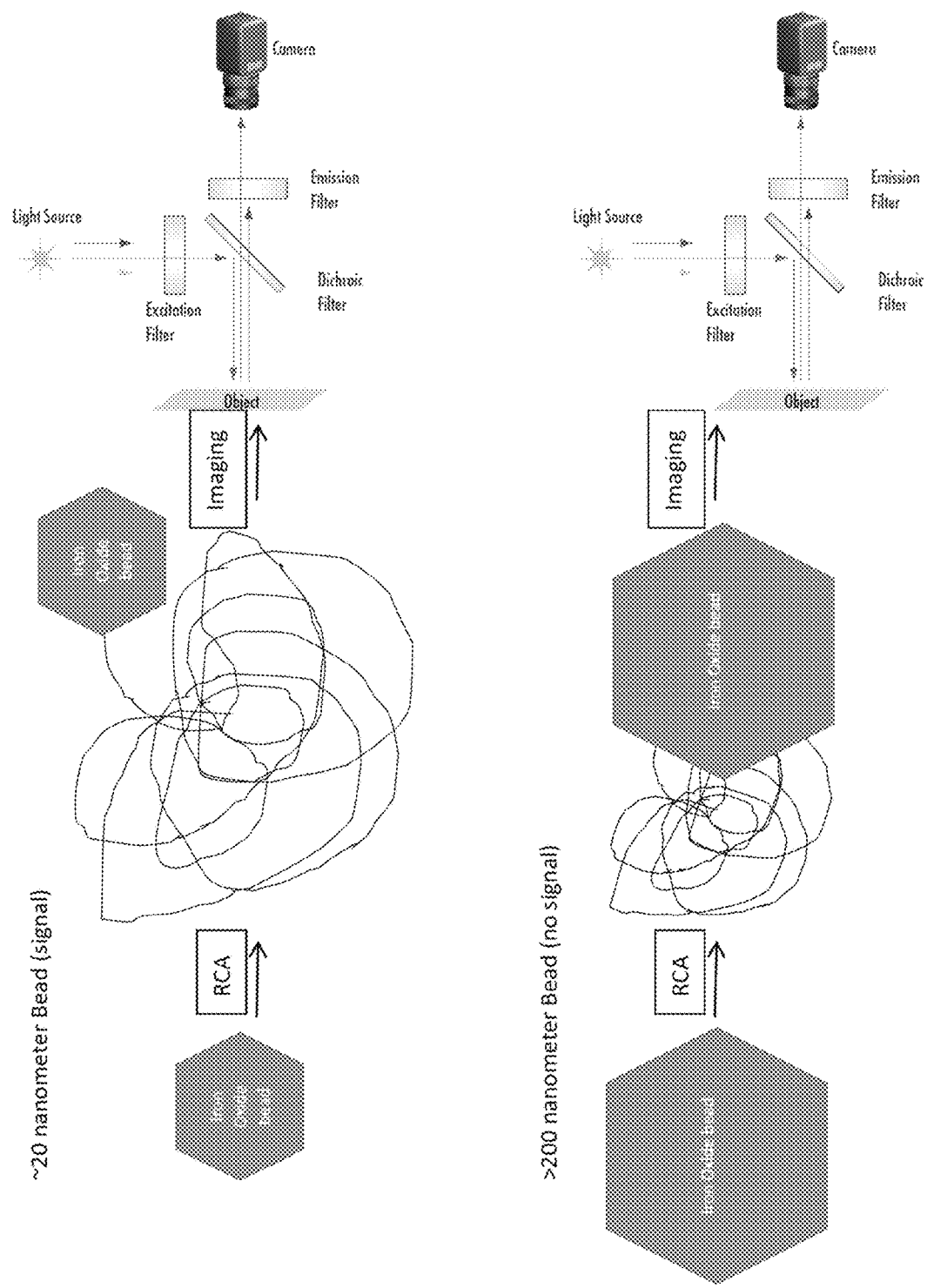
FIG. 52 provides a schematic diagram illustrating the effect of using small nanoparticles, e.g., nanoparticles of about 20 nm diameter, compared to using large nanoparticles, e.g., nanoparticles of greater than about 200 nm. As shown, large nanoparticles can interfere with imaging RCA products.
Figure 53:
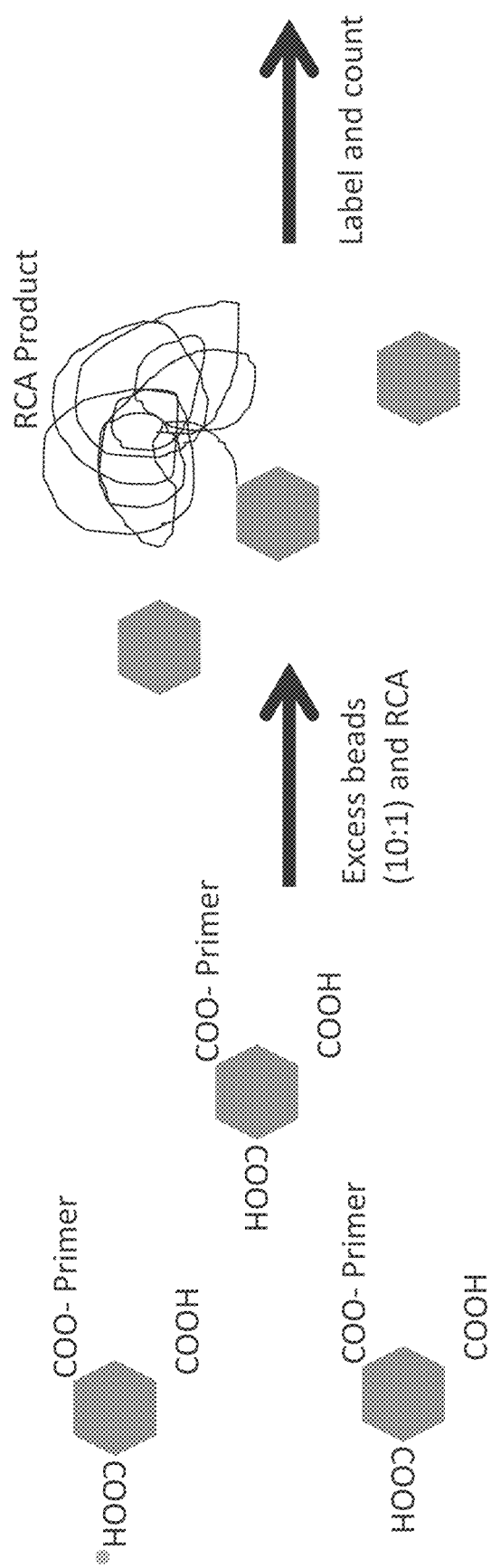
FIG. 53 provides a schematic diagram of an embodiment of the technology in which primers attached to nanoparticles, e.g., small iron oxide nanoparticles, are used to prime RCA amplification to form RCA product attached to nanoparticles.

The results are shown in FIG. 50B. These data show that shaking the RCA step provided the largest improvement in signal across different amounts of input MIPs.

The depletion effect may also be reduced or avoided when the amplification is performed in solution rather than on a fixed surface. Accordingly, in some embodiments, rolling circle amplification may be performed in solution. In some embodiments the resulting product may be localized to a support or surface after amplification, e.g., by hybridization to a probe that is bound to a surface, or by magnetic or centrifugal manipulation of suspended to particles to bring them to a surface, such that detection is done with the products localized to a surface. FIG. 51 shows an example of iron oxide nanoparticles that are derivatized to provide carboxyl groups on the surface. As shown schematically, an oligonucleotide such as a primer may be linked to the nanoparticle via the reactive group.

Paramagnetic particles typically used for nucleic acid manipulations, e.g., for DNA purification or bead-emulsion PCR, are generally much larger than the 10 nm nanoparticles shown in FIG. 51. For example, DYNABEADS magnetic beads are >1 µm in diameter, and surface-activated DYNABEADS comprising carboxyl or other reactive groups (ThermoFisher Scientific, Inc.) come in 1 µm, 2.8 µm, and 4.5 µm sizes. However, as discussed above, products detected by microscopy, e.g., RCA products labeled with fluorescent probes on the surface of a slide or well, are preferably of a one or a few pixels in diameter, with each pixel being approximately 200 nm×200 nm for a light microscope, or 334 nm×334 nm for the IMX4 microscope. Thus, as illustrated schematically in FIG. 52, beads having a diameter of more than about 200 nm can block fluorescence signal from a product across one or more pixels, or can mask the presence of RCA product entirely, making imaging difficult. During development of the technology it has been recognized that use of very small nanoparticles, e.g., paramagnetic particles that are less than a pixel in diameter, preferably less than about 50 nm, more preferably about 20 nm in diameter, may be used in embodiments in which the RCA reaction (or another front-end reaction) may be performed on suspended nanoparticles, such that the reaction kinetics are more similar to a reaction performed in solution, while the reaction product may be manipulated magnetically or by, for example, centrifugation, to localize the products at a surface, e.g., the bottom of a well, for back-end detection, e.g., by microscopy. Use of the very small nanoparticles can reduce or eliminate masking of fluorescence signal by the particle. In other embodiments, reaction products on particles may be measured without such localization, using, e.g., flow cytometry.

In-Solution Amplification

In some embodiments, hybridization of ligated MIPs to immobilized oligonucleotides (e.g., primers attached to a surface) may exhibit reduced efficiency, e.g., because of a lower effective concentration of the immobilized oligonucleotides. Additionally, the primer, MIP and enzyme and need to assemble at the surface, and surface charge and the density of the primers no the surface may also influence the reaction efficiency.

Accordingly, in some embodiments of the technology, oligonucleotides are hybridized to circularized MIPs in solution and are then localized or associated with a surface, e.g., a surface of a well, either before or after a further step, e.g., rolling circle amplification. In certain embodiments, surface-localized RCA products are detected by microscopy, as described hereinabove. Optionally, spacer molecules are included as modifications to primers or to capture oligonucleotides complementary to primers, such that immobilized primers or RCA products are further from the support surface, e.g., during primer extension and/or probe hybridization.

Figure 56:
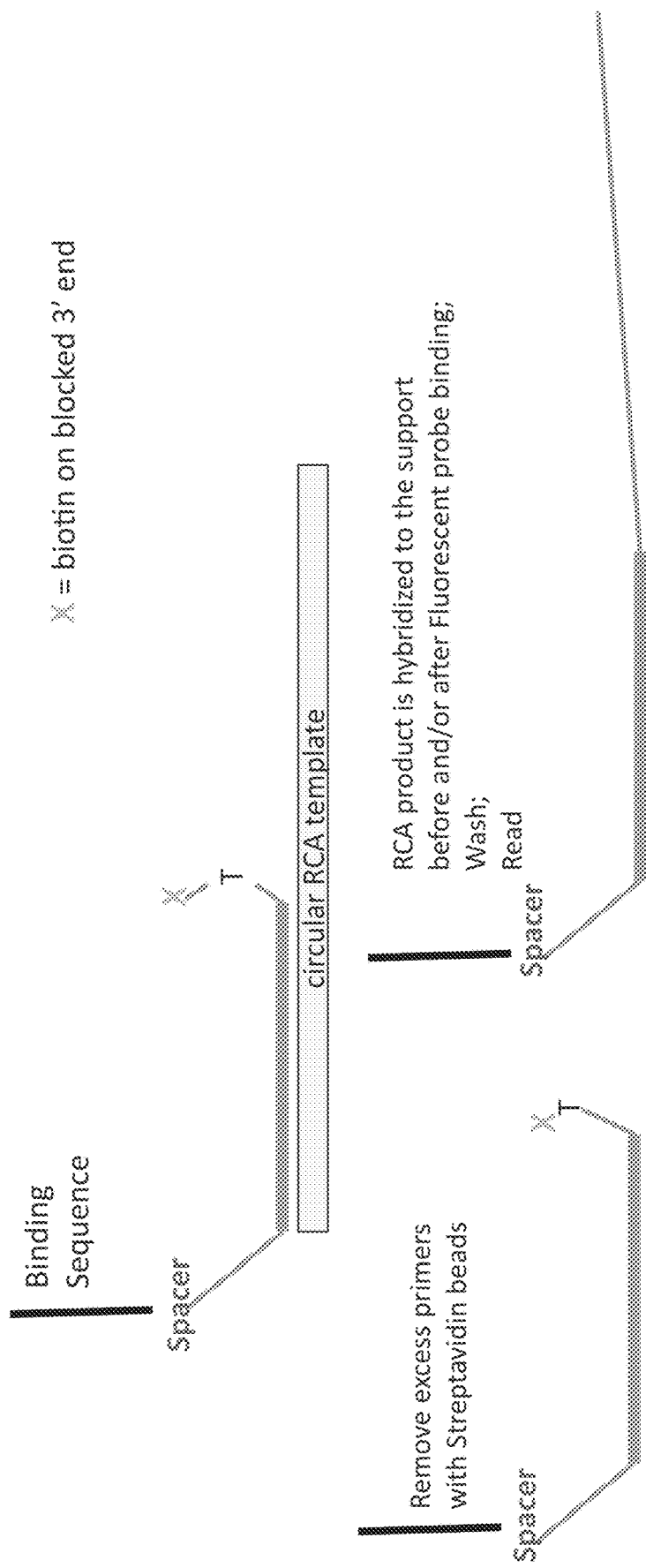
FIG. 56 provides a schematic diagram of an embodiment of the technology in which primers comprise a capture sequence on the 5' end and a biotinylated oligonucleotide block on the 3' end. In the embodiment of the diagram, a primer oligonucleotide hybridizes to s circularized RCA template in solution and the Phi29 polymerase removes the 3' block and extends the primer to form an RCA product. Excess primers that are not extended retain the 3' biotin and may be removed, e.g., with streptavidin-coated beads. The RCA product is captured by hybridization to an immobilized capture oligonucleotide e.g., on a plate or well surface for detection. The RCA product is hybridized with labeled probes, e.g., molecular beacon probes, before or after capture on the surface, the labeled, immobilized complex is washed and detected.

FIG. 56 illustrates an embodiment of the technology detected by hybridization to an RCA primer in solution. In this embodiment, an in-solution primer ("in-sol" primer") is hybridized to a circularized MIP probe (e.g., a padlock probe or other MIP probe that has been successfully ligated after successful specific hybridization to a target nucleic acid in a sample). In the embodiment shown, the primer comprises an unextendible 3' end, e.g., a nucleotide that is mismatched to the MIP template, or that comprises a modification at the 3' position of the ribose. 3' blocking nucleotides can be removed, e.g., by a 3' to 5' exonuclease "proofreading" activity of a DNA polymerase such as Phi29 polymerase, preferably in a template-dependent fashion, to render a template-bound primer extendible, while leaving unhybridized primer oligonucleotides blocked. In some embodiments, proofreading and primer extension are performed by a single enzyme, while in other embodiments, proofreading may be performed by a first enzyme, e.g., an autonomous 3'-5' exonuclease, and extension of the unblocked end may be performed by a second enzyme, a DNA polymerase. The technology is not limited to any particular form of 3' block, and any form of nucleotide that lacks a 3' OH group required for extension by a DNA polymerase may be used. Examples of nucleotides lacking 3' OH groups include dideoxy "chain terminator" nucleotides and nucleotides comprising a 3' group such as a 3' phosphate, 3' hexanediol (6-carbon chain), 3' O-methyl, 3' O-acyl, 3' O-allyl, 3' O-ether, 3' O-methoxymethyl, 3' O-nitrobenzyl, 3' O-azidomethylene, 3' C7-amine, or other substituent in place of the 3' OH group (see, e.g., D. Hutter, et al., *Nucleosides Nucleotides Nucleic Acids.* 29(11):1-18 (2010), which is incorporated herein by reference in its entirety).

In the embodiment shown in FIG. 56, the 3' end comprises a moiety for capturing and removing excess primers. In some embodiments, the 3' end of the primer comprises one or more biotins, (e.g., biotin dT, biotin on a triethyleneglycol (TEG) spacer, dual biotin), which can be used to capture unextended primers, e.g., using streptavidin beads or the primer may comprise a hapten such as 2,4 dinitrophenol (2,4 DNP) or digoxygenin, bindable by an antibody that recognizes the hapten.

EXPERIMENTAL EXAMPLES

Example 1

This example provides examples of work-flows for analysis of DNA, e.g., cfDNA, from a sample such as a blood sample.

Sample Collection

Blood is collected in a standard draw from patient. A 10 mL of blood stored in a Streck blood collection tube or alternative EDTA-containing blood collection tube. The sample is transported into a lab at ambient temperature and processed as follows:
  Centrifuge blood at 2000×g for 20 minutes at room temperature to obtain a plasma fraction from the blood.
  Transfer plasma into a new, sterile, nuclease-free polypropylene tube and centrifuge at 3220×g for 30 minutes.

Cell-Free DNA (cfDNA) Purification

Cell-free DNA is purified from plasma using standard methods, e.g., using a MagMAX Cell-Free DNA isolation kit (Thermofisher Scientific, Cat. No. A29319).

Assay Plate Preparation

Glass bottom microtiter plates are treated to immobilize an oligonucleotide that primes the rolling circle amplification of a circularized MIPs. Several approaches can be used (see, e.g., E. J. Devor, et al., "*Strategies for Attaching Oligonucleotides to Solid Supports,*" Integrated DNA Technologies (2005), which is incorporated herein by reference in its entirety, for all purposes.)

1) Acid Prewash

For each method, glass bottom plates are first acid washed as follows:
  (a) Add 100 µL of 0.5 N sulfuric acid into each well.
  (b) Add foil seal to plate.
  (c) Incubate plate at 37° C. for 2 hours rotating at 300 RPM.
  (d) Remove well contents.
  (e) Wash wells twice with 100 µL molecular-grade water.
  (f) Wash wells twice with 100 µL of 95% ethanol.

2) 3-Aminopropyltriethoxysilane (APTES) Silanization and Streptavidin-Biotin Primer Immobilization:
  (a) Prepare 2% APTES by adding 200 µL 99% APTES (Sigma Aldrich, Cat. No. 440140), 500 µL molecular-grade water, and 9.3 ml 95% ethanol.
  (b) Vortex solution and pipet 100 µL into each well.
  (c) Incubate at room temperature for 15 minutes.
  (d) Remove well contents.
  (e) Wash wells twice with 100 µL of 95% ethanol.
  (f) Remove last wash.
  (g) Incubate plate at 37° C. for 24 hours.
Primer Immobilization
  (h) To the amine-functionalized glass plates, add 1 nanogram of streptavidin in 100 µL of Tris-buffered saline.
  (i) Incubate at room temperature for 1 hour.
  (j) Wash each well three times with 100 µL of TBS.
  (k) Add 100 µL of a 1 µM solution of biotinylated oligonucleotide.
  (l) Incubate at room temperature for 1 hour.
  (m) Wash each well three times with 100 µL of TBS.

3) Acrylic Silanization and Acrydite Primer Immobilization
  (a) Prepare 4% acrylic silane by adding 400 µL 99% acrylic silane (3-(Trimethoxysilyl)propyl methacrylate; Sigma Aldrich, Cat. No. 440159), 1 mL molecular-grade water, and 18.6 mL 100% ethanol.
  (b) Add 100 µL of 4% acrylic silane solution to each well.
  (c) Incubate at room temperature for 15 minutes.
  (d) Remove 4% acrylic silane solution.
  (e) Wash each well four times with 100 µL of 100% ethanol per wash.
  (f) Incubate plate at 37° C. for 24 hours.
  (g) Prepare solution of acrydite-primer by adding
    (i) 250 µL 5×TRIS Boron EDTA (TBE) buffer,
    (ii) 500 µL 40% acrylamide,
    (iii) 17.5 µL 10% ammonium persulfate,
    (iv) 5 µL tetramethylethylenediamine (TEMED),
    (v) 25 µL 100 µM oligonucleotide primer comprising a '5' acrydite (or acrylic-phosphoramidite)
    (vi) 1.7 mL of molecular-grade water.
  (h) Add 25 µL of acrydite primer solution to each well and gently agitate plate to cover well bottom.
  (i) Incubate at room temperature for 30 min.
  (j) Wash wells four times with 100 µL 0.5×TBE, discarding the first three washes and leaving the last wash in well, before continuing to RCA assay.

Primers may be immobilized by other methods, e.g., as described by Devor, et al., supra. In some embodiments, plates are treated with a monomer, e.g., dopamine or a derivative thereof, under conditions wherein a polymerized surface is formed and primers, e.g., primers comprising a 5' amine modification, are conjugated to the polymer surface.

In some embodiments, spacer of various lengths are used between the surface and the oligonucleotide, to increase hybridization efficiency. In some embodiments, the hybridization efficiency is modified, e.g., by modifying primer density on the surface, spacer length, salt, temperature hybridization, etc.

Molecular Inversion Probe Pool

A probe pool is used to capture specific loci in a DNA sample, e.g., a cfDNA sample, and create circularized MIPs for rolling circle amplification. NIPT assays generally comprise a pool of molecular inversion probes. In preferred embodiments, a NIPT assay comprises about 5,000-100,000 molecular inversion probes.

Targeted MIPs are created to target features to be investigated by the assay (e.g., chromosomes 13, 18, 21, X, Y, and CHR22q11.2).

Approximately 5,000 to 100,000 unique MIPs, preferably 5,000 to 50,000, preferably 10,000 to 40,000, preferably 20,000 to 30,000 unique MIPs are created for each feature.

MIPs are mixed together to create a probe pool with each probe at a custom concentration.

MIP Capture of cfDNA and Ligation

MIP Pools are added to the purified cfDNA in the following reaction.

2 µL of AMPligase Buffer (10×), 1 µL of a 10 µM MIP Probe Pool, 16 µL of cfDNA prep, 1 µL of AMPligase (5 units), and 0.5 mM (final concentration) of NAD+ (β-Nicotinamide adenine dinucleotide; New England Biolabs).

Reactions are incubated at 98° C. for 2 to 3 minutes and cooled at 1 degree per minute until they reach 45° C., then held for 2 hours at 45° C. In some embodiments, reactions are cooled at 1 degree per minute to 56° C., held for 120 min., then reduced to 45° C. and held for an additional 120 min. In some embodiments, MIP oligonucleotides hybridized to target regions in, e.g., cfDNA leave a gap in the MIP strand. Thus, in some embodiments, MIP 3' ends are extended, e.g., with a polymerase, to fill the gap and produce a ligatable nick.

In some embodiments, reactions are treated with an exonuclease such as E. coli Exo I, to reduce the amount of unligated MIP probe in the mixture. In preferred embodiments, the technology provides treatment with a nuclease or a cocktail of nucleases, e.g., one or more of Exo I, Exo VII, Exo T, and recJ$_f$ (New England Biolabs, Inc., Ipswich, Mass.) prior to rolling circle amplification. Exonuclease I (Exo I, E. coli) is a DNA-specific exonuclease that catalyzes the removal of nucleotides from single-stranded DNA in the 3' to 5' direction; Exonuclease VII (Exo VII, E. coli) is a DNA-specific, single-strand specific exonuclease that cleaves in both the 3' to 5' and 5' to 3' directions. Exonuclease T (or "RNase T") catalyzes removal of nucleotides from linear single-stranded DNA or RNA in the 3' to 5' direction. RecJ$_f$ is a single-stranded DNA specific exonuclease that catalyzes the removal of deoxynucleotide monophosphates from DNA in the 5' to 3' direction (Lovett, S. T., Kolodner, R. D. (1989). Proc. Natl. Acad. Sci. USA. 86, 2627-2631.) RecJ$_f$ is a recombinant fusion protein of E. coli RecJ and maltose binding protein (MBP). It has the same enzymatic properties as wild-type RecJ, but fusion to MBP enhances RecJ$_f$ solubility.

In preferred embodiments the MIP ligation mixture is treated with a cocktail of 2 or more of Exo I, Exo VII, Exo T, and/or recJ$_f$ nucleases prior to hybridization of the MIPs with primers, e.g., surface immobilized primers. In particularly preferred embodiments, the nuclease-treated MIP ligation mixture is then applied to a surface without intervening purification by, e.g., by spin column, matrix binding, or precipitation. In particularly preferred embodiments, the nucleases are neutralized, e.g., heat killed prior to mixing the ligated, nuclease-treated MIP mixture with additional nucleic acids, e.g., primers.

Molecular Beacon Probes

Examples of molecular beacon probes that find use in the technology are as follows:

```
                                            (SEQ ID NO: 24)
5'Alexa 405-CCTCAGGTGTGTAACTCGATCAGmGmAmGmG-
dabcyl 3'

(SEQ ID NO: 25)
5'Alexa 488-CCTCAATGCTGCTGCTGTACTACmGmAmGmG-
dabcyl 3'

(SEQ ID NO: 26)
5'Alexa 594-CCTCAGGTGTGTAACTCGATCAGmGmAmGmG-BHQ2 3'

(SEQ ID NO: 27)
5'Alexa 647-CCTCAGCGCTGCCTATTCGAACTmGmAmGmG-
BHQ2 3'

(SEQ ID NO: 28)
5'Alexa 750-CCTCAGGTGTGTAACTCGATCAGmGmAmGmG-BHQ3 3'
```

These molecular beacon probes may be used individually or in multiplex combinations.

Fluorophore Labeled Probes

Examples of fluorescently labeled probes (without quencher moieties) that find use in the technology are as follows:

```
                                            (SEQ ID NO: 29)
        5'Alexa 488N/ATGCTGCTGCTGTACTAC 3'

(SEQ ID NO: 30)
        5'Alexa 546N/AGACAGCTAACTCAGACC 3'

(SEQ ID NO: 31)
        5'Alexa 594N/GGTGTGTAACTCGATCAG 3'

(SEQ ID NO: 32)
        5'Alexa 647N/CGCTGCCTATTCGAAC 3'

(SEQ ID NO: 33)
        5'Alexa 700N/CTGAAGTACCGCACGAAT 3'

(SEQ ID NO: 34)
        5'Alexa 750N/CATGGACGAGCTGTACAA 3'
```

These fluorescently labeled probes may be used individually or in multiplex combinations.

Standard Rolling Circle Amplification Assay Conditions

For a 100 µL RCA solution, combine on ice

MIP probe-target DNA preparation (e.g., entire MIP capture/cfDNA preparation described above, approximately 20 µL)

10 µL of 10× Phi29 Buffer for a 1× final concentration

1× Phi29 DNA Polymerase Reaction Buffer 50 mM Tris-HCl 10 mM MgCl$_2$ 10 mM (NH$_4$)$_2$SO$_4$ 4 mM DTT (pH 7.5 @ 25° C.)

200 µM of each dNTP 5 units of Phi29 DNA polymerase 100 nM Beacon probe molecular-grade water to 100 µL Incubate 30° C. to 37° C. for reaction time, e.g., 90 to 120 minutes.

Enhanced RCA (E-RCA) Conditions:

For a 100 µL Enhanced RCA solution, combine on ice

MIP probe-target DNA preparation (e.g., entire MIP capture/cfDNA preparation described above, approximately 20 µL);

10 µL of 10× Phi29 Buffer for a 1× final concentration

800 µM total dNTPs
80 units of Phi29 DNA polymerase
1000 nM Beacon probe
molecular-grade water to 100 µL Incubate 30° C. for reaction time, e.g., 90 to 120 minutes.

One-Step Enhanced Rolling Circle Amplification on a Surface

Prepare Rolling Circle Amplification (RCA) solution
  For a 100 µL RCA solution, combine on ice
    MIP probe-target DNA preparation (e.g., entire MIP capture/cfDNA preparation described above, approximately 20 µL);
    10 µL of 10× Phi29 Buffer for a 1× final concentration
      1× Phi29 DNA Polymerase Reaction Buffer
        50 mM Tris-HCl
        10 mM MgCl$_2$
        10 mM (NH$_4$)$_2$SO$_4$
        4 mM DTT
        (pH 7.5 @ 25° C.)
    4 µL of 10 mM or each dNTPs, for a 0.4 mM total dNTPs final concentration;
    50 µL of filtered 30% PEG 600;
    0.5 µL of 100 µM Molecular Beacon for a final concentration of 0.5 µM
    2-8 µL of Phi29 polymerase (10 units/µL); and
    22.5-28.5 µL of molecular-grade nuclease-free water
  Mix solution, e.g., by vortexing, and pipet onto treated glass surface comprising bound primers, then seal plate;
  Incubate plate on flat bottom heat block of a thermomixer with a thermo-lid, at 45° C. for 90 minutes;
  Remove well contents and wash well two times with 100 µL of 1×TBS; discard wash solution;
  Add 100 µL of 1×TBS, and image in microscope, as described below.

Imaging Samples with IXM4 Microscope (Molecular Devices, San Jose, Calif.)

Typically, 20×, 40×, or 60× objectives are used to capture images.
  Plates are placed in an IXM4 microscope (Molecular Devices, Inc.) and imaged as follows:
    Plates are auto-exposed to ensure a broad dynamic range (maximum range of the camera used such as 16-bit images) in the fluorescence intensity values.
    Each well of the plate is sub-divided into approximately 100 images.
For high-throughput assays, automated microscopes may be used.

Image Analysis
  Images are analyzed as follows:
    Relative fluorescence intensity was determined in images containing no sample (negative control).
    A threshold was determined by multiplying the average relative fluorescent intensity from the negative control by three.
    Spots above the threshold using a localized threshold cutoff calculated above are counted in each channel.

Variations on One-Step Protocol
  Crowding reagent (e.g., PEG) addition: prepare a 30% solution in molecular-grade water; filter with a 0.2 µm pore size filter. Add PEG to the RCA reaction, adjusting the water added to the RCA to maintain consistent volume.
  Beacon: add desired concentration, adjusting the water added to the RCA to maintain consistent volume.
  dNTPs: add desired concentration, adjusting the water added to the RCA to maintain consistent volume.

Detergents and detergent mixtures: Perform a 2-step reaction, adding a detergent or detergent mixture with the labeled probes. In some embodiments, a surface may be washed with a detergent mixture after addition of the labeled probes.

Intermittent mixing: 1-step or 2-step reaction protocols may include intermittent mixing steps (e.g., every 1, 2, 3, 4, 5, 6, 7, 8, 9, 10, 11, 12, 13, 14, 15, etc. minutes) to re-distribute reagents at time points throughout the reaction step incubations (e.g., during probe hybridization, rolling circle amplification, fluorescent probe hybridization, etc.). Mixing is not limited to any particular method and may comprising vortexing, bumping, rocking, tilting, or ultrasonic mixing. See, e.g., Ishigaki and Soto, *Micromachines* 2018, 9:272, which is incorporated herein by reference for all purposes.

Graphene oxide: Perform a 2-step reaction, adding graphene oxide with the labeled probes, as described in Example 2, below.

Example 2

Detection Using Two-Step Rolling Circle Amplification on a Surface

Prepare Rolling Circle Amplification (RCA) solution on ice:
  For a 100 µL RCA solution (without molecular beacon), combine:
    MIP probe-target DNA preparation (e.g., entire MIP capture/cfDNA preparation described above, approximately 20 µL);
    10 µL of 10× Phi29 Buffer for a 1× final concentration
      1× Phi29 DNA Polymerase Reaction Buffer
        50 mM Tris-HCl
        10 mM MgCl$_2$
        10 mM (NH$_4$)$_2$SO$_4$
        4 mM DTT
        (pH 7.5 @ 25° C.)
    4 µL of 10 mM each dNTP, for a 0.4 mM total dNTPs final concentration;
    50 µL of filtered 30% PEG 600;
    2-8 µL of Phi29 polymerase (10 units/µL); and
    23 to 29 µL of molecular-grade water
  Mix solution by vortexing and pipet onto treated glass surface, then seal plate;
  Incubate plate on flat bottom heat block of thermomixer with a thermo-lid, at 45° C. for 90 minutes;
  Remove well contents and wash well three times with 100 µL of 1×TBS; discard wash solution.

Staining Option 1
  Add 50 µL of graphene oxide-molecular beacon solution that comprises:
    5 µL of 10× Phi 29 Buffer for a 1× final concentration
    0.5 µL of 100 µM Molecular Beacon for a final concentration of 0.5 µM
    5 µL of 2 mg/mL graphene oxide solution for a final concentration of 0.2 mg/mL;
    Molecular-grade water to 50 µL
  Incubate reaction for 60 minutes at 37° C.
  Wash three times with 100 µL 1×TBS;
  Wash one time with 100 µL 1×TBS containing 5% w:v Tween 20;
  Wash two times with 100 µL of 1×TBS; discard wash solution;
  Add 100 µL of 1×TBS, and image in microscope, as described above.

Staining Option 2

Add:

5 µL of 10× Phi 29 Buffer for a 1× final concentration 0.5 µL of 100 µM Molecular Beacon or Fluorescent labeled oligo for a final concentration of 0.5

5 µL of 0.1% Teepol detergent for a final concentration of 0.01% Teepol

Molecular-grade water to 50 µL

Incubate reaction for 30 minutes at 37° C.

Wash six times with 100 µL 1×TBS, and image in microscope, as described above.

As discussed above, use of a 2-step protocol may be advantageous for certain modifications, e.g., modifications that may be compatible with one step of the procedure but not compatible with another step.

Variations on the 2-Step Protocol

Intermittent mixing: 1-step or 2-step reaction protocols may include intermittent mixing steps (e.g., every 1, 2, 3, 4, 5, 6, 7, 8, 9, 10, 11, 12, 13, 14, 15, etc. minutes) to re-distribute reagents at time points throughout the reaction step incubations (e.g., during probe hybridization, rolling circle amplification, fluorescent probe hybridization, etc.). Mixing is not limited to any particular method and may comprising vortexing, bumping, rocking, tilting, or ultrasonic mixing. See, e.g., Ishigaki and Soto, *Micromachines* 2018, 9:272, which is incorporated herein by reference for all purposes.

Example 3

Nuclease Digest to Remove Unligated MIP Probes

In some embodiments, ligated MIPs are treated with one or more exonucleases to digest unligated probes. Two exemplary treatment protocols are described below. Reagents

| REAGENT | New England Biolabs Catalog Number |
|---|---|
| 10 × CUTSMART Buffer | B7204S |
| Thermolabile Exo I (20,000 U/mL) | M0568S |
| Rec Jf (30,000 U/mL) | M0264S |
| Exo VII (10,000 U/mL) | M0379S |
| Exo T (5,000 U/mL) | M0265S |

Protocol 1

1. Use protocol below to prepare exo digest master mix:

| Reagent | x1 (uL) | Conc. | 10 |
|---|---|---|---|
| 10 × Cutsmart Buffer | 3 | 1× | 30 |
| Exo T (5,000 U/mL) | 0.75 | 15 U | 7.5 |
| Rec Jf (30,000 U/mL) | 0.75 | 22.5 U | 7.5 |
| Nuclease Free Water | 0.50 | 7.5 U | 7.5 |
| Total Volume | 5.00 | | 52.5 |

2. Vortex master mix and pipet 5 µL of mix into each ligated sample in PCR plate, for a total of 30 µL;
3. Foil seal PCR plate; vortex, then spin plate;
4. Put plate in thermocycler and follow the program below:

| Exo program | |
|---|---|
| 37 C. | 60 min |
| 65 C. | 30 min |
| 4 C. | HOLD |

Protocol 2

1. Use protocol below to prepare exo digest master mix:

| Reagent | x1 (uL) | Conc. | 10 |
|---|---|---|---|
| 10 × Cutsmart Buffer | 3 | 1× | 30 |
| Thermolabile Exo I (20,000 U/mL) | 0.75 | 15 U | 7.5 |
| Rec Jf (30,000 U/mL) | 0.75 | 22.5 U | 7.5 |
| Exo VII (10,000 U/mL) | 0.75 | 7.5 U | 7.5 |
| Total Volume | 5.25 | | 52.5 |

2. Vortex master mix and pipet 5 µL of mix into each ligated sample in PCR plate, for a total of 30.25 µL;
3. Foil seal PCR plate, vortex and spin plate;
4. Put plate in thermocycler and follow the program below:

| Exo program | |
|---|---|
| 37° C. | 60 min |
| 80° C. | 40 min |
| 4° C. | HOLD |

The final high temperature step in each protocol heat denatures the nuclease and the solutions can then be used directly in RCA reactions.

Example 4

Preparation of Chemically Modified Assay Plates and Oligonucleotide Primer Immobilization Provided hereinbelow is an exemplary protocol for chemical modification of assay plates using tannic acid or dopamine, and attachment of oligonucleotides.

| Polytannic Acid Plate Preparation | | | |
|---|---|---|---|
| Mfg: Catalog # | Reagent | Amount | Scale |
| Greiner Bio-One: 655 892 | 96-well Microplate | — | |
| Thermo Fisher: AC419995000 | Tannic Acid | 8 mg | |
| Thermo Fisher: PI17874 | Ammonium Persulfate (APS) | 13 mg | |
| Thermo Fisher: PI17919 | TEMED | 17.2 µL | |
| Thermo Fisher: AA43359AP | Acryl Acid | 550 µL | |
| | $H_2O$ to 10 mL | 9.43 mL | |
| | 15 mL Tube | 1 | |

1. Measure tannic acid and ammonium persulfate into 15 ml Tube (or container)
2. Add nuclease-free $H_2O$ to container
3. Add acrylic acid to solution
4. Add TEMED to solution
5. Vortex to mix
6. Pipette 504, to each well of the plate
7. Incubate at room temperature (25° C.) overnight (protected from UV and other light)

| Polydopamine Plate Preparation | | | |
|---|---|---|---|
| Mfg: Catalog # | Reagent | Amount | Scale |
| Greiner Bio-One: 655 892 | 96-well Microplate | — | |
| SIGMA: H8502 | Dopamine | 22 mg | |
| Thermo Fisher: PI17874 | Ammonium Persulfate (APS) | 13 mg | |
| Thermo Fisher: PI17919 | TEMED | 17.2 µL | |
| SIGMA: 516155-25G | 2-Aminoethylmethacrylamide (AEMA) | 1111 mg | |
| | $H_2O$ | 9.43 mL | |
| | 15 mL Tube | 1 | |

1. Measure AEMA into 15 ml Tube (or container)
2. Add nuclease free $H_2O$ to container
3. Sonicate the container in a sonicating bath for 2 minutes
4. Centrifuge the container at 3500 rpm for 5 minutes
5. Aspirate the supernatant and filter through a 0.2 micron; if needed, add more water to bring volume to 10 mL
6. Add the dopamine to the filtered solution
7. Add APS to solution
8. Add TEMED to solution
9. Vortex to mix
10. Pipette 504, to each well of the plate
11. Incubate at room temperature (25° C.) overnight (protected from UV and other light)

Note: The following steps are identical for either tannic acid or dopamine plate preparation

| Reagent removal and Washing | | | |
|---|---|---|---|
| Mfg: Catalog # | Reagent | Amount | Scale |
| (Any) Thermo Fisher: 10-977-023 | $H_2O$ | 15 mL | |

1. Remove the tannic acid or dopamine solution from wells and dispose into chemical waste
2. Wash the plate with nuclease-free water three (3) times using 100 µL per well. Remove the final wash fluid.
3. Allow plates to dry completely (e.g., overnight incubation at room temperature (25° C.), or in a biological hood in Pre for at least 3 hours before continuing to the oligo conjugation.

| Conjugation of oligonucleotide to prepared assay plate | | | |
|---|---|---|---|
| Mfg: Catalog # | Reagent | Amount | Scale |
| IDT: Custom | Custom Oligo (100 µM) | 10 µL | |
| Thermo Fisher: 22980 | EDC (1-ethyl-3-(3-dimethylaminopropyl)carbodiimide hydrochloride) | 98 mg | |
| Thermo Fisher: 24500 | NHS (N-hydroxysuccinimide) | 57 mg | |
| (Any) Thermo Fisher: 10-977-023 | $H_2O$ | 9,970 µL + 2 mL | |
| (Any) Thermo Fisher: AM12500 | 15 mL Tube | 1 | |

1. Prepare a 100 mM solution of EDC by measuring out 98 mg of EDC and adding 1 mL of $H_2O$.
2. Prepare a 100 mM solution of NHS by measuring out 57 mg of NHS and adding 1 mL of $H_2O$.
3. Combine the following into a 15 ml conical tube (or container)
   a. 100 µL of 100 µM amine-modified oligonucleotide
   b. 1000 µL of 100 mM EDC
   c. 1000 µL of 100 mM NHS
   d. 7900 µL of $H_2O$
4. Vortex to mix
5. Dispense 50 µL of this solution into each well of the plate
6. Incubate the plate at 37° C. for one (1) hour
7. Wash the plate with nuclease-free water three (3) times using 100 µL per well. Remove the final wash fluid.

Plate Quality Control (QC) Check

QC plate with standard RCA performed in triplicates of 10 fmol, 1 fmol, 0.1 fmol, and 0 fmol of standard one color input.

QC reads for dopamine plates should fall around 30,000 spots for 10 fmol, 10,000 spots for 1 fmol, 2000 spots for 0.1 fmol, and 1 spot or less for the no-target control. QC reads for tannic acid plates should fall around 15,000 spots for 10 fmol, 5,000 spots for 1 fmol, 1000 spots for 0.1 fmol, and 1 spot or less for the no-target control.

An example of an amine-modified oligonucleotide for conjugation to a surface is as shown below:

(SEQ ID NO: 17)
5'UniAmM/CGTCGTAGGTCACTTAACATAGAG3'

"5' UniAmM" indicates a 5' Uni-Link™ Amino Modifier (Integrated DNA Technologies, Inc.)

Oligonucleotide modifications suitable for immobilization in the technology are not limited to the modifications on the oligonucleotide shown above. For example, in some embodiments, a spacer is added to an oligonucleotide conjugated to a surface. While not limiting the embodiment to any particular mechanism or effect, an oligonucleotide separated from a plate or bead surface by a spacer would be expected to be further into solution, such that interactions with the support surface are minimized and hybridization of circularized MIPs is enhanced, yielding additional detectable spots.

In some embodiments, multiple amine moieties are added to the oligonucleotides, since a single amine may be in the form $H_3N^+$, which contains a positive charge and may not efficiently react to the NHS ester. By adding additional amine groups, the percentage of oligonucleotides with at least one reactive $H_2N$ is increased, ensuring that a higher percentage of the oligonucleotides are conjugated to the plate during the conjugation reaction.

Oligonucleotides that include spacers and/or additional amino groups include but are not limited to the examples shown below:

(SEQ ID NO: 18)
5'UniAmM/TTTTCGTCGTAGGTCACTTAACATAGAG3'

(SEQ ID NO: 19)
5'UniAmM/T/iUniAmM/T/iUniAmM/T/iUniAmM/TCGTCGTAGGTCACTTAACATAGAG3'

(SEQ ID NO: 20)
5'UniAmM/T/iUniAmM/T/iUniAmM/T/iUniAmM/T/iSp18/iSp18/CGTCGTAGGTCACTTAACATAGAG3'

(SEQ ID NO: 21)
5'UniAmM/T/iUniAmM/T/iUniAmM/T/iUniAmM/T/iSp18/iSp18/iSp18/iSp18/CGTCGTAGGTCACTTAACATAGAG3'

(SEQ ID NO: 22)
5UniAmNA/TTTT/iSp18/iSp18/CGTCGTAGGTCACTTAACATAGAG3'

"iUniAmM" indicates an internal Uni-Link™ Amino Modifier and "iSP18" indicates an internal "Spacer 18," an 18-atom hexa-ethyleneglycol spacer, (Integrated DNA Technologies, Inc.)

Example 5

Rolling Circle Amplification on Iron Oxide Nanoparticles

In some embodiments, rolling circle amplification is performed essentially in solution, e.g., it is performed using primers conjugated to small iron oxide nanoparticles suspended in solution. An exemplary procedure is described below:

A. Conjugation of Amine-Containing Oligonucleotides to Functionalized Iron Oxide Nanoparticles Starting material: Ocean Nanotech catalog number SHP-10-10, 10 nm iron oxide nanoparticles with carboxylic acid reactive groups, provided at 5 mg/mL (Fe) in 2 mL deionized $H_2O$ with 0.02% $NaN_3$, 4.3 nM nmole/mL of nanoparticles. For each oligonucleotide, use 5 μL of the suspension, or about 20 pmoles beads, for 1 pmole of oligonucleotide.

1. Magnetize or spin nanoparticles (standard desktop microcentrifuge at 13,000 RPMs or 20,000 RCF for 5 minutes) and remove storage buffer. Resuspend in 50 μL of nuclease-free water.
2. Magnetize or spin nanoparticles as above and remove supernatant. Resuspend in 50 microliters of a solution containing 0.5 mM EDC and 0.5 mM NHS with 0.1 μM of an amine-containing oligonucleotide.
   a. Freshly prepare a 500 mM concentration of NHS and EDC in nuclease-free water. Combine aliquots with an aliquot of amine-containing oligonucleotide from a 100 μM stock to produce the solution containing 0.5 mM EDC and 0.5 mM NHS with 0.1 μM of an amine-containing oligonucleotide.
3. Incubate nanoparticle-oligonucleotide mixture at 37° C. for 1 hour.
4. Magnetize or spin the nanoparticles as above and remove the supernatant without disrupting the pellet. Add 50 μL of nuclease-free water.
5. Repeat step 4 three times. After the final wash resuspend the nanoparticles in 25 μL of nuclease-free water.

Rolling Circle Amplification with Iron Oxide Nanoparticle-Bound Primer Oligonucleotides The following oligonucleotide was conjugated to iron oxide nanoparticles as described above:

(SEQ ID NO: 35)
5'-/5UniArnM/CGTCGTAGGTCACTTAACATAGAGTT/3BioTEG/-3'

Real-time qRCA reactions were performed with the following variations in reagent concentrations.
  i. Circular Template DNA: 0, 100, 500, or 1000 fmol
  ii. Nanoparticle-primer: 0.5 μM, 1 μM, 5 μM, 10 μM, 15 μM, and 20 μM
  iii. Molecular beacon probe: 0.25 μM, 0.5 μM, 5 μM, 10 μM, 15 μM, and 20 μM 1. Prepare an RCA master mix as follows:

| Master Mix Component | For each reaction |
| --- | --- |
| 10 × Phi29 Buffer | 10 μL |
| 10 mM each dNTP mix | 4 μL |
| 30% PEG Molecular Weight 600 | 50 μL |
| Input MIP 1A (200 fmoles per μL) | 5 μL |
| Iron Oxide nanoparticle-primer | 25 μL |
| Phi29 Polymerase (10 u per μL) | 6 μL |
| Total Vol | 100 μL |

2. Incubated the RCA reactions at 45° C. for 90 minutes, with at-temperature mixing at 1500 rmp for the first 30 seconds of each 15 minute interval.
3. Magnetize or spin nanoparticles as described above and remove the supernatant without disrupting the pellet. Resuspend the nanoparticles in 50 μL of nuclease-free water.
4. Repeat Step 8 three times.

5. Hybridize the RCA products on the nanoparticles to fluorophore-labeled oligonucleotides as described above. For example:
   a. Add 50 µL of molecular beacon solution that comprises:
      i. 5 µL of 10× Phi 29 Buffer for a 1× final concentration
      ii. 0.5 µL of 100 µM Molecular Beacon for a final concentration of 0.5 µM
      iii. Molecular-grade water to 50 µL
   b. Incubate reaction for 60 minutes at 37° C.
   c. Magnetize or spin nanoparticles as described above and remove the supernatant without disrupting the pellet. Resuspend the nanoparticles in 50 µL 1×TBS;
   d. Repeat step c. 2 additional times.
   e. Wash nanoparticles one time with 50 µL 1×TBS containing 5% w:v Tween 20;
6. Wash two times with 50 µL of 1×TBS; as described above, Magnetize or spin nanoparticles as described above and remove the supernatant without disrupting the pellet. Resuspend the nanoparticles in 50 µL of nuclease-free water.
7. Place the nanoparticle solution in a well of a 96 well plate for imaging on a microscope. Magnetize or spin the nanoparticles into a layer on the plate for visualization in the focal plane of the microscope. Count fluorescing nanoparticles.

Figure 54:
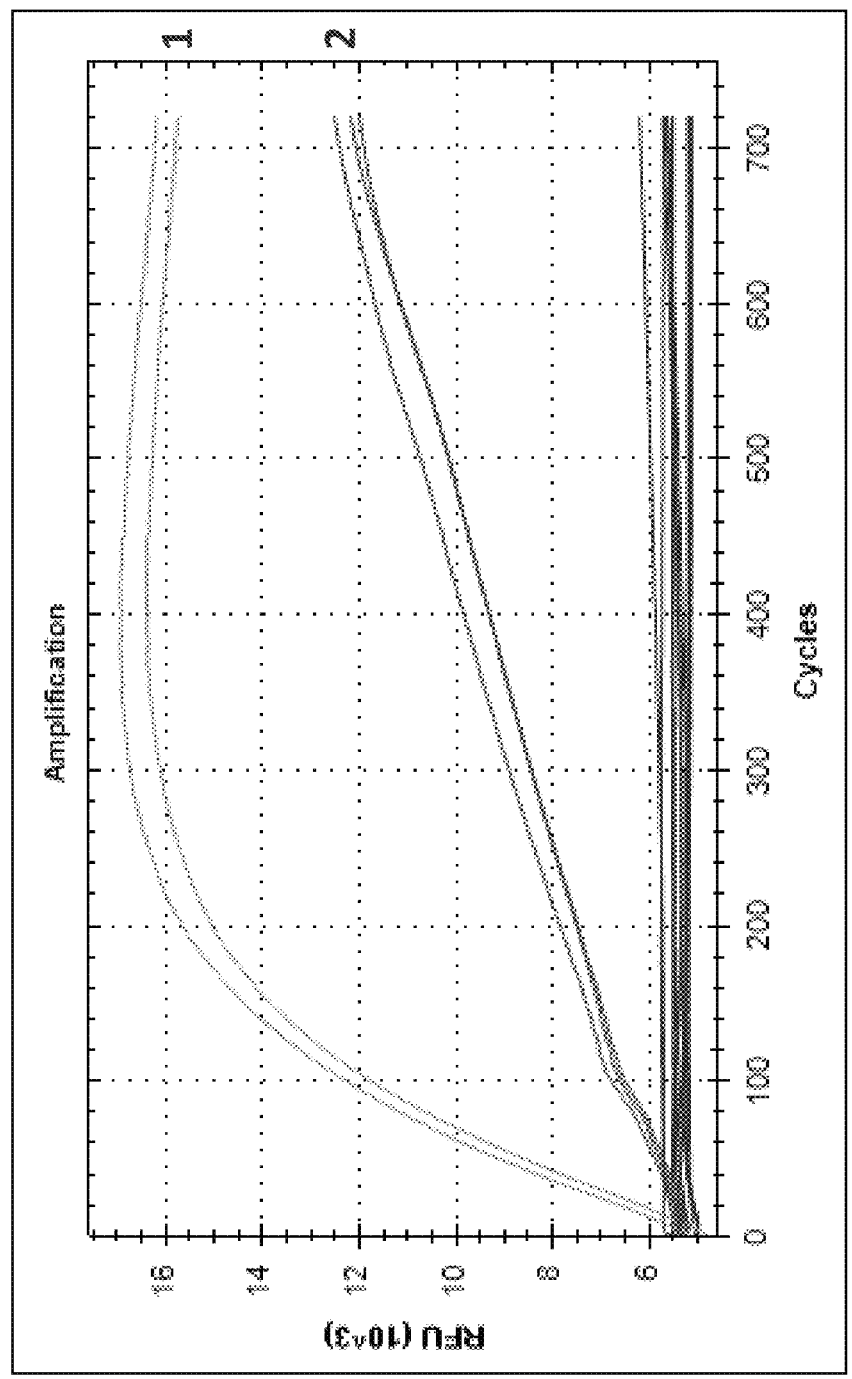
FIG. 54 provides a graph that illustrates that the presence of unlabeled iron oxide nanoparticles (lacking primers) in an RCA reaction mixture do not inhibit RCA amplification (1), and primers attached to iron oxide nanoparticles can prime RCA from a circular template (e.g., a ligated MIP) (2). The RCA reactions were visualized by hybridization of molecular beacon probes.
Figure 55:
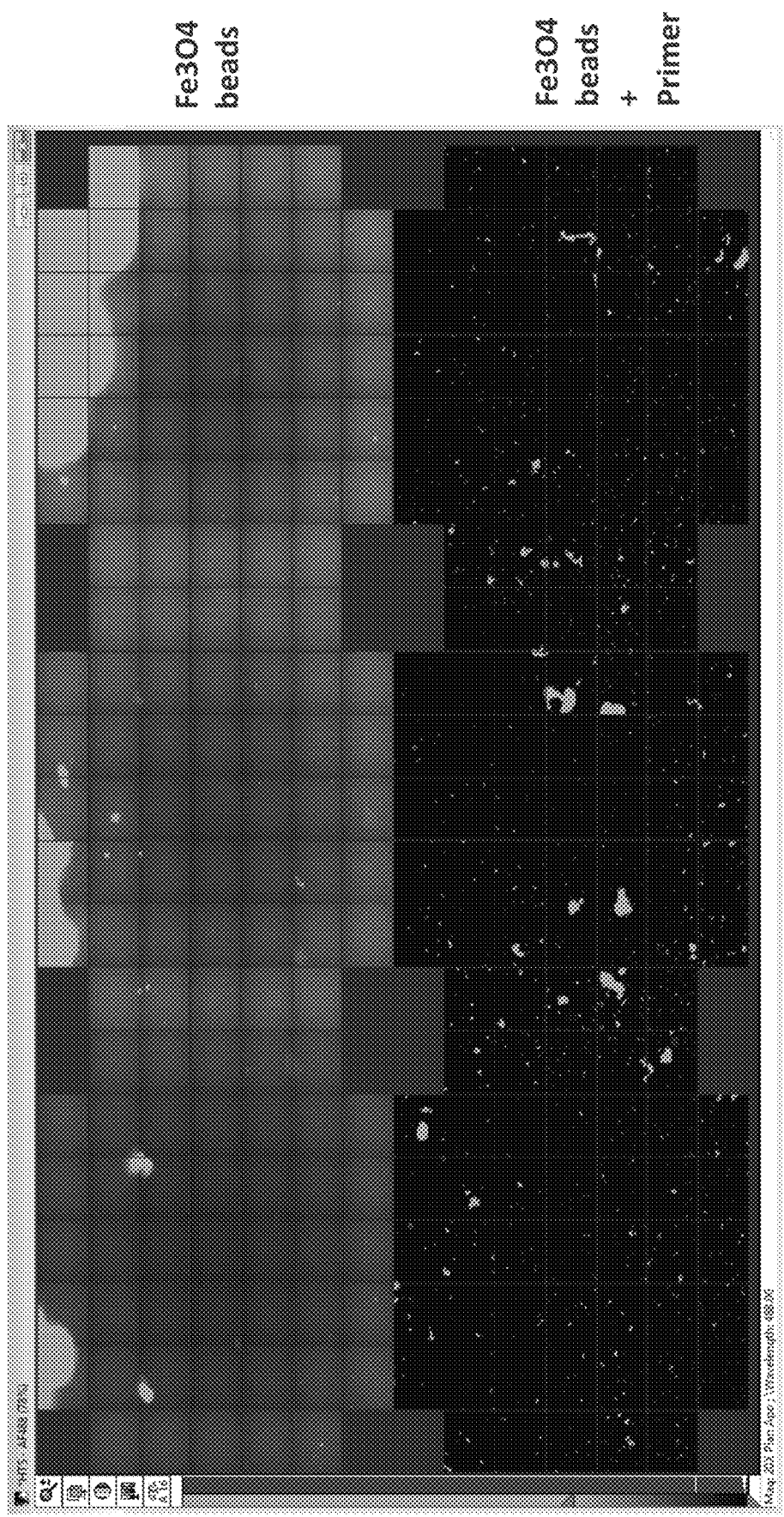
FIG. 55 shows microscope images of surfaces in which iron oxide beads are localized to a surface and imaged with an IXM4 microscope. The top half shows assay wells containing RCA reactions with iron oxide nanoparticles in which the primers were not attached to the nanoparticles, and the bottom half of the figure shows assay wells containing RCA products synthesized using primers attached to iron oxide nanoparticles, in which the RCA products were magnetically localized to the bottom of the well prior to imaging.

For an endpoint read as shown in FIG. 55, the assay plate is imaged directly. For qRCA as shown in FIG. 54, reactions were incubated at 37° C. and the fluorescence was measured at the end of each minute for 720 cycles (approximately 720 minutes).

Example 6

In-Solution Rolling Circle Amplification with Filter Capture

Padlock Probe Ligation
Cf DNA is treated by restriction endonuclease digestion. Following digestion, digested DNA is then combined with
   5 pM each locus-specific probe
   508 nM per backbone ($21 \times 10^{12}$ molecules)
   80 U of Taq DNA Ligase
   1 mM NAD+
   100 mM NaCl
   15 mM $MgCl_2$
   10 mM Tris-HCl pH 8 and 0.11% w/v Tween20

The reaction mixture was incubated at 95° C. for 5 minutes, followed by 10 hours at 56° C. 39 µl of an exonuclease master mix consisting of 20 U Exonuclease I, 5 U Lambda exonuclease, 100 U Exonuclease III, 10 U Uracil dehydrogenase and 28% Tween20 was added to each reaction. The mixture was incubated at 37° C. for 1 hour, followed by 80° C. for 20 minutes.

RCA Reaction
Following Exo III treatment, RCA was performed by adding 11.2 µl RCA master mix consisting of 1.07 µM of an RCA primer oligonucleotide designed to be complementary to a sequence present in the backbone region of each DNA circle, 5.4 mM dNTP solution mix and 20 units of Phi29 DNA polymerase. The reaction was incubated at 37° C. for 1 hour, followed by 65° C. for 10 minutes.

Probe Hybridization
Following RCA, a 12 µl labeling master mix consisting of 60 nM of each fluorescent labeling oligonucleotide complementary to a chromosomal tag in the backbone, 12×SSC (saline sodium citrate) buffer and 0.6% Tween-20. The reaction was incubated at 45° C. for 1 hour. Each reaction was then filtered through a well of a nanofilter detection plate (PerkinElmer), the plate comprising pores selected to retain the labeled RCA products on the upper membrane surface. The membrane was washed twice in 0.5×SSC and the detection plate was moved to a blotting membrane to remove residual liquid. After drying, an optical clearing agent (PerkinElmer) was added to each well and allowed to cure for 10 minutes. The plates were imaged and analyzed using a Vanadis View™ microplate scanner (PerkinElmer).

Example 7

In-Solution Rolling Circle Amplification with Plate Capture

In-sol primers 1, 2, 3, 4, 5, 6, and 7 as shown in FIG. 57A were tested in reactions in which RCA products were formed in solution and captured on a plate for counting. The signal was compared to on-plate RCA performed using on-plate oligonucleotides shown in FIG. 57B. Padlock probe ligation reactions comprised the following:

| [Final] Reagents | ×1 | ×10 |
| --- | --- | --- |
| 1 × Amp Buffer | 2.5 | 25 |
| Water | 1.75 | 17.5 |
| 1 × NAD | 0.25 | 2.5 |
| 1 uM MIP 1B | 5 | 50 |
| 1 uM Target 1T | 15 | 150 |
| Ampligase (0.1 U/µL) | 0.5 | 5 |
| Total Volume | 25 | 250 |

Ligation reactions were incubated at 98° C. for 3 min, then 45° C. 60 min, then held at 4° C. until further processing. In some embodiments, the ligation mixture is treated with exonuclease to remove excess MIP probe. Exonuclease treatment may be omitted when the MIP probes are not present in excess, e.g., when the concentration of target strands (e.g., synthetic target strands) are at about the same concentration as the MIP probes in the ligation mixture, as shown in the table above.

Quantitative RCA (qRCA) reactions comprised the following:

| [Final] Reagents | ×1 | ×10 |
| --- | --- | --- |
| 10 × Phi29 Buffer | 2.5 | 25 |
| Biotin Primer 1:100 | 2.5 | 25 |
| water | 13.25 | 132.5 |
| dNTPs | 1 | 10 |
| 100 uM Beacon | 0.25 | 5 |
| Phi29 Polymerase | 0.5 | 5 |
| Ligated MIP reaction mix | 5 | 50 |
| Total Volume | 25 | 250 |

Reactions were performed in triplicate for each primer type. qRCA reactions were incubated at 45° C. Endpoint results for the in-solution RCA and the on-plate RCA are shown in FIG. 58.

Figure 59:
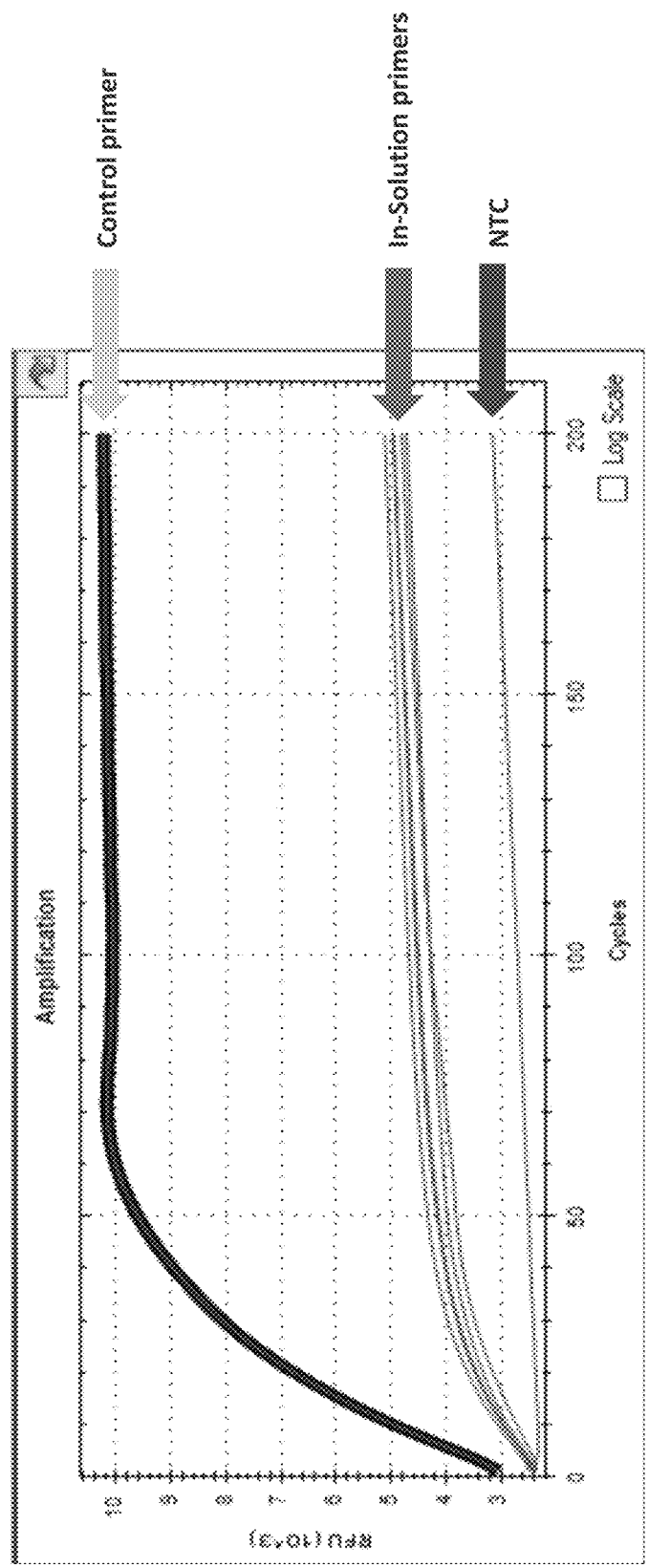
FIG. 59 provides a graph comparing quantitative RCA (qRCA) curves measured using the "in-sol" primers shown in FIG. 57A with qRCA using the control primer (AUP).

RCA efficiency for the in-solution primers was also examined in a standard qRCA reaction, with the results shown FIG. 59, compared to qRCA primed using the AUP control primer shown on FIG. 57B (performed in solution). The presence of 3' biotin on the in-solution primers appears to delay the reaction, resulting in approximately 2-fold less product than that generated by the AUP control primer. For both types of primer, the majority of the RCA product is generated within the first hour The RCA product is generated within the first hour of the RCA step, as indicated by the curve generated by 50 cycles/50 minutes in the qRCA (Note: RCA is performed at a single temperature and each "cycle" refers to a 1 minute interval at that temperature). These data also suggest that the length of the RCA product generated by the current Neverseq Primer (AUP) and the In-solution primers is similar.

Reaction efficiencies for in-solution qRCA performed as described above were examined using the following combinations of reactants:

1. 0, 100, 500 and 1000 fmol DNA input with 0.5 µM of primer, with 0.25 µM beacon probe
2. 0, 100, 500 and 1000 fmol DNA input with 1 µM of primer, with 0.5 µM beacon probe
3. 0, 100, 500 and 1000 fmol DNA input with 5 µM of primer, with 5 µM beacon probe
4. 0, 100, 500 and 1000 fmol DNA input with 10 µM of primer, with 10 µM beacon probe
5. 0, 100, 500 and 1000 fmol DNA input with 15 µM of primer, with 15 µM beacon probe
6. 0, 100, 500 and 1000 fmol DNA input with 20 µM of amine primer, with 20 µM beacon probe Input DNA refers to circularized probe DNA. These reactions showed that under the conditions tested, increasing the concentrations of primer and beacon probe increased the signal up to concentrations of 10 µM of primer and 10 µM beacon probe, above which signal did not increase (data not shown).

It is readily apparent that, provided with the disclosure herein, each of the front-end target recognition systems disclosed may be configured to generate a signal detectable for use with any one of the back-end instruments and systems described above.

ADDITIONAL MATERIALS INCORPORATED HEREIN BY REFERENCE

1. F. Dahl, et al., Imaging single DNA molecules for high precision NIPT; *Nature Scientific Reports* 8:4549 (2018) p1-8
2. R. M. Dirks, et al., Triggered amplification by hybridization chain reaction, *Proc. Natl. Acad. Sci. USA* 101(43): 15275-15278 (2004)
3. T. J. Morin, et al., Nanopore-Based Target Sequence Detection, *PLoS ONE* 11(5):e0154426 (2016)
4. M. Nilsson, et al., Real-time monitoring of rolling-circle amplification using a modified molecular beacon design *Nucleic Acids Research*, 30(14):e66 (2002)
5. J. R. Epstein, et al., High-Density Fiber-Optic Genosensor Microsphere Array Capable of Zeptomole Detection Limits; *Anal. Chem.* 74:1836-1840 (2002)
6. D. M. Rissin and DR Walt, Digital Concentration Readout of Single Enzyme Molecules Using Femtoliter Arrays and Poisson Statistics. *Nano Letters* 6(3):520-523 (2006)
7. R. Roy, et al., A Practical Guide to Single Molecule FRET Nat Methods. 5(6): 507-516 (2008)
8. Z. Li, et al., Detection of Single-Molecule DNA Hybridization Using Enzymatic Amplification in an Array of Femtoliter-Sized Reaction Vessels, *J. Am. Chem. Soc.* 130:12622-12623 (2008)
9. W. Zhang, et al., Automated Multiplexing Quantum Dots in Situ Hybridization Assay for Simultaneous Detection of ERG and PTEN Gene Status in Prostate Cancer. *The Journal of Molecular Diagnostics*, 15(6):754-764 (2013)
10. Quanterix Whitepaper 1.0, Scientific Principle of Simoa (Single Molecule Array) Technology, 1-2 (2013)
11. Quanterix Whitepaper 6.0, Practical Application of Simoa™ HD-1 Analyzer for Ultrasensitive Multiplex Immunodetection of Protein Biomarkers, 1-3 (2015)
12. H. Matsui, et al., Molecular and Biochemical Characterization of a Serine Proteinase Predominantly Expressed in the Medulla Oblongata and Cerebellar White Matter of Mouse Brain, *J. Biol. Chem.*, 275(15):11050-11057 (2000)
13. C. M. Van der Loos, et al., Multiple immunoenzyme staining techniques: Use of fluoresceinated, biotinylated and unlabeled monoclonal antibodies *J. Immunol. Methods* 117:45-52 (1989)
14. J. Hagen, et al., Hapten-Anti-Hapten Technique for Two-Color IHC Detection of Phosphorylated EGFR and $H_2AX$ Using Primary Antibodies Raised in the Same Host Species; *Signal Transduction Immunohistochemistry: Methods and Protocols*, Methods in *Molecular Biology*, vol. 1554:155-160 (Alexander E. Kalyuzhny (ed.)
15. G. K. Geiss, et al., Direct multiplexed measurement of gene expression with color-coded probe pairs; *Nature Biotechnology* 26(3):317-25 (March 2008) and Corrigendum regarding authors' affiliations at 26(6):1 (June 2008)
16. P. N. Hengen, et al., Inventors, U.S. patent application Ser. No. 15/729,421, published Mar. 8, 2018 as U.S. Patent Pub. 2018/0066309 A1 (Nanostring Technogies, Inc.)
17. M. Nilsson, et al. "Padlock probes: circularizing oligonucleotides for localized DNA detection". *Science.* 265 (5181): 2085-2088 (1994)
18. J. Banér, et al., Signal amplification of padlock probes by rolling circle replication *Nucleic Acids Research* 26 (22): 5073-5078 (1998)
19. P.-J. J. Huang, and J. Liu, "Molecular Beacon Lighting up on Graphene Oxide," *Anal. Chem.* 84:4192-4198 (2012)
20. Y. Phillip, et al., "Common Crowding Agents Have Only a Small Effect on Protein-Protein Interactions," *Biophysical Journal* 97: 875-885 (2009)
21. L. M. Dominak, et al., "Polymeric Crowding Agents Improve Passive Biomacromolecule Encapsulation in Lipid Vesicles," *Langmuir* 26(16):13195-13200 (2010)
22. B. Schweitzer, et al., "Immunoassays with rolling circle DNA amplification: A versatile platform for ultrasensitive antigen detection," *Proc. Natl. Acad. Sci. USA* 97(18): 10113-10119 (2000)
23. C. Hong, et al., "Fluorometric Detection of MicroRNA Using Isothermal Gene Amplification and Graphene Oxide," *Anal. Chem.* 88: 2999-3003 (2016)
24. E. J. Devor, et al., "*Strategies for Attaching Oligonucleotides to Solid Supports*," Integrated DNA Technologies (2005)
25. WO 2015/083002 "Multiplex Detection of Nucleic Acids"
26. Steinberg-Tatnab, G., et al., Synthetic Modification of Silica Beads That Allows for Sequential Attachment of Two Different Oligonucleotides, *Bioconjugate Chem.* 2006, 17, 841-848
27. Mahajan, S., et al., Oligonucleotide Microarrays: Immobilization of Phosphorylated Oligonucleotides on Epoxylated Surface, *Bioconjugate Chem.* 2006, 17, 1184-1189
28. Dalsin, J L., et al., Mussel Adhesive Protein Mimetic Polymers for the Preparation of Nonfouling Surfaces, J. AM. CHEM. SOC. 2003, 125, 4253-4258

29. Zhang, D Y., and Liu, B., Detection of target nucleic acids and proteins by amplification of circularizable probes, Expert Rev. Mol. Diagn. 3(2):237-248 (2003)
30. Lee, H., et al., Mussel-Inspired Surface Chemistry for Multifunctional Coatings, *Science* 318, 426 (2007)
31. Koile, R C., et al., Electrochemical Removal of Phenolic Films from a Platinum Anode, ANALYTICAL CHEMISTRY, VOL. 51, NO. 6, May 1979.
32. Li, Y., et al., Electrochemical quartz crystal microbalance study on growth and property of the polymer deposit at gold electrodes during oxidation of dopamine in aqueous solutions, *Thin Solid Films* 497 (2006) 270-278
33. Glass, N R., et al., Organosilane deposition for microfluidic applications, *Biomicrofluidics* 5, 036501-1 to 036501-7 (2011)
34. Kumar, A., et al., Silanized nucleic acids: a general platform for DNA immobilization. Nucleic Acids Res., 28(14) e71: i-vi (2000)
35. Wen, X.-L., Micellar effects on the electrochemistry of dopamine and its selective detection in the presence of ascorbic acid. *Talanta* 50 (1999) 1027-1033
36. Zeng, X., et al., Synthesis and Characterization of DOPA-PEG Conjugates, *Polymer Preprints* 2000, 41(1), 989
37. Lee H., et al., Facile Conjugation of Biomolecules onto Surfaces via Mussel Adhesive Protein Inspired Coatings, *Adv Mater.* 2009 January 26; 21(4): 431-434
38. U.S. Pat. No. 7,618,937B2, Messersmith, et al., Peptidomimetic polymers for antifouling surfaces
39. U.S. Pat. No. 7,858,679B2, Messersmith, et al., Polymeric compositions and related methods of use
40. U.S. Pat. No. 8,541,060B2, Messersmith, et al., Surface-independent, surface-modifying, multifunctional coatings and application thereof
41. U.S. Pat. No. 8,815,793B2, Messersmith, et al., Polymeric compositions and related methods of use
42. U.S. Pat. No. 9,637,597B2, Messersmith, et al., DOPA-melanin formation in high ionic strength solutions
43. US20030087338A1, Messersmith, et al., Adhesive dopa-containing polymers and related methods of use.
44. US20060009550A1, Messersmith, et al., Polymeric compositions and related methods of use
45. US20080247984A1, Messersmith, et al., Dopa-functionalized, branched, poly(alkylene oxide) adhesives
46. US20100330025A1, Messersmith, et al., Surface Independent, Surface-Modifying, Multifunctional Coatings and Applications Thereof
47. WO2006091226A2, Messersmith, et al., Polymeric compositions and related methods of use
48. WO2008049108A1, Messersmith, et al., Surface-independent, surface-modifying, multifunctional coatings and applications thereof
49. WO2008091386A2, Messersmith, et al., Biomimetic modular adhesive complex: material, methods and applications therefore
50. WO2009062146A2, Messersmith, et al., Substrate-independent layer-by-layer assembly using catechol-functionalized polymers
51. WO2012125693A2, Messersmith, et al., Multifunctional metal nanoparticles having a polydopamine-based surface and methods of making and using the same
52. WO2014116812A2, Messersmith, et al., Phenolic coatings and methods of making and using same
53. WO2015148503A1, Messersmith, et al., Dopa-melanin formation in high ionic strength solutions
54. WO2017147145A1, Messersmith, et al., Macrocyclic polyphenols for universal coatings
55. WO2019036378A1, Messersmith, et al., Bioinspired supramolecular medical adhesives
56. J. Jiang, et al., Surface Characteristics of a Self-Polymerized Dopamine Coating Deposited on Hydrophobic Polymer Films, *Langmuir* 27:14180-14187 (2011)
57. N. Orishchin, et al., Rapid Deposition of Uniform Polydopamine Coatings on Nanoparticle Surfaces with Controllable Thickness, *Langmuir* 33:6046-6053 (2017)
58. H. M. Hegab, et al., Single-Step Assembly of Multifunctional Poly(tannic acid)—Graphene Oxide Coating To Reduce Biofouling of Forward Osmosis Membranes, *ACS Appl. Mater. Interfaces,* 8:17519-17528 (2016)
59. L. Pan, et al., Tannic-Acid-Coated Polypropylene Membrane as a Separator for Lithium-Ion Batteries, *ACS Appl. Mater. Interfaces,* 7:16003-16010 (2015)
60. H. Lee, et al., Mussel-Inspired Surface Chemistry for Multifunctional Coatings, *Science* 318(5849): 426-430 (2007)
61. WO 2019/195346 A1 to Sekedat, et al., Methods, Systems, and Compositions for Counting Nucleic Acids (2019)

All literature and similar materials cited in this application, including the publications described in the Bibliography above, and including but not limited to patents, patent applications, articles, books, treatises, and internet web pages, are expressly incorporated by reference in their entireties for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, molecular diagnostics, nucleic acids structure, biochemistry, medical science, or related fields are intended to be within the scope of the claims.

We claim:

1. A method for nucleic acid molecule analysis, comprising:
   a) providing a plurality of molecular inversion probes (MIPs) and a sample of nucleic acid molecules;
   b) hybridizing MIPs of the plurality of MIPs to the nucleic acid molecules to generate hybridized MIPs;
   c) in a reaction mixture, circularizing hybridized MIPs to form a plurality of circularized nucleic acid probes;
   d) treating the reaction mixture with more than one exonuclease, wherein circularized nucleic acid probes are not a substrate for the more than one exonucleases;
   e) forming a plurality of complexes comprising a plurality of primers hybridized to a plurality of circularized nucleic acid probes from the reaction mixture following d), wherein the plurality of primers is bound to a solid support;
   f) extending the plurality of primers in the plurality of complexes in an amplification reaction to form a plurality of amplification products immobilized to the solid support;
   g) in a presence of a detergent, hybridizing a set of labeled probes to the plurality of amplification products to generate a plurality of amplification products comprising hybridized labeled probes, wherein the set of labeled probes comprises five or more different labels; and
   h) using imaging to count the plurality of amplification products comprising hybridized labeled probes based on detecting the five or more different labels.

2. The method of claim 1, wherein the more than one exonucleases comprise Rec Jf.

3. The method of claim 1, wherein the more than one exonucleases comprise Exo VII.

4. The method of claim 1, wherein the more than one exonucleases comprise Exo I.

5. The method of claim 4, wherein the more than one exonucleases comprise Thermolabile Exo I.

6. The method of claim 1, wherein the more than one exonucleases comprise Rec Jf, Exo VII, and Exo I.

7. The method of claim 1, wherein the more than one exonucleases comprise Rec Jf, Exo VII, and Thermolabile Exo I.

8. The method of claim 1, further comprising, between d) and e), inactivating the more than one exonucleases.

9. The method of claim 8, wherein the inactivating comprises heat-inactivating.

10. The method of claim 1, wherein the solid support comprises tannic acid.

11. The method of claim 1, wherein the solid support comprises acrylic acid.

12. The method of claim 1, wherein the solid support comprises a homopolymeric coating.

13. The method of claim 1, wherein the plurality of primers is bound to the solid support by a 5' terminal amine modification.

14. The method of claim 1, wherein the plurality of primers is covalently bound to the solid support.

15. The method of claim 1, wherein the solid support comprises glass.

16. The method of claim 1, wherein the solid support comprises an assay plate.

17. The method of claim 16, wherein the assay plate is a multi-well assay plate.

18. The method of claim 1, wherein in f) the plurality of amplification products immobilized to the solid support are in a solution comprising a crowding agent.

19. The method of claim 18, wherein the crowding agent comprises polyethylene glycol (PEG).

20. The method of claim 19, wherein the PEG has an average molecular weight between 200 and 8000.

21. The method of claim 19, wherein the PEG is at a concentration of at least 12%.

22. The method of claim 1, wherein the plurality of primers are bound to the solid support in an irregular dispersal.

23. The method of claim 1, wherein the five or more different labels comprise five or more different fluorescent labels.

\* \* \* \* \*

SEQUENCE LISTING

<160> NUMBER OF SEQ ID NOS: 35

<210> SEQ ID NO 1
<211> LENGTH: 24
<212> TYPE: DNA

<213> ORGANISM: Artificial sequence
<220> FEATURE:
<223> OTHER INFORMATION: Synthetic

<400> SEQUENCE: 1
agtctaggat tcggcgtggg ttaa                                              24

<210> SEQ ID NO 2
<211> LENGTH: 31
<212> TYPE: DNA
<213> ORGANISM: Artificial sequence
<220> FEATURE:
<223> OTHER INFORMATION: Synthetic

<400> SEQUENCE: 2
ggtggcttcc ttggccgaag tgcggggacc g                                      31

<210> SEQ ID NO 3
<211> LENGTH: 56
<212> TYPE: DNA
<213> ORGANISM: Artificial sequence
<220> FEATURE:
<223> OTHER INFORMATION: Synthetic

<400> SEQUENCE: 3
agtctaggat tcggcgtggg ttaaggtggc ttccttggcc gaagtgcggg gaccgc           56

<210> SEQ ID NO 4
<211> LENGTH: 100
<212> TYPE: DNA
<213> ORGANISM: Artificial sequence
<220> FEATURE:
<223> OTHER INFORMATION: Synthetic

<400> SEQUENCE: 4
ccttcgactt caagagacca tgagttgtgc ggtccccgca cttcggccaa ggaagccacc       60
atcatcagta gtgtgatggc agcctagcac gggcattagc                            100

<210> SEQ ID NO 5
<211> LENGTH: 48
<212> TYPE: DNA
<213> ORGANISM: Artificial sequence
<220> FEATURE:
<223> OTHER INFORMATION: Synthetic

<400> SEQUENCE: 5
ttaacccacg ccgaatccta gactcaaagt agtctaggat tcggcgtg                    48

<210> SEQ ID NO 6
<211> LENGTH: 48
<212> TYPE: DNA
<213> ORGANISM: Artificial sequence
<220> FEATURE:
<223> OTHER INFORMATION: Synthetic

<400> SEQUENCE: 6
agtctaggat tcggcgtggg ttaacacgcc gaatcctaga ctactttg                    48

<210> SEQ ID NO 7
<211> LENGTH: 28
<212> TYPE: DNA
<213> ORGANISM: Artificial sequence
<220> FEATURE:
<223> OTHER INFORMATION: Synthetic
<220> FEATURE:
<221> NAME/KEY: misc_feature

```
<222> LOCATION: (1)..(1)
<223> OTHER INFORMATION: n is a, c, g, t or u

<400> SEQUENCE: 7
ncgtcgtagg tcacttaaca tagaguuu                                              28

<210> SEQ ID NO 8
<211> LENGTH: 24
<212> TYPE: DNA
<213> ORGANISM: Artificial sequence
<220> FEATURE:
<223> OTHER INFORMATION: Synthetic

<400> SEQUENCE: 8
ctctatgtta agtgacctac gacg                                                  24

<210> SEQ ID NO 9
<211> LENGTH: 25
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 9
ncgtcgtagg tcacttaaca tagag                                                 25

<210> SEQ ID NO 10
<211> LENGTH: 41
<212> TYPE: DNA
<213> ORGANISM: Artificial sequence
<220> FEATURE:
<223> OTHER INFORMATION: Synthetic

<400> SEQUENCE: 10
tcggtccgag ggtctcgtcg taggtcactt aacatagagt t                               41

<210> SEQ ID NO 11
<211> LENGTH: 41
<212> TYPE: DNA
<213> ORGANISM: Artificial sequence
<220> FEATURE:
<223> OTHER INFORMATION: Synthetic

<400> SEQUENCE: 11
tgggttgccg tggttcgtcg taggtcactt aacatagagt t                               41

<210> SEQ ID NO 12
<211> LENGTH: 44
<212> TYPE: DNA
<213> ORGANISM: Artificial sequence
<220> FEATURE:
<223> OTHER INFORMATION: Synthetic

<400> SEQUENCE: 12
ttcatttggc agtgggtccg tcgtaggtca cttaacatag agtt                            44

<210> SEQ ID NO 13
<211> LENGTH: 44
<212> TYPE: DNA
<213> ORGANISM: Artificial sequence
<220> FEATURE:
<223> OTHER INFORMATION: Synthetic
```

<400> SEQUENCE: 13
tggaaagagg ctgctagtcg tcgtaggtca cttaacatag agtt        44

<210> SEQ ID NO 14
<211> LENGTH: 46
<212> TYPE: DNA
<213> ORGANISM: Artificial sequence
<220> FEATURE:
<223> OTHER INFORMATION: Synthetic

<400> SEQUENCE: 14
gtcgtttact gtccatttgc cgtcgtaggt cacttaacat agagtt      46

<210> SEQ ID NO 15
<211> LENGTH: 46
<212> TYPE: DNA
<213> ORGANISM: Artificial sequence
<220> FEATURE:
<223> OTHER INFORMATION: Synthetic

<400> SEQUENCE: 15
ctgcgctagt cattcatttg cgtcgtaggt cacttaacat agagtt      46

<210> SEQ ID NO 16
<211> LENGTH: 33
<212> TYPE: DNA
<213> ORGANISM: Artificial sequence
<220> FEATURE:
<223> OTHER INFORMATION: Synthetic

<400> SEQUENCE: 16
tttttttcgt cgtaggtcac ttaacataga gtt        33

<210> SEQ ID NO 17
<211> LENGTH: 24
<212> TYPE: DNA
<213> ORGANISM: Artificial sequence
<220> FEATURE:
<223> OTHER INFORMATION: Synthetic

<400> SEQUENCE: 17
cgtcgtaggt cacttaacat agag              24

<210> SEQ ID NO 18
<211> LENGTH: 28
<212> TYPE: DNA
<213> ORGANISM: Artificial sequence
<220> FEATURE:
<223> OTHER INFORMATION: Synthetic

<400> SEQUENCE: 18
ttttcgtcgt aggtcactta acatagag          28

<210> SEQ ID NO 19
<211> LENGTH: 27
<212> TYPE: DNA
<213> ORGANISM: Artificial sequence
<220> FEATURE:
<223> OTHER INFORMATION: Synthetic

<400> SEQUENCE: 19
ttttcgtcgt aggtcactta acataag           27

<210> SEQ ID NO 20
<211> LENGTH: 28

<212> TYPE: DNA
<213> ORGANISM: Artificial sequence
<220> FEATURE:
<223> OTHER INFORMATION: Synthetic

<400> SEQUENCE: 20
ttttcgtcgt aggtcactta acatagag                                              28

<210> SEQ ID NO 21
<211> LENGTH: 28
<212> TYPE: DNA
<213> ORGANISM: Artificial sequence
<220> FEATURE:
<223> OTHER INFORMATION: Synthetic

<400> SEQUENCE: 21
ttttcgtcgt aggtcactta acatagag                                              28

<210> SEQ ID NO 22
<211> LENGTH: 28
<212> TYPE: DNA
<213> ORGANISM: Artificial sequence
<220> FEATURE:
<223> OTHER INFORMATION: Synthetic

<400> SEQUENCE: 22
ttttcgtcgt aggtcactta acatagag                                              28

<210> SEQ ID NO 23
<211> LENGTH: 86
<212> TYPE: DNA
<213> ORGANISM: Artificial sequence
<220> FEATURE:
<223> OTHER INFORMATION: Synthetic

<400> SEQUENCE: 23
cctcccatca tattaaaggc ctctatgtta agtgacctac gacgatgctg ctgctgtact           60
acgaggctaa ggcattctgc aaacat                                                86

<210> SEQ ID NO 24
<211> LENGTH: 27
<212> TYPE: DNA
<213> ORGANISM: Artificial sequence
<220> FEATURE:
<223> OTHER INFORMATION: Synthetic

<400> SEQUENCE: 24
cctcaggtgt gtaactcgat caggagg                                               27

<210> SEQ ID NO 25
<211> LENGTH: 27
<212> TYPE: DNA
<213> ORGANISM: Artificial sequence
<220> FEATURE:
<223> OTHER INFORMATION: Synthetic

<400> SEQUENCE: 25
cctcaatgct gctgctgtac tacgagg                                               27

<210> SEQ ID NO 26
<211> LENGTH: 27
<212> TYPE: DNA
<213> ORGANISM: Artificial sequence
<220> FEATURE:
<223> OTHER INFORMATION: Synthetic

<400> SEQUENCE: 26
cctcaggtgt gtaactcgat caggagg                                    27

<210> SEQ ID NO 27
<211> LENGTH: 27
<212> TYPE: DNA
<213> ORGANISM: Artificial sequence
<220> FEATURE:
<223> OTHER INFORMATION: Synthetic

<400> SEQUENCE: 27
cctcagcgct gcctattcga actgagg                                    27

<210> SEQ ID NO 28
<211> LENGTH: 23
<212> TYPE: DNA
<213> ORGANISM: Artificial sequence
<220> FEATURE:
<223> OTHER INFORMATION: Synthetic

<400> SEQUENCE: 28
cctcaggtgt gtaactcgat cag                                        23

<210> SEQ ID NO 29
<211> LENGTH: 18
<212> TYPE: DNA
<213> ORGANISM: Artificial sequence
<220> FEATURE:
<223> OTHER INFORMATION: Synthetic

<400> SEQUENCE: 29
atgctgctgc tgtactac                                              18

<210> SEQ ID NO 30
<211> LENGTH: 18
<212> TYPE: DNA
<213> ORGANISM: Artificial sequence
<220> FEATURE:
<223> OTHER INFORMATION: Synthetic

<400> SEQUENCE: 30
agacagctaa ctcagacc                                              18

<210> SEQ ID NO 31
<211> LENGTH: 18
<212> TYPE: DNA
<213> ORGANISM: Artificial sequence
<220> FEATURE:
<223> OTHER INFORMATION: Synthetic

<400> SEQUENCE: 31
ggtgtgtaac tcgatcag                                              18

<210> SEQ ID NO 32
<211> LENGTH: 16
<212> TYPE: DNA
<213> ORGANISM: Artificial sequence
<220> FEATURE:
<223> OTHER INFORMATION: Synthetic

<400> SEQUENCE: 32
cgctgcctat tcgaac                                                16

<210> SEQ ID NO 33
<211> LENGTH: 18

```
<212> TYPE: DNA
<213> ORGANISM: Artificial sequence
<220> FEATURE:
<223> OTHER INFORMATION: Synthetic

<400> SEQUENCE: 33
ctgaagtacc gcacgaat                                               18

<210> SEQ ID NO 34
<211> LENGTH: 18
<212> TYPE: DNA
<213> ORGANISM: Artificial sequence
<220> FEATURE:
<223> OTHER INFORMATION: Synthetic

<400> SEQUENCE: 34
catggacgag ctgtacaa                                               18

<210> SEQ ID NO 35
<211> LENGTH: 26
<212> TYPE: DNA
<213> ORGANISM: Artificial sequence
<220> FEATURE:
<223> OTHER INFORMATION: Synthetic

<400> SEQUENCE: 35
cgtcgtaggt cacttaacat agagtt                                      26
```